United States Patent
Joseph et al.

(10) Patent No.: US 10,518,153 B2
(45) Date of Patent: Dec. 31, 2019

(54) SYSTEM AND METHOD FOR IMPROVING A BASKETBALL PLAYER'S SHOOTING INCLUDING A TRACKING AND CONTROL SYSTEM FOR TRACKING, CONTROLLING AND REPORTING STATISTICS

(71) Applicant: Shoot-A-Way, Inc., Upper Sandusky, OH (US)

(72) Inventors: John G. Joseph, Upper Sandusky, OH (US); Troy David Geiser, Findlay, OH (US); Albert Charles Abnett, Nevada, OH (US)

(73) Assignee: Shoot-A-Way, Inc., Upper Sandusky, OH (US)

( * ) Notice: Subject to any disclaimer, the term of this patent is extended or adjusted under 35 U.S.C. 154(b) by 0 days.

(21) Appl. No.: 14/984,051

(22) Filed: Dec. 30, 2015

(65) Prior Publication Data
US 2016/0166907 A1 Jun. 16, 2016

Related U.S. Application Data

(63) Continuation of application No. 13/529,903, filed on Jun. 21, 2012, now Pat. No. 9,233,292, which is a
(Continued)

(51) Int. Cl.
*A63B 69/00* (2006.01)
*A63B 69/40* (2006.01)
(Continued)

(52) U.S. Cl.
CPC ...... *A63B 69/0071* (2013.01); *A63B 24/0021* (2013.01); *A63B 24/0075* (2013.01);
(Continued)

(58) Field of Classification Search
CPC ............ A63B 69/0071; A63B 24/0021; A63B 24/0075; A63B 47/002; A63B 47/02;
(Continued)

(56) References Cited

U.S. PATENT DOCUMENTS

| 1,223,386 | A | 4/1917 | Handelan |
| 2,908,266 | A | 10/1959 | Cooper |

(Continued)

FOREIGN PATENT DOCUMENTS

| EP | 2271414 B1 | 6/2014 |
| RU | 2026104 | 1/1995 |

(Continued)

OTHER PUBLICATIONS

Brochure entitled "Sniper: The Ultimate Basketball Trainer." before Oct. 22, 1995, 5 pages including the cover letter.
(Continued)

*Primary Examiner* — Mitra Aryanpour
(74) *Attorney, Agent, or Firm* — Standley Law Group LLP

(57) ABSTRACT

A device for assisting a user during basketball practice is disclosed. The device includes an ejector that launches a basketball, a control system that detects and records shooting data and programs the ejector, and an interface that has a plurality of indicia and communicates with the control system. A report generator is included that generates a report on the shooting data. In exemplary embodiments, a tracking device may detect the location of the basketball and a sensor may detect if the basketball passes through the goal.

14 Claims, 88 Drawing Sheets

Related U.S. Application Data continuation-in-part of application No. 12/420,122, filed on Apr. 8, 2009, now Pat. No. 8,206,246.

(51) Int. Cl.
| | |
|---|---|
| *A63B 63/08* | (2006.01) |
| *A63B 71/02* | (2006.01) |
| *A63B 71/06* | (2006.01) |
| *A63B 47/02* | (2006.01) |
| *G09B 19/00* | (2006.01) |
| *G06F 19/00* | (2018.01) |
| *G01S 13/58* | (2006.01) |
| *G01S 13/88* | (2006.01) |
| *A63B 24/00* | (2006.01) |
| *A63B 63/00* | (2006.01) |
| *A63B 47/00* | (2006.01) |

(52) U.S. Cl.
CPC ............ *A63B 47/02* (2013.01); *A63B 63/083* (2013.01); *A63B 69/40* (2013.01); *A63B 71/022* (2013.01); *A63B 71/0616* (2013.01); *A63B 71/0619* (2013.01); *G01S 13/582* (2013.01); *G01S 13/88* (2013.01); *G06F 19/3481* (2013.01); *G09B 19/0038* (2013.01); *A63B 47/002* (2013.01); *A63B 2024/0034* (2013.01); *A63B 2024/0056* (2013.01); *A63B 2063/001* (2013.01); *A63B 2071/025* (2013.01); *A63B 2071/0694* (2013.01); *A63B 2207/02* (2013.01); *A63B 2210/50* (2013.01); *A63B 2220/13* (2013.01); *A63B 2220/17* (2013.01); *A63B 2220/20* (2013.01); *A63B 2220/802* (2013.01); *A63B 2220/805* (2013.01); *A63B 2220/89* (2013.01); *A63B 2225/20* (2013.01); *A63B 2225/50* (2013.01)

(58) Field of Classification Search
CPC ..... A63B 63/083; A63B 69/40; A63B 71/022; A63B 71/0616; A63B 71/0619; A63B 2024/0034; A63B 2024/0056; A63B 2063/001; G09B 19/0038
USPC ....... 473/433, 422, 447, 431, 432, 479–481, 473/467
See application file for complete search history.

(56) References Cited

U.S. PATENT DOCUMENTS

| | | | |
|---|---|---|---|
| 3,776,550 | A | 12/1973 | McNabb |
| 3,802,703 | A | 4/1974 | Van Tassel |
| 3,878,828 | A | 4/1975 | Francesco |
| 4,168,695 | A | 9/1979 | Haller et al. |
| 4,262,648 | A | 4/1981 | Wegener et al. |
| 4,269,163 | A | 5/1981 | Feith |
| 4,471,746 | A | 9/1984 | Ando |
| 4,579,340 | A | 4/1986 | Jenkins et al. |
| 4,667,957 | A | 5/1987 | Joseph |
| 4,678,189 | A | 7/1987 | Koss |
| 4,714,248 | A | 12/1987 | Koss |
| 4,747,149 | A | 1/1988 | Juhl |
| 4,913,431 | A | 4/1990 | Jakobs |
| 4,936,577 | A | 6/1990 | Kington et al. |
| 4,940,231 | A | 7/1990 | Ehler |
| 4,955,605 | A | 9/1990 | Goldfarb |
| 5,016,875 | A | 5/1991 | Joseph |
| 5,125,651 | A | 6/1992 | Keeling et al. |
| 5,312,099 | A | 5/1994 | Oliver, Sr. |
| 5,342,041 | A | 8/1994 | Aguinek et al. |
| 5,365,427 | A | 11/1994 | Soignet et al. |
| 5,393,049 | A | 2/1995 | Nelson |
| 5,409,211 | A | 4/1995 | Adamek |
| 5,417,196 | A | 5/1995 | Morrison et al. |
| 5,540,428 | A | 7/1996 | Joseph |
| 5,647,747 | A | 7/1997 | Macri et al. |
| 5,676,120 | A | 10/1997 | Joseph |
| 5,681,230 | A | 10/1997 | Krings |
| 5,746,668 | A | 5/1998 | Ochs |
| 5,768,151 | A | 6/1998 | Lowy et al. |
| 5,776,018 | A | 7/1998 | Simpson et al. |
| 5,813,926 | A | 9/1998 | Vance |
| 5,842,699 | A | 12/1998 | Mirando et al. |
| 6,224,503 | B1 | 5/2001 | Joseph |
| 6,241,628 | B1 * | 6/2001 | Jenkins .............. A63B 69/0071 473/422 |
| 6,389,368 | B1 | 5/2002 | Hampton |
| 6,707,487 | B1 | 3/2004 | Aman et al. |
| 6,731,316 | B2 | 5/2004 | Herigstad et al. |
| 6,746,397 | B2 | 6/2004 | Lee et al. |
| 7,094,164 | B2 | 8/2006 | Marty et al. |
| 7,850,552 | B2 | 12/2010 | Marty et al. |
| 7,854,669 | B2 | 12/2010 | Marty et al. |
| 7,927,237 | B2 | 4/2011 | Jenkins et al. |
| 7,938,746 | B2 | 5/2011 | Chipperfield |
| 8,016,687 | B2 | 9/2011 | Martin et al. |
| 8,123,634 | B1 | 2/2012 | Lovett |
| 8,147,356 | B2 | 4/2012 | Campbell et al. |
| 8,206,246 | B2 | 6/2012 | Joseph et al. |
| 8,408,982 | B2 | 4/2013 | Marty et al. |
| 8,409,024 | B2 | 4/2013 | Marty et al. |
| 8,540,560 | B2 | 9/2013 | Crowley et al. |
| 8,579,632 | B2 | 11/2013 | Crowley |
| 8,617,008 | B2 | 12/2013 | Marty et al. |
| 8,622,832 | B2 | 1/2014 | Marty et al. |
| 8,852,030 | B2 | 10/2014 | Campbell et al. |
| 9,010,309 | B2 | 4/2015 | Lewis et al. |
| 9,017,188 | B2 | 4/2015 | Joseph et al. |
| 9,233,292 | B2 | 1/2016 | Joseph et al. |
| 9,248,368 | B2 | 2/2016 | Stimac |
| 9,724,584 | B1 | 8/2017 | Campbell et al. |
| 9,808,696 | B2 | 11/2017 | Campbell et al. |
| 2002/0010032 | A1 | 1/2002 | Stiteler |
| 2003/0023145 | A1 | 1/2003 | Lee et al. |
| 2006/0160639 | A1 | 7/2006 | Klein |
| 2007/0026975 | A1 | 2/2007 | Marty et al. |
| 2008/0015061 | A1 | 1/2008 | Klein |
| 2008/0200287 | A1 | 8/2008 | Marty et al. |
| 2008/0254866 | A1 | 10/2008 | Young et al. |
| 2008/0261726 | A1 | 10/2008 | Chipperfield |
| 2008/0312010 | A1 | 12/2008 | Marty et al. |
| 2009/0137347 | A1 | 5/2009 | Jenkins et al. |
| 2010/0259412 | A1 | 10/2010 | Pagonakis |
| 2011/0294585 | A1 | 12/2011 | Penna et al. |
| 2012/0115651 | A1 | 5/2012 | Chipperfield |
| 2013/0095959 | A1 | 4/2013 | Marty et al. |
| 2013/0130845 | A1 | 5/2013 | Marty et al. |
| 2013/0172058 | A1 | 7/2013 | Marty et al. |
| 2014/0092253 | A1 | 4/2014 | Marty et al. |
| 2014/0200692 | A1 | 7/2014 | Thurman et al. |
| 2015/0265897 | A1 | 9/2015 | Gordon et al. |
| 2016/0325168 | A1 | 11/2016 | Campbell et al. |

FOREIGN PATENT DOCUMENTS

| | | |
|---|---|---|
| WO | 9530872 A1 | 11/1995 |
| WO | 9532033 | 11/1995 |
| WO | 2005062841 | 7/2005 |
| WO | 2009126982 A2 | 10/2009 |

OTHER PUBLICATIONS

The Gun 6000 Series, Shoot-A-Way, Inc. Upper Sandusky, Ohio, http://www.shootaway.com/Gun1.htm/, at least as early as Jun. 2000.

Dr. Dish™, Airborne Athletics Inc., Belle Plaine, Minnesota, http://www.drdishbasketball.com/, at least as early as Jul. 29, 2003.

IMake™, Airborne Athletics Inc., Belle Plaine, Minnesota, www.imakebasketball.com. (The iMake has a menu drive programming board allowing the user to select a shooting range by selecting a left

(56) References Cited

OTHER PUBLICATIONS and a right limit. The user is given the ability to select spots between said shooting range in spaced increments for the machine to tire balls in that direction. ) At least as early as Jun. 2008.
Vorelco, The Sniper Basketball Training System, https://www.youtube.com/watch?v=X9SqMy8xdf4, Uploaded on Jul. 5, 2008.

* cited by examiner

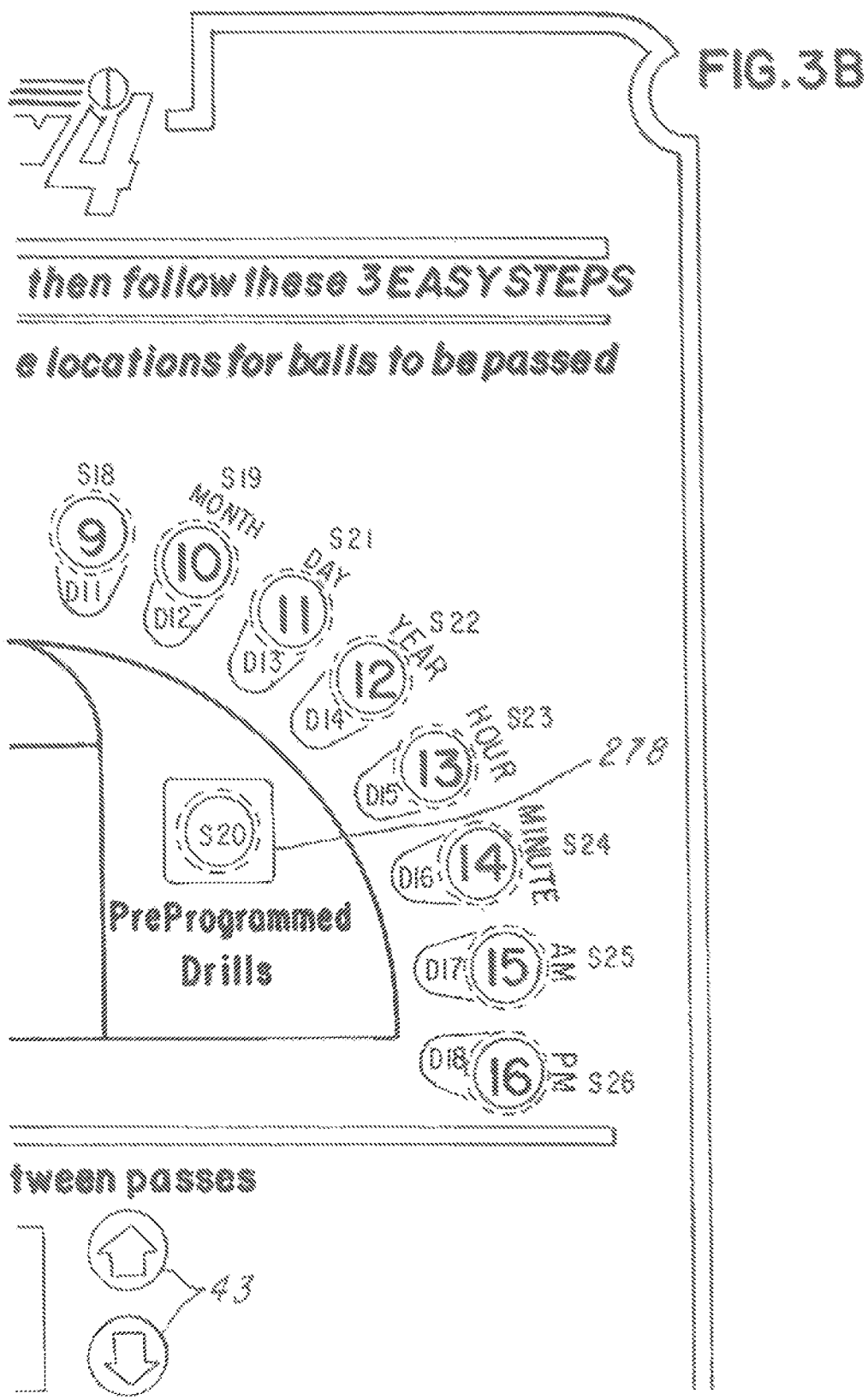

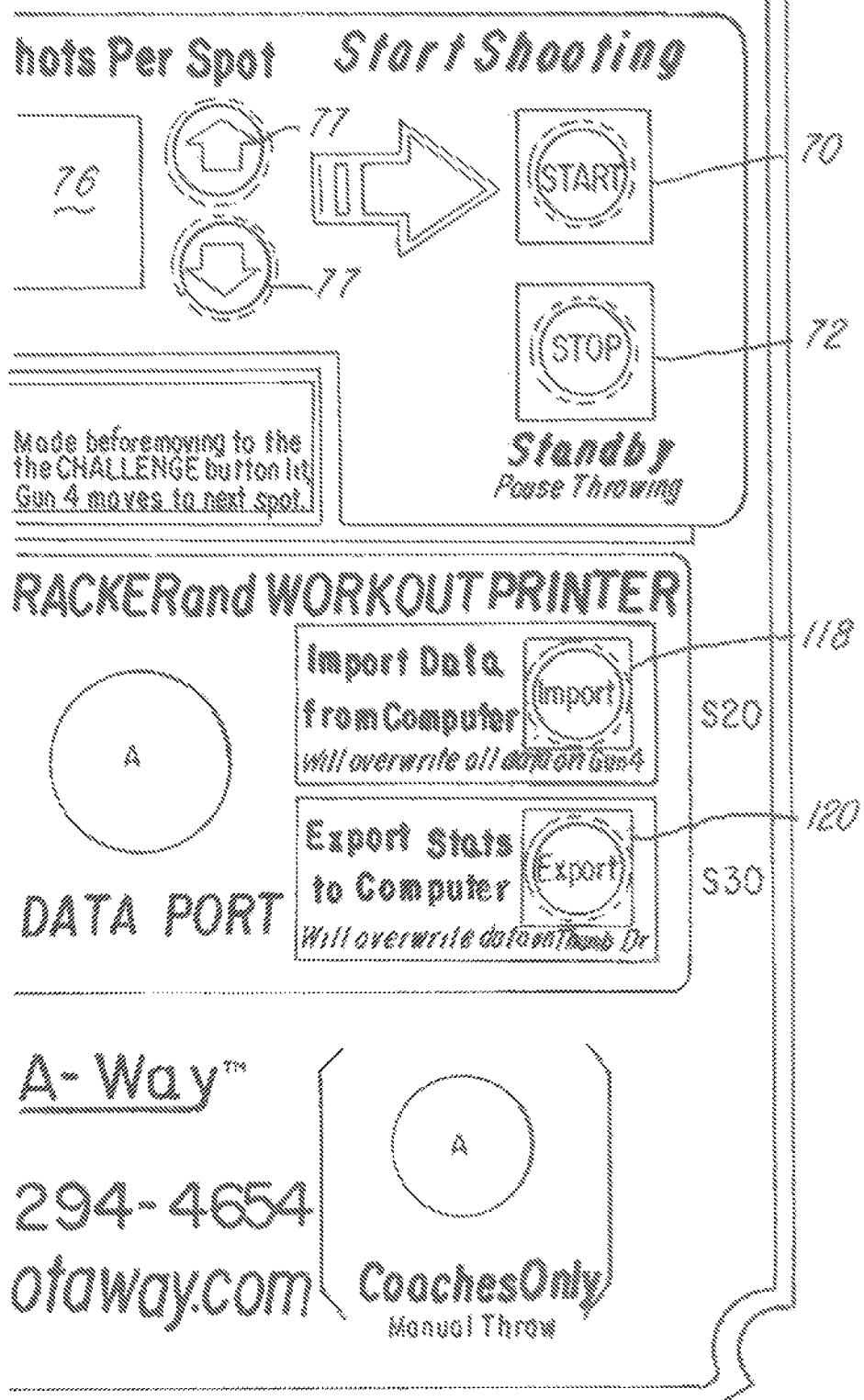

| SHOT | MAKES | TOTAL ATTEMPTS | MAKES IN A ROW | TOTAL MAKES | PERCENTAGE TOTAL MAKES / TOTAL ATTEMPTS |
|---|---|---|---|---|---|

USER NAME: JOHN SMITH – USER DEFINED PERIOD

Fig. 6: Example Printout

Shooting Workout Printout

User: Joe Thomas
User defined Time Period: 1/1/09 to 3/26/09

| Spot | Makes | Total Shots | Percentage |
|------|-------|-------------|------------|
| 0 | 453 | 634 | 71.5% |
| 1 | 200 | 234 | 85.5% |
| 2 | 100 | 243 | 41.2% |
| 3 | 121 | 323 | 37.5% |
| 4 | 123 | 232 | 53.0% |
| 5 | 105 | 234 | 44.9% |
| 6 | 178 | 343 | 51.9% |
| 7 | 186 | 343 | 54.2% |
| 8 | 543 | 1006 | 54.0% |
| 9 | 66 | 132 | 50.0% |
| 10 | 80 | 232 | 34.5% |
| 11 | 109 | 343 | 31.8% |
| 12 | 243 | 545 | 44.6% |
| 13 | 116 | 343 | 33.8% |
| 14 | 298 | 545 | 54.7% |
| 15 | 100 | 232 | 43.1% |
| 16 | 180 | 423 | 42.6% |
| TOTAL | 3201 | 6387 | 50.1% |

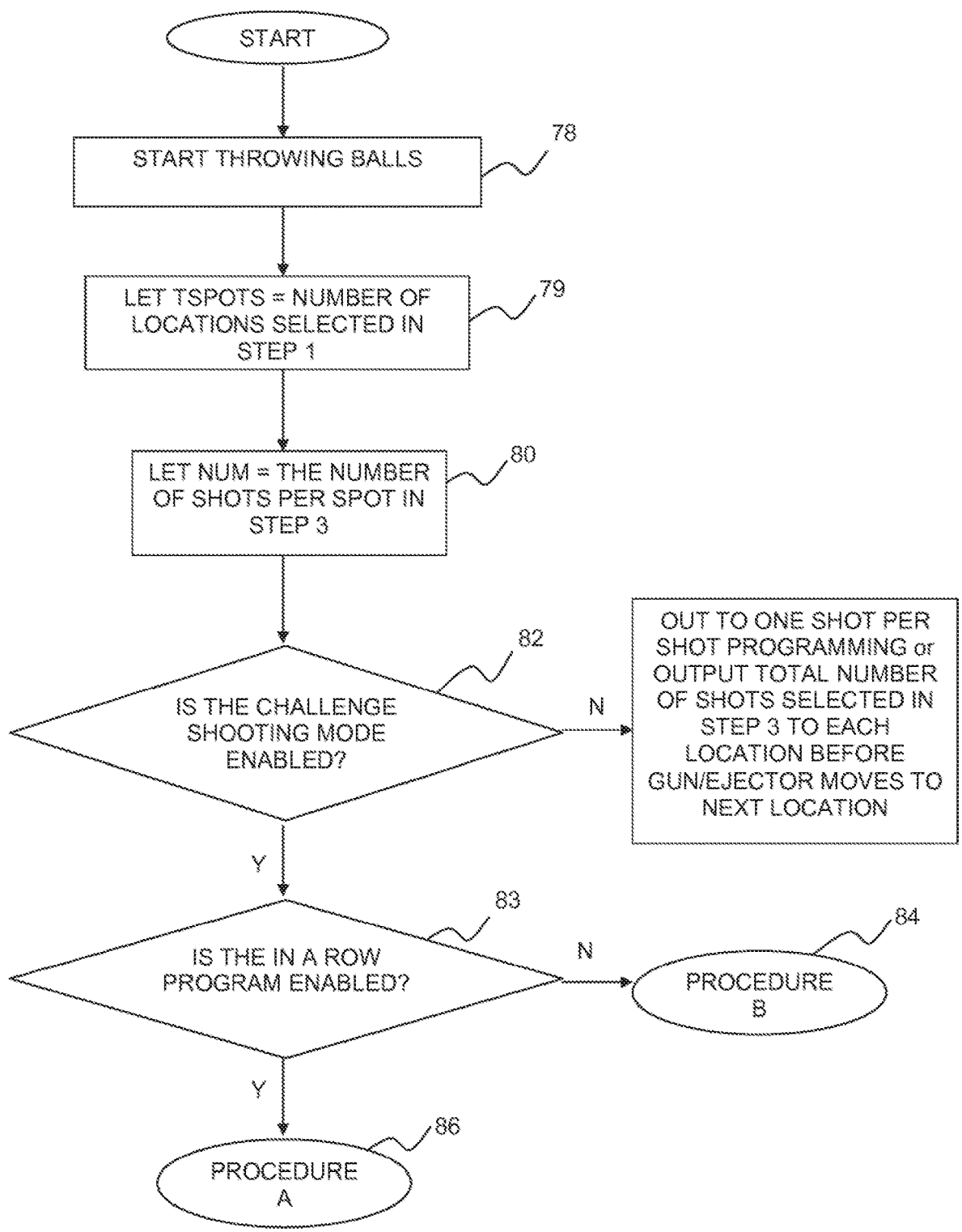

CHALLENGE SHOOTING ACCURACY - PROCEDURE A

Challenge Shooting Accuracy - Procedure B

Multi Shots which MUST BE MADE at 1 or Each Spot

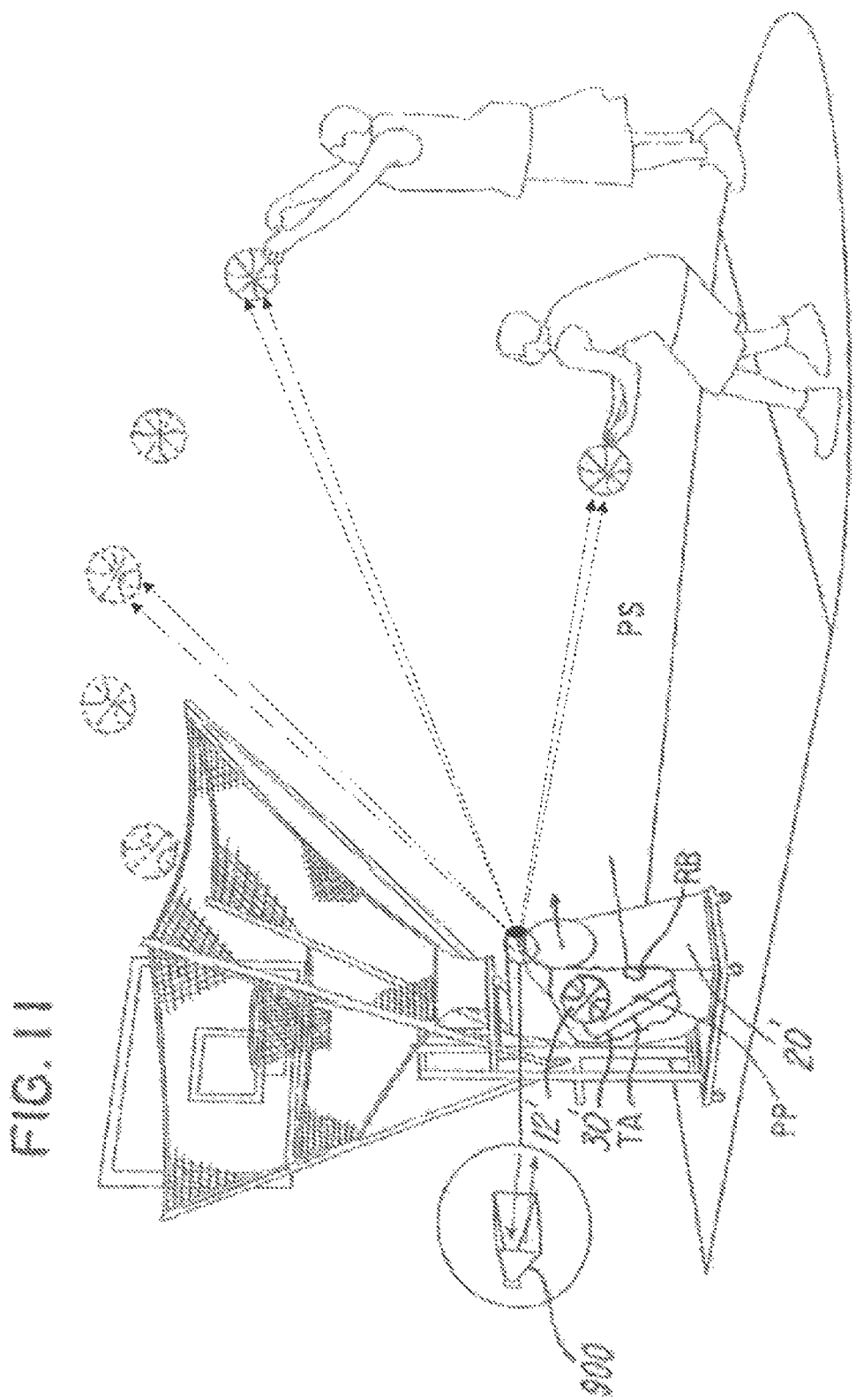

AT ANY POINT P:
(1) $Y = V_{oy}T - 1/2 gT^2$
(2) $X = V_{ox}T$  OR  $T = X/V_{ox}$

Y IS VERTICAL POSITION
X IS HORIZONTAL POSITION
$V_{oy}$ IS VERTICAL VELOCITY COMPONENT, UPON SHOOTING
$V_{ox}$ IS HORIZONTAL VELOCITY COMPONENT, UPON SHOOTING

WHEN BALL REACHES BASKET, $Y = D_B$ AND $X = D$

COMBINE EQUATIONS (1) AND (2): $Y = (X V_{oy} / V_{ox}) - 1/2 g (X^2 / V_{ox}^2)$    (3)

SUBSTITUTE VALUES OF X AND Y AT BASKET:

$$D_B = (D V_{oy} / V_{ox}) - 1/2 g (D^2 / V_{ox}^2) \quad (3A)$$

MULTIPLY BY $V_{ox}^2$ AND RE-ARRANGE $$V_{oy} = (D_B V_{ox}^2 + 1/2 g D^2) / D V_{ox} \quad (4)$$

FOR A GENERALIZED BODY TRAVELLING VERTICALLY TO A HEIGHT H
$(1/2) M V^2 = M g H$  WHERE M IS MASS, g IS ACCELERATION OF GRAVITY
AND V IS VERTICAL VELOCITY.

THAT IS, THE BODY INITIALLY HAD ONLY KINETIC ENERGY
AND ALL THAT IS CONVERTED INTO POTENTIAL ENERGY.

SOLVE FOR H    $H = V^2/2g$

SUBSTITUTE $D_A$ FOR H AND $V_{cy}$ FOR V:    $D_A = V_{cy}^2/2g$    (5)

FIG. 13I
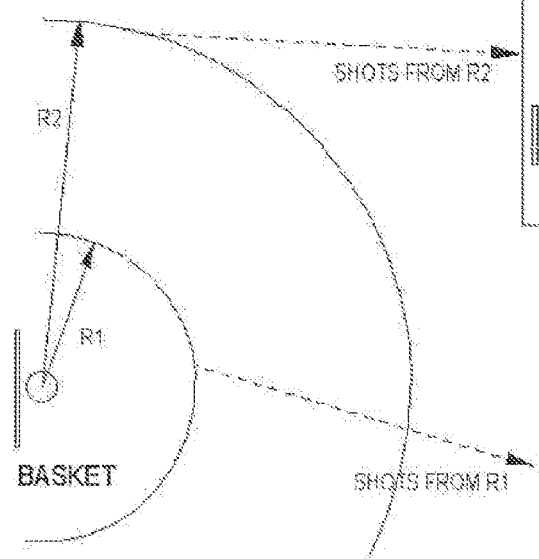
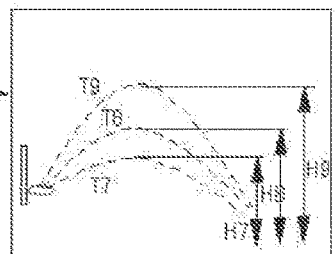
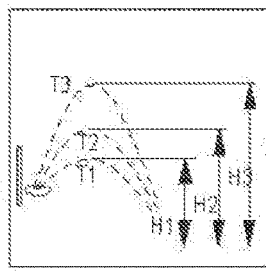
TABLE
R1 T1 H1
R1 T2 H2
R1 T3 H3
R2 T7 H7
R2 T8 H8
R2 T9 H9
YOU KNOW DISTANCE, R, AND TIME, T, FOR A GIVEN SHOT.
YOU THEN LOOK UP THAT R AND THAT T IN THE TABLE, TO FIND H.
SO INSTEAD OF COMPUTING H, IT IS FOUND THROUGH A LOOK-UP.

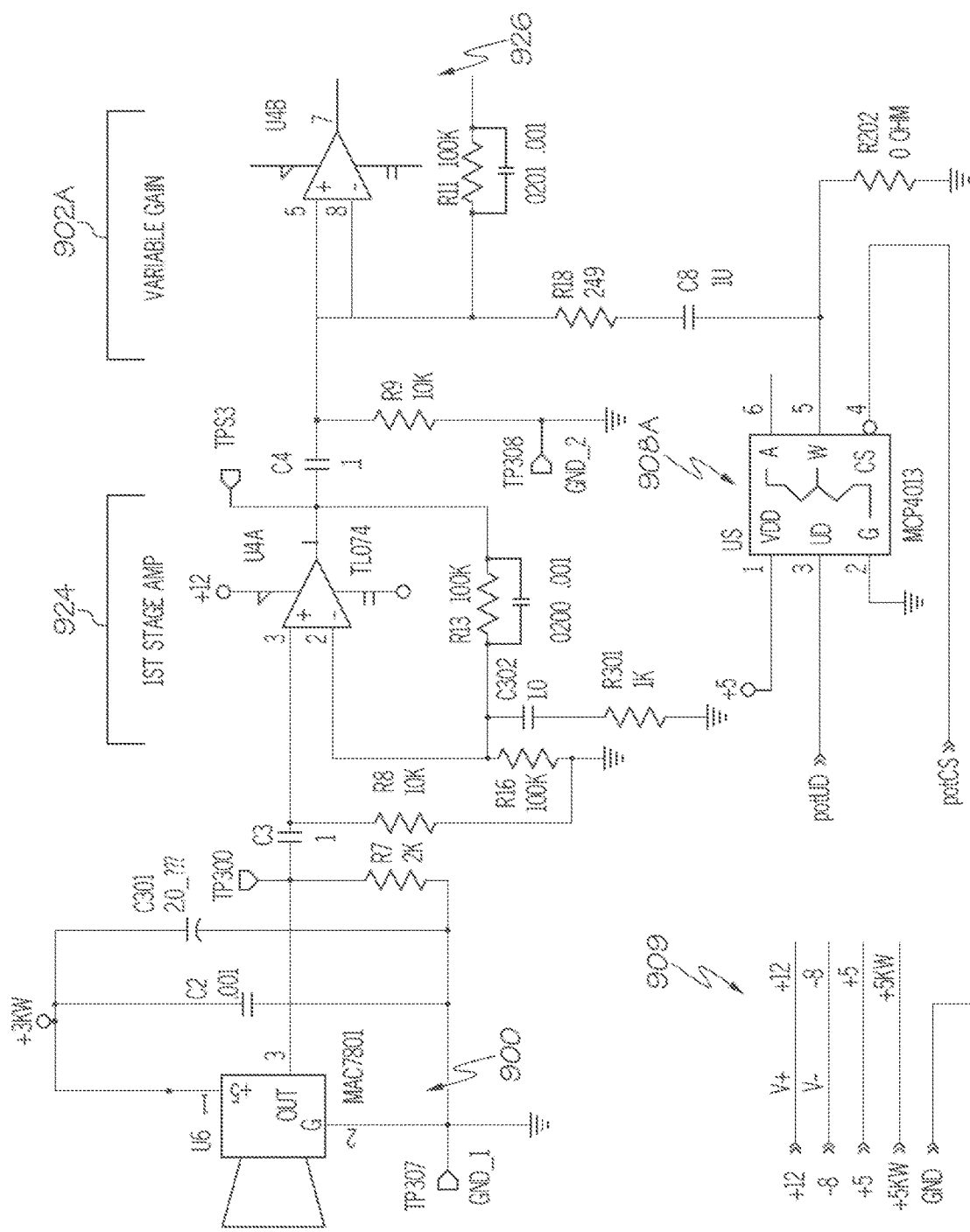
FIG. 15A1

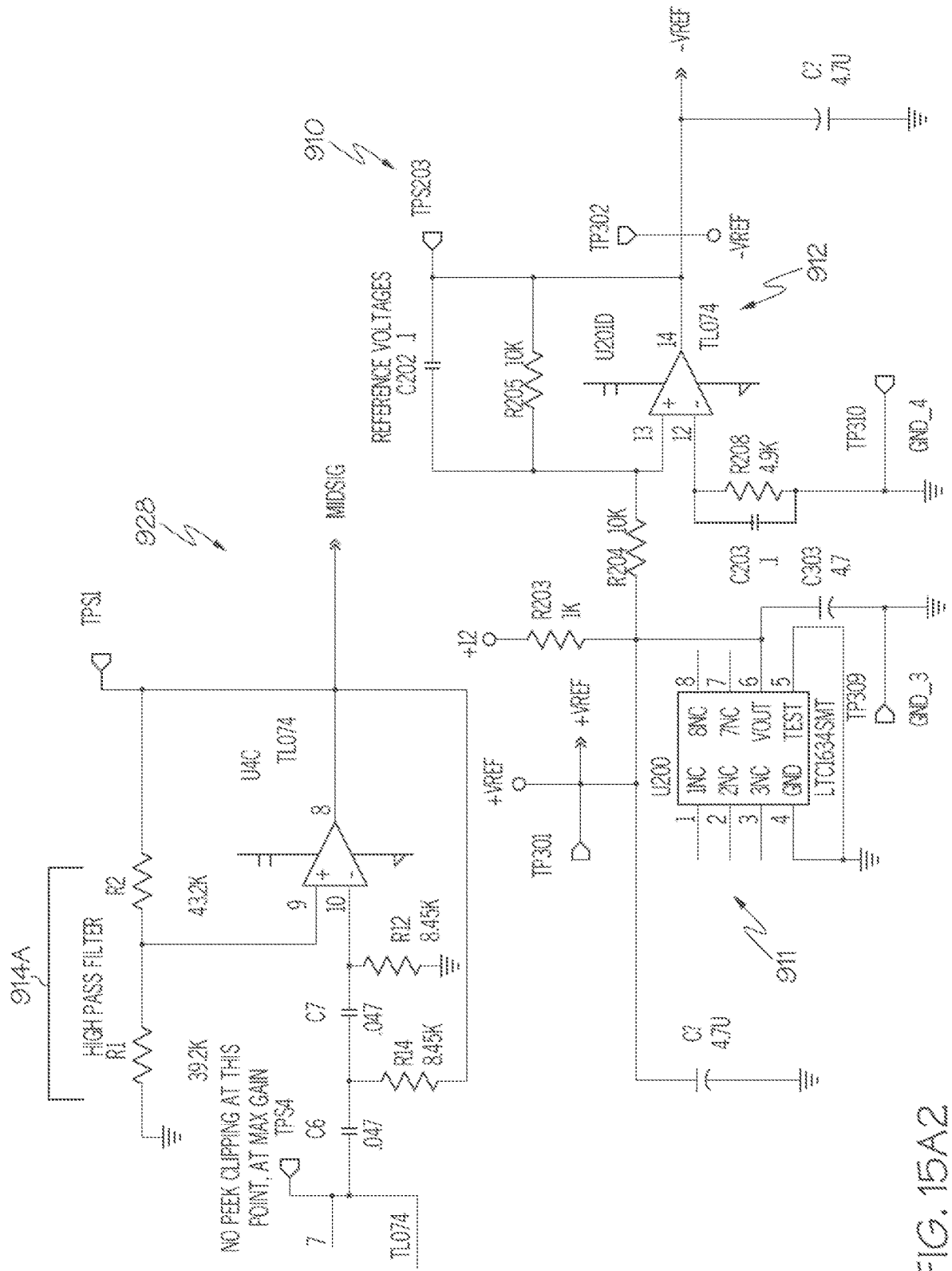
FIG. 15A2

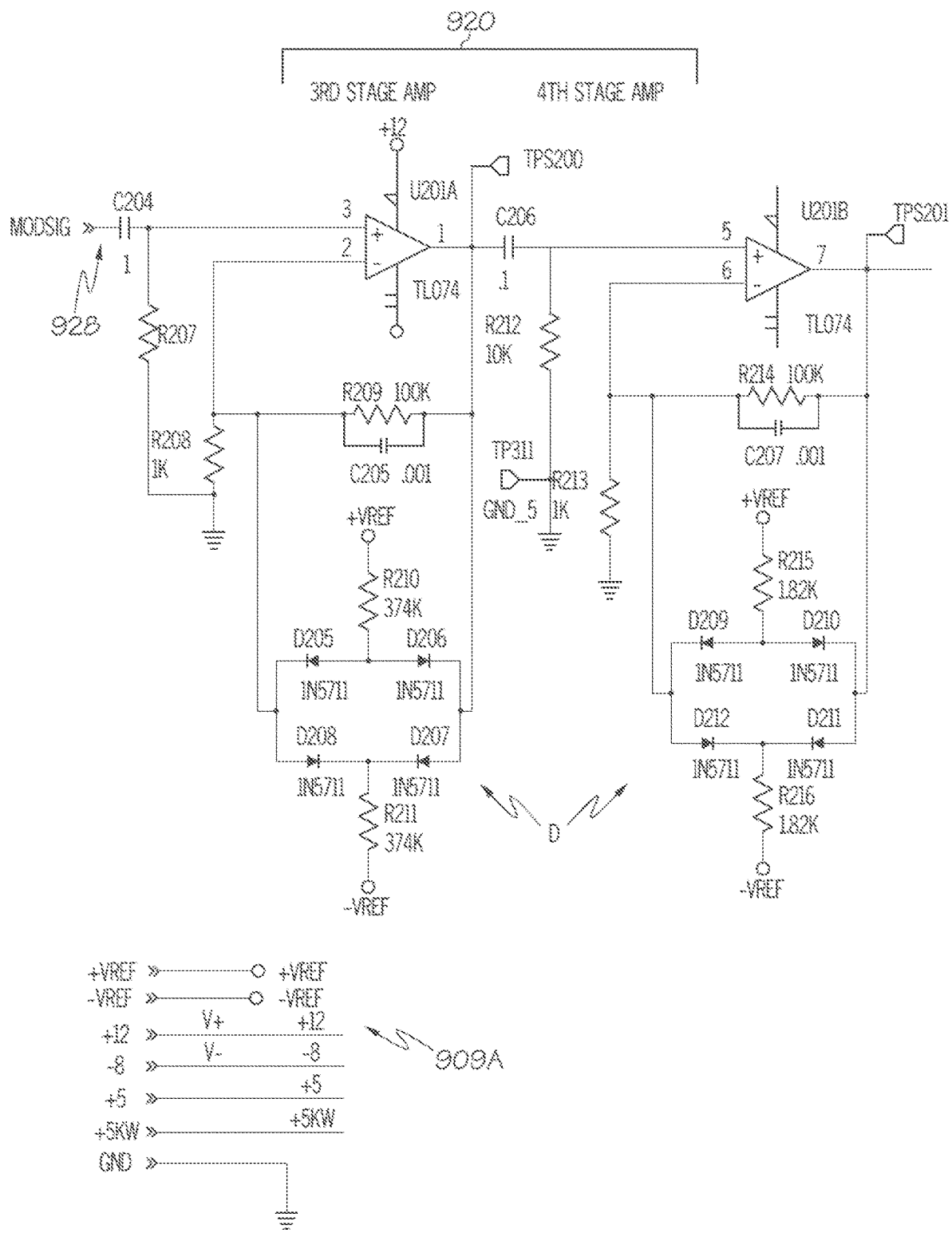
FIG. 15B1

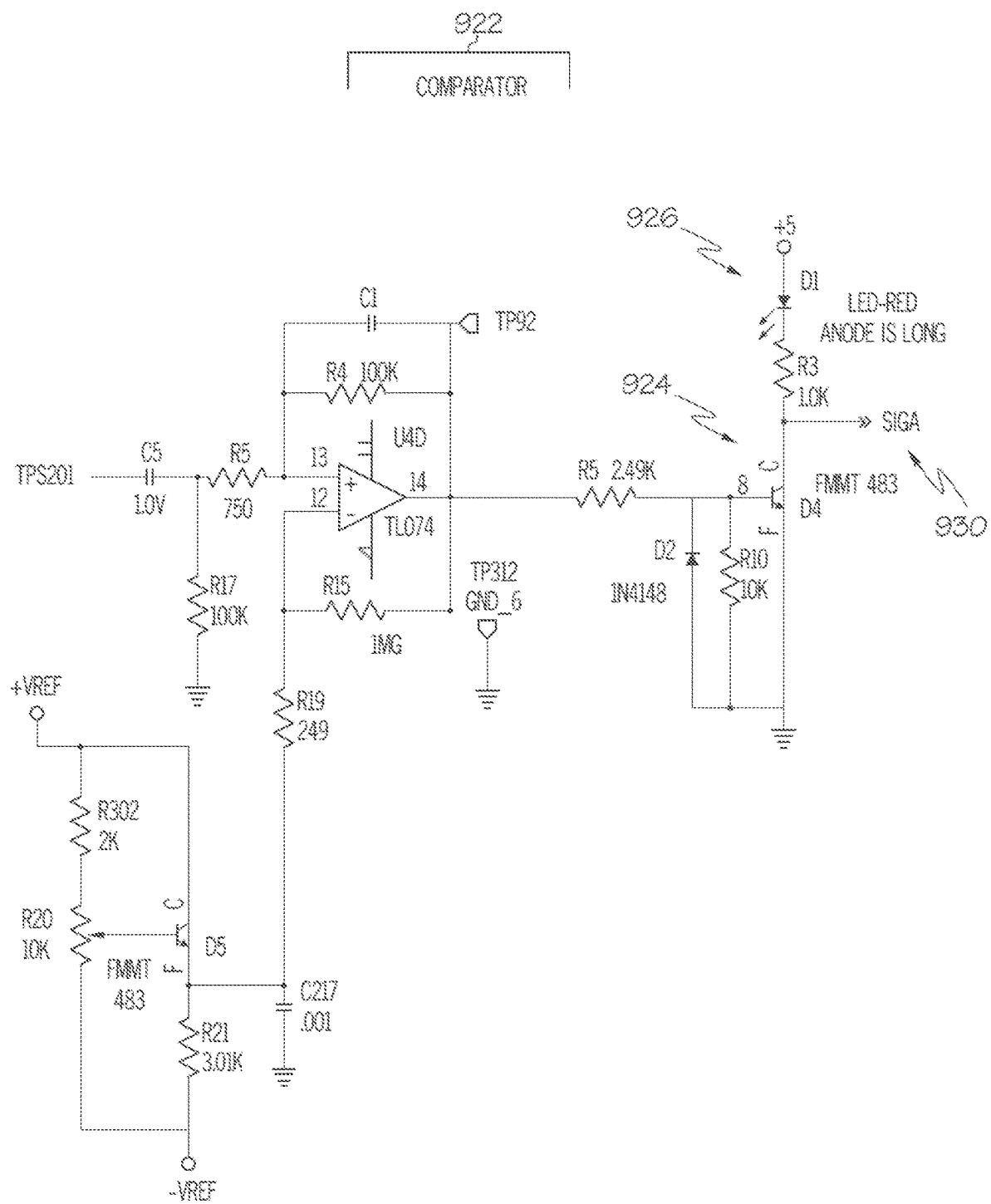
FIG. 15B2

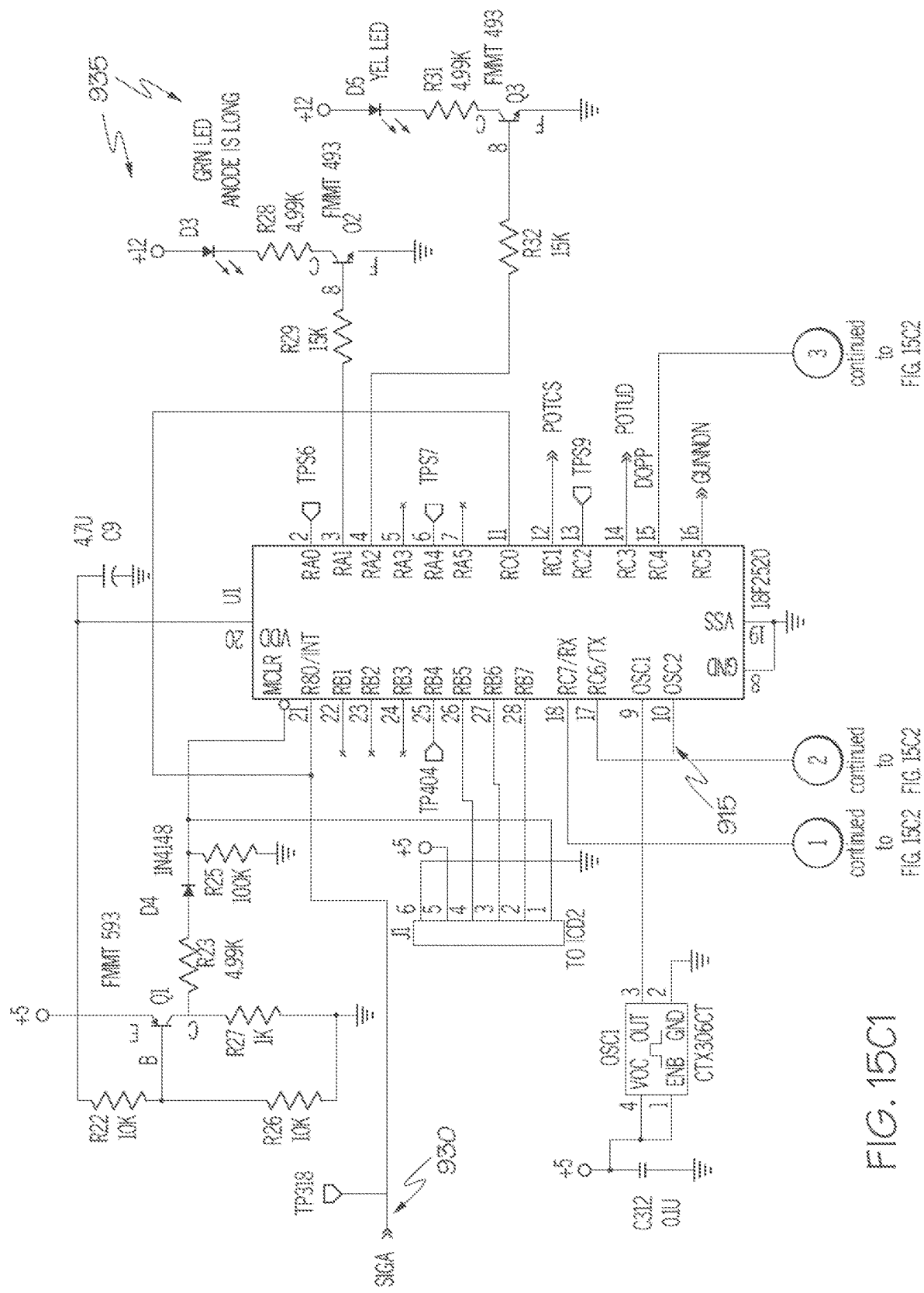
FIG. 15C1

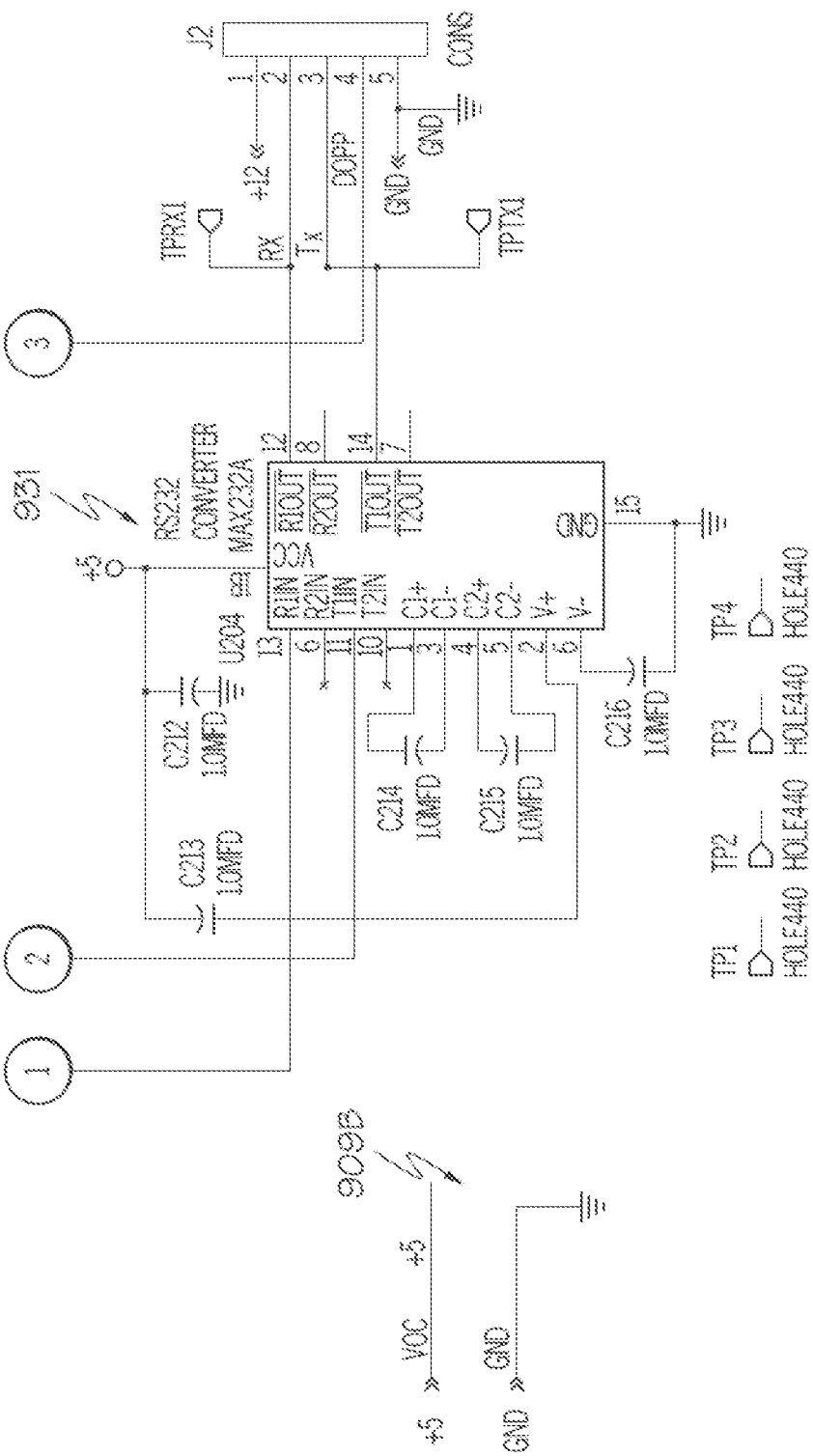
FIG. 15C2

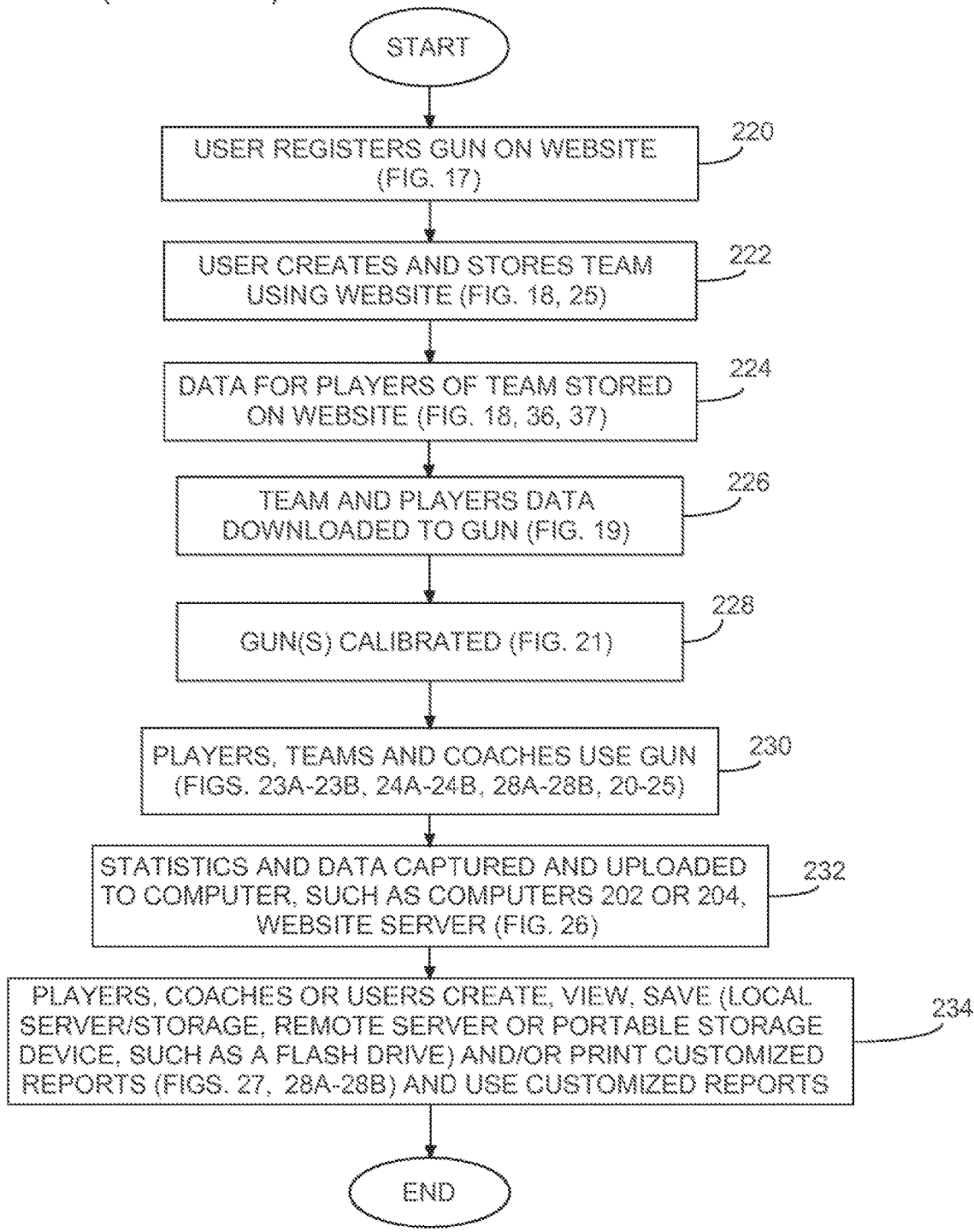
FIG. 16 (OVERALL)

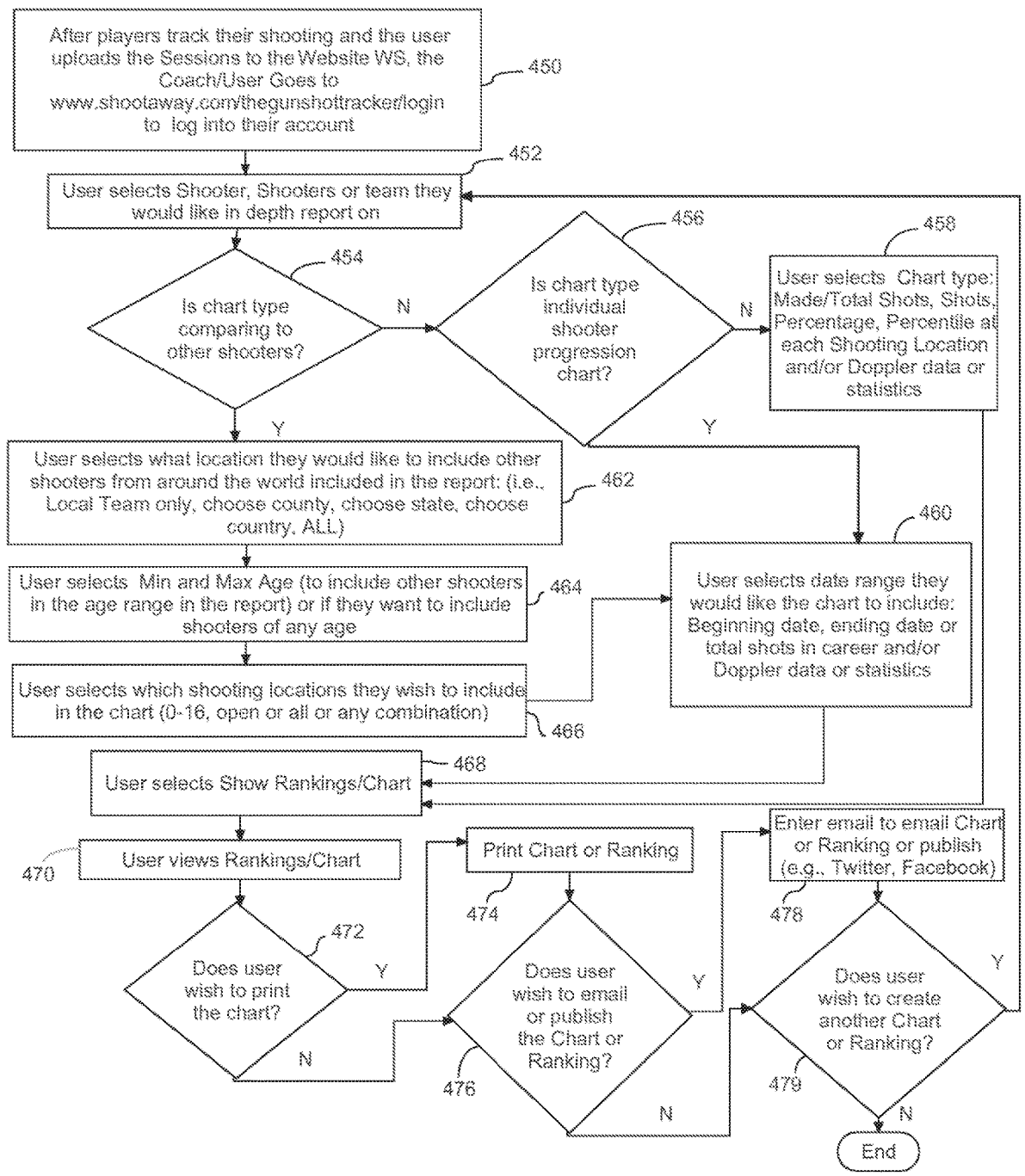

NOT DEPENDENT ON DOPPLER
PROCEDURE TO USE REAL TIME CHALLENGE MODE ON THE GUN FOR TWO PLAYERS TO LOG INTO THE SAME GUN AND SHOOT AGAINST EACH OTHER

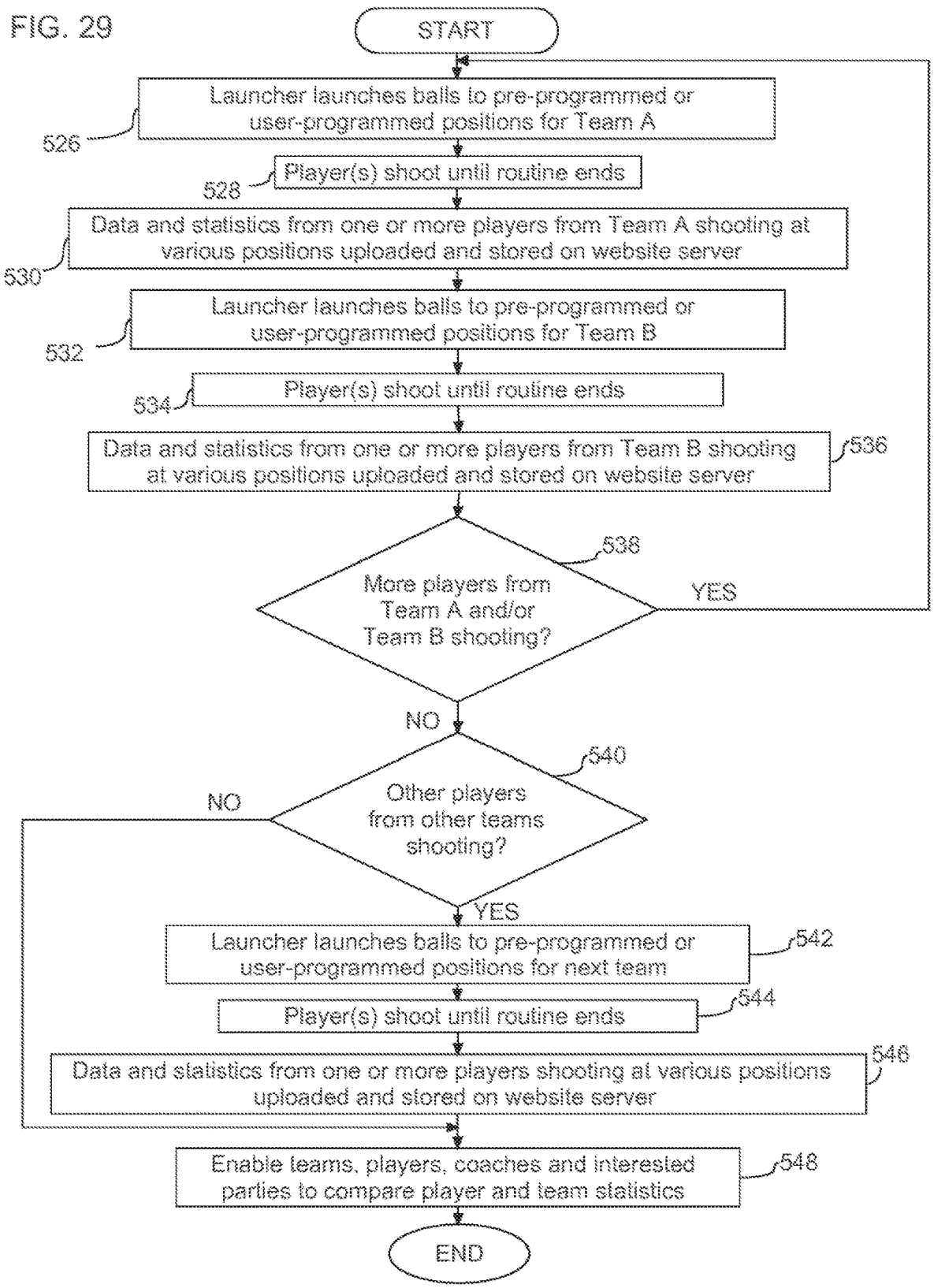

FIG. 44

*Not dependant on doppler (Please note ROMs 1.6 will not actually be in Session upload file)*

Example Sessions file for upload from the Gun to the internet site

| Player or Players logged in | Time Stamp | | | | | | | | | | | | | | | | | | | | | |
|---|---|---|---|---|---|---|---|---|---|---|---|---|---|---|---|---|---|---|---|---|---|---|
| P0 PowerUp | | | | | | | | | | | | | | | | | | | | | | |
| P223 Joe Jones | 05/20/2010 - 00:53:44 | | | | | | | | | | | | | | | | | | | | | |
| P214 Kevin Curtis | 05/20/2010 - 00:56:28 | | | | | | | | | | | | | | | | | | | | | |
| P224 Katie Bassey | 05/20/2010 - 00:58:04 | | | | | | | | | | | | | | | | | | | | | |
| P223 Joe Jones | 05/20/2010 - 01:00:18 | | | | | | | | | | | | | | | | | | | | | |
| P744 Michelle Eschenan | 05/20/2010 - 01:01:14 | | | | | | | | | | | | | | | | | | | | | |
| P214 Kevin Curtis | 05/20/2010 - 01:02:42 | | | | | | | | | | | | | | | | | | | | | |
| P0 PowerUp | 05/20/2010 - 01:05:24 | | | | | | | | | | | | | | | | | | | | | |
| Gun Life 346 | SerialNumber | 99999 | | | | | | | | | | | | | | | | | | | | |
| Gun Life 346 | SerialNumber | 99999 | | | | | | | | | | | | | | | | | | | | |

FIG. 45

Doppler Dependant (Please note ROWs 1-5 will not actually be in Session upload file)
Example Sessions file for upload from the Gun to the internet site
The Gun will track six facts for every shoot a logged in player shoot. They are:
1) Shooting Location, 2) Distance of shot, 3) is it a make or miss, 4) release time, 5) release angle and 6) entry angle into the basket
1 of shot in shooting session ————————>

720

|  |  |  | SHOT #1 | | | | | | SHOT #2 | | | | | | SHOT #3 | | | | | |
|---|---|---|---|---|---|---|---|---|---|---|---|---|---|---|---|---|---|---|---|---|
| Player code # | Player logged in | Time Stamp | Shooting Location | Distance of shot in Ft | Made =1, Miss = 0 | release time | release angle | entry angle | Shooting Location | Distance of shot in Ft | Made =1, Miss = 0 | release time | release angle | entry angle | Shooting Location | Distance of shot in Ft | Made =1, Miss = 0 | release time | release angle | entry angle |
| P0 | PowerUp | 05/20/2010 - 00:53:44 | | | | | | | | | | | | | | | | | | |
| P223 | Joe Jones | 05/20/2010 - 00:56:28 | 0 | 15 | 1 | 0.301 | 55 | 45 | 1 | 15 | 1 | 0.302 | 54 | 44 | 2 | 16 | 1 | 1.000 | 54 | 43 |
| P214 | Kevin Curtis | 05/20/2010 - 00:58:04 | 8 | 15 | 1 | 0.230 | 53 | 43 | 6 | 15 | 1 | 0.244 | 53 | 43 | 8 | 15 | 0 | 0.224 | 52 | 42 |
| P724 | Katie Bassey | 05/20/2010 - 01:00:18 | | | | | | | | | | | | | | | | | | |
| P223 | Joe Jones | 05/20/2010 - 01:01:14 | | | | | | | | | | | | | | | | | | |
| P744 | Michelle Escherman | 05/20/2010 - 01:02:42 | | | | | | | | | | | | | | | | | | |
| P214 | Kevin Curtis | 05/20/2010 - 01:04:06 | | | | | | | | | | | | | | | | | | |
| P0 | PowerUp | 05/20/2010 - 01:05:24 | | | | | | | | | | | | | | | | | | |
| Gun Lifetime | | 346 SerialNumber | 99999 | | | | | | | | | | | | | | | | | |
| Gun Lifetime | | 346 SerialNumber | 99999 | | | | | | | | | | | | | | | | | |

722

|  |  |  | SHOT #4 | | | | | | SHOT #N+1 | | | | | |
|---|---|---|---|---|---|---|---|---|---|---|---|---|---|---|
| Player code # | Player logged in | Time Stamp | Shooting Location | Distance of shot in Ft | Made =1, Miss = 0 | release time | release angle | entry angle | Shooting Location | Distance of shot in Ft | Made =1, Miss = 0 | release time | release angle | entry angle |
| P0 | PowerUp | 05/20/2010 - 00:53:44 | | | | | | | | | | | | |
| P223 | Joe Jones | 05/20/2010 - 00:56:28 | 3 | 14 | 0 | 0.400 | 60 | 50 | 4 | 15 | 1 | | | |

FIG. 46

Not Dependant on Doppler
Player/Team or USA the World Rankings        Sorting variables to create custom charts

| Headings | Quantifiers | Explanation of Quantifiers |
|---|---|---|
| 1. Choose Player | Roster List | Chose any player on your roster or entire team |
| 2. Minimum Age | Any | range from 1 - 150 <= Maximum Age |
| 3. Maximum Age | Any | range from 1 - 150 >= Minimum Age |
| 4. Beginning Date | All | Beginning date <= Ending date |
| 5. Ending Date | All | Ending date >= Beginning date |
| 6. Gender | Both, M, F | Male, Female or include all shooters |
| 7. Enter Shooting Locations | All | 0 through 17 |
| 8. Chart Type | Makes/Total Shots/% | Sort based on makes, total shots or shooting % |
| 9. City | All | Choose City |
| 10. County | All | Choose County |
| 11. State | All | Choose State |
| 12. Country | All | Choose Country |

Example #1

(Example 1 INPUT Information)

| | | |
|---|---|---|
| 1 | Choose Player | John Drew |
| 2 | Minimum Age | 14 |
| 3 | Maximum Age | 25 |
| 4 | Beginning Date | 6/1/2009 |
| 5 | Ending Date | 12/15/2010 |
| 6 | Gender | M |
| 7 | Enter Shooting Locations | All |
| 8 | Chart Type | Total Shots |
| 9 | City | All |
| 10 | County | All |
| 11 | State | All |
| 12 | Country | United States |

Player/Team or USA vs the World Rankings
*(Example #1 Custom Created Report)*
*Total Shots from all shooting locations from 6/1/09 to 12/15/10 for males age range 24-25 for John Drew*

| Rank | Name | State | School | Total |
|---|---|---|---|---|
| 1 | Ted Robinson | AR | Bison | 623,567 |
| 2 | Mike Johnson | TN | Cordova | 511,343 |
| 3 | Tim Worley | KS | Kansas University | 198,565 |
| 4 | Ron Jefferson | NM | Gallup HS | 191,223 |
| 5 | Ted Jackson | NC | UNCC | 190,343 |
| 6 | Mary Fredrick | TN | Memphis HS | 185,343 |
| 7 | Heather Jones | CA | Jackson | 183,232 |
| 8 | Frank Tedford | AZ | Home Skills | 180,232 |
| 9 | Robert Lie | OH | Upper Defense | 177,656 |
| 10 | Tiffany Robinson | CA | Point Arena HS | 165,454 |
| 11 | Tom Watson | CA | Foothill HS | 161,232 |
| 12 | Mike Jackson | TX | Alto HS | 160,334 |
| 13 | John Drew | CO | Georgia | 155,343 |
| 14 | Tim Whamson | GE | Whownad | 154,343 |
| 15 | Mak Ames | FL | Florida Gators | 150,232 |
| 16 | Joetta Cooley | AZ | Scottsdale AZ | 145,343 |
| 17 | Joe Drew | CO | Sangre de Cristo | 141,223 |
| 18 | Mike Watson | MI | St. Louis HS | 139,343 |
| 19 | Heather Johnson | OH | Lima HS | 135,354 |
| 20 | Kevin Curtis | CA | USC | 134,232 |
| 21 | Jeff George | MN | St. Paul West HS | 131,232 |
| 22 | Jermaine Watson | SC | Myrtle Beach HS | 129,434 |
| 23 | Avery Elliot | NC | Durham HS | 128,343 |
| 24 | Christy Robinson | TX | Union City HS | 125,324 |
| 25 | Michael Drew | SD | Howard | 119,232 |

Example #2

(Example #2 INPUT Information)

| | |
|---|---|
| 1. Choose Player | TEAM Sangre |
| 2. Minimum Age | all |
| 3. Maximum Age | all |
| 4. Beginning Date | all |
| 5. Ending Date | all |
| 6. Gender | M |
| 7. Enter Shooting Locations | spot 8 |
| 8. Chart Type | Total Makes |
| 9. City | All |
| 10. County | All |
| 11. State | Colorado |
| 12. Country | United States |

FIG. 50

(Example #2 Custom Created Report)
Player/Team or USA vs the World Rankings
Total Makes for all states from shooting location 8 for Colorado Male teams.

| Rank | Team | State | Total |
|---|---|---|---|
| 1 | Alamosa | CO | 623,567 |
| 2 | Sangre | CO | 511,343 |
| 3 | Sargent | CO | 198,565 |
| 4 | Stratton | CO | 191,233 |
| 5 | Pagosa | CO | 190,343 |
| 6 | Centauri | CO | 185,343 |
| 7 | Creed | CO | 183,232 |
| 8 | Custer | CO | 180,232 |
| 9 | Monte Vista | CO | 177,656 |
| 10 | Bana Vista | CO | 165,454 |
| 11 | Denver East | CO | 161,292 |
| 12 | Denver West | CO | 160,334 |
| 13 | Pueblo East | CO | 155,343 |
| 14 | Sierra Grande | CO | 154,343 |
| 15 | Mt. Valley | CO | 150,232 |
| 16 | Grand Junction | CO | 145,343 |
| 17 | Wray | CO | 141,223 |
| 18 | Eads | CO | 139,343 |
| 19 | Swink | CO | 135,354 |
| 20 | Simla | CO | 134,232 |
| 21 | La Junta | CO | 131,232 |
| 22 | Lamar | CO | 129,434 |
| 23 | John Mall | CO | 128,343 |
| 24 | La Veta | CO | 125,324 |
| 25 | Sanford | CO | 119,232 |

Doppler Dependant
Player/Team or USA the World Rankings        Sorting variables to create custom charts → 742

| Headings | Quantifiers | Explanation of Quantifiers |
|---|---|---|
| 1. Choose Player | Roster List | Chose any player on your roster |
| 2. Minimum Age | Any | range from 1 - 150 <= Maximum Age |
| 3. Maximum Age | Any | range from 1 - 150 >= Minimum Age |
| 4. Beginning Date | All | Beginning date <= Ending date |
| 5. Ending Date | All | Ending date >= Beginning date |
| 6. Gender | Both, M, F | Male, Female or include all shooters |
| 7. Enter Shooting Locations | All | 0 through 17 |
| 8. Shooting Distance | All | 13, 14, 15, 16, 17, 18, 19, 20, 21+, all |
| 9. Chart Type | Makes/Total Shots/% | Sort based on makes, total shots or shooting % |
| 10. City | All | Choose City |
| 11. County | All | Choose County |
| 12. State | All | Choose State |
| 13. Country | All | Choose Country |

FIG. 52

Example #1
(Example #1 INPUT Information)

| | |
|---|---|
| 1 Choose Player | John Drew |
| 2 Minimum Age | 14 |
| 3 Maximum Age | 25 |
| 4 Beginning Date | 6/1/2009 |
| 5 Ending Date | 12/15/2010 |
| 6 Gender | M |
| 7 Enter Shooting Locations | All |
| 8 Shooting Distance | 20 feet away |
| 9 Chart Type | Total Shots |
| 10 City | All |
| 11 County | All |
| 12 State | All |
| 13 Country | United States |

FIG. 53

Player/Team or USA vs the World Rankings (Example #1 Custom Created Report)

Total Shots from all shooting locations from 6/1/09 to 12/15/10 for males age range 16-25 at a distance of 20 feet for John Drew

| Rank | Name | State | School | Total |
|---|---|---|---|---|
| 1 | Ted Robinson | AR | Risers | 623,567 |
| 2 | Mike Johnson | TN | Cordova | 511,343 |
| 3 | Tim Worley | KS | Kansas University | 198,565 |
| 4 | Ken Jeffersson | NM | Gallup HS | 193,233 |
| 5 | Ted Jackson | NC | UNCC | 190,343 |
| 6 | Mary Fredrick | TN | Memphis HS | 185,343 |
| 7 | Heather Jones | CA | Jackson | 183,232 |
| 8 | Frank Tedford | AZ | Horse Skills | 180,232 |
| 9 | Robert Ele | OH | Upper Defense | 177,656 |
| 10 | Tiffany Robinson | CA | Point Arena HS | 165,454 |
| 11 | Tom Watson | CA | Foothill HS | 161,232 |
| 12 | Mike Jackson | TX | Alto HS | 160,334 |
| 13 | *John Drew* | CO | *Scorgim* | *155,343* |
| 14 | Tim Wheaton | GE | Wilwood | 154,343 |
| 15 | Mak Ames | FL | Florida Gators | 150,232 |
| 16 | Joetta Cooley | AZ | Scottsdale AZ | 145,343 |
| 17 | Joe Drew | CO | Sangre de Cristo | 141,223 |
| 18 | Mike Watson | MS | St. Louis HS | 139,343 |
| 19 | Heather Johnson | OH | Lima HS | 135,354 |
| 20 | Kevin Curtis | CA | USC | 134,232 |
| 21 | Jeff George | MN | St. Paul West HS | 133,353 |
| 22 | Jermaine Watson | SC | Myrtle Beach HS | 129,434 |
| 23 | Avery Elliot | ME | Durham HS | 128,343 |
| 24 | Chrissy Robinson | TX | Unicorn City HS | 125,334 |
| 25 | Michael Drew | SD | Howard | 119,232 |

Example #2
(Example #2 INPUT Information)

| | |
|---|---|
| 1. Choose Player | TEAM Sangre |
| 2. Minimum Age | all |
| 3. Maximum Age | all |
| 4. Beginning Date | all |
| 5. Ending Date | all |
| 6. Gender | M |
| 7. Enter Shooting Locations | spot 8 |
| 8. Shooting Distance | 15 feet |
| 9. Chart Type | Total Makes |
| 10. City | All |
| 11. County | All |
| 12. State | Colorado |
| 13. Country | United States |

FIG. 55

*(Example #2 Custom Created Report)*

Player/Team or USA vs the World Rankings

*Total Makes for all dates from shooting location 8 for Colorado Male teams at a distance of 15 feet*

| Rank | Team | State | Total |
|---|---|---|---|
| 1 | Alamosa | CO | 623,567 |
| 2 | Sangre | CO | 511,343 |
| 3 | Sargent | CO | 198,565 |
| 4 | Stratton | CO | 191,233 |
| 5 | Pagosa | CO | 190,343 |
| 6 | Centauri | CO | 185,343 |
| 7 | Creed | CO | 183,232 |
| 8 | Center | CO | 180,232 |
| 9 | Monte Vista | CO | 177,656 |
| 10 | Buna Vista | CO | 165,454 |
| 11 | Denver East | CO | 161,232 |
| 12 | Denver West | CO | 160,334 |
| 13 | Pueblo East | CO | 155,343 |
| 14 | Sierra Grande | CO | 154,343 |
| 15 | Mt. Valley | CO | 150,232 |
| 16 | Grand Junction | CO | 145,343 |
| 17 | Wray | CO | 141,223 |
| 18 | Eads | CO | 139,343 |
| 19 | Swink | CO | 135,354 |
| 20 | Simla | CO | 134,232 |
| 21 | La Junta | CO | 131,232 |
| 22 | Lamar | CO | 129,434 |
| 23 | John Mall | CO | 128,343 |
| 24 | La Veta | CO | 125,324 |
| 25 | Sanford | CO | 119,232 |

(This chart is a list of top 20 rankings for shooters using the Gun on a given day)

Top 20 National Rankings for Team Upper Sandusky, Ohio
Date: December 15, 2011

| Ranking | Total Shots Taken | State | School | Number |
|---|---|---|---|---|
| 1 | M. Johnson | PA | East HS | 8,543 |
| 2 | T. Tedford | OH | Upper Sandusky | 7,644 |
| 3 | H. Mikelson | TX | Wattford | 6,445 |
| 4 | J. Johnson | IL | Sangre | 5,434 |
| 5 | L. Berry | CA | Monte Vista | 5,344 |
| 6 | M. Terry | CA | West HS | 5,000 |
| 7 | M. Robinson | MD | Metford | 4,567 |
| 8 | S. Adams | WA | Johnson | 4,322 |
| 9 | M. Curtis | NE | Eastbay | 3,400 |
| 10 | K. Prior | MO | Sandusky | 3,000 |
| 11 | T. Allen | ND | St. Pats | 2,545 |
| 12 | K. Clair | FL | Jefferson | 2,400 |
| 13 | B. Brown | CA | Pueblo West | 2,234 |
| 14 | S. Heard | CO | Denver East | 2,112 |
| 15 | M. Lopez | TN | Knoxville | 2,000 |
| 16 | T. Vandouk | TX | Austin Central | 1,923 |
| 17 | B. Simpson | OR | Medford | 1,901 |
| 18 | M. Leach | TX | Lubbock | 1,899 |
| 19 | J. Crawford | MN | St. Paul | 1,823 |
| 20 | M. Eddy. | OH | Carey | 1,800 |
| 643 | M. Jones | OH | Upper Sandusky | 543 |
| 822 | T. Whenton | OH | Upper Sandusky | 344 |
| 12,500 | H. Duncan | OH | Upper Sandusky | 123 |
| 21,356 | J. Dudley | OH | Upper Sandusky | 100 |
| 40,343 | M. Anderson | OH | Upper Sandusky | 70 |
| 59,943 | T. Martinez | OH | Upper Sandusky | 65 |
| 123,134 | M. Davis | OH | Upper Sandusky | 0 |

| Ranking | Total Shots Made | State | School | Number |
|---|---|---|---|---|
| 1 | M. Johnson | PA | East HS | 6,407 |
| 2 | T. Tedford | OH | Upper Sandusky | 5,733 |
| 3 | H. Mikelson | TX | Wattford | 4,834 |
| 4 | J. Johnson | IL | Sangre | 4,076 |
| 5 | L. Berry | CA | Monte Vista | 4,008 |
| 6 | M. Terry | CA | West HS | 3,750 |
| 7 | M. Robinson | MD | Metford | 3,425 |
| 8 | S. Adams | WA | Johnson | 3,242 |
| 9 | M. Curtis | NE | Eastbay | 2,550 |
| 10 | K. Prior | MO | Sandusky | 2,250 |
| 11 | T. Allen | ND | St. Pats | 1,909 |
| 12 | K. Clair | FL | Jefferson | 1,800 |
| 13 | B. Brown | CA | Pueblo West | 1,676 |
| 14 | S. Heard | CO | Denver East | 1,584 |
| 15 | M. Lopez | TN | Knoxville | 1,500 |
| 16 | T. Vandouk | TX | Austin Central | 1,442 |
| 17 | B. Simpson | OR | Medford | 1,426 |
| 18 | M. Leach | TX | Lubbock | 1,424 |
| 19 | J. Crawford | MN | St. Paul | 1,367 |
| 20 | M. Eddy | OH | Carey | 1,350 |
| 643 | M. Jones | OH | Upper Sandusky | 407 |
| 822 | T. Whenton | OH | Upper Sandusky | 258 |
| 12,500 | H. Duncan | OH | Upper Sandusky | 92 |
| 21,356 | J. Dudley | OH | Upper Sandusky | 75 |
| 40,343 | M. Anderson | OH | Upper Sandusky | 53 |
| 59,943 | T. Martinez | OH | Upper Sandusky | 49 |
| 123,134 | M. Davis | OH | Upper Sandusky | 0 |

| Ranking | Percentage | State | School | Number |
|---|---|---|---|---|
| 1 | H. Brown | PA | East HS | 99.90% |
| 2 | M. Watson | OH | Upper Sandusky | 99.85% |
| 3 | S. Terry | TX | Wattford | 99.00% |
| 4 | M. Applewood | IL | Sangre | 97.65% |
| 5 | H. Jacobson | CA | Monte Vista | 97.50% |
| 6 | | | | |
| 7 | | | | |
| 8 | | | | |
| 9 | | | | |
| 10 | | | | |
| 11 | | | | |

(This chart is a list of top 20 rankings for shooters using the Gun for a given AGE range)

Top 20 National Rankings for Team Upper Sandusky, Ohio
Age range of Shooters in the Ranking
Min Age: 16          Max Age 18

| Ranking | Total Shots Taken | State | School | Number |
|---|---|---|---|---|
| 1 | M. Johnson | PA | East HS | 1,122,233 |
| 2 | T. Tedford | OH | Upper Sandusky | 993,343 |
| 3 | H. Mikelson | TX | Wattford | 894,343 |
| 4 | J. Johnson | IL | Sangre | 785,454 |
| 5 | L. Berry | CA | Monte Vista | 734,469 |
| 6 | | | | |
| 7 | | | | |
| 8 | | | | |
| 9 | | | | |
| 10 | | | | |
| 11 | | | | |

(This chart is a list of top 20 rankings for shooters using the Gun for a given DATE range)

Top 20 National Rankings for Team Upper Sandusky, Ohio
Date Range: December 23, 2011 - December 22, 2012

| Ranking | Total Shots Taken | State | School | Number |
|---|---|---|---|---|
| 1 | M. Johnson | PA | East HS | 1,122,233 |
| 2 | T. Tedford | OH | Upper Sandusky | 993,343 |
| 3 | H. Mikelson | TX | Wattford | 894,343 |
| 4 | J. Johnson | IL | Sangre | 785,454 |
| 5 | L. Berry | CA | Monte Vista | 734,469 |
| 6 | ................ | | | |
| 7 | ................ | | | |
| 8 | ................ | | | |
| 9 | ................ | | | |
| 10 | ................ | | | |
| 11 | ................ | | | |

(Not Dependant on Doppler – This chart shows rankings from a shooting area)
Player/Team vs the Nation Shooting Report for Kevin Curtis, Team Upper Sandusky, OH
December 15, 2011
Shooting Location 8  (could also be on locations 0-16)

Local Shooting (Team Upper Sandusky) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 1st | 1st | 1st | 1st |
| Total Upper Sandusky Shooters | 6 | 12 | 14 | 55 | 132 |

Regional Shooting (Wyandot County) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 2nd | 1st | 1st | 1st |
| Total Wyandot Shooters | 864 | 1,432 | 5,348 | 15,343 | 34,766 |

Statewide Shooting (Ohio) Rankings for Kevin Curtis

| RANKINGS | Today | Week | Month | Year | Lifetime |
|---|---|---|---|---|---|
| Total Shots | 4th | 1st | 9th | 5th | 543rd |
| Total Shots Made | 3rd | 1st | 9th | 4th | 342nd |
| Shooting % | 2nd | 5th | 2nd | 2nd | 434th |
| Total Ohio Shooters | 12,121 | 25,344 | 33,434 | 49,343 | 85,434 |

National Shooting (USA) Rankings for Kevin Curtis

| RANKINGS | Today | Week | Month | Year | Lifetime |
|---|---|---|---|---|---|
| Total Shots | 28th | 1st | 21st | 10th | 123231st |
| Total Shots Made | 9th | 1st | 17th | 8th | 9,384th |
| Shooting % | 3rd | 29th | 5th | 3rd | 7,859th |
| Total United States Shooters | 50,123 | 112,123 | 123,323 | 213,432 | 987,433 |

International Shooting (World) Rankings for Kevin Curtis

| RANKINGS | Today | Week | Month | Year | Lifetime |
|---|---|---|---|---|---|
| Total Shots | 32nd | 1st | 23rd | 12th | 232,234th |
| Total Shots Made | 11th | 1st | 18th | 9th | 11,232nd |
| Shooting % | 3rd | 34th | 5th | 3rd | 8,453rd |
| Total Internation Shooters | 65,434 | 132,332 | 155,234 | 244,002 | 1,323,323 |

FIG. 61

(Not dependant on Doppler)
Player/Team vs the Nation Shooting Report for Kevin Curtis, Team Upper Sandusky
December 15, 2011

770

Local Shooting (Team Upper Sandusky) Rankings for Kevin Curtis — 770a

| RANKINGS | Today | Percentile | Week | Percentile | Month | Percentile | Year | Percentile | Lifetime | Percentile |
|---|---|---|---|---|---|---|---|---|---|---|
| Total Shots | 1 | 83.3% | 1 | 91.7% | 1 | 92.9% | 1 | 98.2% | 1 | 99.2% |
| Total Shots Made | 1 | 83.3% | 1 | 91.7% | 1 | 92.9% | 1 | 98.4% | 1 | 99.2% |
| Shooting % | 1 | 83.3% | 1 | 91.7% | 1 | 92.9% | 1 | 98.2% | 1 | 99.2% |
| Total Upper Sandusky Shooters | 6 | | 12 | | 14 | | 55 | | 132 | |

Regional Shooting (Wyandot County) Rankings for Kevin Curtis — 770b

| RANKINGS | Today | Percentile | Week | Percentile | Month | Percentile | Year | Percentile | Lifetime | Percentile |
|---|---|---|---|---|---|---|---|---|---|---|
| Total Shots | 1 | 99.9% | 1 | 99.9% | 1 | 100.0% | 1 | 100.0% | 1 | 100.0% |
| Total Shots Made | 1 | 99.9% | 1 | 99.9% | 1 | 100.0% | 2 | 100.0% | 2 | 100.0% |
| Shooting % | 1 | 99.9% | 2 | 99.9% | 1 | 100.0% | 1 | 100.0% | 1 | 100.0% |
| Total Wyandot Shooters | 864 | | 1,432 | | 5,345 | | 15,343 | | 34,766 | |

Statewide Shooting (Ohio) Rankings for Kevin Curtis — 770c

| RANKINGS | Today | Percentile | Week | Percentile | Month | Percentile | Year | Percentile | Lifetime | Percentile |
|---|---|---|---|---|---|---|---|---|---|---|
| Total Shots | 4 | 100.0% | 1 | 100.0% | 9 | 100.0% | 5 | 100.0% | 543 | 99.4% |
| Total Shots Made | 3 | 100.0% | 1 | 100.0% | 9 | 100.0% | 4 | 100.0% | 342 | 99.6% |
| Shooting % | 2 | 100.0% | 5 | 100.0% | 2 | 100.0% | 2 | 100.0% | 434 | 99.5% |
| Total Ohio Shooters | 12,123 | | 25,344 | | 33,434 | | 49,343 | | 65,434 | |

National Shooting (USA) Rankings for Kevin Curtis — 770d

| RANKINGS | Today | Percentile | Week | Percentile | Month | Percentile | Year | Percentile | Lifetime | Percentile |
|---|---|---|---|---|---|---|---|---|---|---|
| Total Shots | 28 | 99.9% | 1 | 100.0% | 21 | 100.0% | 10 | 100.0% | 123,231 | 86.7% |
| Total Shots Made | 9 | 100.0% | 1 | 100.0% | 17 | 100.0% | 8 | 100.0% | 9,384 | 99.0% |
| Shooting % | 3 | 100.0% | 29 | 100.0% | 5 | 100.0% | 3 | 100.0% | 7,855 | 99.1% |
| Total United States Shooters | 53,123 | | 112,123 | | 123,323 | | 213,434 | | 923,434 | |

International Shooting (World) Rankings for Kevin Curtis — 770e

| RANKINGS | Today | Percentile | Week | Percentile | Month | Percentile | Year | Percentile | Lifetime | Percentile |
|---|---|---|---|---|---|---|---|---|---|---|
| Total Shots | 32 | 100.0% | 1 | 100.0% | 23 | 100.0% | 12 | 100.0% | 232,234 | 82.5% |
| Total Shots Made | 11 | 100.0% | 1 | 100.0% | 18 | 100.0% | 9 | 100.0% | 11,232 | 99.2% |
| Shooting % | 3 | 100.0% | 34 | 100.0% | 5 | 100.0% | 3 | 100.0% | 8,453 | 99.4% |
| Total International Shooters | 65,434 | | 132,332 | | 155,234 | | 244,002 | | 1,323,323 | |

FIG. 62

*(Chapter dependent - This chart could be a comparison of shots take from 15 ft. It could also be shots of different distances for example 15-18 ft. or 19ft etc.)*

Player/Team vs the Nation Shooting Report for Kevin Curtis, Team Upper Sandusky, OH 772a → December 15, 2011

Distance: 15 Feet  (could also be from 15-18 feet, or 19.9+ feet)

Local Shooting (Team Upper Sandusky) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 1st | 1st | 1st | 1st |
| Total Upper Sandusky Shooters | 6 | 12 | 14 | 55 | 132 |

Regional Shooting (Wyandot County) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 2nd | 1st | 1st | 1st |
| Total Wyandot Shooters | 864 | 1,432 | 5,345 | 13,343 | 34,768 |

Statewide Shooting (Ohio) Rankings for Kevin Curtis

| RANKINGS | Today | Week | Month | Year | Lifetime |
|---|---|---|---|---|---|
| Total Shots | 4th | 1st | 9th | 5th | 543rd |
| Total Shots Made | 3rd | 1st | 9th | 4th | 342nd |
| Shooting % | 2nd | 5th | 2nd | 2nd | 434th |
| Total Ohio Shooters | 12,121 | 25,344 | 33,434 | 49,343 | 85,434 |

National Shooting (USA) Rankings for Kevin Curtis

| RANKINGS | Today | Week | Month | Year | Lifetime |
|---|---|---|---|---|---|
| Total Shots | 28th | 1st | 21st | 10th | 123231st |
| Total Shots Made | 9th | 1st | 17th | 8th | 9,384th |
| Shooting % | 3rd | 29th | 5th | 3rd | 7,859th |
| Total United States Shooters | 50,123 | 112,123 | 123,333 | 213,432 | 987,433 |

International Shooting (World) Rankings for Kevin Curtis

| RANKINGS | Today | Week | Month | Year | Lifetime |
|---|---|---|---|---|---|
| Total Shots | 32nd | 1st | 23rd | 12th | 232,234th |
| Total Shots Made | 11th | 1st | 18th | 9th | 11,232nd |
| Shooting % | 3rd | 34th | 5th | 3rd | 8,453rd |
| Total International Shooters | 65,434 | 132,332 | 155,234 | 244,002 | 1,323,323 |

FIG. 63
Doppler Dependent Report

774

(Doppler Dependent - This chart shows rankings from a shooting area along with distance)
Player/Team vs the Nation Shooting Report for Kevin Curtis, Team Upper Sandusky, OH
December 15, 2011

Shooting Location 8, from 15-19 feet (could also be on locations 0-26 & other distance range)

774a  Local Shooting (Team Upper Sandusky) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 1st | 1st | 1st | 1st |
| Total Upper Sandusky Shooters | 6 | 12 | 14 | 55 | 132 |

774b  Regional Shooting (Wyandot County) Rankings for Kevin Curtis

| RANKINGS | Today | Week | Month | Year | Lifetime |
|---|---|---|---|---|---|
| Total Shots | 1st | 1st | 1st | 1st | 1st |
| Total Shots Made | 1st | 1st | 1st | 2nd | 2nd |
| Shooting % | 1st | 2nd | 1st | 1st | 1st |
| Total Wyandot Shooters | 864 | 1,432 | 5,345 | 15,343 | 34,766 |

774c  Statewide Shooting (Ohio) Rankings for Kevin Curtis

| RANKINGS | Today | Week | Month | Year | Lifetime |
|---|---|---|---|---|---|
| Total Shots | 4th | 1st | 9th | 5th | 543rd |
| Total Shots Made | 3rd | 1st | 9th | 4th | 342nd |
| Shooting % | 2nd | 5th | 2nd | 2nd | 434th |
| Total Ohio Shooters | 12,121 | 25,344 | 33,434 | 49,343 | 85,434 |

774d  National Shooting (USA) Rankings for Kevin Curtis

| RANKINGS | Today | Week | Month | Year | Lifetime |
|---|---|---|---|---|---|
| Total Shots | 28th | 1st | 21st | 10th | 123231st |
| Total Shots Made | 9th | 1st | 17th | 8th | 9,384th |
| Shooting % | 3rd | 29th | 5th | 3rd | 7,955th |
| Total United States Shooters | 50,123 | 112,123 | 123,323 | 213,432 | 987,433 |

774e  International Shooting (World) Rankings for Kevin Curtis

| RANKINGS | Today | Week | Month | Year | Lifetime |
|---|---|---|---|---|---|
| Total Shots | 32nd | 1st | 23rd | 12th | 232,234th |
| Total Shots Made | 11th | 1st | 18th | 9th | 11,232nd |
| Shooting % | 3rd | 34th | 5th | 3rd | 6,453rd |
| Total Internation Shooters | 65,434 | 132,332 | 155,234 | 244,002 | 1,323,323 |

SYSTEM AND METHOD FOR IMPROVING A BASKETBALL PLAYER'S SHOOTING INCLUDING A TRACKING AND CONTROL SYSTEM FOR TRACKING, CONTROLLING AND REPORTING STATISTICS

CROSS-REFERENCE TO RELATED APPLICATION

This application is a continuation of U.S. patent application Ser. No. 13/529,903, filed Jun. 21, 2012, which is a continuation-in-part of U.S. patent application Ser. No. 12/420,122, filed Apr. 8, 2009, which is incorporated herein by reference and made a part hereof.

BACKGROUND OF THE INVENTION

1. Field of the Invention

A system and method for improving a player's shooting and for collecting and tracking shooting statistics (such as made shots, entry angle and release angle, get-off or release speed, measurements of distance degree of arch and the like) and data regarding a player's shooting.

2. Description of the Related Art

In the past, various devices have been used to throw basketballs at a player so that the player can practice shooting the basketballs from a location and toward a basketball hoop on a basketball backboard. Several devices are offered by the assignee of the present application and marketed under the trademark THE GUN. For example, The Gun 6000 Series available from the assignee hereof provides a player with a high performance gun or ejector that a player and his or her coach can use during shooting practice. Other ball throwing devices are also available, such as the Dr. Dish™ product available from Airborne Athletics, Inc. of Belle Plaine, Minn., that are used during basketball practice.

One problem or deficiency of the prior art devices is that while they can be programmed to eject basketballs toward a player at a particular location, they were not capable of challenging the shooter's accuracy by, for example, making the shooter successfully shoot a number of shots, either consecutively or non-consecutively, at one location before the gun or ejector caused balls to be ejected or thrown to the next spot or location. Moreover, the devices fail to simulate a playing environment wherein a player feels pressure or a pressure-simulated is provided.

In shooting systems of the past, a launcher may launch balls to various positions on the basketball floor for shooting by a player. The player would then shoot the balls. In general, there were no means or devices for collecting, recording and/or tracking data associated with the shots and passes to the player, such as the distance from the launcher that the player was positioned, the arc of the player's shot after the player received the basketball and whether the player made the shot or missed the shot. There was also no means provided for recording the time it took to launch the ball to the player, a time that it took the player to get the shot off and then the time it took for the shot to travel to the basket, all of which can be important data and statistics for improving the player's shooting.

Moreover, there have been no means or systems or methodologies in the past for providing an automated system for repeating the same shot to the same player, multiple players from the same team or even players from different teams and then comparing the shooting data and statistics for the players.

The basketball practice systems of the prior art also lack the ability to track, measure or record the shooting distance and/or a shooting location (such as a shooting location along a vector associated with a basketball hoop) and, therefore, are incapable of providing comparable measurements or statistics for comparison.

There is, therefore, a need for a system and method for not only improving the player's efficiency in shooting the basketball, but also for providing a system and method for repeatedly launching the same shot to the same or different players so that data and statistics, such as data and statistics relative to the shots that the player made, misses and the like, and to provide the player, coaches and other interested persons the ability to compare statistics by the same player, by different players on the same team or by different players from different teams.

SUMMARY OF THE INVENTION

One object of an embodiment is to provide a system and process for improving a player's shooting ability.

Another object is to provide a system and method for challenging a shooter.

Still another object is to provide a system and method for monitoring a player's shooting performance, such as shots made in a row and/or total cumulative shots made.

Another object of the invention is to provide a system and method for determining when a basketball that has been shot by a player has been made or has been missed.

Another object of the invention is to provide a system and method for comparing statistics regarding shots by a player.

Still another object of the invention is to provide a system and method for gathering, collecting and tracking data and statistics regarding shots from different players on the same team, the same player, or different players from different teams.

Yet another object of the invention is to provide a system and method for comparing data generated by at least one or a plurality of players, regardless of whether those players are on the same or different teams and/or providing means for accessing that comparison data over the internet.

Still another object of the invention is to provide means for downloading, exporting, saving (on a permanent or portable storage device 210, such as a USB drive) the data and statistics, including the comparison data and statistics, for at least one or a plurality of players.

In one aspect, this invention comprises a system for improving a player's efficiency in shooting a basketball toward a basketball hoop on a basketball backboard associated with a basketball playing area, the system comprising a basketball ejector for ejecting a basketball to a plurality of predetermined different locations on the basketball playing area, a sensor associated with the basketball hoop for sensing when the basketball goes through the basketball hoop and a controller coupled to the basketball ejector and the sensor, the controller causing the basketball ejector to eject a predetermined number of balls to a player located at a first one of the plurality of predetermined different locations for a predetermined shooting challenge, and after the predetermined shooting challenge is met by the player shooting a number of balls that the sensor senses passing through the basketball hoop, the controller causes the basketball ejector to eject balls toward at least one second one of the plurality of predetermined different locations.

The above mentioned aspects and the embodiments shown and described herein could be used alone or together and/or in combination with one or more of the features covered by one or more of the claims set forth herein, including but not limited to one or more of the following features or steps:

The system wherein the predetermined shooting challenge is a total number of made shots challenge and the controller causes the basketball ejector to eject basketballs to the player at the at least one second one of the plurality of predetermined different locations only after the player makes a predetermined number of total shots at the first one of the plurality of predetermined different locations.

The system wherein the controller causes the basketball ejector to delay ejecting the basketball to the at least one second one of the plurality of predetermined different locations a predetermined delay time when the player has made the predetermined number of total shots less one.

The system wherein the predetermined delay time is at least 1 second.

The system wherein the predetermined shooting challenge is a total number of made shots in a row challenge and the controller causes the basketball ejector to eject a predetermined number of balls to the player at the at least one second one of the plurality of predetermined different locations only after the player has made a predetermined number of shots in a row at the first one of the plurality of predetermined different locations.

The system wherein the system comprises a user interface for selecting the predetermined shooting challenge, wherein the predetermined shooting challenge is at least one of a total number of made shots at each of the plurality of predetermined different locations or a total number of made shots in a row at each of the plurality of predetermined different locations.

The system wherein the system comprises at least one storage device coupled to the controller for storing data associated with the player's performance during the predetermined shooting challenge, the controller further comprising a shooting efficiency calculator for calculating the player's shooting efficiency during the predetermined shooting challenge using the data.

The system wherein the system comprises at least one storage device coupled to the controller for storing data associated with the player's performance during the predetermined shooting challenge, the controller further comprising a shooting efficiency calculator for calculating the player's shooting efficiency using the data.

The system wherein the shooting efficiency calculator calculates the player's shooting efficiency for each of the first one of the plurality of predetermined different locations and the at least one second one of the plurality of predetermined different locations.

The system wherein the shooting efficiency calculator calculates the player's cumulative shooting efficiency for each of the first one of the plurality of predetermined different locations and the at least one second one of the plurality of predetermined locations over the player's cumulative total number of attempts for each of the first one of the plurality of predetermined different locations and the at least one second one of the plurality of predetermined locations.

The system wherein the shooting efficiency calculator calculates the player's cumulative shooting efficiency at each of the plurality of different locations for all attempts the player has made at each of the plurality of predetermined different locations.

The system wherein the system comprises a printer for printing the player's shooting efficiency.

The system wherein the printer prints a ticket of the player's shooting efficiency.

The system wherein the player's shooting efficiency comprises a completion percentage calculated by the total number of shots the player has made over the total number of shots the player has attempted during the predetermined shooting challenge.

The system wherein the player's shooting efficiency comprises a completion percentage calculated by the total number of shots the player has made over the total number of shots the player has attempted during all times the player performed the predetermined shooting challenge.

In another aspect, this invention comprises a system for assisting basketball practice, comprising a) a launcher which is programmable to make a series of different passes to a player; b) a control system which i) determines a location where the player shot from and whether the player successfully scores a goal from the location and ii) records, in a computer, the percentage or number of shots made from each location.

The above mentioned aspects and the embodiments shown and described herein could be used alone or together and/or in combination with one or more of the features covered by one or more of the claims set forth herein, including but not limited to one or more of the following features or steps:

A system in which the control system places data recorded about the player's performance onto a website available on the Internet.

A system in which the control system records at least one distance from which a shot was taken, an arch of the shot or release time.

A system in which the control system places data recorded about the player's performance onto a website available on the Internet.

A system wherein the control system comprises a measurement system that measures a distance from which the player shot the basketball, with the measurement being recorded in the computer.

A system wherein the measurement system comprises a Doppler system.

A system wherein the launcher launches balls along at least one vector selected by a user, the measurement system measuring the shots along the at least one vector.

In still another aspect, this invention comprises an apparatus for assisting basketball practice, comprising a) a system which i) launches a basketball along a flight path for a player; ii) issues a score signal which indicates whether the player scored a goal after a catch and b) a control system which i) controls launching by a launcher, ii) receives the score signal, iii) records data comprising (A) the location of the catch and (B) whether the goal was scored and iv) stores the data recorded, and delivers the data at a later time.

The above mentioned aspects and the embodiments shown and described herein could be used alone or together and/or in combination with one or more of the features covered by one or more of the claims set forth herein, including but not limited to one or more of the following features or steps:

The apparatus in which the control system repeats processes described in paragraphs (a) and (b).

The apparatus in which the control system places the data recorded onto a website, to thereby make the data available to other parties.

In still another aspect, this invention comprises a system for assisting basketball practice, comprising a) a launcher which launches a succession of passes, to different locations, for a player to catch; b) a control system which i) determines whether each pass resulted in a goal made by the player; ii) records data indicating the events of paragraphs (b)(i) and (b)(ii); and iii) makes the data available to remote parties.

The above mentioned aspects and the embodiments shown and described herein could be used alone or together and/or in combination with one or more of the features covered by one or more of the claims set forth herein, including but not limited to one or more of the following features or steps:

The system in which the data is placed onto a website.

The system wherein the control system senses and records a distance between from which a shot was taken and the rim.

The system wherein the control system comprises a plurality of launchers located at a plurality of locations, wherein the control system is adapted to cause the plurality of launchers to launch basketballs to the same relative shooting position at a different plurality of locations.

The system wherein the control system is adapted to enable shooting data associated with shooting at the plurality of locations to be uploaded to a website and compared.

The system wherein the data comprises cumulative shooting statistics for shooting by each player by at least one of each player or each shooting location.

The system wherein the data comprises cumulative shooting statistics for a plurality of shooting distances.

The system wherein the shooting statistics are at least one of a player, a team, a geographic region, an age or a league.

In yet another aspect, this invention comprises a system, comprising a) at a first location, a first apparatus which i) launches a first basketball along a first flight path for a first player; ii) detects whether the first player subsequently scores a goal using the first basketball and iii) maintains first data which indicates whether a goal was scored by the first basketball; b) at a second location, a second apparatus which i) launches a second basketball along a second flight path for a second player; ii) detects whether the second player subsequently scores a goal using the first basketball and iii) maintains second data which indicates whether a goal was scored by the second basketball.

The above mentioned aspects and the embodiments shown and described herein could be used alone or together and/or in combination with one or more of the features covered by one or more of the claims set forth herein, including but not limited to one or more of the following features or steps:

A system in which the first apparatus makes the first data available to remote parties.

A system in which the second apparatus makes the second data available to remote parties.

A system in which A) the first apparatus makes the first data available on the Internet, and B) the second apparatus makes the second data available on the Internet.

A system in which the data includes at least one: (1) distance, (2) angle of the launch, or (3) release time.

In another aspect, this invention comprises a basketball tracking system comprising a plurality of user interfaces for accessing a website adapted to receive statistics and data from at least one launcher for launching basketballs to at least one player during at least one shooting session, a report generator for generating at least one report in response to a selection of a plurality of criteria selected by a user using at least one of the plurality of user interfaces, the at least one report comprising a ranking of the at least one player based upon the player's shooting performance.

The above mentioned aspects and the embodiments shown and described herein could be used alone or together and/or in combination with one or more of the features covered by one or more of the claims set forth herein, including but not limited to one or more of the following features or steps:

The basketball tracking system wherein the website comprises an associated server or database for storing the statistics and data, at least one of the plurality of user interfaces enabling the statistics and data to be uploaded to the website, the statistics and data comprising at least one of the following: distance measurements for each location that the at least one player took a shot; minimum age, maximum age, beginning date, ending date, gender, shooting locations, shooting distance, city, county, state, country.

The basketball tracking system wherein the website maintains cumulative data and statistics for the at least one player.

The basketball tracking system wherein the plurality of criteria comprise a plurality of the following: player, minimum age, maximum age, beginning date, ending date, gender, shooting locations, shooting distance, city, county, state, country.

The basketball tracking system wherein at least one of the plurality of criteria is a shooting distance, the at least one report showing the at least one player's shooting accuracy at the shooting distance.

The basketball tracking system wherein at least one of the plurality of criteria is a shooting distance, the at least one report showing a comparison of the at least one player's shooting accuracy to at least one other player at the shooting distance.

The basketball tracking system wherein the at least one player and the at least one other player are on the same team.

The basketball tracking system wherein the at least one player and the at least one other player are on different teams.

The basketball tracking system wherein the at least one other player is located in the same county as the at least one player.

The basketball tracking system wherein the at least one other player is located in a different county as the at least one player.

The basketball tracking system wherein the at least one other player is located in a different country as the at least one player.

The basketball tracking system wherein the at least one other player is located in a different states as the at least one player.

The basketball tracking system wherein the statistics and data comprises sessions data generated by a single launcher used during a single shooting session.

The basketball tracking system wherein the statistics and data comprises sessions data generated by a single launcher used during a multiple shooting sessions.

The basketball tracking system wherein the statistics and data comprises sessions data generated by a plurality of launchers; the plurality of user interfaces being adapted to permit the sessions data from each of the plurality of launchers to be uploaded to the website at the same or different times.

The basketball tracking system wherein at least one of the plurality of user interfaces is adapted to permit the user to create a roster of players for downloading to the at least one launcher.

The basketball tracking system wherein the roster of players is stored on the website, the plurality of user interfaces and the website being adapted to store cumulative data relative to a plurality of players' shooting statistics and data for comparisons by other users authorized to access the website.

A basketball tracking system wherein the system further comprises a plurality of launchers, each adapted to collect a plurality of statistics and data associated with a plurality of players' shooting, the website storing the plurality of statistics and data so that comparisons thereof can be made on the website and printed out if desired.

The basketball tracking system wherein each of the plurality of launchers comprises a user interface having a plurality of buttons arranged in a layout on the user interface that generally corresponds to a plurality of locations from which a player may shoot a basketball.

The basketball tracking system wherein each of the plurality of launchers causes a plurality of basketballs to be launched to a plurality of the plurality of locations in the order in which the plurality of buttons were actuated by the user on the interface.

The basketball tracking system wherein at least one of the plurality of user interfaces is adapted to enable a user to view the reports and print them.

The system wherein at least one of the at least one report comprises a mapping report or scatter diagram shooting a shooting accuracy for a plurality of distances along a vector extending from the launcher.

In another aspect, this invention comprises an apparatus which enables a player to practice basketball, comprising a) a gun or ejector which i) has an interface that is programmable for selecting a number of basketball passes and ii) launches the basketball passes for the player to catch; b) a detector which i) for each of the basketball passes, ascertains whether the player succeeded in making a goal; and ii) for all of the basketball passes, creates a visual matrix, graph, scatter diagram or chart which describes (A) data describing the basketball passes, and (B) for each of the basketball passes, data describing the player's response.

The above mentioned aspects and the embodiments shown and described herein could be used alone or together and/or in combination with one or more of the features covered by one or more of the claims set forth herein, including but not limited to one or more of the following features or steps:

The apparatus in which the selected number of basketball passes specifies passes to different locations on a basketball court.

The apparatus in which the selected number of basketball passes specifies a generally radial array of passes originating from a pass launcher.

The apparatus and further comprising a communication system which transmits the data to a web site, which displays the visual matrix, graph, scatter diagram or chart to parties who visit the web site.

The apparatus and further comprising a communication system which transmits, directly or indirectly, a list to a system at a remote location, which comprises c) a second gun or ejector which i) accepts the list; and ii) launches each pass on the list for a second player to catch; d) a detector which i) for each pass, ascertains whether the second player succeeded in making a goal; and ii) for all passes, creates a visual matrix, graph, scatter diagram or chart which describes (A) data describing all passes, and (B) for each pass, data describing the second player's response.

The apparatus in which the data describing the player's response includes (1) height of shot, (2) distance of player from goal, (3) release angle, and (4) entry angle into goal.

The apparatus in which the data describing the second player's response includes (1) height of shot, (2) distance of player from goal, (3) release angle, and (4) entry angle into goal.

In another aspect, this invention comprises a basketball tracking system comprising a plurality of user interfaces for accessing a website adapted to receive statistics and data from at least one launcher for launching basketballs to at least one player during at least one shooting session, a report generator for generating at least one report in response to a selection of a plurality of criteria selected by a user using at least one of the plurality of user interfaces, the at least one report comprising a ranking of the at least one player based upon the at least one player's shooting performance.

The above mentioned aspects and the embodiments shown and described herein could be used alone or together and/or in combination with one or more of the features covered by one or more of the claims set forth herein, including but not limited to one or more of the following features or steps:

The basketball tracking system wherein the website comprises an associated server or database for storing the statistics and data at least one of the plurality of user interfaces enabling the statistics and data to be uploaded to the website, the statistics and data comprising at least one of the following: distance measurements for each location that the at least one player took a shot; minimum age, maximum age, beginning date, ending date, gender, shooting locations, shooting distance, city, county, state, country.

The basketball tracking system wherein the website maintains cumulative data and statistics for the at least one player.

The basketball tracking system wherein the plurality of criteria comprise a plurality of the following: player, minimum age, maximum age, beginning date, ending date, gender, shooting locations, shooting distance, city, county, state, country.

The basketball tracking system wherein at least one of the plurality of criteria is a shooting distance, the at least one report showing the at least one player's shooting accuracy at the shooting distance.

The basketball tracking system wherein at least one of the plurality of criteria is a shooting distance, the at least one report showing a comparison of the at least one player's shooting accuracy to at least one other player at the shooting distance.

The basketball tracking system wherein the at least one player and the at least one other player are on the same team.

The basketball tracking system wherein the at least one player and the at least one other player are on different teams.

The basketball tracking system wherein the at least one other player is located in the same county as the at least one player.

The basketball tracking system wherein the at least one other player is located in a different county as the at least one player.

The basketball tracking system wherein the at least one other player is located in a different country as the at least one player.

The basketball tracking system wherein the at least one other player is located in a different state as the at least one player.

The basketball tracking system wherein the statistics and data comprises sessions data generated by a single launcher used during a single shooting session.

The basketball tracking system wherein the statistics and data comprises sessions data generated by a single launcher used during multiple shooting sessions.

The basketball tracking system wherein the statistics and data comprises sessions data generated by a plurality of launchers; the plurality of user interfaces being adapted to permit the sessions data from each of the plurality of launchers to be uploaded to the website at the same or different times.

The basketball tracking system wherein at least one of the plurality of user interfaces is adapted to permit the user to create a roster of players for downloading to the at least one launcher.

The basketball tracking system wherein the roster of players is stored on the website, the plurality of user interfaces and the website being adapted to store cumulative data relative to a plurality of players' shooting statistics and data for comparisons by other users authorized to access the website.

The basketball tracking system wherein a distance sensor measures a distance along each of a plurality of different vectors.

The basketball tracking system wherein a distance sensor measures a distance at fixed positions along each of a plurality of vectors.

The basketball tracking system wherein the distance sensor comprises a Doppler measurement system that measures the distances of between 3 feet and 25 feet from the launcher.

These and other objects and advantages of the invention will be apparent from the following description, the accompanying drawings and the appended claims.

BRIEF DESCRIPTION OF THE ACCOMPANYING DRAWINGS

FIGS. 3A-3D are views of a user interface or display in accordance with one embodiment of the invention;

FIG. 6 is a view of various statistics and data and a printout for the player over a preselected period, illustrating the player's percentage of made shots relative to total shots at one or more of each of the plurality of different locations;

FIG. 7 is a schematic of a challenge shooting accuracy main procedure routine;

FIG. 11 is a partial fragmentary view showing a throwing arm and vibration limit sensor in the embodiment shown in FIG. 10 and the player shoots from a distance;

FIGS. 13A-13I are various formulas, calculations and algorithms used to generate Doppler measurements in the embodiment being illustrated;

FIGS. 15A-15D are one form of a Doppler circuit used in the embodiment shown in FIG. 10;

FIG. 16 is an overall view of the use of the embodiment shown in FIG. 10;

FIG. 27 is a general procedure for creating customized reports;

FIG. 29 is another illustrative challenge for different players on different teams at different locations using different guns or ejectors;

FIG. 44 is an example of a "SESSIONS" file for uploading from the gun or ejector;

FIG. 45 is an example of the "SESSIONS" file from the gun or ejector to the website WS;

FIG. 46 is an example of various sorting variables or selection criteria for use by a user;

FIG. 47 is an illustrative input selected criteria in one example;

FIG. 48 is an illustrative chart resulting from the selections made and shown in FIG. 47;

FIG. 49 is another example of input selection criteria or information selected by a user in the example;

FIG. 50 is the report or chart shown from the selections made and shown in FIG. 49;

FIG. 51 is a listing of the sorting variables or selection criteria that a user may use, which in the embodiment shown includes Doppler measurements;

FIG. 52 is another illustrative example of selected criteria or input information, including Doppler measurement of shooting distance;

FIG. 53 is a chart or report created by the website WS in response to the selected criteria in FIG. 52;

FIG. 54 is still another example of selected input information or criteria;

FIG. 55 is a chart or report created by the website WS in response to the criteria or information selected in FIG. 54; and FIGS. 56-63 are various charts and reports showing illustrative comparisons and rankings of players and teams, where such players are from the same or different teams, same or different regions, skill levels and the like.

DETAILED DESCRIPTION OF THE PREFERRED EMBODIMENTS

Figure 3:
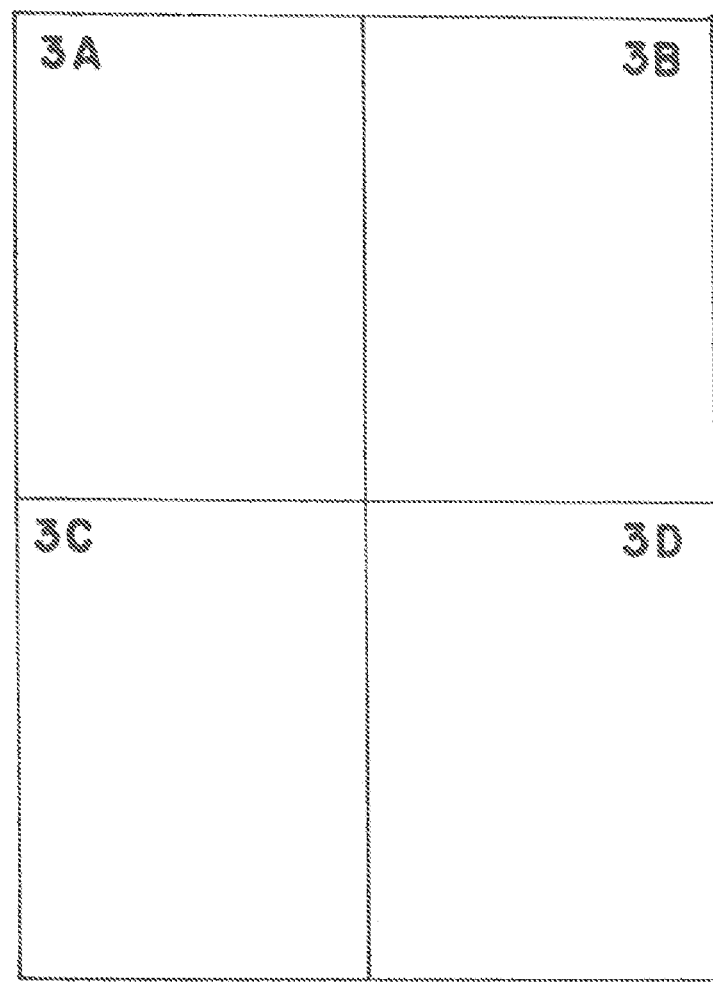
FIG. 3 is a view showing the layout of FIGS. 3A-3D.

Referring back to FIG. 1, the system 10 comprises a user interface 40 and a front display 42. The user interface 40 in the illustration being described is shown in more detail in FIGS. 3A-3D and will be described later herein. For ease of illustration, FIG. 3 illustrates the interface 40 with various portions of the interface shown in FIGS. 3B-3D. The system 10 further comprises a storage device 44, such as an electronic storage device or other electronic storage, for storing data relative to the player's efficiency, such as data regarding the player's performance during one or more of the shooter challenge routines 32*a* and even historical or cumulative information regarding a player's performance over a predetermined period or even a player's career in shooting using the system 10.

The gun or ejector 20 is a conventional ball ejecting machine and comprises a frame 24 having a plurality of wheels 26. The gun or ejector 20 has a conventional ball ejector 28 that is pivotally mounted on the frame 24 and can throw or eject basketballs 12 in the direction A. The gun or ejector 20 comprises a drive motor and linkage 30 for pivotally driving the ball ejector 28 in the direction of double arrow B in FIG. 1 so that a direction of thrown balls can be changed. The system 10 comprises a circuit board (not shown) having the controller 32 that is coupled to and controls the operation of the drive motor and linkage 30, gun or ejector 20 as shown.

Note that the gun or ejector 20 also comprises a ball retrieval or net system 34 which facilitates gathering basketballs 12 that are thrown toward the hoop 14 in a manner conventionally known. As also illustrated, the gun or ejector 20 may further comprise a shoot or guide 36 for facilitating guiding basketballs 12 into an inlet 38 connected to a housing 29, where said housing 29 rotates with said gun or ejector 20. The basketballs 12 can be ejected by the gun or ejector 20 through the outlet 39 in the housing 29 and toward a basketball player P.

A photo sensor 33 is coupled to the hoop 14 and electronically coupled to the controller 32. The photo sensor 33 senses when the player P has successfully shot the basketball through the hoop 14.

In the embodiment being described several conventional guns/ejectors 20 may be used, including The Gun 6000 Series available from Shoot-a-Way, Inc. of Upper Sandusky, Ohio. An alternative gun or ejector 20 may be the Dr. Dish™ product available from Airborne Athletics, Inc. of Belle Plaine, Minn.

In the illustration being described, the controller 32 comprises a plurality of routines or algorithms for improving the player P's shooting efficiency. The routines include a shooter challenge routine 32*a* for challenging the player P in shooting a basketball 12 towards the at least one or a plurality of different areas 22. The shooter challenge routine 32*a* facilitates improving a player's efficiency in that they provide a player P with feedback as to his or her shooting accuracy. With the feedback, the player P can focus his or her shooting practice on those areas where the player's efficiency is below a predetermined or preselected efficiency percentage. In the illustration being described, the predetermined efficiency may be any desired or selected shooting efficiency, such as 30% or 40%. For example, if a player's shooting efficiency falls below the predetermined threshold, such as 40% in the illustration being described, the player P may forces his or her practice on the areas where the player P needs to improve his or her shooting efficiency.

Referring back to FIG. 1, the controller 32 further comprises means or apparatus for calculating the shooting efficiency using a shooting efficiency calculator 32*b*. The shooting efficiency calculator 32*b* calculates a shooting efficiency of the player P at the at least one or a plurality of the plurality of different positions 22 where the player P shot the basketball 12. The shooting efficiency calculator 32*b* may provide shooting efficiency statistics and data during one or more of the shooter challenge routines 32*a* mentioned later herein, but it is also capable of providing historical or cumulative data regarding a player's lifetime or career shooting statistics at each of the plurality of different locations 22. Again, the player P or a coach (not shown) may use the information, statistics or data as feedback in order to improve the player's efficiency in shooting the basketball 12 at the one or more of the plurality of different locations 22.

Referring back to FIG. 1, the system 10 comprises a user interface 40 and a front display 45. The user interface 40 in the illustration being described is shown in more detail in FIG. 3 and will be described later herein. The system 10 further comprises a storage device 44, such as an electronic storage device or other electronic storage, for storing data relative to the player's efficiency, such as data regarding the player's performance during one or more of the shooter challenge routines 32*a* and even historical or cumulative information regarding a player's performance over a predetermined period or even a player's career in shooting using the system 10.

Figure 1:
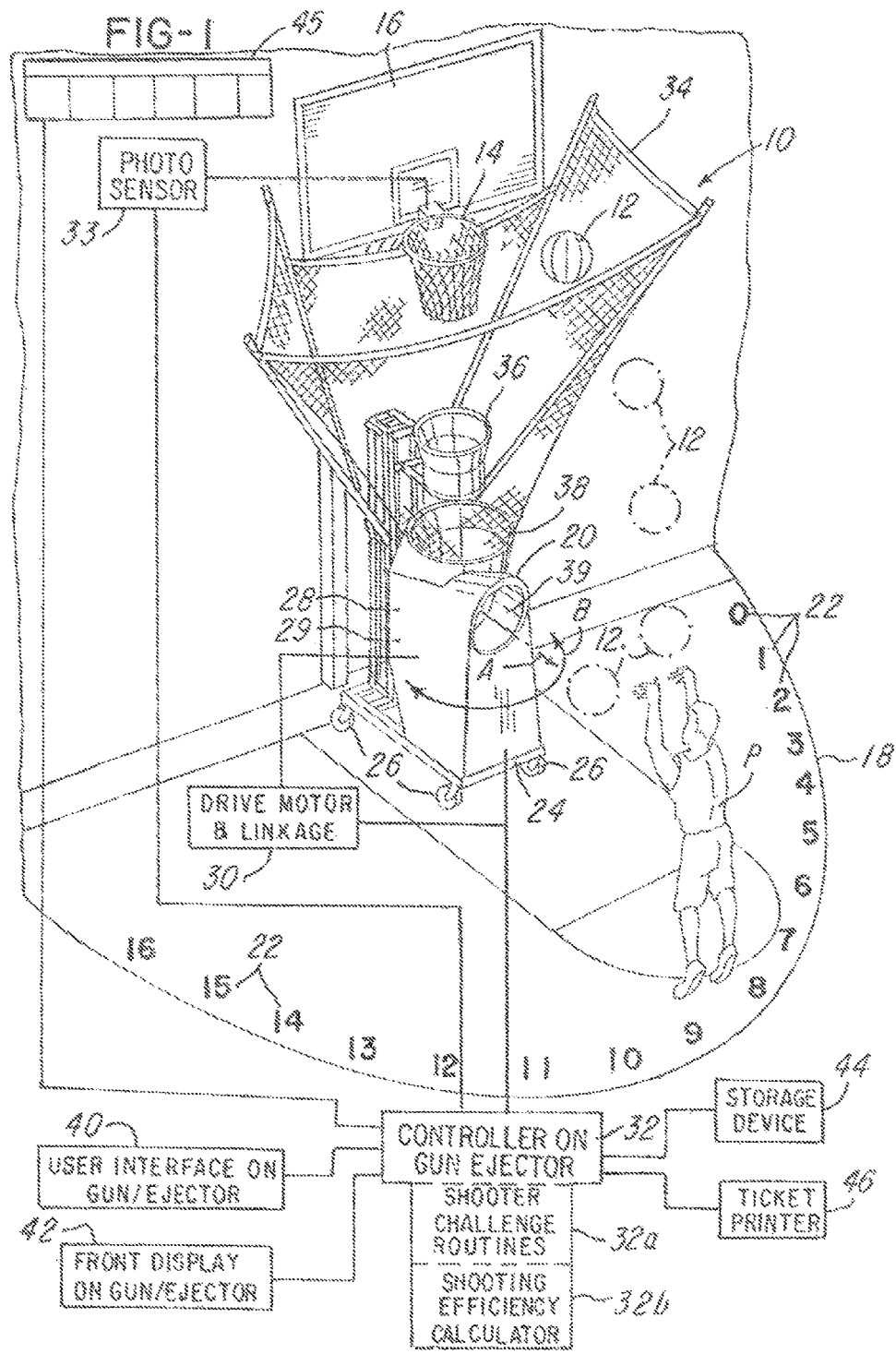
FIG. 1 is a perspective view of a system in accordance with one embodiment of the invention where a player is shooting a basketball from a first position at a playing area.
Figure 2:
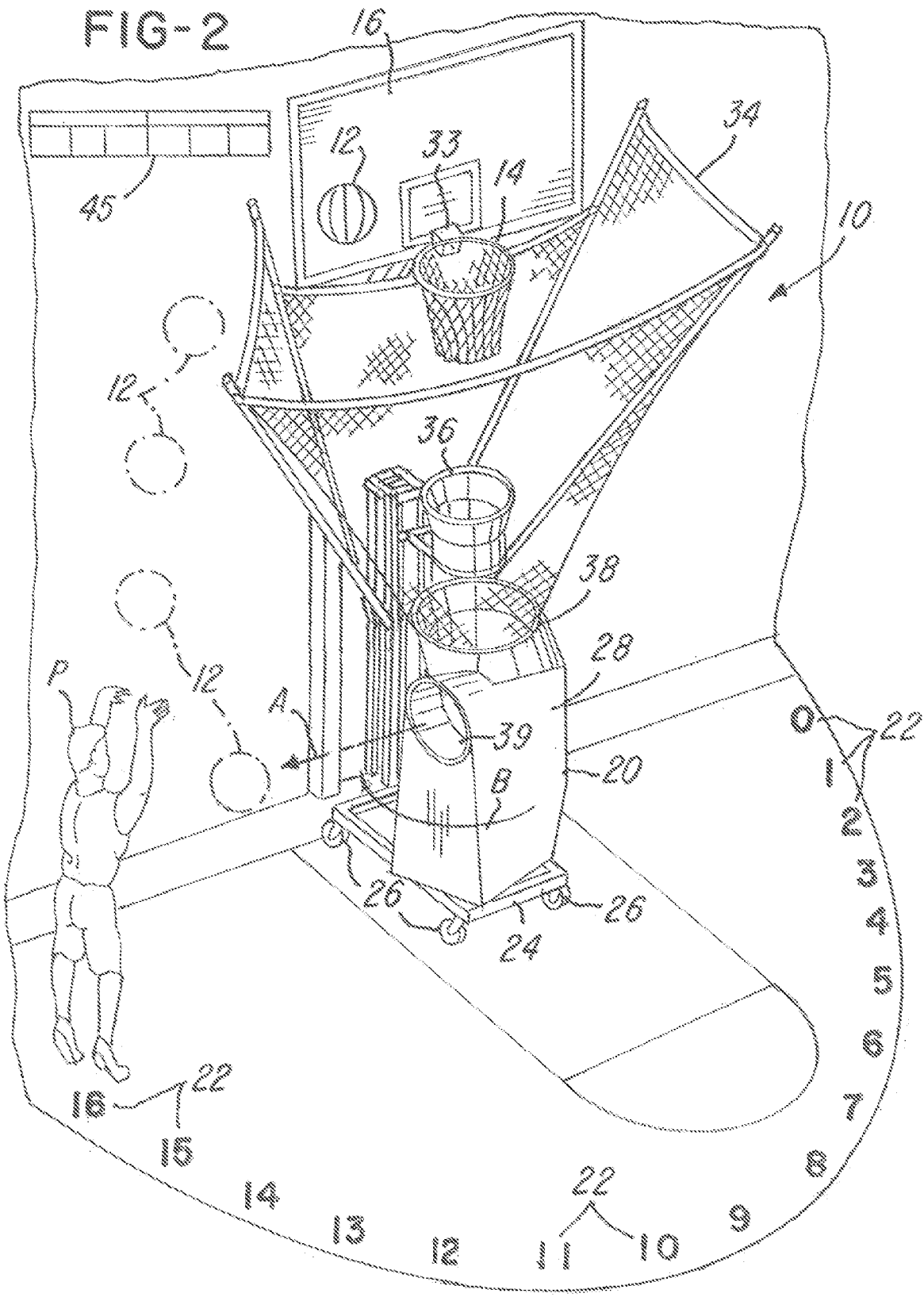
FIG. 2 is a view similar to FIG. 1 after the player has successfully performed one or more shooting accuracy routines at a first position (such as FIG. 9 and FIG. 1) and after a gun or ejector has automatically pivoted to eject or throw a basketball to another position, such as position 16 in the illustration.

As further illustrated in FIG. 1, the system 10 further comprises a ticket printer 46 which is coupled to the controller 32 and which is capable of printing a ticket 48 (FIG. 6). In the illustration being described, the ticket 48 comprises a plurality of information fields 50. In the illustration being described, the information fields 50 may include a player's name 52, time and date or period the player P practiced which could be a single day or date or could be a date span over a period of time during which the player P used the system 10. Note in the illustration being described, the ticket 48 comprises information fields 50 that also include information relevant to the player P's shooting performance. In the illustration being described, the ticket 48 comprises a spot column 55 which identifies the at least one or a plurality of predetermined locations 22 at which the player P shot the basketball 12. A total shots column 56 which identifies the number of shots attempted at the associated spot listed in the spot column 55. The ticket 48 information fields 50 also comprises a number of shots made column 58. Finally, a percentage column 60 is provided so that a player P can view the percentage of shots made at a given spot relative to the total number of shots taken over the time period 54 selected by the player P.

As mentioned earlier, a predetermined or desired efficiency threshold, such as 40% in the illustration being described, may be selected. The player P can use the information fields 50, such as the percentage column 60, and identify those spots where the player P's shooting efficiency dropped below the predetermined or desired efficiency threshold. In the illustration shown in FIG. 6, note that the highlighted areas 62 each identify spots, such as spots 3, 10, 11, and 13, at which the player P's efficiency dropped below 40%. Using this information, the player P or his or her coach (not shown) may then program the controller 32 using the user interface 40 (FIGS. 3A-3D) to direct one or more respected shots to those particular spots where the player P's efficiency dropped below the predetermined threshold. In a manner conventionally known, the player P may select a number of shots to shoot at the one or more of predetermined plurality of different locations 22 or alternatively, the player P may select initially or after reviewing his or her efficiency percentages to shoot a number of shots at each of the plurality of different locations 22 where the player P's performance efficiency was deficient using one or more of the shooter challenge routines 32a. These routines will not be described relative to FIGS. 7-9.

In the illustration being described, the shooter challenge routines 32a are programs stored in a read only memory (not shown) on the board (not shown) and under control of the controller 32.

Before beginning the shooter challenge routines 32a, the player P or the coach uses the interface 40 to program the controller 32. In this illustration, the controller 32 is programmed in multiple steps. First, the user selects one or more of the plurality of different locations 22 (0-16, in the illustration being described) during a first step or does not select a location thus the Gun will throw to the direction it is pointing. Note that the interface 40 may have the steps labeled for easy access. During a second step, the user programs the controller 32 and selects a time delay between passes or the time between which the gun or ejector 20 ejects basketballs 12. In one embodiment, the time delay is predetermined and set to at least one second. The third conventional step is programming the controller 32 with the number of shots for each of the plurality of different locations 22 selected in Step 1. Again, the player P can start the shooting by pressing the start button 70 and can stop shooting by pressing the stop button 72 (FIG. 3D).

The player P or a coach may select a challenge shooting accuracy button 74 (FIGS. 3A-3D) whereupon the controller 32 will begin the shooter challenge routines 32a. A multiple shots in a row routine requires the player P to make the number of shots consecutively before the gun/ejector 20 is caused to throw basketballs 12 at the next programmed spot. A total number of shots routine requires the player P to make the total number of shots before the gun/ejector 20 begins throwing basketballs 12 at the next programmed spot. During this routine, the player P does not have to make the number of shots consecutively. In this regard, if the player P selects the challenge shooting accuracy button 74, then the controller 32 prompts the user using the screen 76 to determine whether the player P desires to make multiple shots in a row or multiple shots at each spot before the gun/ejector 20 is caused to pivot and throw basketballs 12 to the next position, without the requirement that the shots be made in a row.

A main routine will now be described. If the challenge shooter accuracy button 74 is not pressed and the player P or his or her coach presses the start button 70, the controller 32 begins at block 78 (FIG. 7) by starting to throw basketballs 12 toward the player P at one of the plurality of different locations 22 as selected by the player P during step 1 (FIGS. 3A-3D). The routine continues to block 79 where the controller 32 assigns a TSPOTS variable to the number of locations selected in step 1. The routine continues to block 80 where the controller 32 assigns a NUM variable to the number of shots per spot selected by the player P in step 3. At decision block 82, it is determined whether the challenge shooting mode was enabled by the player P by pressing button 74 (FIGS. 3A-3D). If it was not, then the controller 32 energizes the gun/ejector 20 to output one shot for each spot selected by the player P. In another embodiment, the controller 32 energizes the gun/ejector 20' to output the total number of shots selected in step 3 to each location before the gun/ejector 20' moves to the next location. If a decision at block 82 was affirmative, then it is determined at decision block 83 whether the player P selected the multiple shots must be made in a row routine where the player P must make the selected number of shots in a row at each of the plurality of different locations 22 selected by the player P in step 1. If the decision at block 83 was negative, then the routine continues (block 84) to the multiple shots which must be made at one or each of the plurality of different locations 22 selected by the player P in step 1 which is illustrated in FIG. 9. If the decision at decision block 83 was affirmative, then the routine continues (block 86) to the multiple shots which must be made in a row at the at least one or each of the plurality of different locations 22 selected by the player P in step 1, which is illustrated in FIG. 8 and which will now be described.

Figure 8:
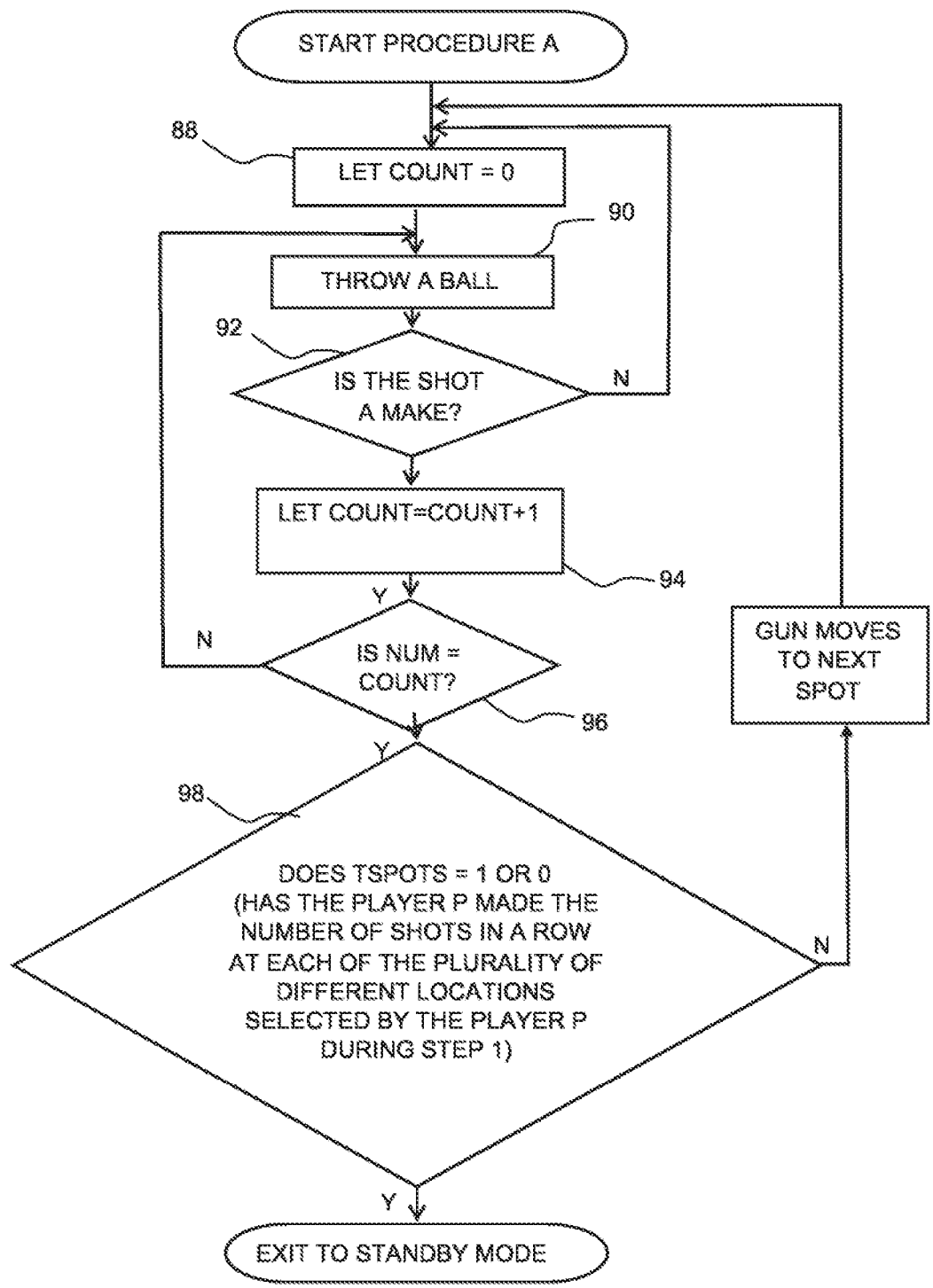
FIG. 8 is a schematic of a challenge shooting accuracy routine wherein multiple shots must be made in a row.
Figure 9:
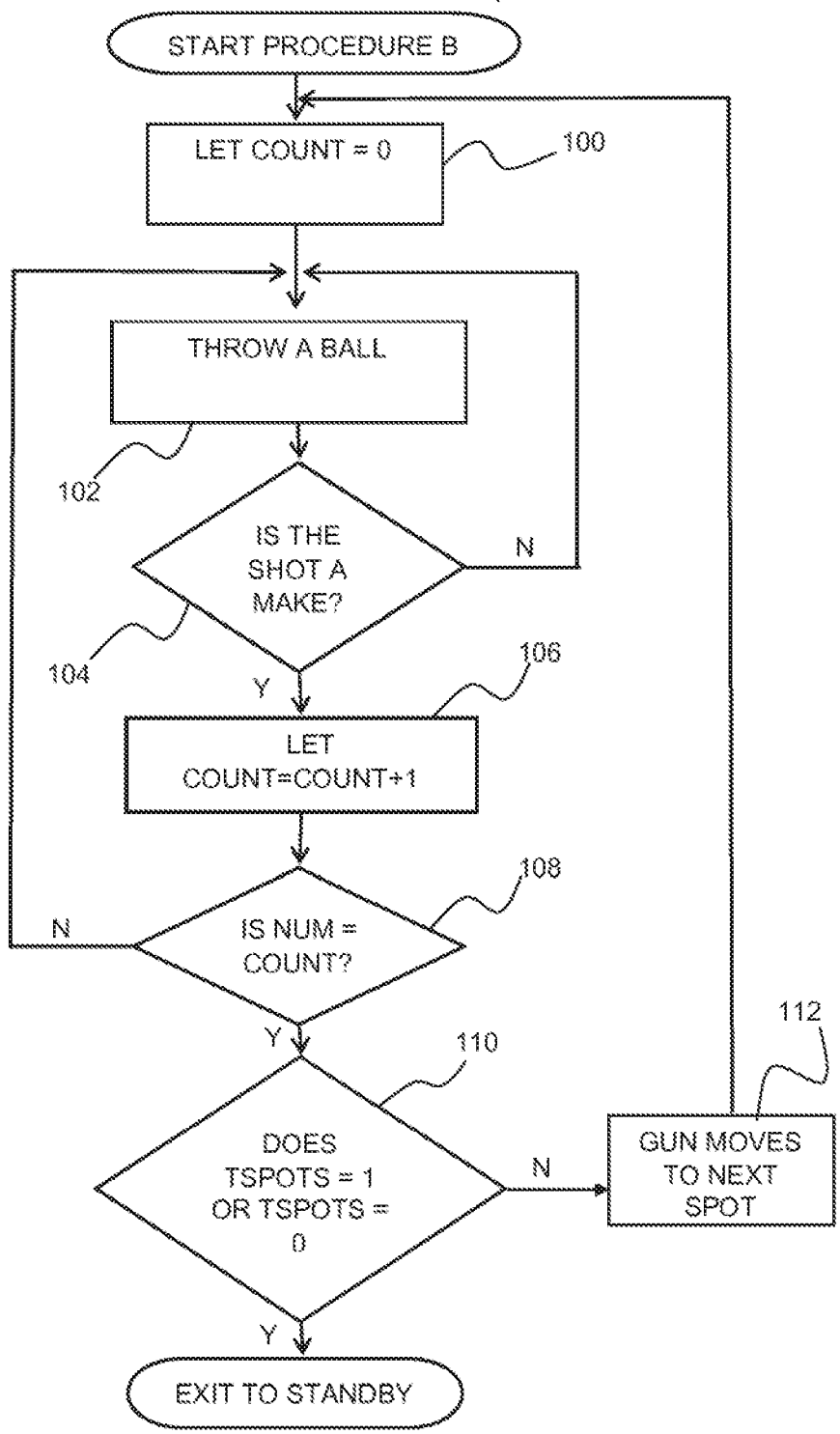
FIG. 9 is a schematic of a challenge shooting accuracy routine wherein multiple shots must be made at a particular location, but not necessarily in a row.

If the player P selected challenge shooter accuracy routine in which the player P must make multiple shots in a row at the least one or a plurality of different locations 22 selected by the player P, then the controller 32 begins the routine illustrated in FIG. 8 (block 88) and the routine continues to block 90 where the controller 32 energizes the gun or ejector 20 to throw a basketball 12 toward the first spot selected by the player P during step 1.

Figure 3A:
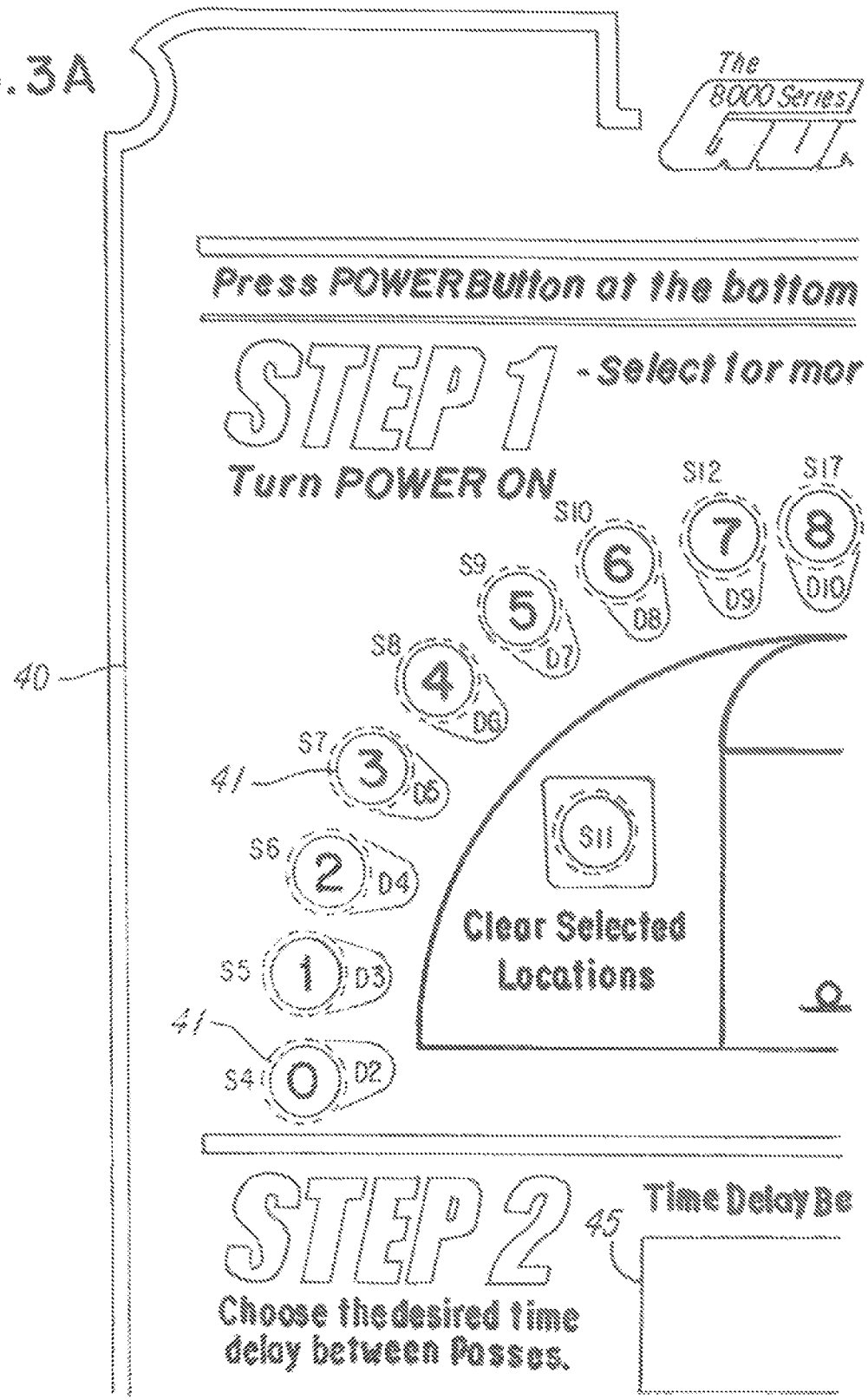

The photo sensor 33 senses when a basketball 12 passes through the hoop 14 (FIG. 5) and therefore when a shot by a player P has been made. At decision block 92 (FIG. 8), the photo sensor 33 determines whether the shot was made by the player P and if it was not then the routine loops back to block 88 as shown. If the shot was made, the controller 32 increments the count by one (block 94) and it is determined at decision block 96 whether or not the total number, which is the number that the player P has programmed during step 3 using the interface 40. It should be understood that if the player P has selected the challenge shooting accuracy button 74 and been prompted to enter during step 3 the number of shots that must be made in a row using the buttons 77 (FIGS. 3A-3D), with the total number of shots displayed in the display 76. If the controller 32 determines that the total number of shots made, as represented by the COUNT variable, is equal to the predetermined number of shots to be made as selected by the player P at decision block 96, then the routine continues to decision block 98, otherwise it loops back to block 90 as shown.

Thereafter, the controller 32 determines (block 98) whether or not the total number of spots (TSPOTS) equals one or zero. If the decision at decision block 98 is negative, then the player P has made the number of shots in a row at the location which the player P is shooting the ball, so the controller 32 energizes drive motor and linkage 30 to pivotally drive the gun or ejector 20 so that it will eject basketballs 12 toward the next spot which was selected by the player P in step 1. If the decision at decision block 98 if affirmative then the routine exits to a standby mode as shown.

Another shooter challenge routine 32a (FIG. 1) may be selected by the player P as mentioned earlier. During this routine, a player must shoot multiple shots at the at least one or at each of the plurality of different locations 22 that are selected by the player P, without the limitation or qualification that the shots be made in a row. If this shooter challenge routine 32a is selected, controller 32 starts the routine in FIG. 9 wherein it sets a COUNT equal to zero at block 100. The controller 32 energizes the gun or ejector 20 to throw a basketball 12 (block 102) toward the first of the at least one or a plurality of the plurality of different locations 22 selected by the player P at block 102. At decision block 104, it is determined whether the shot is made and if it is not it loops back to block 102 as shown. If the shot is made, the controller 32 increments the COUNT by one (block 106) and then proceeds to decision block 108 where it is determined whether the total number of shots made is equal to the COUNT. If it is not, then the routine loops back to block 102 where another basketball 12 is thrown. If the decision at decision at decision block 108 is affirmative, then the routine proceeds to decision block 110 where it is determined if the TSPOTS equals one or is TSPOTS equals zero. Thus, it is determined at decision block 110 if TSPOTS equals one or is TSPOTS equals zero which signify that player P has only selected one spot or the direction the gun or ejector 20 is currently pointing (zero spots) to shoot his number of makes at this spot (i.e. there is no other locations selected so the gun goes in standby mode). If it is not, then the controller 32 energizes the drive motor and linkage 30 to pivotally drive the gun or ejector 20 so that it throws a basketball 12 to the next spot selected by the player P at block 112 and the routine then proceeds back to block 100 as shown. If the decision at decision block 110 is affirmative, then the routine exits to standby mode as shown.

Figure 3C:
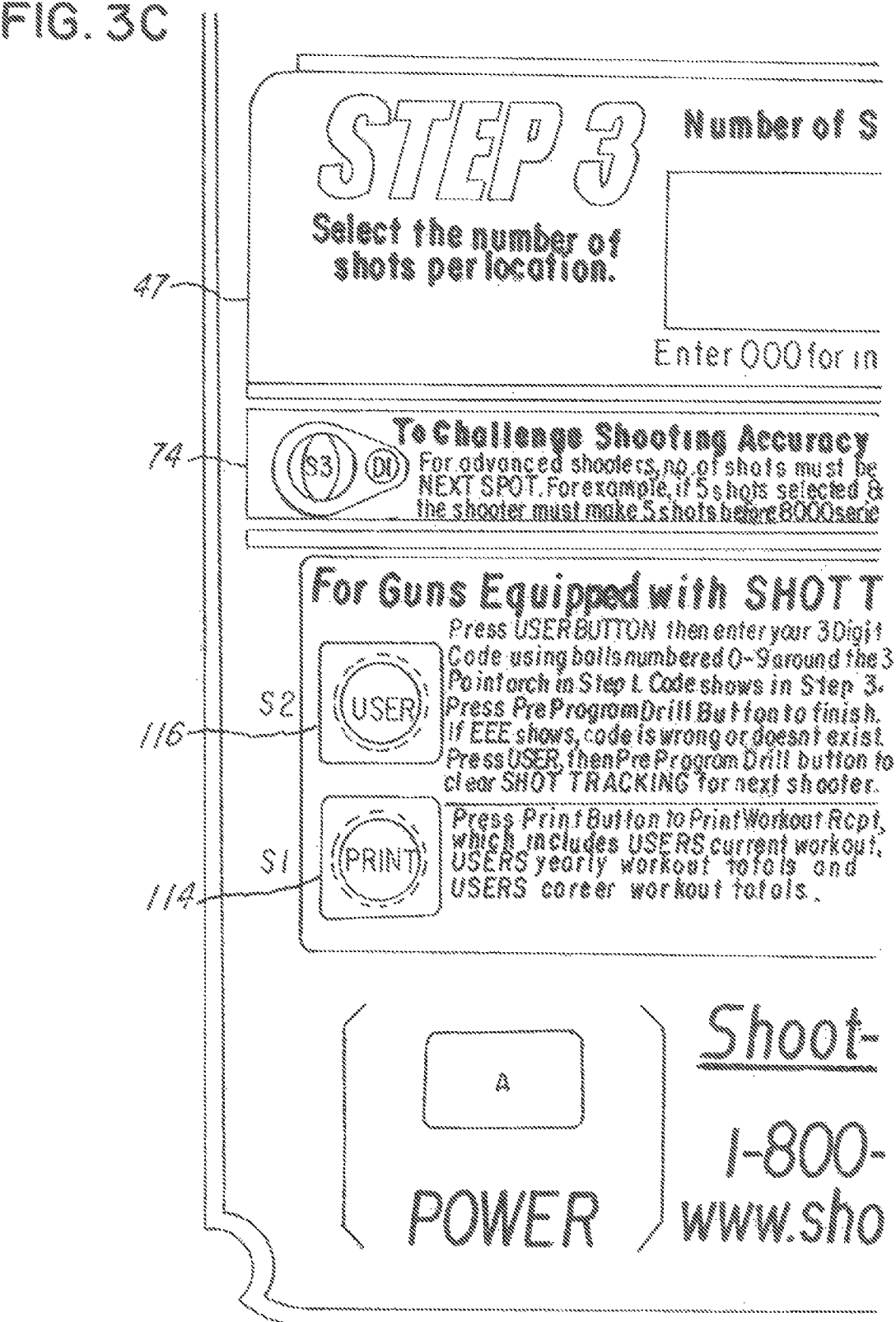
Figures 4, 5:
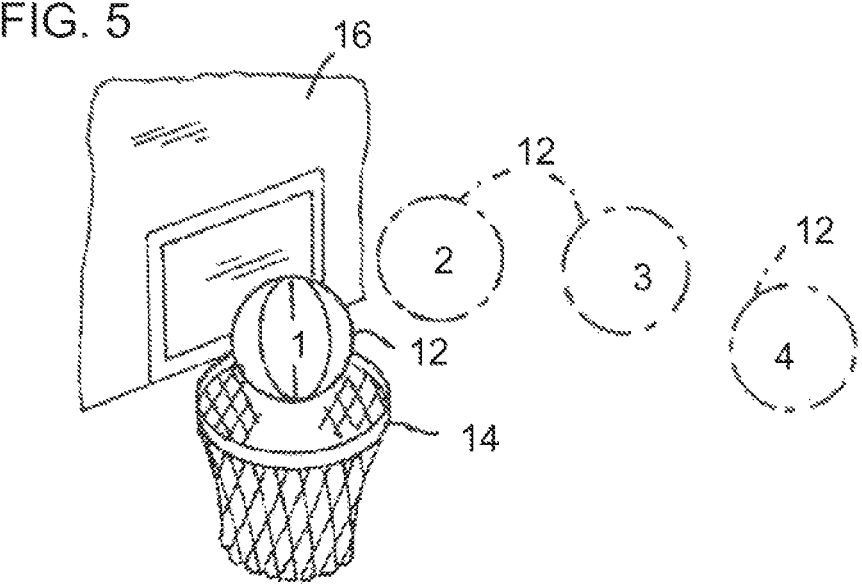
FIG. 4 is an enlarged view showing details of a display shown in FIG. 1.
FIG. 5 is a simplified view of a plurality of basketballs made in a row in the simplified illustration.

After the player P has used the system 10, it may output the shooting efficiency statistics to the ticket printer 46 by selecting the print button 114 (FIG. 3C). The user can display shooting statistics either by the ticket printer or by exporting them to a secondary device like a computer and see them there.

In the illustration being described, the controller 32 may be programmed with one or more player's names, such as the players P on any given team and their information stored in the electronic storage device 44. When a particular player P is using the system 10 he can retrieve his user information using the user button 116 (FIGS. 3A-3D) which the controller 32 could cause a directory of players to be displayed so that the user can select the player P that will be using the system 10. In one illustration, each player will have a 3 digit code tied to his name which will be initially set up on a computer and dropped down on the gun/ejector 20 by an import button 118 (FIGS. 3A-3D). When player P wants to use the system 10, he will enter his three digit code. This code will be displayed on the front scoreboard display 45 (FIGS. 1 and 4) when the system 10 is in standby mode and for a set time, such as at least 4 seconds, in the STEP 3 (76 in FIGS. 3A-3D) three digit display. Although not shown, the system 10 may include the ability to load/enter the shooter's number or name at the gun/ejector 20 and have it displayed on the front board and/or on the control board, thus not having to import it from a computer. The statistics relative to a player P may also be imported and stored using the button 118 (FIG. 3D), which a coach uses to load players into the system each tagged with a 3 digit code or if the coach has to edit a certain player's shooting data on a given workout. Moreover, the user can export data associated with one or more players P using the export stats button 120 (FIG. 3D). In this regard, the controller 32 may have an input/output interface that enables, for example connection to permanent or portable storage devices, such as CD, DVD, USB interface for smart drives, flash drives and the like. The information can then be loaded onto other computers (not shown) for evaluation and use by other users, such as coaches, trainers and the like.

During use of the system 10, it may be desirable to provide a display 45 (FIGS. 1 and 3A-3D) which can be wired or wireless and in communication with the controller 32 so as to enable a player P or his or her coach to view the performance and efficiency during the player P's use of the system 10.

In general, the system 10 comprises the user interface 40 that enables the user to select the shooting practice that the user desires. During the first step, the user turns the power to the gun or ejector 20 and the controller 32 on and selects either the pre-programmed drills or the user can select at least one or a plurality of different locations 22 at which the player P will shoot the basketball 12. In the illustration being described, for example, the user would select the various positions by depressing one or more of the buttons 41 (FIG. 3A) which are arranged on the interface 40 to generally correspond to the positions 22 labeled in FIG. 1. The controller 32 receives the selected positions information and stores it in memory (not shown). During a second step, labeled as step 2 on the user interface 40, the user selects the time delay between passes using the buttons 43 and display 45. The time delay represents the amount of time that the gun or ejector 20 allows to lapse before ejecting basketballs 12.

During the third step, the user uses the button 77 and display 47 to select the number of shots at each of the locations selected during step 1. The user may begin a practice by depressing the start button 70 and may end the practice by depressing the stop button 72.

During this third step, the user may also elect to challenge the shooting accuracy. The shooter challenge routines 32a are stored in the electronic storage device 44. It should be understood that the shooter challenge routines 32a facilitate improving the player P's shooting efficiency by providing a number of shooting challenges to the player P at one or more of the plurality of different locations 22. By challenging the shooter accuracy and then evaluating a shooter's statistics during the challenges, the shooter's performance can be evaluated. If the shooter's shooting efficiency is below a predetermined threshold or is deficient as determined by the player P or his or her coach, then during the player P's next shooting practice the player P can use the information and program the system 10 to throw basketballs 12 at one or more of the plurality of different locations 22 where the player P's performance was deficient, thereby improving the player P's shooting accuracy in general and also improving the player P's accuracy at one or more of the plurality of different locations 22.

Advantageously, this system 10 and method provide means for improving the player P's efficiency at shooting the basketball 12 at one or more of the plurality of different locations 22.

The system and method enables a player to select S number of shots and N number of positions at which the player will shoot at least one basketball.

The system and method further permits repeating the throwing, sensing and causing steps until the player has shot S number of shots at each of N number of position, wherein S is at least one of a total number of shots made at each of N number of positions or a total number of shots made in a row at each of N number of positions.

Figure 10:
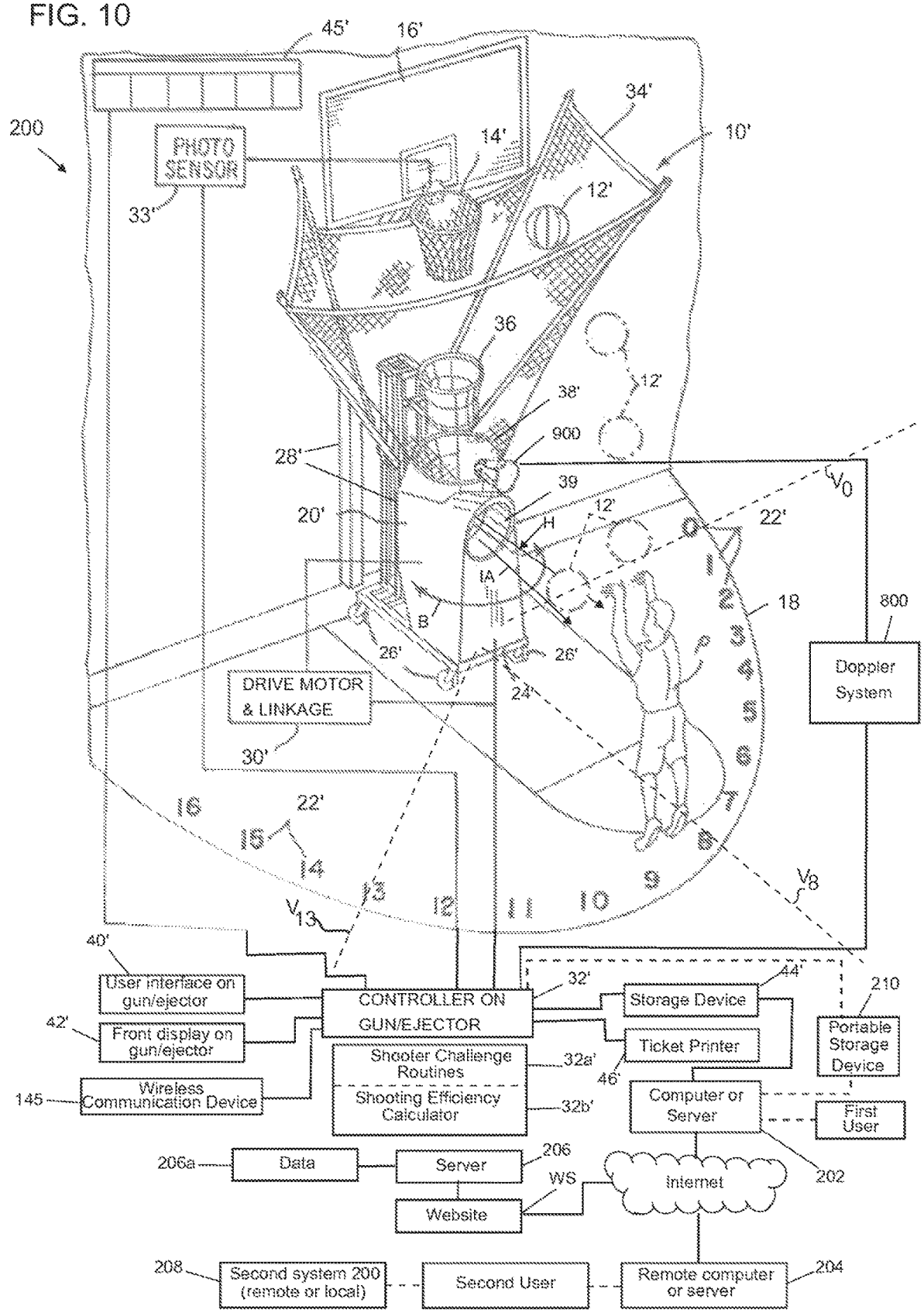
FIG. 10 is a perspective view of a system in accordance with another embodiment of the invention where a basketball is launched to a player and the player shoots the basketball from a position on the basketball floor.

Referring now to FIGS. 10-63, other embodiments of the invention will now be presented and described. An overview of these embodiments will now be described. In the embodiments, like parts are identified with the same part numbers, except a prime ("'") has been added to the parts described in this embodiment. Notice in FIG. 10 some additional components relative to the embodiment of FIG. 1 are shown. In this embodiment, a system 200 is provided for training players from the same or different teams and for training players or teams practicing at the same or different locations. In one embodiment shown in FIGS. 10-62, the system 200 comprises a Doppler measuring system 800 and means for measuring or calculating various measurements, such as a player's release time, a player's distance between a position from which the player shoots to the rim 14', a release arc associated with the player's release of the ball 12', and an entry arc are associated with the angle at which the ball 12' enters the hoop 14', as will be described later herein.

In another embodiment, the system and methods described herein provides means, procedure and tracking system for calculating, comparing and tracking shooting statistics and data of players from the same team or different teams regardless of whether those players or teams are located at the same shooting location or at different shooting locations and regardless of whether the players or teams are shooting at the same time or at different times. In other words, the system allows, for example, a player, a coach or other interested person on one team of players to view that player's shooting statistics and also to compare those statistics against other shooters' statistics on the same team or comparing that shooter's statistics against statistics of shooters from different teams.

In the examples shown, it is important to note that the players on the different teams could be, for example, in the same league, in different leagues, of the same age group or different age groups or could be different skill levels (e.g., high school vs. college, college vs. pros, high school vs. pros). The comparisons and reports or chart, can be created using various criteria, such as age (e.g., comparison of a player age fifteen to a comparison of shooting statistics from other players of the same age or in the same age group.) It is also envisioned that gender could also be a criterion for comparison so, for example, girls or women could be compared against other girls or women from other teams in the same or different age groups. Moreover, the female shooter statistics could be compared against male shooter statistics.

In FIG. 10, a player P identifies himself to the computer 202 and then a computer 202 initiates a series of drills for the player P. During the drills, the gun or ejector 20' selects at least one spot, area or position 22' on the basketball floor and causes the ball launcher, gun or ejector 20', described earlier herein, to pass basketball(s) 12' to one or more spots or locations selected by the user or that are part of the pre-programmed drills. A measurement system, such as a Doppler measurement system 800 described earlier measures various Doppler data described later herein, such as a speed of the basketball 12' as it leaves the gun or ejector 20'. The player P responds by moving to one of the spots or positions 22' and catches the basketball 12'. The ball launcher, gun or ejector 20' and other components may be the same or similar to the gun or ejector 20 and other parts described earlier and may have feature of the embodiment described earlier.

In short, the system and methods described herein permit a player, coach or other interested person or user to compare a shooter's statistics based on a number of selected or predetermined criteria which will be described later herein. For ease of description, the term "user" will be used herein and refers to any interested person, such as a player, trainer, coach, scout, family member or any other interested user.

Referring back to FIG. 10, the method and system 200 also provides means and apparatus for uploading and downloading information and data between the gun or ejector 20' and a website WS using a computer (such as computer 202 or 204) via the internet, wirelessly, or using other devices (e.g., computer 204). The website WS has an associated server 206 that permits the user to upload and download information to and from the website WS using the computer 202 in the manner described later herein.

The system comprises the computer 202 which is coupled to the local server or storage device 44' which was described earlier herein relative to FIG. 1. In the example, the computer 202 is used by a first user and a second computer, such as computer 204, could be used by a second user so that the second user could also access the website WS via the internet. Of course, multiple users could access and use the website WS from other computers (not shown) or devices, such as smart devices like iPad, iPhone, Blackberry and the like. For ease of illustration, the second user is shown in FIG. 10 as being associated with a remote or second system 204, but it should be understood that the second user could also be utilizing the computer 204 directly, wirelessly or via the internet. Note also that the first user could access the computer 202 directly or via the internet as shown. It is also important to understand that the second user could be utilizing the system 200 located at the same geographic location and same system 200 that is used by the first user. Alternatively, the second user could be utilizing a different launcher 20' with a different backboard 14' at a different geographic location remote from the first location of the system 200 and computer 202 that the first user is using. For ease of description, the second system comprising the same components as the system 200 will be collectively referred to as system 208 (FIG. 10).

In the illustration being described, the first and second systems 200 and 208, respectively, are calibrated as described herein so that shooting positions and statistics gathered from the various shooting positions using the first and second systems 200 and 208 can be compared. For example, a player A using system 200 and shooting at a location, such as at location 8 (FIG. 10), as identified by button 8 shown in the interface 40 in FIG. 3, will be shooting from location 8 at the basketball playing area shown. The gun or ejector 20' will shoot or launch balls to the position 8 as selected, the shooter A will shoot from that position and the system 200 will measure and calculate statistics and data, described later herein, relating to player A's shooting at the position 8. A player B using the second system 208, which can be at the same or different geographic location, that has been programmed to launch balls or that launches ball to the same position 8, the system 200 will measure, calculate and generate data and statistics relative to the second player B's shooting efficiency at the position 8. In one illustrative embodiment that the players could be shooting at the same time or at different times and that the system 200 and second system 208 could be located at the same or different geographic locations. Thus, the players may not know that they are competing against each other, whereas in other illustrative embodiments, the players may desire a competition and use the systems 200 and 208 to compete directly against each other at the same or different times or locations.

As mentioned, one embodiment includes the Doppler measurement system for generating various data and statistics to be described herein. The general measurements will be described relative to FIGS. 12A-12C and 13A-13G. Features of a Doppler system and circuit will be described later herein relative to FIGS. 15A-15D.

Figure 12A:
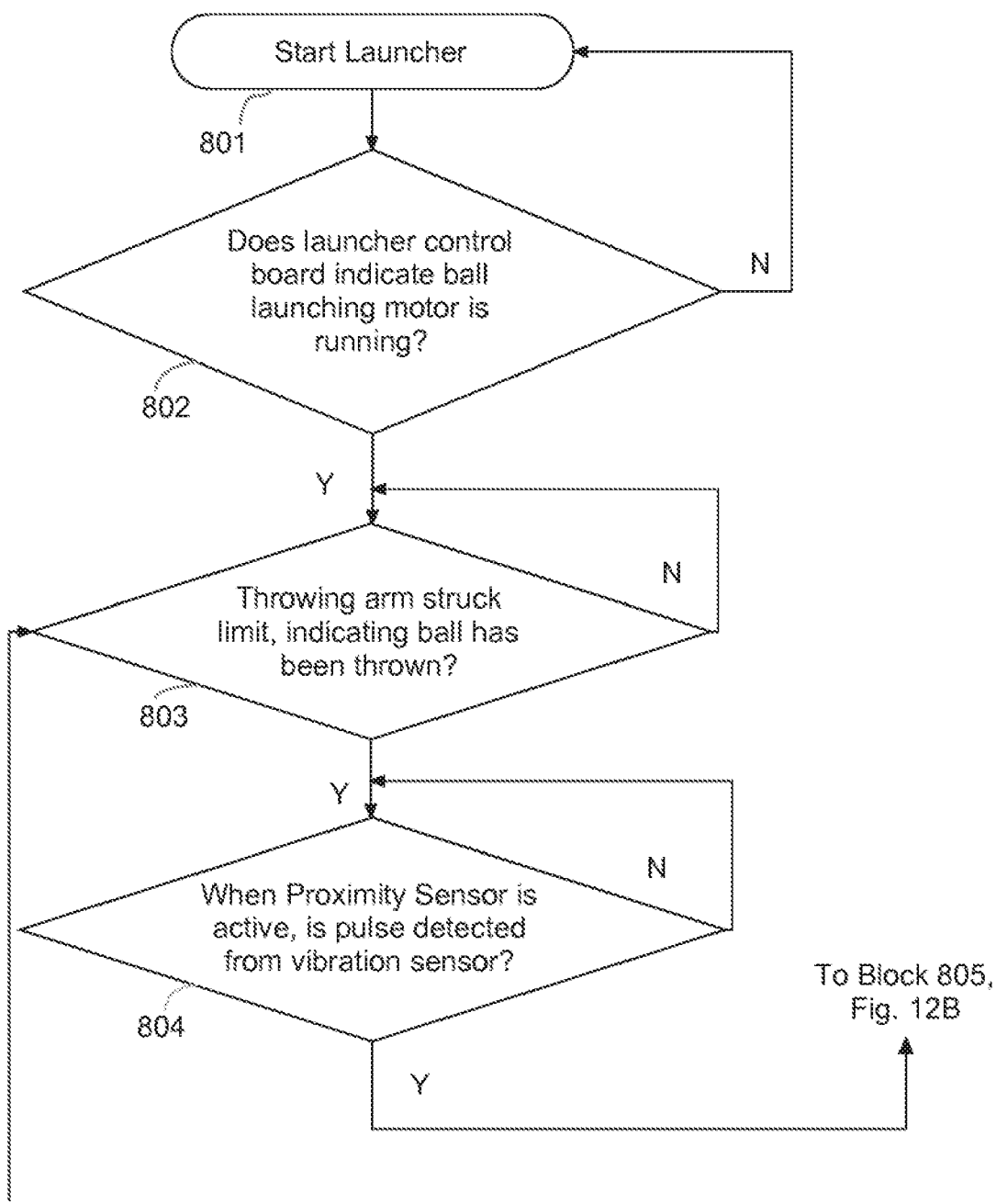
FIGS. 12A-12C illustrate a Doppler procedure or algorithm for generating various Doppler statistics.
Figure 12B:
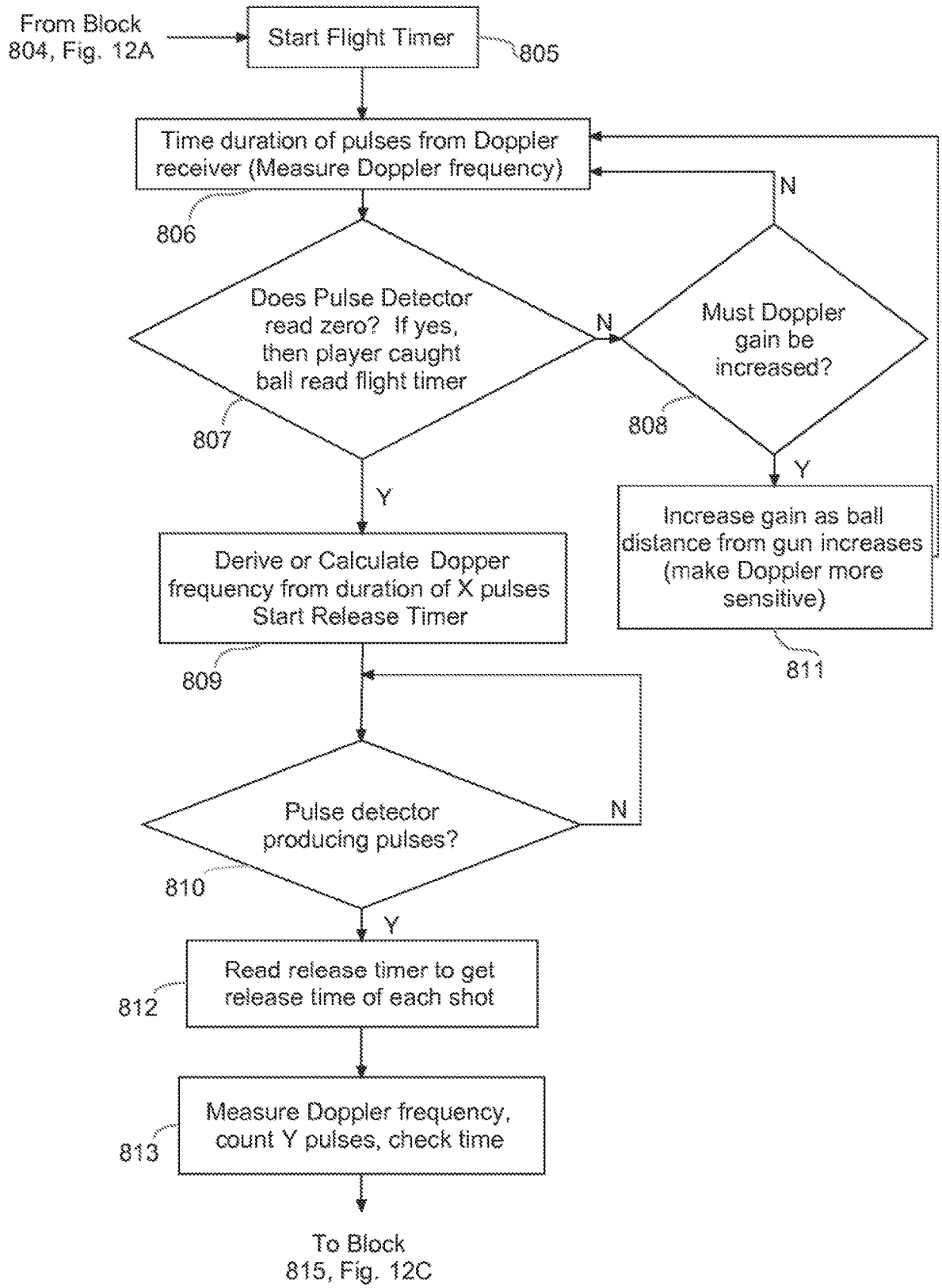
Figure 12C:
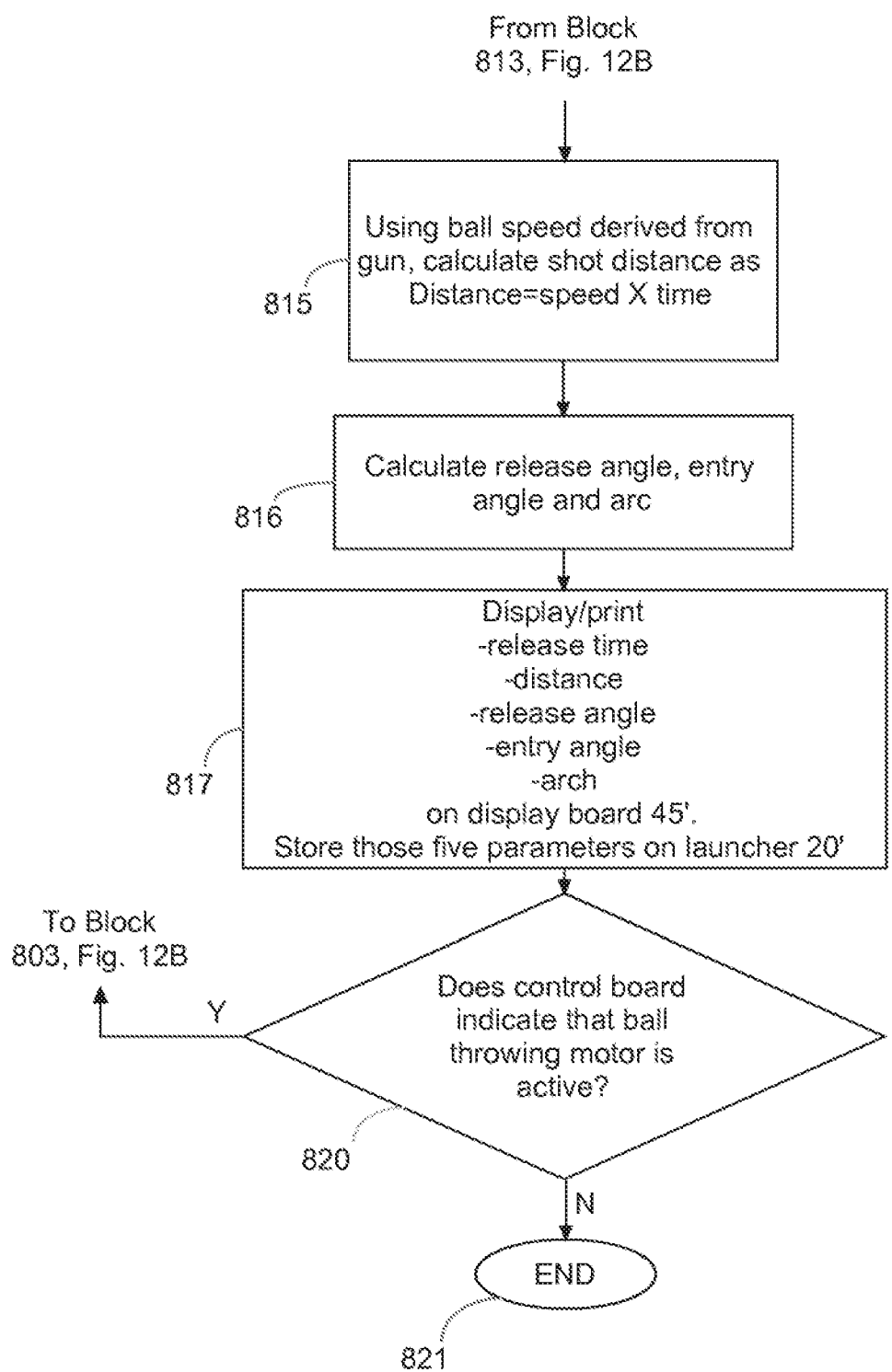

FIGS. 12A-12C are flow charts which illustrate processes undertaken by one form of the invention showing a general operation of the Doppler system 800.

In FIG. 12A, execution begins at block 801. Block 802 then inquires whether the motor which launches the basketball 12 is running. If not, the NO branch is taken, and the logic idles in the NO branch until the motor is detected as running.

When the running motor is detected, the YES branch is taken, and the logic reaches block 803, which inquires whether a throwing arm TA (FIG. 11) in the gun or ejector 20', powered by the motor 30' (FIG. 10), has struck its limiting stop, which is a rubber limit bumper RB (FIG. 11). If not, the NO branch is taken, and the logic idles in the NO branch until a strike of the limit-bumper is detected by a proximity sensor PS (FIG. 11) having a proximity pickup PP. Note in FIG. 15C, the microprocessor pin labeled RC4 obtains signal from proximity sensor PS from connector J2.

It is pointed out that at least some of the idling in the NO branch occurs during the travel of the throwing arm from its rest position en route to the limit-bumper RB.

When striking of the rubber limit-bumper RB is detected, the YES branch is taken from block 803, and block 804 is reached. Block 804 inquires whether a pulse is detected from the proximity sensor LBS, which indicates that the throwing arm TA has struck the limit-bumper, indicating that the ball 12' has been launched. If no pulse is detected, the NO branch is taken, and the logic idles in the NO branch until the pulse is detected.

When the pulse is detected, indicating that the arm TA has struck the limit-bumper RB, the YES branch is taken, which leads to block 805 in FIG. 12B. In block 805, a flight timer is started in microprocessor 910 (FIG. 14) described later herein. To repeat: the pulse of block 804 in FIG. 12A indicates that the launching arm has reached the limit of its travel, and thus a ball has been launched. The flight timer is now started at this initiation of the launch, as indicated in block 805 of FIG. 12B.

Next, block 806 is reached, in which the duration of X number of pulses is measured. This allows computation of the time interval T between adjacent pulses to be measured, which allows determination by microprocessor 910 of the pulse frequency, which is the inverse of T, or 1/T. This is an indicator of the Doppler frequency, although in the digital domain.

Next, the logic reaches block 807 in FIG. 12B, which inquires whether the measured speed of the ball 12' has reached zero. If not, the NO branch is taken, and the logic reaches block 808, which inquires whether the gain of the amplifiers described later herein which amplify the Doppler signal should be increased. If not, because the amplification is sufficient, the NO branch is taken from block 808 and leads to block 806.

If block 808 indicates that amplification must be increased, the YES branch is taken, leading to block 811, where an amplifier gain is increased. The logic returns to block 806.

If, in block 807, the ball velocity is detected as zero, indicating that the player has caught the ball 12', then the YES branch is taken. Block 809 is reached, wherein the Doppler frequency, mentioned in connection with block 806, is actually computed. Also, a release timer is triggered.

At this time, it is assumed that the player has caught the ball, because the measured velocity of the ball is zero. It is desired to now learn how fast the player can get off a shot, also referred to herein as release time, so a release timer RT is initiated in microprocessor 910 described later herein.

The logic then proceeds to block 810, which asks whether pulses are received which indicate that a Doppler frequency has resumed. To repeat: during the flight of the ball to the player, the Doppler pulses dropped to zero when the player caught the ball 12'. Now, as the player holds the ball 12' momentarily, block 810 waits for the pulses to resume, indicating that the player has made a shot. The logic idles in the NO branch of block 810 until ball 12' motion, indicating a shot is detected.

When the pulses are detected, the YES branch is taken from block 810, and block 812 is reached. That block ascertains the count value of the release timer which was initiated in block 809. The count value indicates the time delay between (1) the time when the player caught the ball and (2) the time the player makes a shot.

Next, block 813 is reached, which measures the speed of the shot made by the player in the manner of block 806.

Next, block 815 in FIG. 12C is reached, which computes a distance of the player from the hoop or rim 14', based on the measured speed of the ball and the time of flight of the ball.

Next, block 816 calculates the release angle, entry angle to the basket, and the arc height, or peak altitude, of the ball.

Next, block 817 displays, or prints, or both, the five indicated parameters which were computed, and stores those values.

Next, block 820 inquires whether the ball throwing motor is active. If not, the NO branch is taken, and the processing ends, as indicated by block 821. If so, the YES branch is taken, and the logic returns to block 803 in FIG. 12A.

Figure 13A:
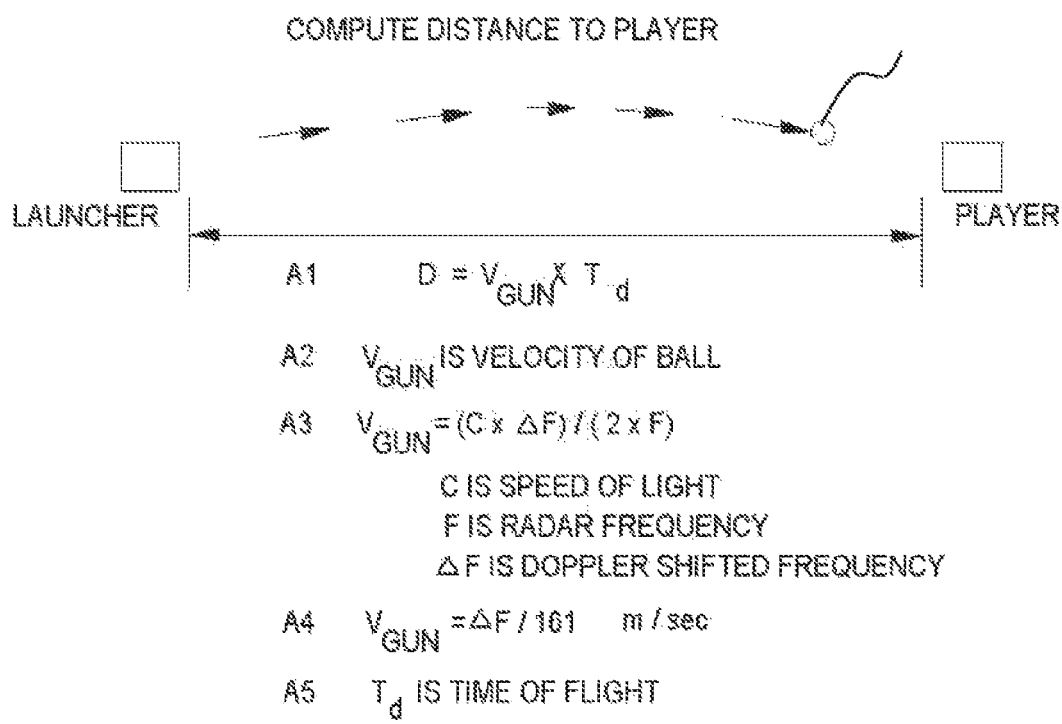
Figure 13B:
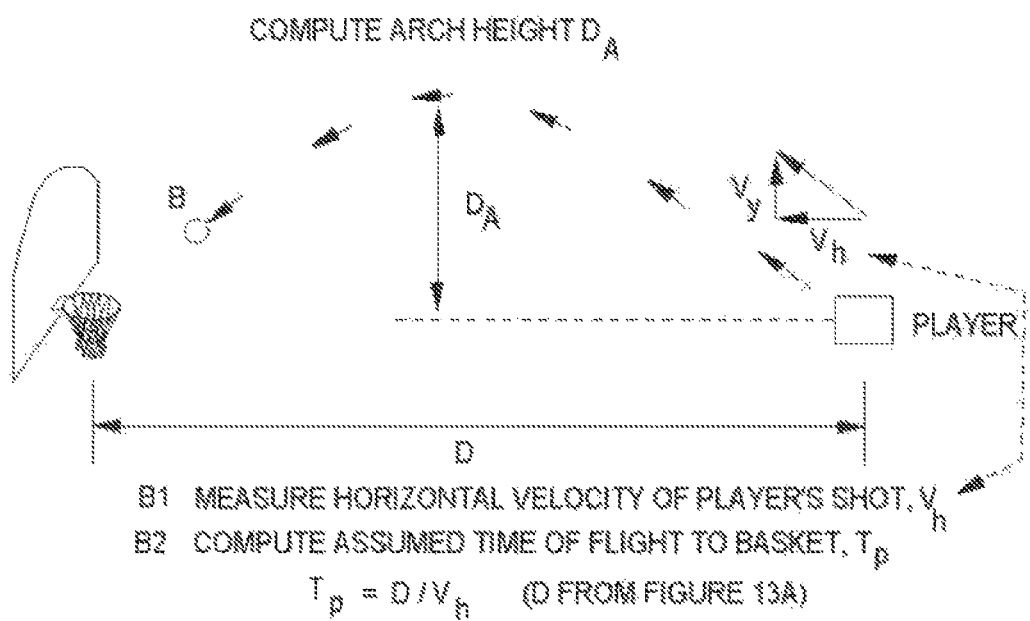
Figure 13C:
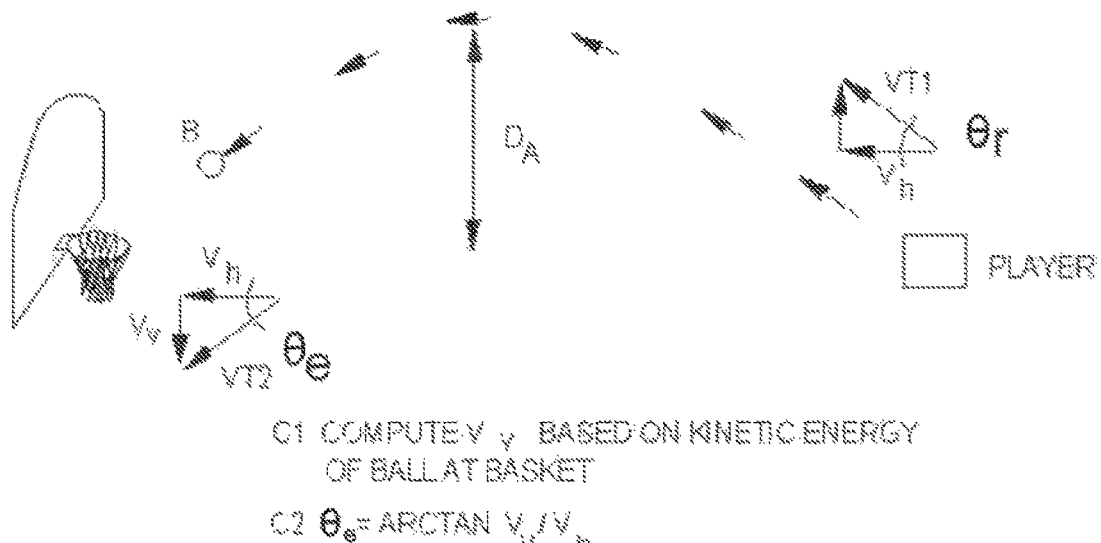

FIGS. 13A, 13B and 13C provide an overview of the computations used to gather various Doppler measurements referred to herein. These algorithms are programmed into microprocessor 910 (FIG. 14) described later herein. FIGS. 13D-13H provide greater detail referred to in the description relative to FIGS. 14 and 15A-15C and elsewhere herein.

In FIG. 13A, the ball 12' travels toward the player. The following equations are used:

$$D = V_{GUN} \times T_d \quad \text{A1}$$

$$V_{GUN} \text{ is velocity of ball} \quad \text{A2}$$

$$V_{GUN} = (C \times \Delta F)/(2 \times F) \quad \text{A3}$$

C=Speed of Light
F=Radar Frequency (24.15 GHz)
ΔF=Doppler Shifted Frequency $$V_{GUN} = \Delta F/161 \text{ m/sec} \quad \text{A4}$$

$$T_d = \text{Time of Flight} \quad \text{A5}$$

In FIG. 13A, the ball B travels toward the player. The distance to the player is given by equation A1, and is the standard equation of distance equaling velocity multiplied by time. The time $T_d$ is defined in equation A5.

$V_{GUN}$ is the velocity of the ball, as indicated by equation A2. Equation A3 gives a standard Doppler equation. Equation A4 is a simplification of equation A3, in which the constants F and C have been inserted. It is seen that velocity, in meters per second, equals the measured frequency shift divided by 161.

In FIG. 13B, the arc height $D_A$ (or $D_{Arch}$) is computed using the following equations:

$$\text{measure horizontal velocity of player's shot}, V_h \qquad \text{B1}$$

$$\text{compute assumed time of flight to basket}, T_p \qquad \text{B2}$$

$$T_p = D/V_h (D \text{ from FIG. 13A})$$

In FIG. 13B, the arch height $D_A$ (or $D_{Arch}$) is computed. $D_A$ is the height above the point at which the player releases the ball, as shown in FIG. 13E, and not the height of the arch above the ground.

In equation B1 in FIG. 13B, the horizontal velocity component, $V_h$, is measured by the radar gun, as described herein. Equation B2 computes the assumed time of flight, $T_p$, to the basket. $V_h$ becomes $V_{ox}$ later. $V_v$ becomes $V_{oy}$ later.

Figure 13D:
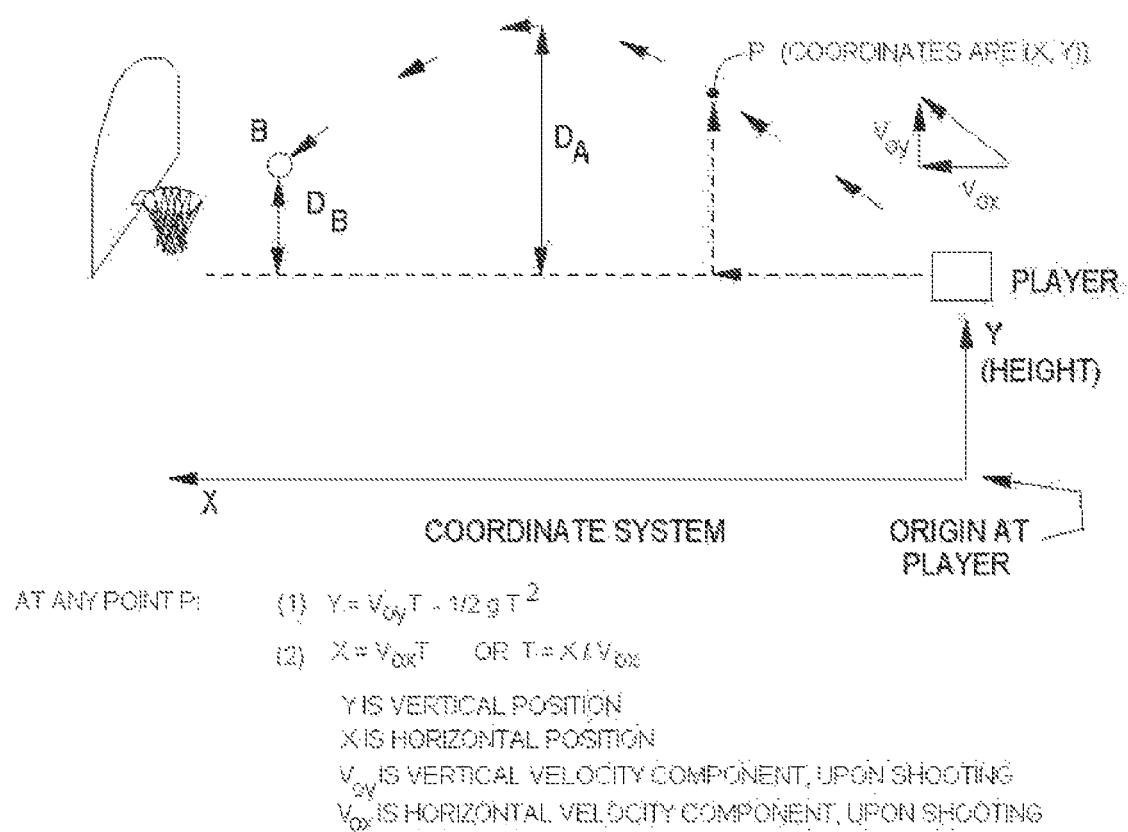
Figure 13E:
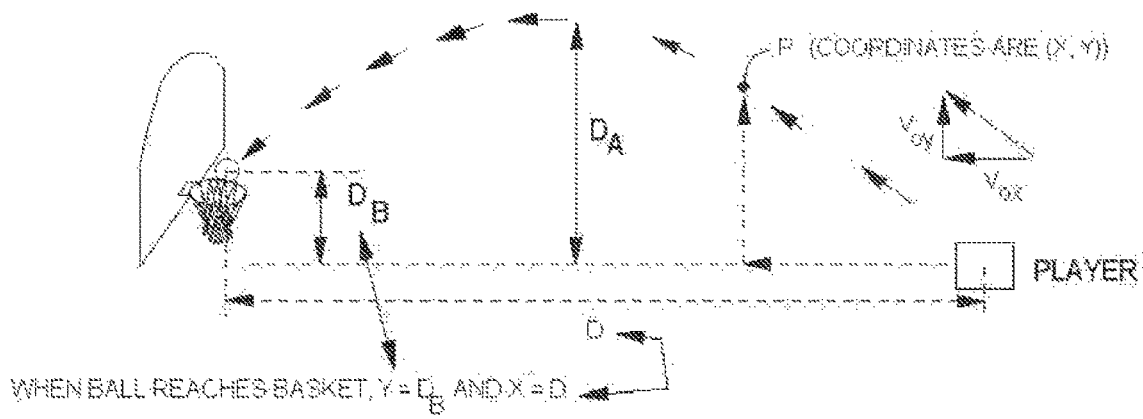

The vertical velocity in that equation, $V_y$, is computed in FIG. 13E, equation 4. It is preferred to compute $D_A$ as shown in equation 5, which is explained later with reference to FIG. 13G.

In FIG. 13C, the entry angle theta$_e$, $\theta_e$ is computed, as is the release angle theta$_r$, $\theta_r$. The following equations are used:

$$\text{compute } V_v \text{ based on kinetic energy of ball at basket} \qquad \text{C1}$$

$$\theta_e = \arctan V_v/V_h \qquad \text{C2}$$

Phrase C1 indicates that the vertical component, $V_v$, of the ball's velocity is computed. Equation C2 then computes theta$_e$. Theta$_r$ is computed in a similar way. $V_v$ ("v" for vertical) is a generalized variable, and a specific instance later will be $V_{by}$ ("y" for y-axis). Similarly, $V_h$ ("h" for horizontal) in FIG. 13C is a generalized variable, and a specific instance later will be $V_{bx}$ ("x" for x-axis).

FIGS. 13D-H will provide details of the computations just outlined.

In FIG. 13D, an x-y coordinate system is shown, wherein x represents horizontal distance and y represents height. For any point P on the path of the ball B, equations 1 and 2 apply.

Equation 1 is the difference between (1) the vertical distance covered because of the initial velocity of the ball, namely, $V_{oy}T$ and (2) the deceleration of the ball due to gravity, namely, $\frac{1}{2} g T^2$. From another point of view, equation 1 is the sum of (1) distance travelled upward at any given time T, plus the superposition of (2) the distance travelled downward at that same time T. Equation 1 gives the y-coordinate of the ball.

Equation 2 gives the x-coordinate of the ball, and is the simple velocity-multiplied-by-time function.

In FIG. 13E, equation 3 is the result of combining equations 1 and 2 of FIG. 13D. In equation 3A, the known values of x and y are substituted for the condition where point P is located at the basket. That is, at the basket, the value of x is D and the value of y is $D_B$ (or $D_{Basket}$). Those values are substituted into equation 3, to produce equation 3A, as indicated.

Equation 4 is a reduction, in which equation 3A is multiplied by $V_{ox}^2$, and re-arranged, as indicated. Equation 4 allows computation of $V_{oy}$, which is the vertical component of the ball's velocity.

Figure 13F:
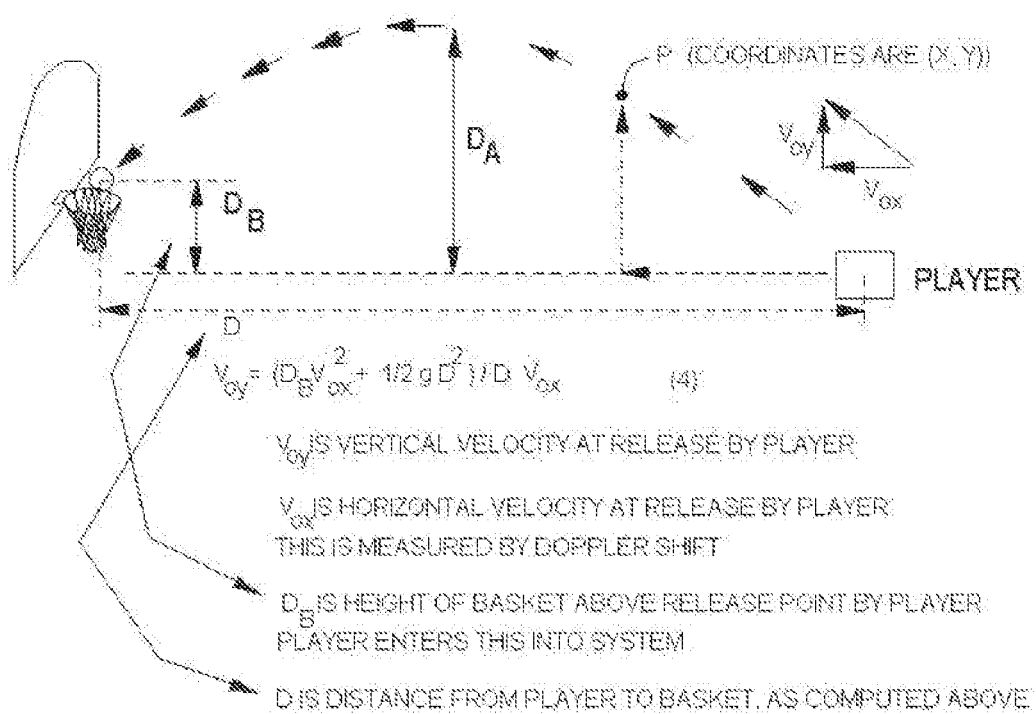

FIG. 13F is a further illustration of the content of Equation 4, which is repeated in the Figure. $V_{oy}$, the vertical component of velocity of the ball, is computed from $D_B$, $V_{ox}$, D, and g. $D_B$ is the height of the ball, at the basket, above the player's release height. The player enters $D_B$ into the system upon initialization. Of course, $D_B$ will, in general, be larger for a player who is short of stature, compared to a taller player.

$V_{ox}$ is the x-component of velocity of the ball, and is measured by the Doppler shift. D is the distance between the player and the basket. The parameter g is the acceleration due to gravity.

Figure 13G:
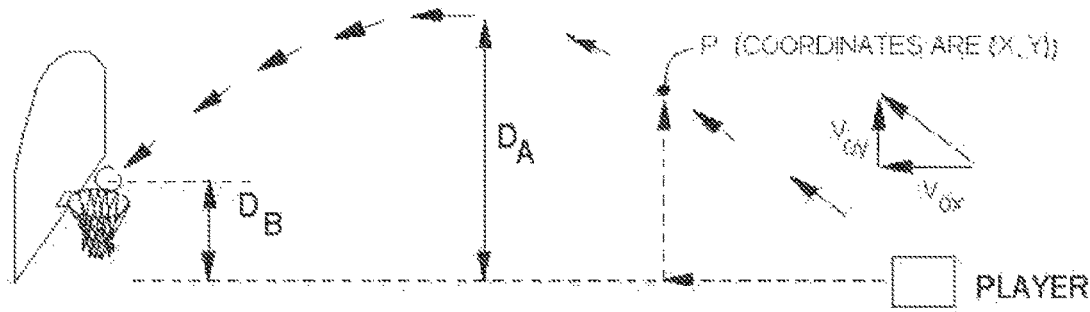

FIG. 13G produces equation 5, which allows computation of $D_A$, the arch height, based on $V_{oy}$. Equation 5 results from solving the equation $(\frac{1}{2})MV^2 = MgH$ for H, and making the substitution indicated.

Figure 13H:
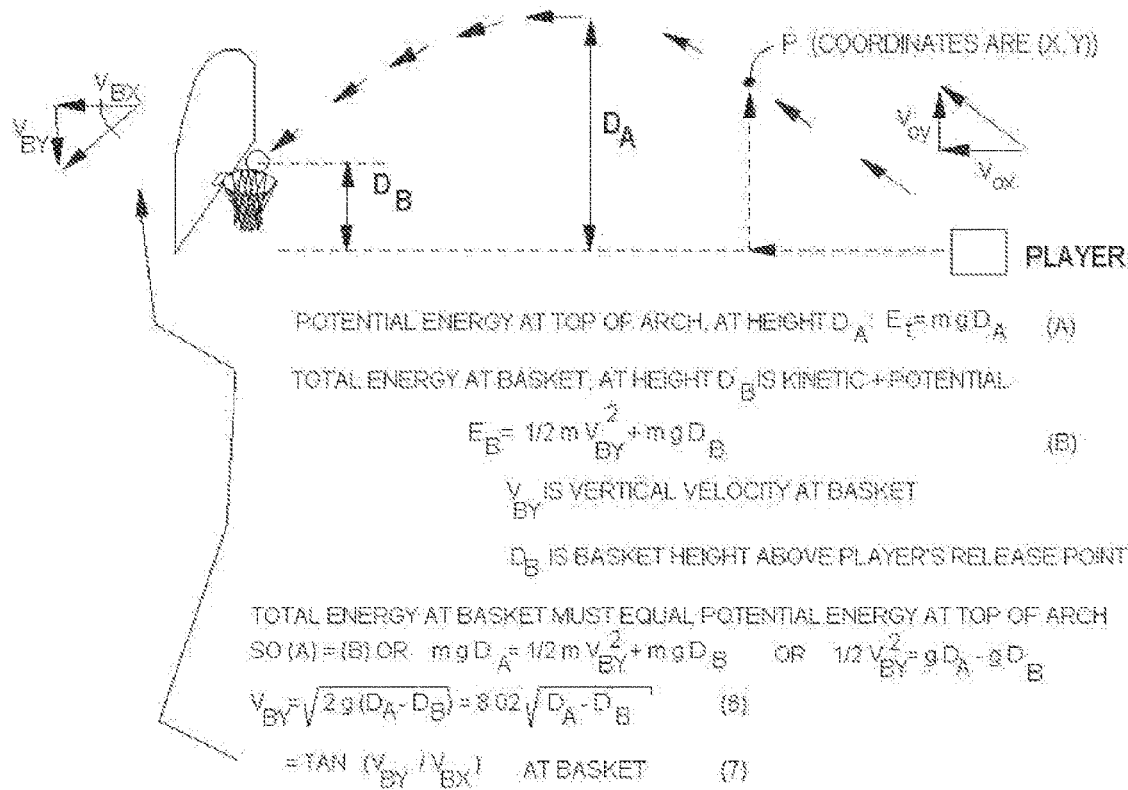

FIG. 13H uses the preceding values computed to obtain the angle theta, the entry angle of the ball into the basket. Equation A indicates the potential energy of the ball at the top of the arch, that is, at height $D_A$ (or $D_{Arch}$). Equation B indicates the total energy (kinetic plus potential, in the y-direction) of the ball at the basket, at height $D_B$ (or $D_{Basket}$). It is assumed that $V_{bx} = V_{ox}$, since air drag is ignored. This assumption is considered tenable, since at a typical ball velocity of 13 feet per second, the speed reduction due to drag is about 0.9 percent, that is, less than one percent.

Another embodiment for determination of arch height is shown in FIG. 13I. In this embodiment, the distance to the player is known and whether the player is at R1 or R2. So, in advance, a player makes a series of shots at each of R1 and R2, with different arch heights. The shot for each different arch height will have a different flight time. A look-up table may be created and stored in memory on the gun. Then, during play, for each shot, the distance (R1 or R2 in the illustration) and the flight time is ascertained. An arch height for that type of shot is "looked-up" in the look-up table, which eliminates the need to compute the value. This is illustrated in FIG. 13I.

The total energy of the ball (in the y-direction) at the basket equals the potential energy at the peak of the arch, that is, at the height $D_A$. Thus, equation A is set equal to equation B, and solved for $V_{By}$, producing equation 6. $V_{By}$ is the vertical component of velocity at the basket.

Equation 7 then uses $V_{by}$ and $V_{bx}$ to compute the entry angle of the ball at the basket.

An exemplary calculation using typical values will now be given. The following assumptions are made:
1. Velocity of ball as shot from the gun, $V_{gun}$, is 20 feet per second.
2. The distance D from gun to player is 18 feet.
3. The hold time by the player is 0.45 seconds, that is, slightly less than one-half second.
4. The horizontal velocity of the player's shot, $V_{ox}$, is 13 feet per second.
5. The height of the basket above the player's release height, $D_b$, is 3 feet.

The following calculations are thus made.
A. The flight time to the player is 18 feet/(20 feet/second), or 0.9 second. Thus, T=0.9 second.
B. From Equation 4 in FIG. 13E, $V_{oy} = [(D_B)(V_{ox}^2) + \frac{1}{2} g D^2]/D V_{ox}$. In this example, $V_{ox} = 13$ feet/second, $D_B = 3$ feet, $D = 18$ feet, and $g = 32.2$ feet/second$^2$.

Thus, $V_{oy}$, vertical velocity of the player's shot, equals 24.46 feet per second.

C. From Equation 5 in FIG. 13G, $D_A=(V_{oy}^2/2g)=9.29$ feet. Since the height of the basket is known to be ten feet, the ball release height is seven feet. The arch is thus 6.29 feet above the basket (ie, 9.29−3.0).

D. The entry angle, theta, in FIG. 13H is calculated from Equation 6 in that Figure. $V_{by}=8.02$ SQRT($D_A-D_B$)=20.1 feet per second. Theta is ARCTAN($V_{by}/V_{bx}$)=ARCTAN(20.1/13)=57.1 degrees.

The system 200 and Doppler system 800 comprise a Doppler circuit for capturing and/or calculating the various Doppler measurements that will now be described.

Figure 14:
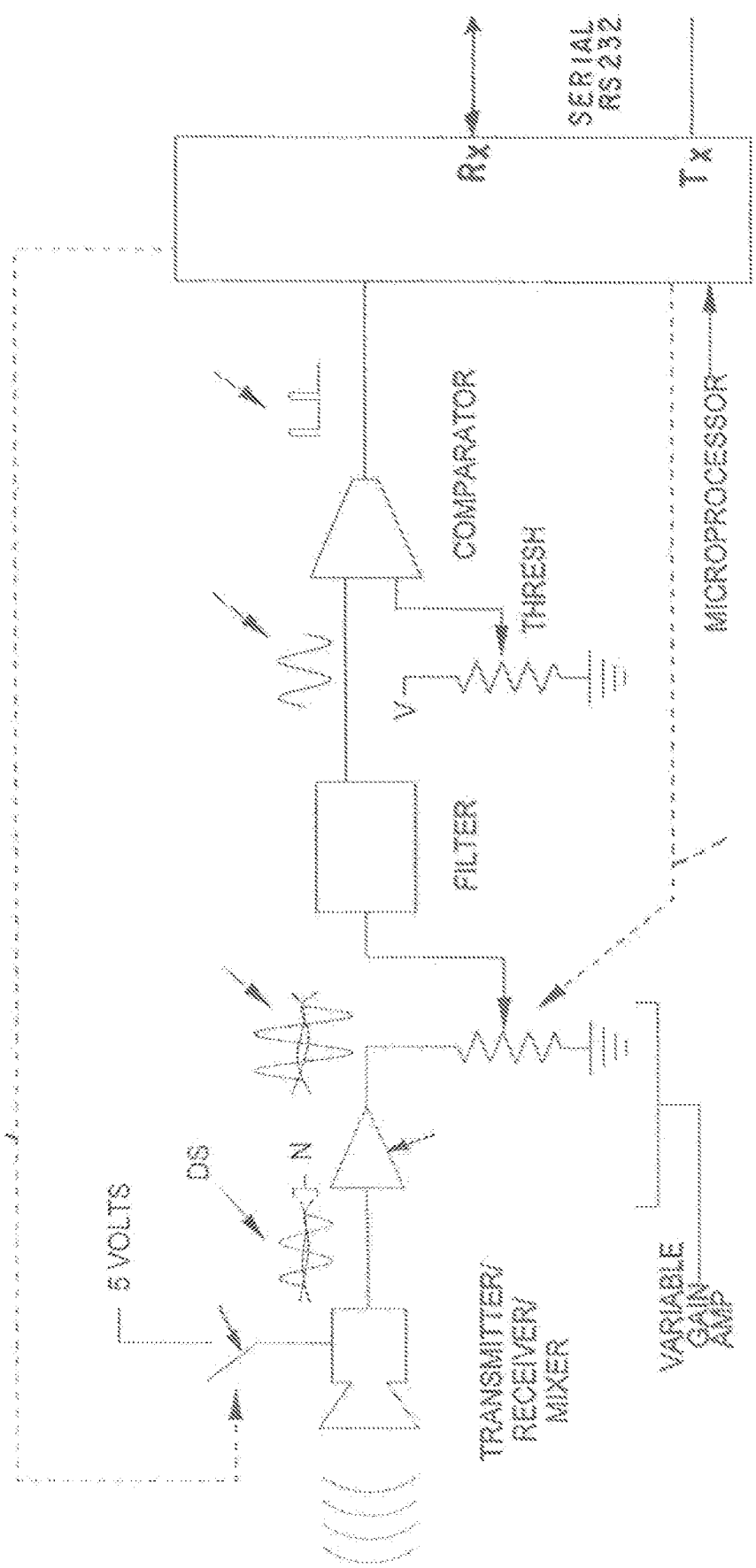
FIG. 14 is a simplified schematic of the Doppler circuit shown in FIGS. 15A-15D.

FIG. 14 is a high-level diagram of a circuit which detects the speed of the ball 12' as it exits the launcher. FIGS. 15A-15D are more detailed diagrams of the circuit.

Horn 900 in FIGS. 10, 11 and 14 is mounted adjacent an exit port on the gun, ejector or launcher 20'. Horn 900 in FIG. 14 generically represents a radar gun having a Gunn diode (not shown) in the illustration. It should be understood that a conventional radar gun may be used.

Horn 900 includes (1) a radar transmitter which transmits bursts of energy at 24 GHz, (2) a receiver, or detector, which detects reflected radar energy, and (3) a mixer (also called a multiplier or heterodyne circuit) which produces a signal which indicates the difference in frequency, due to Doppler shift, between the transmitted signal and the received signal.

The difference signal, indicated as waveform DS in FIG. 14, will most often lie in the range of about 200 to 1200 Hz. The difference signal DS will probably be contaminated with low frequency noise N.

A variable gain amplifier 902 amplifies the difference signal DS. Waveform 904 represents the amplified signal. The amplifier is represented as an amplifier 906 symbolically followed by a variable potentiometer 908. The latter operates as a voltage divider and picks off a signal which is a percentage of the output signal produced by the amplifier 906. Thus, as a hypothetical example, if the gain of amplifier 906 is 10, and potentiometer 908 picks off 80 percent of the amplified signal, the net amplification is 8.

The gain of the variable gain amplifier 902 is controlled by microprocessor 910, as indicated by dashed line 912. One reason for using variable gain is that the strength of the reflected signal received by horn 900 will depend on the distance to the object (the basketball 12' in this context) causing the reflection.

For example, if the object is located ten feet from the horn, the reflected signal received by the horn will have a certain strength. If the object is located twenty feet from the horn, the reflected signal received by the horn will have a smaller strength because the reflected signal travelled a longer distance.

In order to compensate for this reduced signal strength due to distance, the gain of amplifier 902 is adjusted during the flight of the radar pulse. The following simplified Table 1 illustrates some principles involved in this compensation. All units are arbitrary for simplicity.

TABLE 1

| Row 100 | Distance to Object | Time of Flight of Radar Pulse | Strength of Received Signal | Gain of Amplifier |
|---|---|---|---|---|
| 1 | 10 | 1 | 5 | 1 |
| 2 | 20 | 2 | 4 | 5/4 |
| 3 | 30 | 3 | 3 | 5/3 |
| 4 | 40 | 4 | 2 | 5/2 |

As Table 1 indicates, the time of flight of the radar pulse (that is, the round-trip time which includes the time of flight to the object, plus the time of flight back to the horn 900) is proportional to the distance to the object. The strength of the received signal is arbitrarily indicated as the sequence 5, 4, 3, 2.

It is pointed out that the flight time of the ball-pass described earlier is not the time of flight in Table 1, but is one-half of the time of flight of Table 1.

The gain of the amplifier 902 is adjusted so that the signal strength produced by the amplifier 906 remains at unity. For example, for the object at 10 distance units, the received signal strength is 5, and the gain is unity.

For the object at 20 distance units, the gain is 5/4, or 1.25. When this gain is applied to the received signal strength of 4, the resulting signal strength is 4×5/4, or 5, making the received signal strength, after amplification, the same as the signal strength for the object at 10 distance units.

Further, the sequence of operation is significant. Row 1 represents an elapsed time of 1 unit after transmission of a radar burst. The gain is 1 at this time. If a reflected signal is received at this time, it is amplified by this gain.

Row 2 represents an elapsed time of 2 units after transmission of this radar burst. The gain is 5/4 at this time. If a reflected signal is received at this time, it is amplified by this gain.

Row 3 represents an elapsed time of 3 units after transmission of this radar burst. The gain is 5/3 at this time. If a reflected signal is received at this time, it is amplified by this gain, and so on.

Thus, for each radar pulse transmitted, the microprocessor 910 in FIG. 14 adjusts the gain of amplifier 902 according to the sequence listed in the Table above, based on the time elapsed since the pulse was transmitted. At time 1, the gain is 1; at time 2, the gain is 5/4; at time 3, the gain is 5/3, and so on. This sequence is repeated for each successive pulse.

In the immediately preceding discussion, a single speed of the ball-pass. However, if a faster pass is made, then, at any given time after launch, the ball will be farther away than the same ball passed at a slower speed.

To repeat: at any given time after launch, such as Y milliseconds, the reflected radar signal from the faster ball, when received, will be smaller than the reflected radar signal from the slower ball, when received. The reason is that, after Y milliseconds, the faster ball is farther away.

Accordingly, Table 1 above can be modified. The progressive reduction of signal strength in the received burst will depend on the distance which the burst traveled (that is, the total distance to the basketball, plus the return distance). That distance will equal (1) the speed of the basketball multiplied by (2) the time of travel of the basketball.

The basketball's speed is known to the microprocessor 910 in FIG. 14. The time of travel is also known because that is simply the time elapsed since the launch of the basketball, called the pass flight time above.

Therefore, the distance to the basketball 12', in the second column of Table 1, in principle, will be known by multiplying the speed of the basketball 12' times the time elapsed since the radar pulse was transmitted. A radar pulse will travel twice this distance. The attenuation of the radar signal will depend on this distance.

Consequently, the time elapsed since the launch of the basketball is used to determine the gain of variable gain amplifier 902 in FIG. 14.

This can be illustrated by Table 2.

TABLE 2

| Row | Speed of Ball | Distance to Object | Time of Flight of Radar Pulse |
|---|---|---|---|
| 1 | 20 | 10 | 1 |
| 2 | 20 | 20 | 2 |
| 3 | 20 | 30 | 3 |
| 4 | 20 | 40 | 4 |

Assume that the speed of the ball 14' is 20, as indicated. In Row 1, the time of flight represents a trip to the ball, plus the return trip, for a distance of 20. Since the speed is 20, the time of flight is 1, as indicated.

In row 2, the speed is still 20, but the total distance is 40, corresponding to the time shown of 2, and so on.

In another embodiment, the gain selected for each time instant after launch of the basketball 12' need not be a linear function of time.

Therefore, the distance to the ball 12' is, in principle, used to adjust the gain of the amplifier 902 in FIG. 14. That distance can be inferred based on speed of the ball, and time elapsed since the ball was launched. Thus, for a given ball launch speed, a given sequence of gains is computed, or retrieved from memory. One gain is used at each time interval, as indicated by the Tables above. For another ball launch speed, another sequence of gains is computed, or retrieved from memory, and so on.

In one form of one embodiment of the invention, the goal is to maintain the signal received by horn 900 as constant as possible. The gain required at each instant can be determined experimentally in a simple manner, since the distances involved are not large. For example, if the basketball is launched for different distances of 5 feet, then 6 feet, then 7 feet, and then in one foot increments up to 100 feet, and the signal attenuation measured for each launch, that represents 96 launches, which can be done in a short time. The necessary signal gain is immediately apparent for each launch, based on the signal received for each.

After the gain is adjusted in pursuit of maintaining a constant received amplitude, the signal is filtered. In FIG. 14, the output of variable amplifier 902 is fed to a block 914, which represents components, later described, which perform multiple functions. One function is that block 914 extracts the amplified difference signal DS, and suppresses low frequency noise N. A second function is that block 914 performs amplification.

The output of block 914 is indicated as waveform 916, which represents the extracted difference signal DS.

The output of block 914 is fed to a comparator 918, which compares this output to a threshold voltage THRESH, which is produced by a potentiometer 920. Potentiometer 920 is manually adjustable. The adjustable voltage THRESH determines the trip point of the comparator 918.

Each time the voltage THRESH is exceeded, comparator 918 produces a pulse, thereby producing a pulse train 922 having a frequency identical to that of waveform 916, which frequency is identical to the difference frequency DS. This frequency indicates the speed of the object which reflected the radar pulse produced by horn 900

Microprocessor 910 counts the number of pulses occurring in pulse train 922 per second, and thereby deduces the frequency of the pulse train 922.

Switch 923 is controlled by the microprocessor 910, as indicated by dashed line 925. Switch 923 turns the transmitter within horn 900 on and off periodically.

One reason is that the transmitter utilizes a Gunn diode to generate radar energy. Gunn diodes can draw significant amounts of current, and the current can cause heating of the Gunn diode, which will increase the temperature of the Gunn diode. The increase in temperature can cause a drift in frequency of the Gunn diode.

Therefore, in one form of one embodiment of the invention, the microprocessor 910 turns on the Gunn diode, through switch 923, only just prior to transmission of a radar burst, and shuts down the Gunn diode immediately afterward.

Figure 15A:
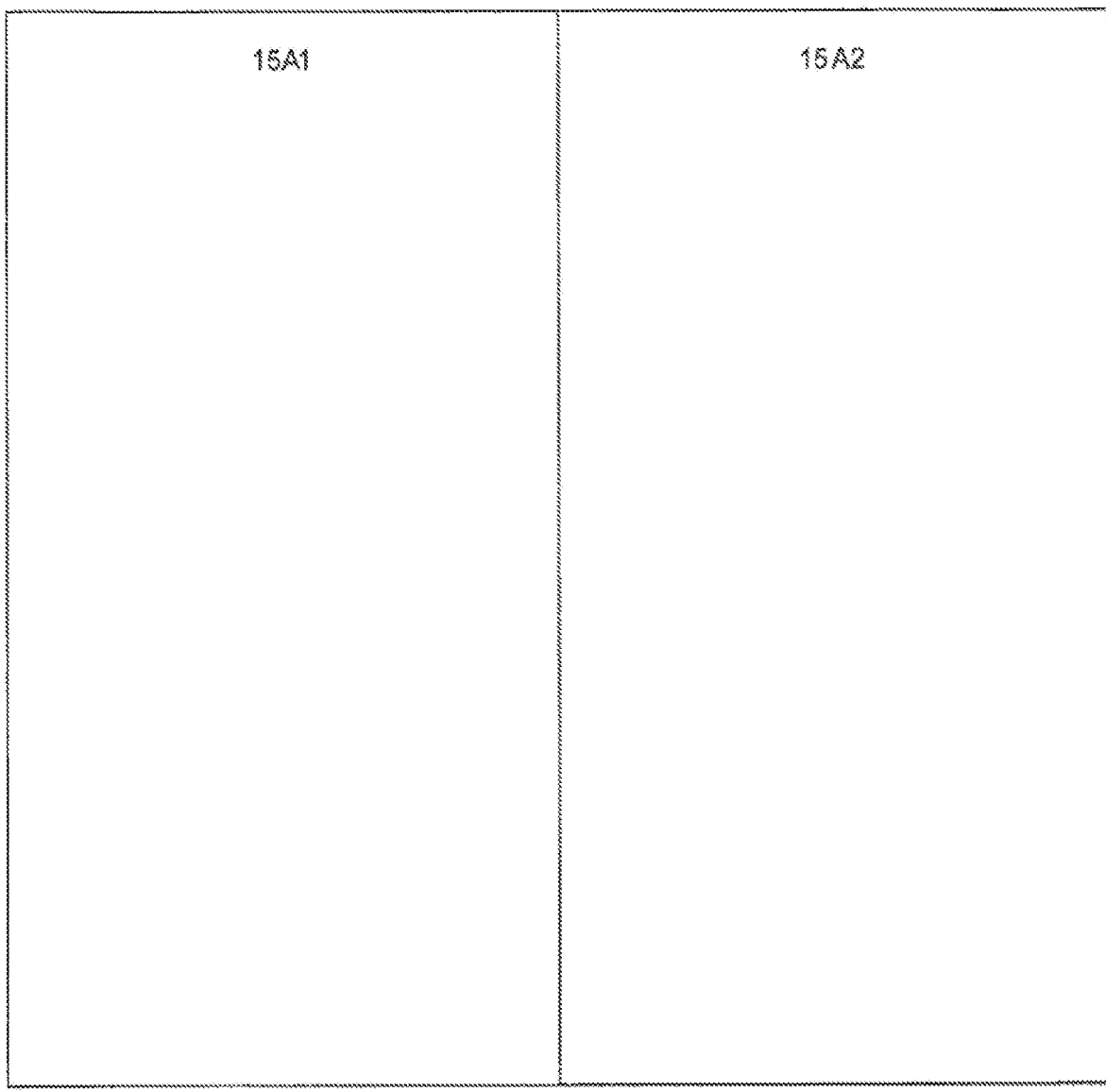
Figure 15B:
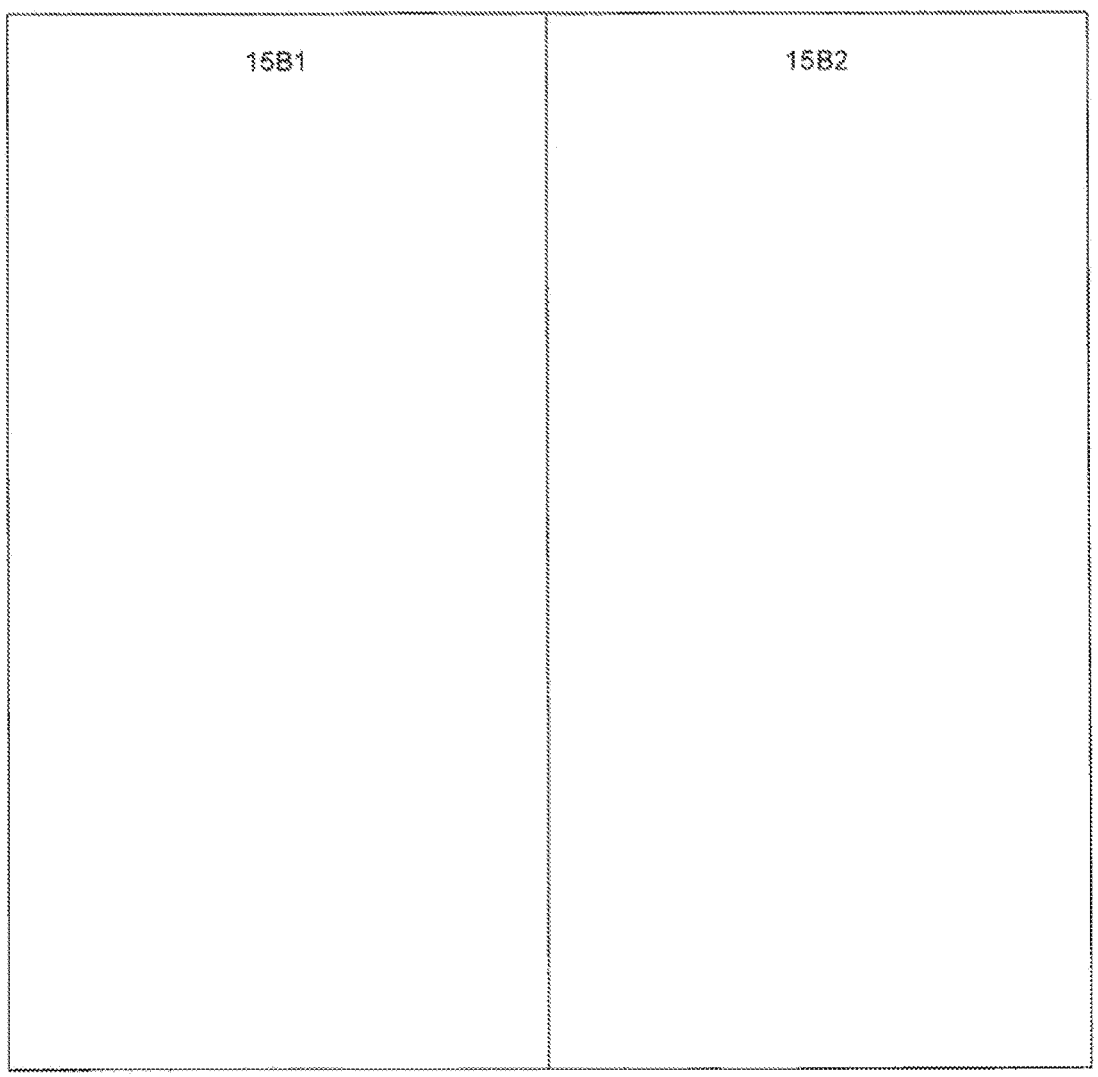

FIGS. 15A-15C are more detailed circuit diagrams of the speed measuring circuitry of FIG. 14. Horn 900 in FIG. 15A corresponds to the transmitter/receiver horn 900 of FIG. 14 described above.

In FIG. 15A, and other figures, resistors are labeled with the symbol "R," followed by another symbol, such as "7," as in "R7" adjacent, and to the right of, horn 900. These symbols are not used as reference indices for explanations given in the text of this Specification for the functions provided by the associated resistors. Instead, the symbols are used for internal consistency in the drawings. For example, if R7 appears in two different places in the drawings, the symbol R7 indicates that the same resistor is shown in those two places. A similar comment applies to capacitors and other elements.

In FIG. 15A, a first stage amplifier 924 (not individually indicated in FIG. 14) receives the signal from horn 900. The amplifier is AC coupled, and has a gain of 100.

The symbolic variable gain amplifier 902 of FIG. 14 is indicated in FIG. 15A as amplifier 902A. The variable gain is provided by a digitally variable resistor 908A, which alters the feedback network of individual amplifier 926, which alters the overall gain of the amplifier stage 902A.

Digitally variable resistor 908A in FIG. 15A functions as the symbolic potentiometer 908 in FIG. 14, and is under control of the microprocessor 910 in FIG. 14. Digitally variable resistors are known in the art, and one suitable version is model number MCP 4013, available from Microchip Technologies, Inc.

In FIG. 15A, filter 914A is contained in block 914 in FIG. 14. The output line 928 in FIG. 15A leads to the same line 928 in FIG. 15B.

Lines 909 represent power lines which receive voltages from sources external to the components of FIG. 15A. The voltages are delivered to those components, via lines which are not shown. Item 909A in FIG. 15B and item 909B in FIG. 15C represent similar power lines.

Circuit 910 supplies reference voltages which are used throughout FIG. 15. It includes a precision shunt voltage reference 911, such as model number LTC 1634, available from Linear Technologies, Inc., which feeds an operational amplifier 912, such as model number TL074, available from Texas Instruments Corporation.

In FIG. 15B, amplifier stages 920 amplify the signal on line 928. The eight diodes D (only two of them are labeled) act as clippers to eliminate low level noise when no signal is received on line 928, as when no ball-pass has been made by the ball launcher, which is shown in other figures.

Comparator 922 determines when the output of amplifiers 920 exceed a threshold and, if so, feeds a signal to transistor 924. The signal is indicated by LED 926.

The signal on line 930 is fed to microprocessor 915 in FIG. 15C, which is an industry standard PIC 18F9140. An RS232 converter 931 enables serial communication with the processor 910. LEDs 935 are used for diagnostic purposes.

Figure 15D:
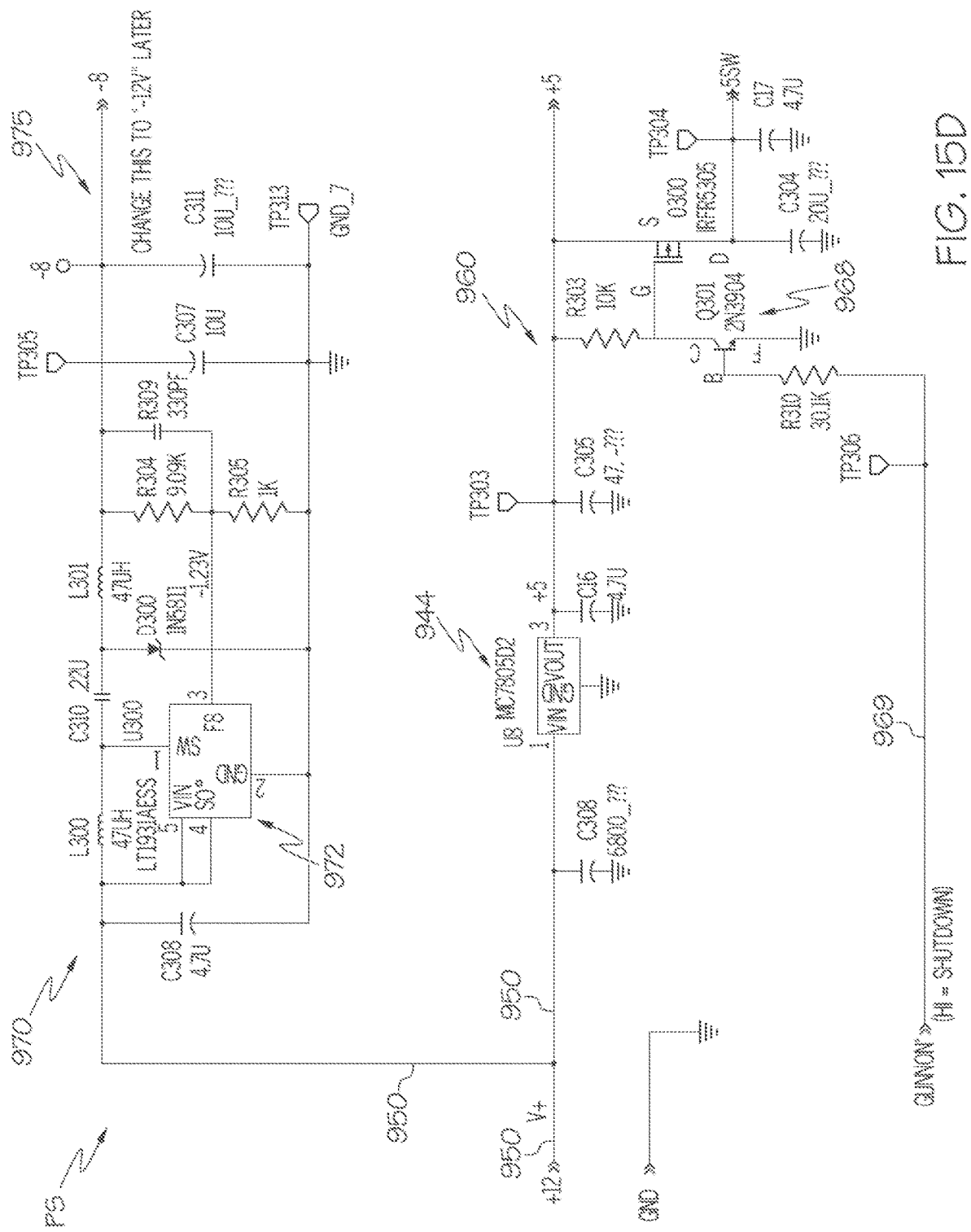

FIG. 15D illustrates a power supply PS which powers the circuits described above. Twelve volts DC are applied to lines 950. Lines 950 deliver power to voltage regulator 944, which is an industry standard model 7805 regulator, which delivers five volts, regulated, on terminal 960. A shut-down switch 968 is activated by a signal on line 969.

Terminals 950 also power a DC/DC converter circuit 970, which contains the industry standard LT1931 DC/DC converter 972, which produces negative 8 volts on line 975. Other embodiments of the invention may utilize 12 volts on this line 975, and yet other voltages in other cases.

A significant feature of one form of the invention is that the microprocessor 910 in FIGS. 14, 15A makes the computations described herein based, in essence, on only two external inputs. One external input is the pulse train 922 of FIG. 14, which, after processing, appears on the line labeled SigA in FIG. 15C. That line SigA is a single line, carrying a single pulse train.

That pulse train 922 indicates the Doppler shift of the radar signal, which is Delta-F in equation A3 in FIG. 13A. That Doppler shift is used to compute the parameters of (1) distance to the player, (2) arch height $D_A$ in FIGS. 13B and 13E, and (3) release angle and entry angle in FIG. 13D.

The other external data used is $T_p$, elapsed time of the player's shot, as in equation B2 in FIG. 13B. This is computed as the time interval between (1) the time of initiation of the shot, as indicated by resumption of the Doppler signal, and (2) the arrival of the ball at the basket, which is detected as described herein.

So long as the user has entered $D_h$ (the difference between the height of the ball at the release point and the loft rim), the only external values used by the microprocessor are (1) the Doppler shift and (2) the flight time of the player's shot, $T_p$.

Another time, $T_d$ in equation A1 in FIG. 13A is used, namely, the time of flight of the pass to the player. But $T_d$ is an internally computed value, using the internal dock of the microprocessor 910 or using another device associated with the microprocessor 910. The beginning of the time interval $T_d$ is known to the microprocessor 910 because the microprocessor 910 initiates the pass. The end of the time interval $T_d$ is known from the time when the Doppler shift drops to zero. This is sensed by the proximity sensor LBS in FIG. 11, when the arm TA hits the stop RB.

To recapitulate: the Doppler shift, indicated in pulse train 922 in FIG. 14, is used to measure the initial speed of the launched ball. When the Doppler shift indicates that the speed of the launched ball falls to zero, it is assumed that the player has caught the ball. The time between launch and catch, $T_d$ is then computed.

When the Doppler shift indicates that the ball is again in motion, it is assumed that the player has shot the ball. The Doppler shift is then taken as indicating the horizontal velocity $V_h$ in FIG. 13D. When the ball reaches the basket, the time of flight of the ball, $T_p$ can be computed.

The Doppler shift and $T_p$, the time of flight of the player's shot, are values determined by external events. The flight time of the pass to the player, $T_d$ is computed internally, as the interval between (1) initiation of the launch of the ball, which is under control of the microprocessor 910, and (2) the drop of the Doppler shift to zero, indicating zero speed in the ball. In one embodiment of the Doppler, the signal is continuous. It transmits a continuous 24 GHz signal. The signal it receives back from a moving target is slightly shifted in frequency above or below 24 GHz according to the velocity of the target. When mixed together (transmitted and received signal), a difference signal results. The frequency of this difference signal is proportional to target speed. The difference signal is what is input to the first amplifier stage of the gun or ejector 20' circuit. So the changes in amplification occur as a function of time from an event, the Gun throwing the ball in the first case, and the player shooting the ball in the second case.

In one embodiment, the gun or ejector 20' which launches a basketball pass at a time T1, a radar gun which measures speed S of the basketball upon launch and a control which knows time T1, identifies a time T2, when the speed measured by the radar gun falls below a first threshold, detects a time T3, occurring after time T2, when speed measured by the radar gun rises above a second threshold, learns that the basketball scored a goal at time T4 after a shot by the player, computes a pass flight time PFT, based on the equation PFT=T2−T1, computes a distance D based on the equation D=PFT×S, computes a hold time H based on the equation H=T3−T2, and computes a shot flight time SFT based on the equation SFT=T4−T3. In another embodiment, SFT can be computed by dividing the Distance, D (already computed) by the Player's horizontal velocity, Vox. It should be understood that SFT could be measured by the means written if every shot was a make.

Thus, to repeat, the computations of FIGS. 13A through 13G are based on only two variables whose values depend on external events, and those variables are (1) DELTA-F in equation A3 in FIG. 13A and (2) $T_p$ in equation B2 in FIG. 13B, which is the flight time of the player's shot.

The use of the measurements and calculations (e.g., in customized comparison reports) is described later herein.

Referring back to FIG. 10, as with the embodiment shown relative to FIG. 1, note that the gun or ejector 20' has the storage device 44' for storing information, data and statistics regarding the player's shooting. As with the embodiment described earlier herein, a portable storage device 210, such as a USB drive, flash drive or other memory or storage device may be used to enable the user to port to a USB port (not shown) on the gun or ejector 20' and download information, such as a player roster, upload the statistics and data from the gun or ejector 20' to the computer 202. The first user or users may then access the website WS via the internet using the computer 202 and upload those statistics to a server 206 associated with the website WS for use as described herein. Alternatively, the gun or ejector 20' may include a conventional wireless communication device 145' to enable the user to wirelessly transmit the data and statistics from the gun or ejector 20' directly to the computer 202 or other device or directly to the website WS. Similarly, the second computer 204 may upload data and statistics from the second system 208, for example, using another portable storage device 210 and the remote computer or server 204 (or wirelessly) to the website WS and the computer 206 associated therewith.

After the data and statistics from one or more players, such as Players A and B, is captured or measured and has have been uploaded to the website WS and its associated server 206, the first and second users can elect to make the data and statistics public so that they can be used by others, elect to keep the data and statistics private for use only by themselves or some combination thereof. The first and second users may also view, save (locally or on a remote server, such as the website WS server, or portable storage device), create and print customized reports, use customized reports regarding a player using the data and statistics. Comparison reports and charts of players' data, statistics and rankings from the same or different teams, the same or different geographic territories or other criteria, such as gender, age or skill level may also be created, viewed, stored, printed and used as described and shown later herein.

Advantageously, therefore, the system according to another embodiment enables a user to improve the player's shooting efficiency by, among other things, comparing shooting statistics and rankings of players, regardless of whether the players are using the same gun or ejector 20', using different guns or ejectors 20', shooting at the same or different times, shooting at the same or different geographic locations, or the like.

Referring now to FIG. 16, an overall schematic view of the methodology and process for using the system 200 is shown. Initially, the user registers (block 220) the gun or ejector 20' by accessing the website WS, which will be described later herein relative to FIG. 17. The user creates and stores team information (block 222) using by accessing the website WS using, for example, computer 202 and such process is described later herein relative to FIGS. 35 and 18. The user creates and stores a team roster and its players, and that data for players of the team is stored on the website WS (block 224), which is described later herein relative to FIGS. 36, 37 and 18. After the user has stored the information and data on the website WS, the team and player data information may be downloaded (block 226 in FIG. 16) to the gun or ejector 20 and this procedure is described relative to FIG. 19.

Figure 20:
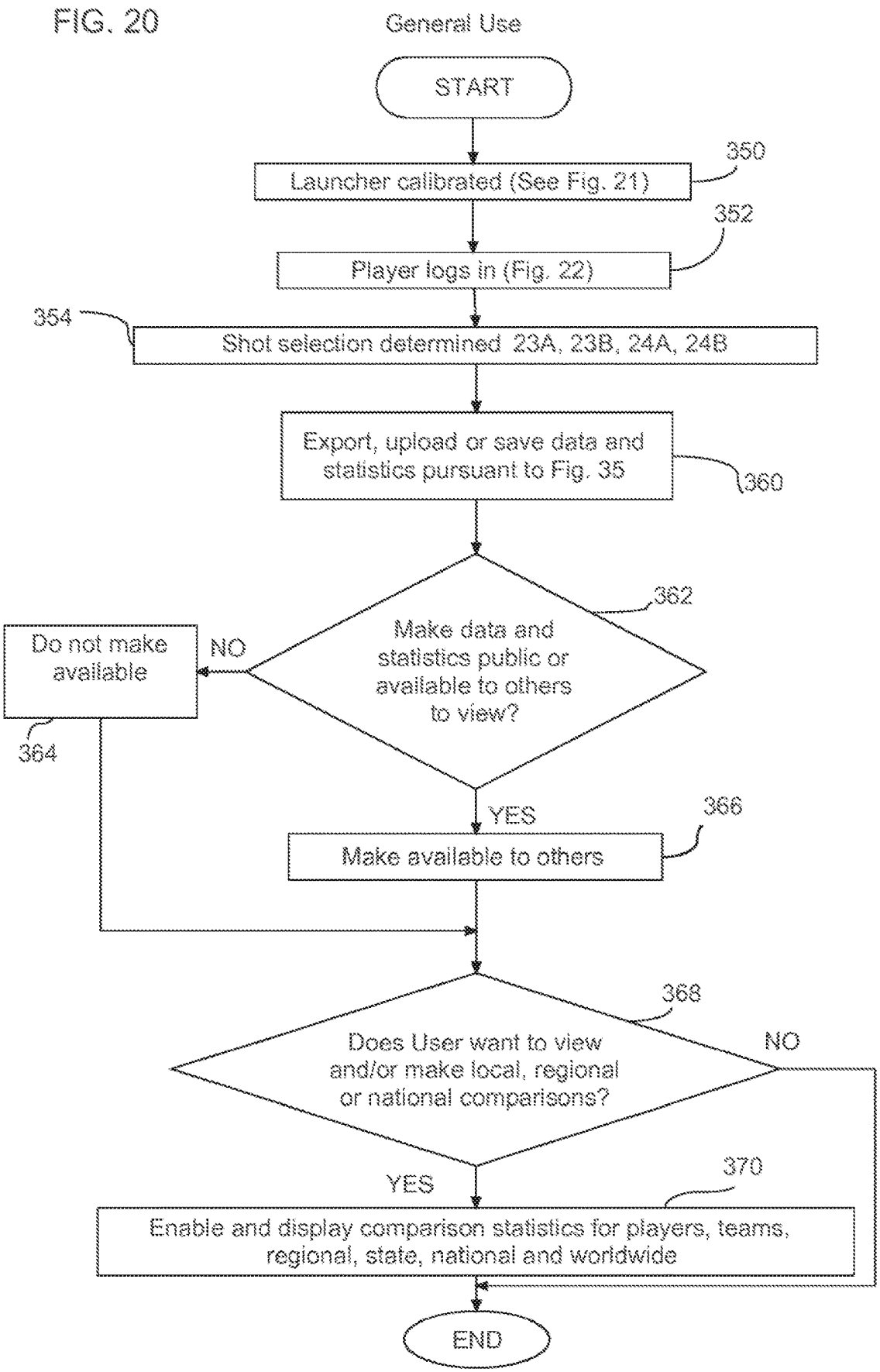
FIG. 20 is a general use of the embodiment shown in FIG. 10.
Figure 21:
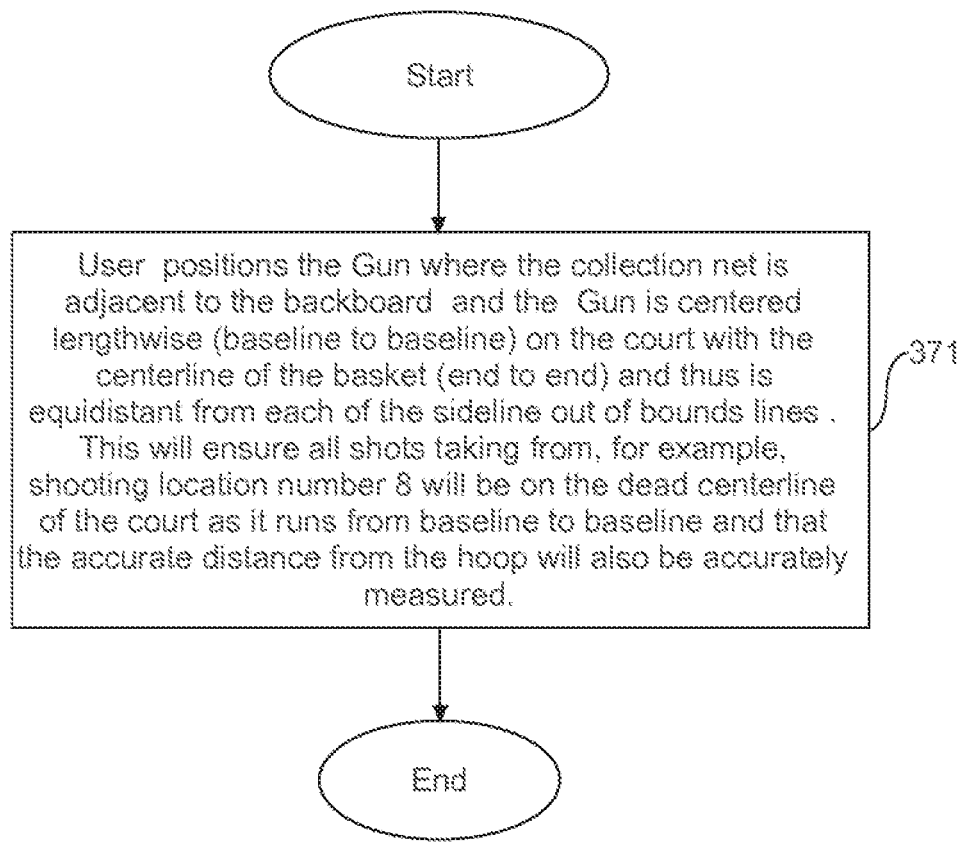
FIG. 21 is an illustrative procedure for calibrating the gun or ejector.

In order to utilize and compare statistics or data from shooters using multiple guns or ejectors 20' which are situated at the same or different geographic locations, it is necessary to calibrate each gun or ejector 20' (block 228), and this procedure is described in more detail relative to FIG. 21. After the gun or ejector(s) 20' is/are calibrated, the players, teams, coaches and other users may use the gun or ejector 20' (block 230). In this regard, the players, teams and coaches may use the gun or ejector 20' in a traditional manner, as described earlier herein relative to FIGS. 1-9, including utilizing the shooter challenge routines 32a', the other shooting challenges, or the gun or ejector 20' may be used by the same or different teams. In general, the use of the gun or ejector 20' is described later herein relative to FIG. 20.

Returning to the overview description in FIG. 16, after the gun or ejector 20' as described is used, shooting statistics and data are captured by the gun or ejector 20' (block 232 in FIG. 16), those statistics or data may then be used, uploaded to the portable storage device 210, computer 202, transmitted or uploaded to website WS server 206 in a manner described later herein relative to the procedure shown in FIG. 26. After the statistics and data described earlier herein are captured and uploaded to the website WS server 206, the user (such as players, coaches or other interested users or persons) may create, view, download, save them on a local server or storage associated with the computers 202, 204, remote server or portable storage device (such as a flash drive), publish, share and/or print customized reports using the data and statistics. The creation and use of customized reports and use is described in more detail herein relative to FIGS. 27, 28A-28B and use the customized reports created to improve the players' shooting and basketball playing ability and skills (block 234). The overall procedure and use of the system then ends. More detailed descriptions of the foregoing will now be provided.

Figure 17:
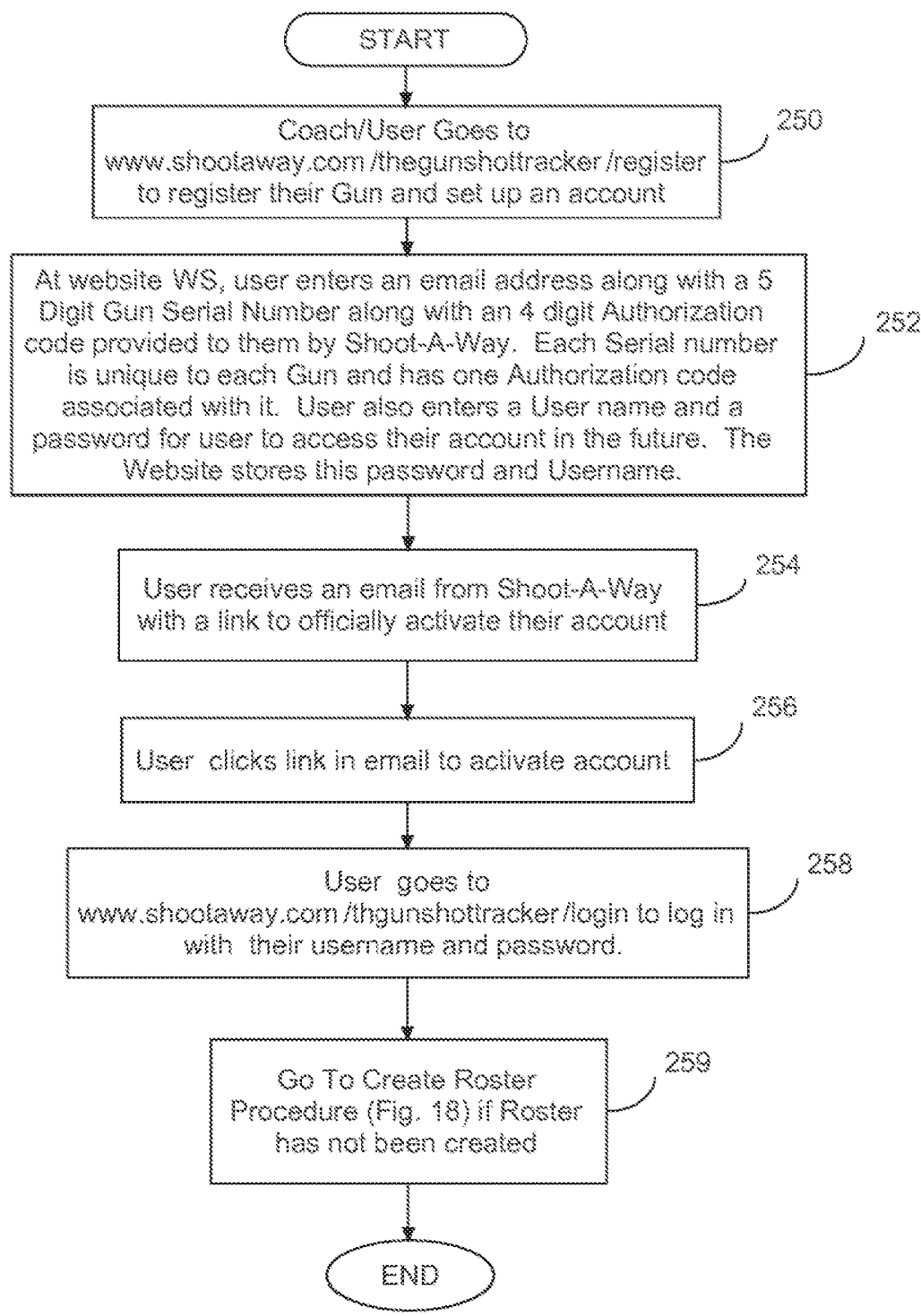
FIG. 17 is a general procedure and method for a coach to register the gun or ejector.
Figure 18:
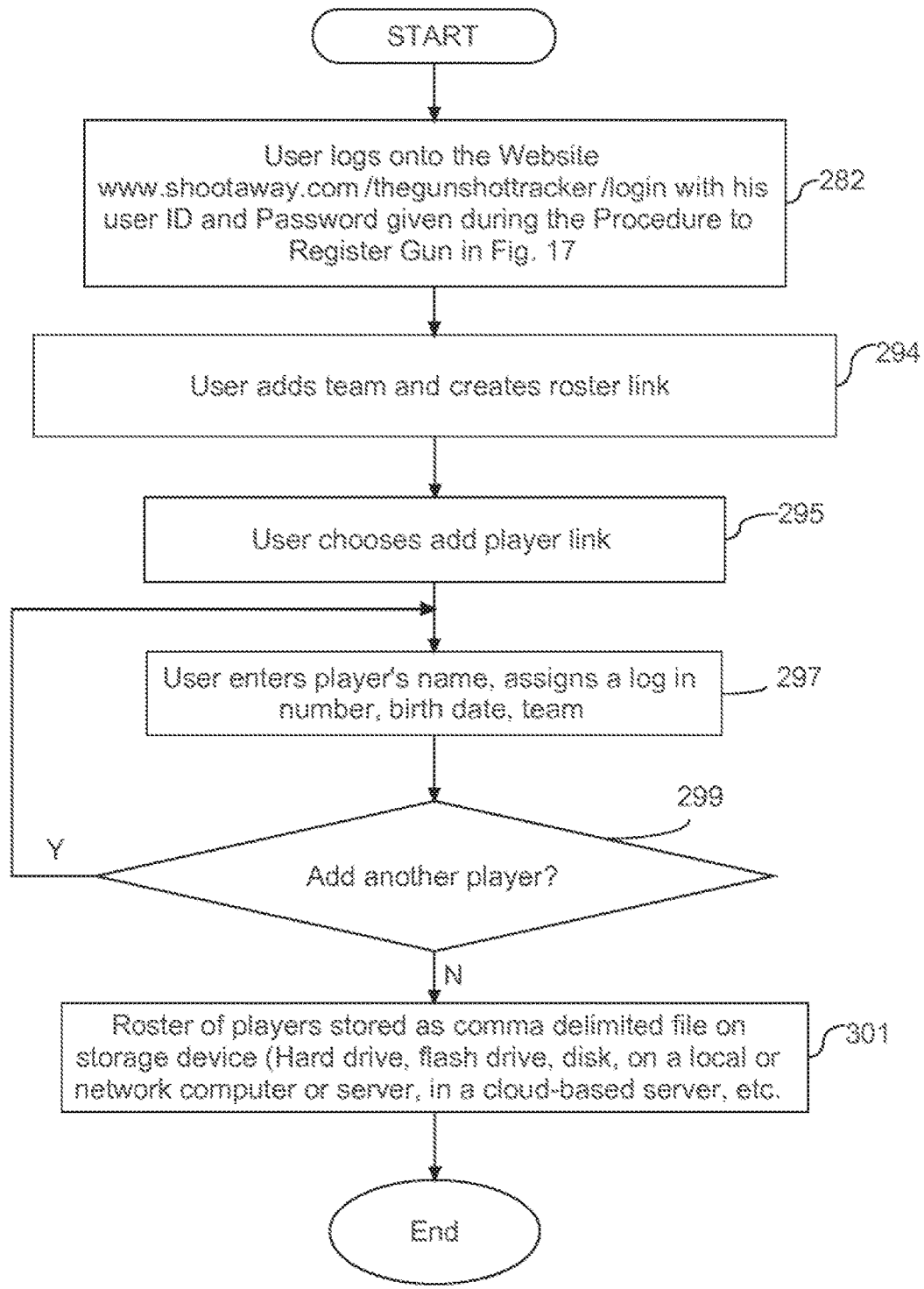
FIG. 18 is an illustrative procedure for creating a roster on a website for downloading to the gun or ejector.
Figure 19:
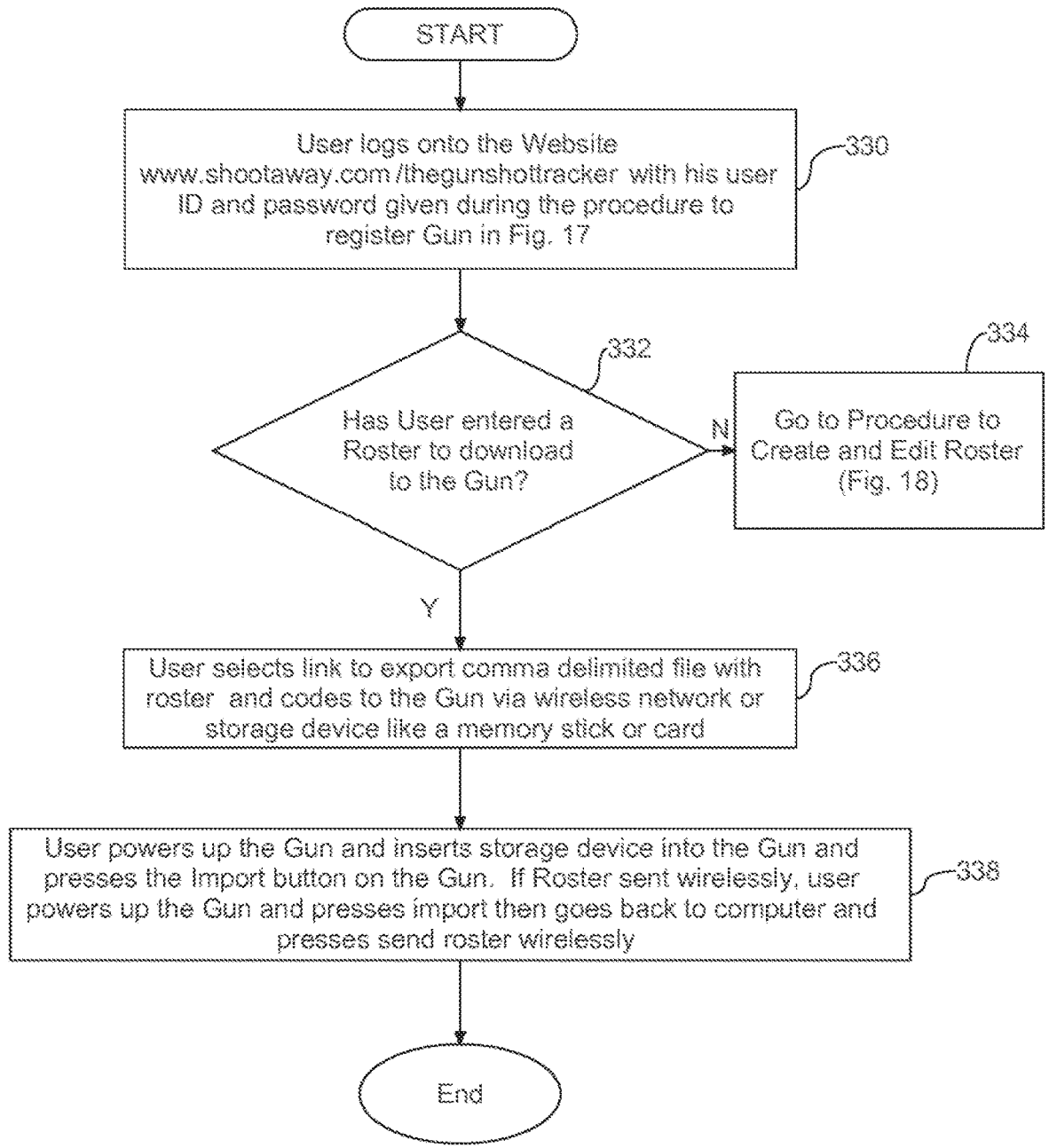
FIG. 19 is a illustrative procedure for downloading the rosters created relative to FIG. 18 to the gun or ejector.
Figure 30:
FIGS. 30-41 are illustrative graphical user interfaces or screenshots in accordance with one embodiment of the invention.
Figure 31:

Referring now to FIGS. 17-19, a process and procedure for registering a gun or ejector 20' and for creating and downloading a team roster of players to the gun or ejector 20', along with a plurality of associated graphical user interfaces, shown in FIGS. 30-41, will now be described. Referring to FIG. 17, the coach or user accesses the website WS, which is shown in the illustration as being the website located at the domain name www.shootaway.com. The screen shots or graphical user interfaces in FIGS. 30-41 are presented to the user when he or she accesses the website S. Once the website WS is accessed (block 250 in FIG. 17), the user is presented with and uses the graphical user interface 260 (FIG. 30) and enters the serial number of the gun or ejector 20' and an authentication number at the locations 262 and 264 on the graphical user interface as Illustrated in FIG. 30 (block 252 in FIG. 17). In the illustration being described, the authorization code inserted in the area 264 in FIG. 30 is provided by the manufacturer of the gun or ejector 20'. In this regard, each individual gun or ejector 20' has a unique serial number and has the authorization code associated with it. The user is provided this authorization code as a means of securely accessing the website WS. The user may be assigned and be required to enter a use name and a password for the user to access their account in the future. This user name and password may be communicated or provided to the user, for example, in an email message 266 (FIG. 33) communicated to the user. In a conventional manner, the website WS presents the user with a graphical user interface 268 (FIG. 31) after the serial number and authorization code are accepted by the website WS whereupon the user can enter his or her name, create a user name and password and have an assigned email address as illustrated in the FIG. 31. In this regard, at using the graphical user interface 268, the user can enter his or her first and last name, user name, password and an email address and then create and account at the website WS by actuating the electronic "create account" button 270 in FIG. 31. Once the information is entered, the user can create the account by clicking the electronic "create account" button 270 in FIG. 31 whereupon the website WS creates a user account for the user.

Figure 32:
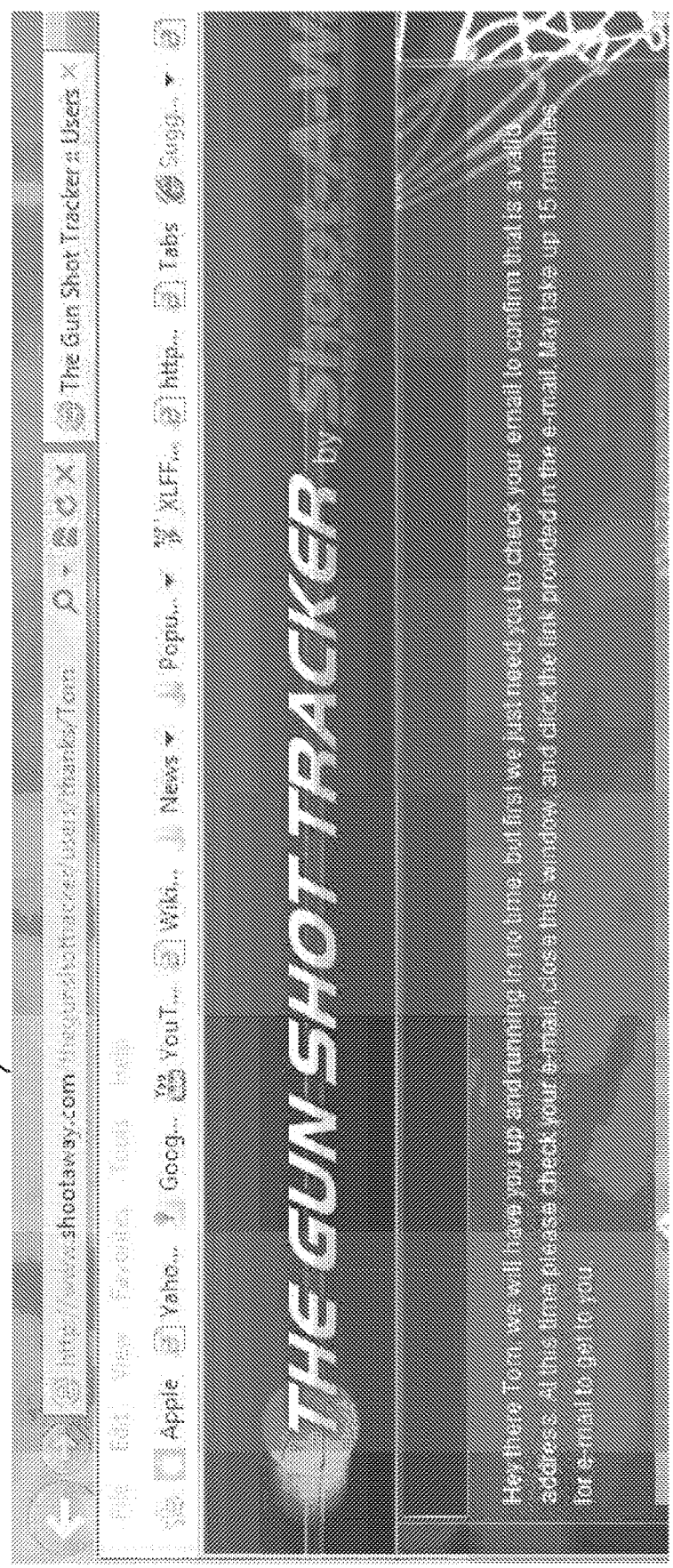
Figure 33:
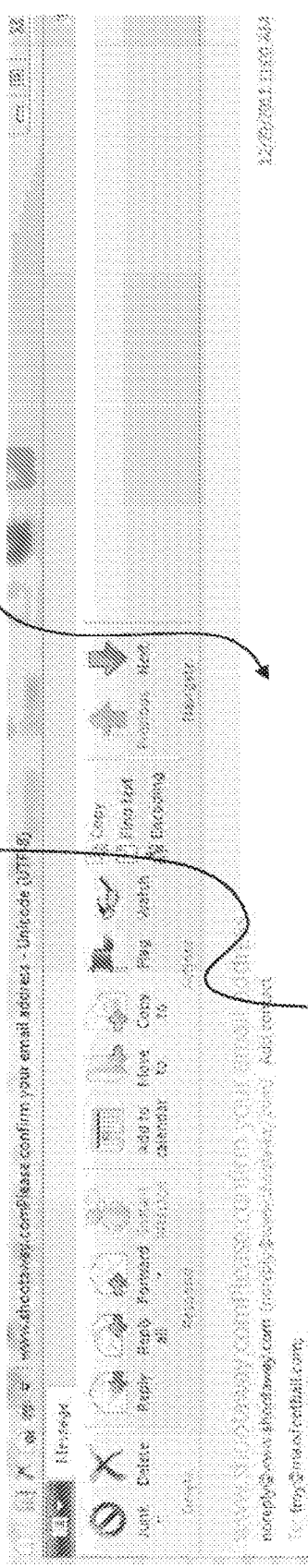
Figure 34:
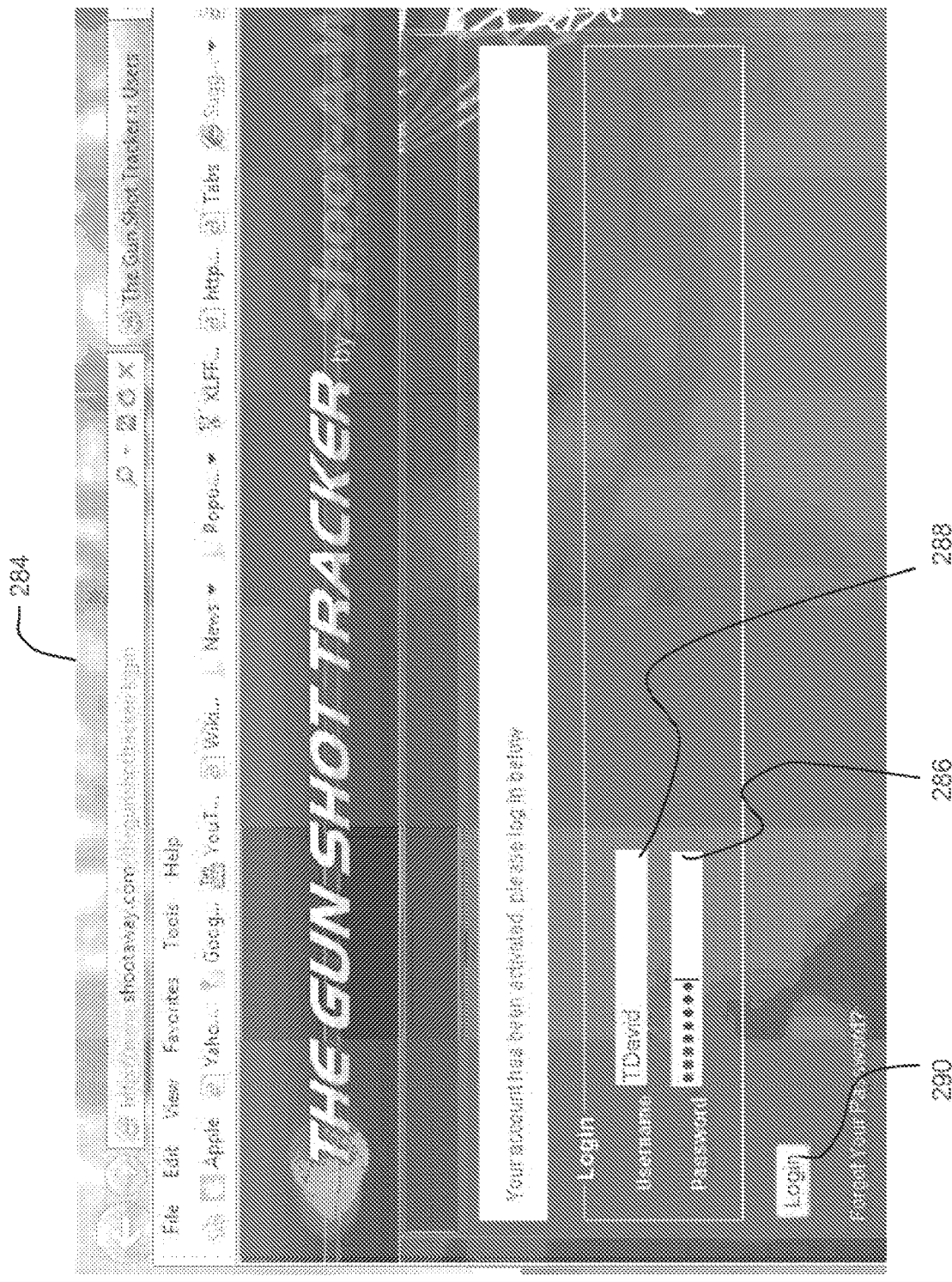

In response to this input, the website WS generates a message, which is illustrated in FIG. 32 on the graphical user interface 272, which informs the user to check his or her email address, one illustrative email confirmation or notice is shown in the FIG. 33 (block 254 in FIG. 17) which informs the user of the general overview of the system 200 as well as provides an electronic link 267 in FIG. 32 (block 256 in FIG. 17) for enabling the user to log on to the account that the website WS created and associated with the user.

Once an account is created, the user may go to the website WS (block 258 in FIG. 17) and log in using their newly created user name and password. The first time the user accesses the website WS he or she is directed to a "create roster" procedure or routine which will now be described relative to FIG. 18 (block 259 in FIG. 17).

In one illustrative embodiment and after registering the gun or ejector 20', the user is enabled to create rosters and add teams and players, for example, up to twenty-seven players per team, although the number of players could be more or fewer, using the website WS. Each player is assigned a digital or numeric code that they will use to enter each time they use the gun or ejector 20'. Once the roster has been entered by the user on the website WS, the user will be prompted to and may export it (or save it) to a portable storage device 210, such as a USB drive, thumb drive, flash drive or the like. The gun or ejector 20' comprises a port or interface (not shown) that receives the portable storage device 210 so that the data thereon can be downloaded to the gun or ejector 20' using the import button 118 mentioned earlier herein relative to FIG. 3.

In one illustrative embodiment, two groups or teams of players within, for example, a school or organization can be tracked by one gun or ejector 20', and the website WS will allow for at least two groups or teams to be tagged to each gun or ejector 20' that was entered into the area 262 on the website WS associated with the gun or ejector 20'. For example, if a high school boys and girls teams purchased a single gun or ejector 20' together, the gun or ejector 20' will track twenty-seven players for the boy's team and twenty-seven players for the girl's team. In this regard, the system 200 contemplates that each of the boys and girls teams has created an account tied to the gun or ejector 20' serial number and authentication code that was provided as mentioned earlier herein. In one illustrative embodiment, only two individuals, such as coaches, may be registered or associated with one gun or ejector 20' when accessing the website WS. A third or other user may be associated with the gun or ejector 20', but only if one of the prior two users has been deleted or disassociated with the gun or ejector 20' serial number.

In the manner described later herein, once the gun or ejector 20' is registered using the procedure in FIG. 17 and the roster is created using the website WS, including team and players (for example, up to twenty-seven players in one illustrative embodiment), the user(s) will be allowed to log onto and use the gun or ejector 20' by using the interface 40 (FIGS. 3-3D) and input the roster onto the gun or ejector 20'. In this regard, it is important to note that once the team or player information and data is stored by the user on the website WS, it may be imported into the gun or ejector 20'. Individual players can be selected by using the digital code that is assigned to each player at the time the roster is created in the manner described later herein. In this regard, the user uses the interface 40 and depresses a button such as the pre-programmed drills button 278 (FIG. 3B) which is a button used for both selecting pre-programmed drills and selecting the player who is shooting. Once the pre-programmed drills button 278 is depressed, a player's three-digit code will appear on the display 45'. If necessary, the user may toggle the pre-programmed drills button 278 to scan through and select one digital number assigned to the desired player. In the illustration being described, the digital code is displayed on the display 45' and if the user scrolls through the digital code and leaves the digital code on the front scoreboard display 45' for two or more seconds, the gun or ejector 20' will recognize the player and will begin tracking and storing that player's shooting statistics and data. After the gun or ejector 20' recognizes the player, the pre-programmed drills button 278 may be used in a conventional manner to select one or more pre-programmed drills that are stored on the gun or ejector 20'.

As will be described in more detail later herein, after a shooting session, the statistics and data associated with the team or one or more players may be uploaded to the website WS. In this regard, the portable storage device 210 mentioned earlier herein, such as a USB flash drive, may be inserted into the port, such as a conventional USB port (not shown) on the gun or ejector 20', and the export button 120 on interface 40 may be actuated so that the shooting statistics and data associated with a shooting session may be downloaded or exported to the portable storage device 210. The portable storage device 210 may then be ported to a storage device or computer, such as computers 202 or 204 (FIG. 10), and the shooting statistics and data uploaded to the user's account at the website WS. In this regard, a session file, which is a comma delimited file containing the data and shooting statistics associated with a session of shooting, may then be uploaded to the website WS using an import button 280 (FIG. 35) on the graphical user interface 292.

Figure 35:
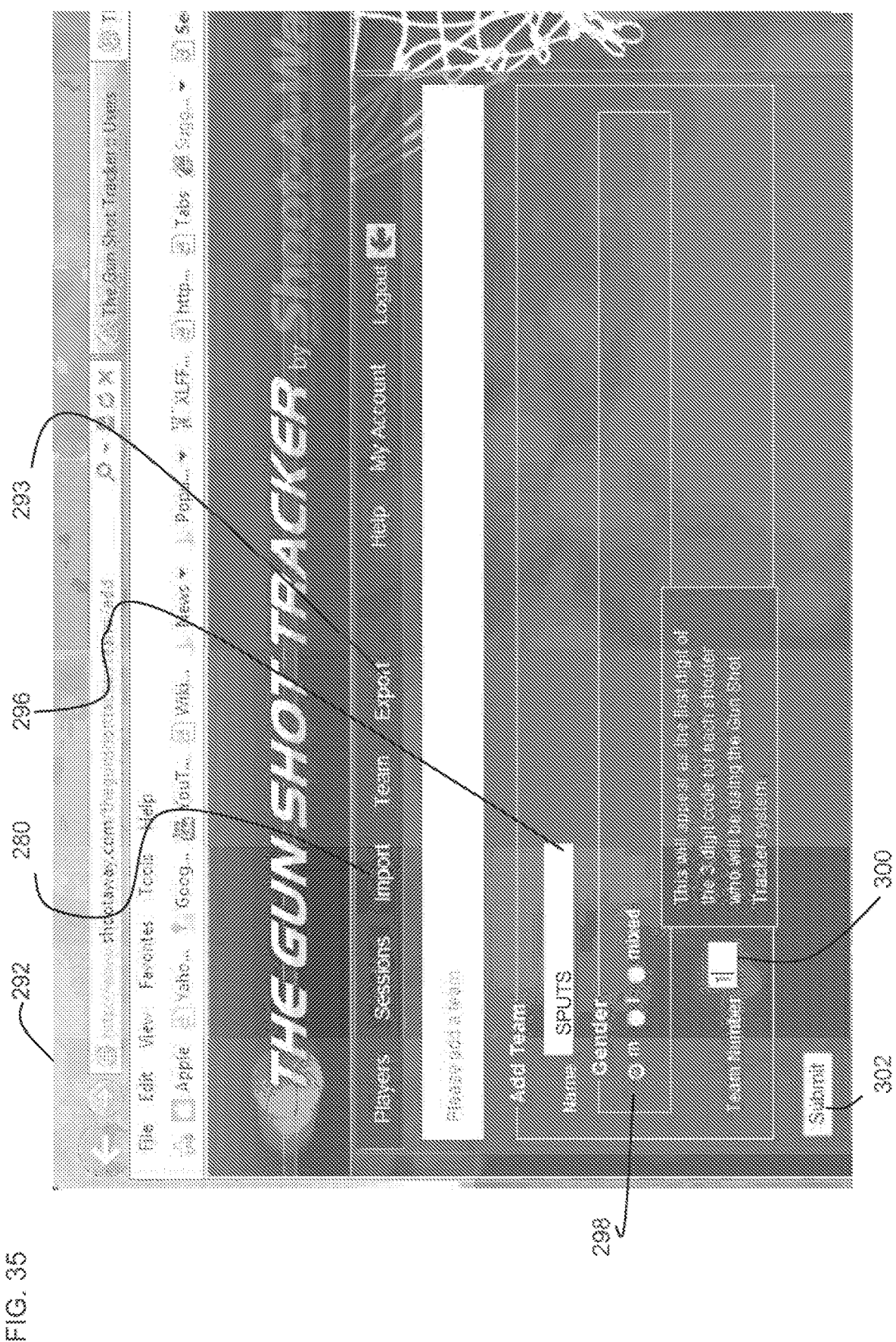

Having described the procedure for registering the gun or ejector 20' and provided a general overview of the tracking system and features of the embodiment being described, a more detailed description of various features of embodiments will now be described. As mentioned earlier, it is necessary to create a roster of teams and players on the website WS and that roster of teams and players may then be downloaded to the gun or ejector 20'. Again, after the gun or ejector 20' is used during a shooting session, the data and statistics may be uploaded to the website WS, for example, using the import button 280 (FIG. 3) which is provided in the graphical user interface 292 (FIG. 35). The user logs onto the website WS (block 282—FIG. 18) using the graphical user interface 284 (FIG. 34) which is provided by the website WS after the user has created his user account as will now be described. After the gun or ejector 20' is registered, a roster is created using the procedure to create a roster of team(s) and players, which will now be described relative to FIG. 18.

As illustrated in FIG. 18, the user enters his username and password in the areas 286 (FIG. 34) and 288, respectively, and then actuates the login button 290. The user will be presented first with the ability to add a team (block 294 in FIG. 18) and create a roster link using the graphical user interface 292 (FIG. 35) presented by the website WS. After log in, the user uses the graphical user interface 292 and enters a team or group name ("SPUTS" in the example) at area 296 and identifies an associated gender using the electronic buttons 298. The website WS also asks the user to identify a team number from 0-9 in the area 300 of the graphical user interface 292. It is important to note that this single-digit number will appear as the first digit of the digital code assigned by system 200 to each shooter who will be using the shot tracking system in accordance with the illustration being described. The digital code in the illustration associated with each player is a three digit code in the embodiment being described, but it could be another alphanumeric or digital code of longer or shorter length.

Figure 36:
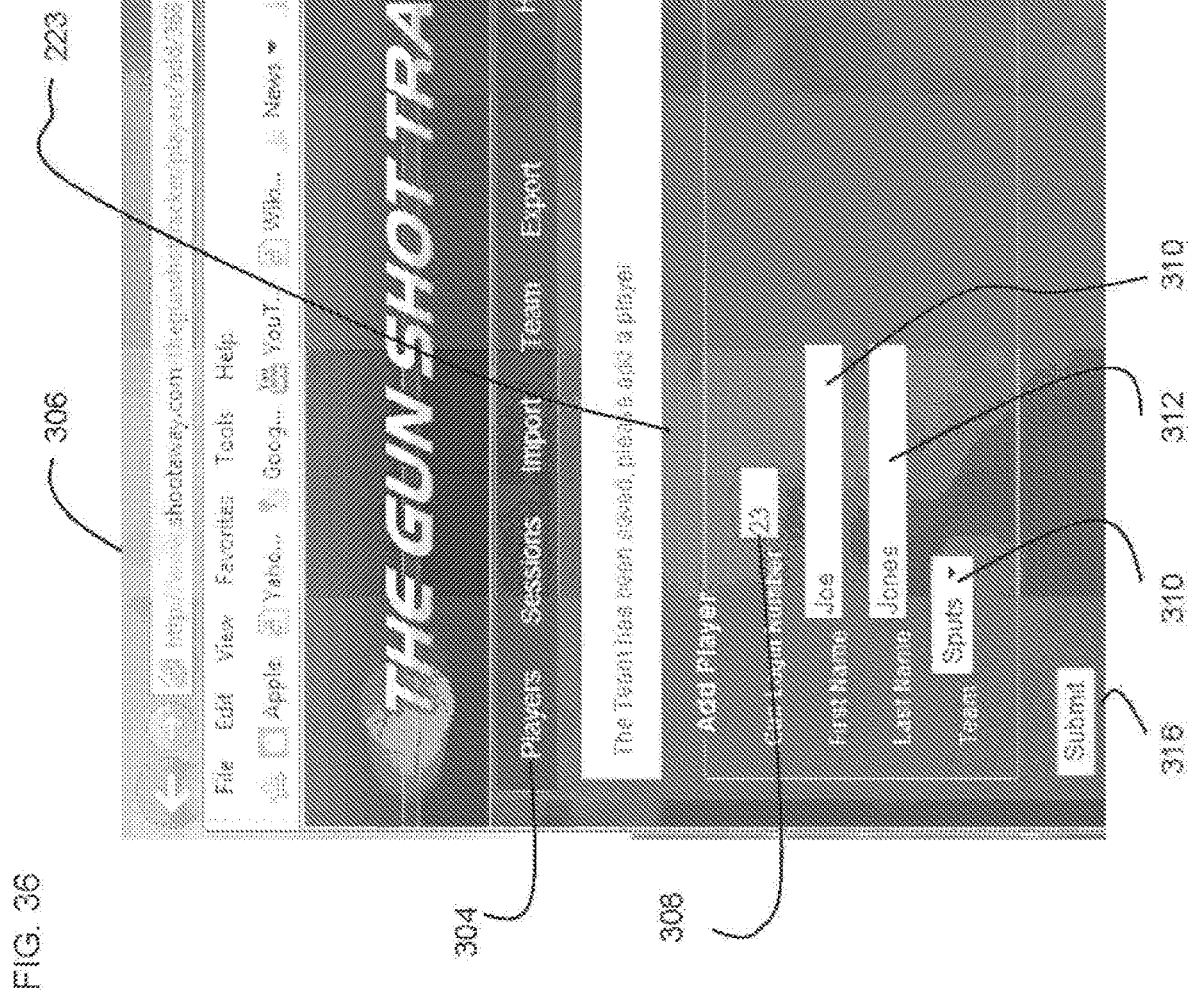

Once the team, gender and team number is assigned by the user, the user actuates (block 294 in FIG. 18) the electronic submit button 302 (FIG. 35) whereupon the team is created. Once a team has been created, the user may select a players link button 304, which is the electronic link labeled "Players" in the top banner portion of the graphical user interface 306 (FIG. 36). Whereupon the user is presented with the graphical user interface 306 which enables the user to link or associate players with the team that was created using the graphical user interface 292 in FIG. 35. Thus, at block 295 (FIG. 18), the user chooses the add player link 304 (FIG. 36) whereupon the user is presented with area 223 (FIG. 36) containing the gun login number area 308, first name area 310, last name area 312 and a drop down menu 314 for selecting the team. Note that a gun login number entered in the area 308 of interface 306 is a number associated with the player and that player will use when logging onto and using the gun or ejector 20' to collect data and shooting statistics during a shooting session. In the illustration being described, the gun login number will be assigned by the user by selecting a number from 0-99, which will be combined with the team number prefix digit, mentioned earlier relative to area 300 in FIG. 35, to create the three-digit code. In one illustrative embodiment, the number of players associated with a team is limited to 27, but it is to be understood that more or fewer players may be assigned to a team if desired.

The information is submitted to the website WS by actuating the electronic submit button 316 (FIG. 36). In response, the website WS presents the user with a graphical user interface 318 illustrated in FIG. 37 which shows the team and the players that are associated with the team in the area 320 of the graphical user interface 318.

Referring back to FIG. 18, after the user enters the players name, assigns a login number, birth date and associates the player with a team (block 297 in FIG. 18), it is determined at decision block 299 whether the player wishes to add another player. If yes, then the routine loops back to block 297 as shown, but if not, the routine proceeds to block 301 in FIG. 18 where the roster of players is stored on the website WS as a comma delimited file in the illustration being described. In this regard, the information or data associated with the roster may be stored on the local computer 202, 204 and/or the remote server 206 associated with the website WS. Alternatively, the data may be stored on a portable storage device 210 of the type mentioned and described earlier herein.

After the roster is created as described relative to FIG. 18, the roster may be downloaded to the gun or ejector 20' which will now be described relative to FIG. 19.

Referring now to FIG. 19, the rosters are downloaded to the gun or ejector 20' after the rosters are created and the procedure for downloading will now be described. The procedure begins by the user logging onto the website WS using the graphical user interface 284 (FIG. 34) and actuating the electronic button 290 (block 330 in FIG. 19). At decision block 332, it is determined whether the user has entered a roster to download to the gun 20', if not then the user uses the procedure described relative to FIG. 18 to create a roster on the website WS (block 334 in FIG. 19). If the decision at decision block 332 is affirmative, then the user selects the export link 293 (FIG. 35) at block 336 in FIG. 19. Once the user selects the export link 293 in the graphical user interface 292, the user is presented with a graphical user interface 292 (FIG. 38) by the website WS. The user is provided with the ability to export or save the play list file of the roster which includes the data and information relating to a team and its players, onto a storage device 210 (FIG. 10). In this regard, the player is provided with the graphical user interface 340 (FIG. 39) showing storage areas on his or her computer, such as computer 202 or 204, or other device the user uses to access the website WS. The user selects the player list file (identified in the FIG. 39 as "plyrlist") and saves it out using the electronic button 342 (FIG. 39) onto the portable storage device 210 of the type mentioned earlier herein. The "plyrlist" file, which comprises the information regarding the team, the players identification code, name, and the like, are imported to the gun or ejector 20' using the USB port (not shown) using the import button 118 (FIG. 3) mentioned earlier herein. Although the embodiment being described herein discusses or utilizes the portable storage device 210 for importing and exporting data and statistics to and from, respectively, the gun or ejector 20', it is important to understand that these functions and features could be done wirelessly with conventional wireless technology. Also, it is envisioned that the gun or ejector 20' could comprise means and apparatus for uploading and downloading information directly to the website WS to the computers 202 or 204 and the like using conventional wired or wireless technology, thereby reducing or eliminating the need for the use of the portable storage device 210. It is also important to note that the computers 202 and 204 may be stand alone computers, portable computers or smart phones or devices, such as an Apple iPhone, Android, iPad, Blackberry, smart phone or other similar smart device that is capable of receiving and transmitting information to and from the website WS.

In the illustration using portable storage device 210, the user inserts the device to a port (not shown) on the gun or ejector 20' and actuates the import button 118 (FIG. 3D), which causes the "plyrlist" data to the downloaded onto the gun 20' This is done at block 338 in FIG. 19.

After the rosters are downloaded to the gun or ejector 20', the routine in FIG. 19 ends. It is important to understand that once the gun or ejector 20' has been programmed with the roster(s) of teams and/or player(s), the gun or ejector 20' is ready to use and collect statistics as provided herein. A general description of use will now be described relative to FIG. 20.

The procedure starts at block 350 (FIG. 20) where the gun or ejector 20' is calibrated at the geographic location where it is located, such as a gymnasium or basketball floor. The calibration procedure is described later herein relative to FIG. 21. The calibration procedure is important so that the data and statistics captured or collected regarding a shooting session for one or more players using the same or different guns or ejectors 20' will be comparable. For example, the data and statistics associated with a player shooting at a particular position, such as along a vector associated with the position 8 (FIGS. 2 and 10 and the button labeled 8 in FIG. 10) will be comparable to a second player B who is shooting from that same position, position 8 in the example.

Once the gun or ejector 20' is calibrated, then shooting data and statistics may be compared with reasonable reliability and relatively low margin of error. As mentioned earlier, the players A and B may be on the same team shooting at the same location, may be on the same team shooting at different locations, may be on the same team shooting at the same time, may be on the same or different teams using the same gun or ejector 20', on different teams using different guns or ejectors 20', may be on different teams using different guns or ejectors 20' at the same or different times, and the like.

Returning to FIG. 20, the player selects at least one or a plurality of positions from which to shoot (block 354), which is described later herein relative to FIGS. 23A, 23B, 24A and 24B. The player shoots until the selected routine, whether it be a pre-programmed drill routine or a user-programmed drill routine, ends at block 356. In one embodiment, the gun or ejector 20' may be programmed to eject balls 12' in the order in which the buttons 41 (FIG. 3A) are selected. In other words, the controller 32' on the gun or ejector 20' will cause the balls to be ejected from the gun or ejector 20' in the order in which the buttons were selected. The system 200 stores the plurality of positions selected and then the gun or ejector 20' ejects the correct number of balls to those locations in the order they were programmed. It may also eject the balls in order from left to right as viewed on the interface 40 as far as the plurality of the positions no matter the order they were programmed. For example, if the user selected or actuated buttons 0, 11, 5 and 16 (FIGS. 3A-3B) on interface 40 in this order, then the controller 32' would cause the balls to be ejected from the gun or ejector 20' to the corresponding location 0, 11, 5 and 16 (FIG. 10) in the order in which the buttons 41 (FIG. 3A) were selected, thereby enabling the user to program the positions in a non-serial order which enables the gun or ejector 20' to accurately simulate game-playing situations. This programming ability enables the user to create millions of possible shooting drills or routines.

After the shot selection is determined and the player shoots until the routine ends (FIGS. 23A, 23B and 24A, 24B), it is determined whether or a not a new shooter, the same shooter or whether the shooter(s) are done shooting. If they are the same or if there are new shooters, then the routine loops back to block 354 as shown, but if the shooting is done, then the user may export the data and statistics regarding the shooting session (block 360), which is described later herein relative to FIG. 25. At decision block 362 (FIG. 20), the user who is exporting, uploading or saving the data or statistics may decide to make the data or statistics public or available for use or to view by others at decision block 362. If the decision is not to make them available, then the routine proceeds to block 364, but if the decision is to make them available, then the procedure enables the data and statistics to be made available for use by others at block 366, and this procedure is described later herein relative to FIG. 25.

It is then determined whether the user wants to view and/or make local, regional, national or international comparisons of the data or statistics from a shooting session at decision block 368. If the user does not, then the procedure ends, but if the user does wish to view, print and/or make local, regional, national or international comparisons, then the routine proceeds to block 370 (FIG. 20) wherein the system proceeds to block 434 in FIG. 25.

As referenced in FIG. 20, block 350 and for the reasons mentioned earlier, the gun or ejector 20' is preferably calibrated and the procedure to calibrate the gun or ejector 20' is shown in FIG. 21, which will now be described. The calibration procedure starts by the user positioning the gun or ejector 20' underneath the net or rim 14' adjacent to the backboard 16'. The gun or ejector 20' is centered lengthwise (baseline to baseline) on the basketball playing area or court with a center line of the basket (end to end) and thus is equidistant from each of sidelines and side edges of the backboard, all of which is shown in block 371. Calibrating the gun or ejector 20' in this manner facilitates ensuring that all shots taken from, for example, a shooting location such as the shooting location associated with the button labeled 8 (FIG. 3A) associated with the position 8 (FIG. 10), will be on a dead-center line of the court as it bisects a baseline where the gun or ejector 20' is located to the opposing baseline at the opposite end of the court. Accurately positioning the gun or ejector 20' also assures accurate measurements by the Doppler System 800 (FIG. 10) and comparisons.

Figure 22:
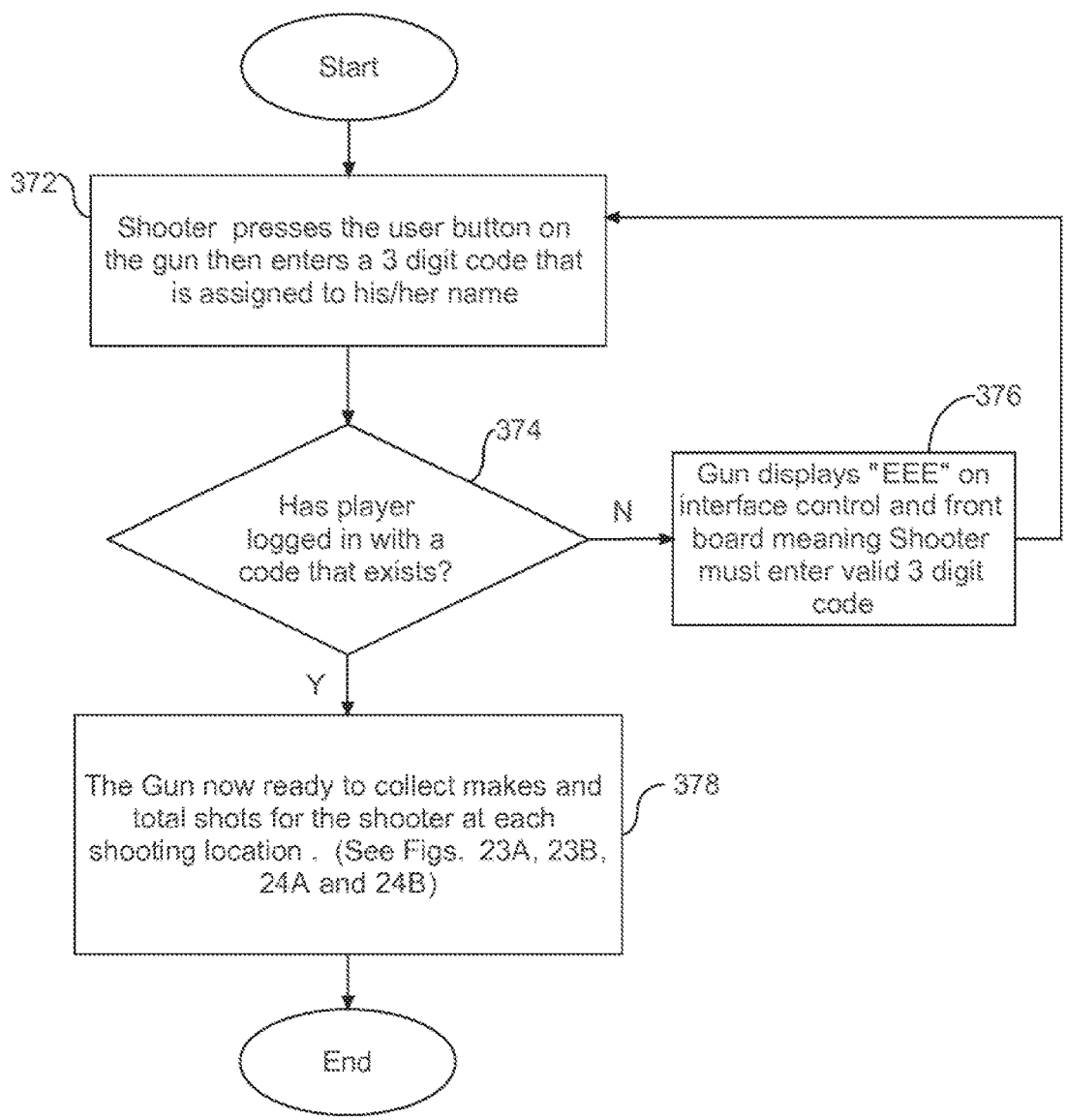
FIG. 22 is a general illustrative procedure for players to log onto the gun or ejector in the embodiment shown in FIG. 10.

As shown in block 352 in FIG. 20, after the gun or ejector 20' is calibrated, the player may log in and use the gun or ejector 20' and the procedure for log in will now be described relative to FIG. 22. The player starts by using the pre-programmed drills button 278 on the interface 40. In the example, the user enters his 3 digit code by first pressing the user button 116 in FIG. 3C the pressing the number of balls in FIGS. 3A and 3B until he/she has entered the complete code. The user then presses the Pre-Programmed Drills button 278 (FIG. 3B) to enter that code. The user could also depress and hold the user button in FIG. 3C for 4 seconds, for example. If this is done, the system 200 enables the user to scroll through all the user codes using the up/down arrows 43 (FIG. 3B). When they see their code, the user actuates or presses the Pre-Programmed Drills button to enter it. Thereafter, it is determined at block 372 (FIG. 22) whether the player logged in with a code that exists (as downloaded and stored to the gun or ejector 20' by the user) or that has been programmed into the gun or ejector 20' at decision block 374. If he or she has not logged in properly, then the gun displays an error code, which in one embodiment is the three letters "EEE" on the interface 40' on the display 42' (FIG. 10) at decision block 376.

If the decision at decision block 374 (FIG. 22) is affirmative, then the gun or ejector 20' is ready to use and collect data and statistics (block 378) for the player regarding the player's makes and total shots for the player at each shooting location from where the player shot at block 378. Thereafter the routine ends.

It is important to understand that once the gun or ejector 20' has been calibrated and the player has logged in, the player may begin a shooting session and shoot until the shooting session ends, as mentioned earlier relative to block 356 in FIG. 20. For ease of description and illustration, it is to be understood that the Doppler System 800 described earlier herein may be used during a shooting session, although it is not mandatory. Thus, measurement and calculations from the Doppler System 800 may be used alone or in combination with other features of other embodiments described herein. For ease of description, various procedures will be described herein as being Doppler dependent, which means that the procedures are conducted using the Doppler System 800 and measurements sensed and calculated therefrom. Some of the features or embodiments of the invention will be repeated, but without use of the Doppler System 800. Accordingly, it should be understood that while some of the embodiments utilize the Doppler System 800 and its calculations or measurements, it is not mandatory and there are features of various embodiments that are not dependent on the measurements performed by the Doppler System 800. For further ease of illustration and description, some of the procedures and embodiments described herein will be first described as without the use of the Doppler System 800, followed by a description of a similar embodiment but using the Doppler System 800.

Figure 23A:
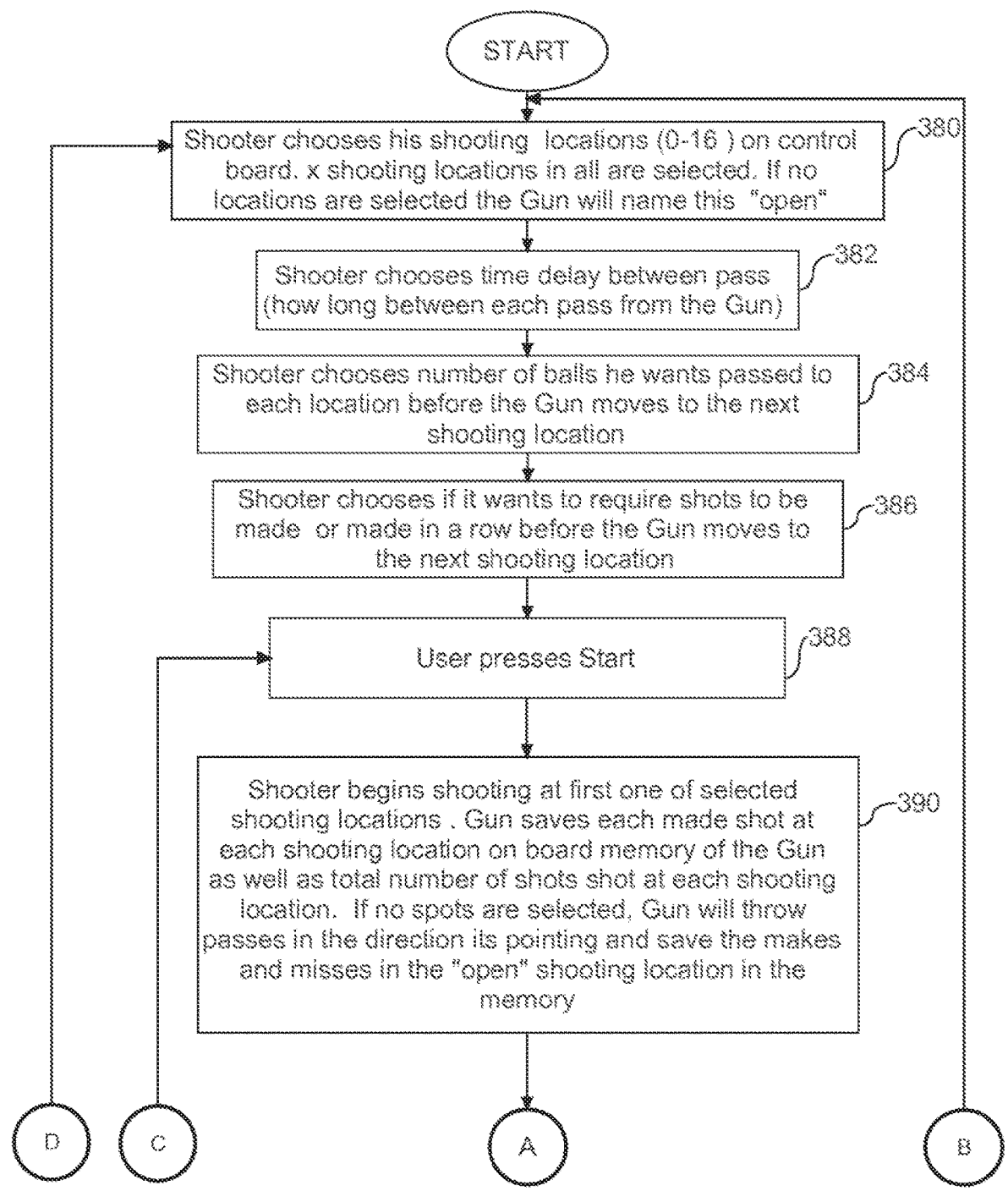
FIGS. 23A-23B illustrate a general procedure for a shooting workout in accordance with another embodiment of the invention wherein the procedure is not dependent upon Doppler measurements.
Figure 23B:
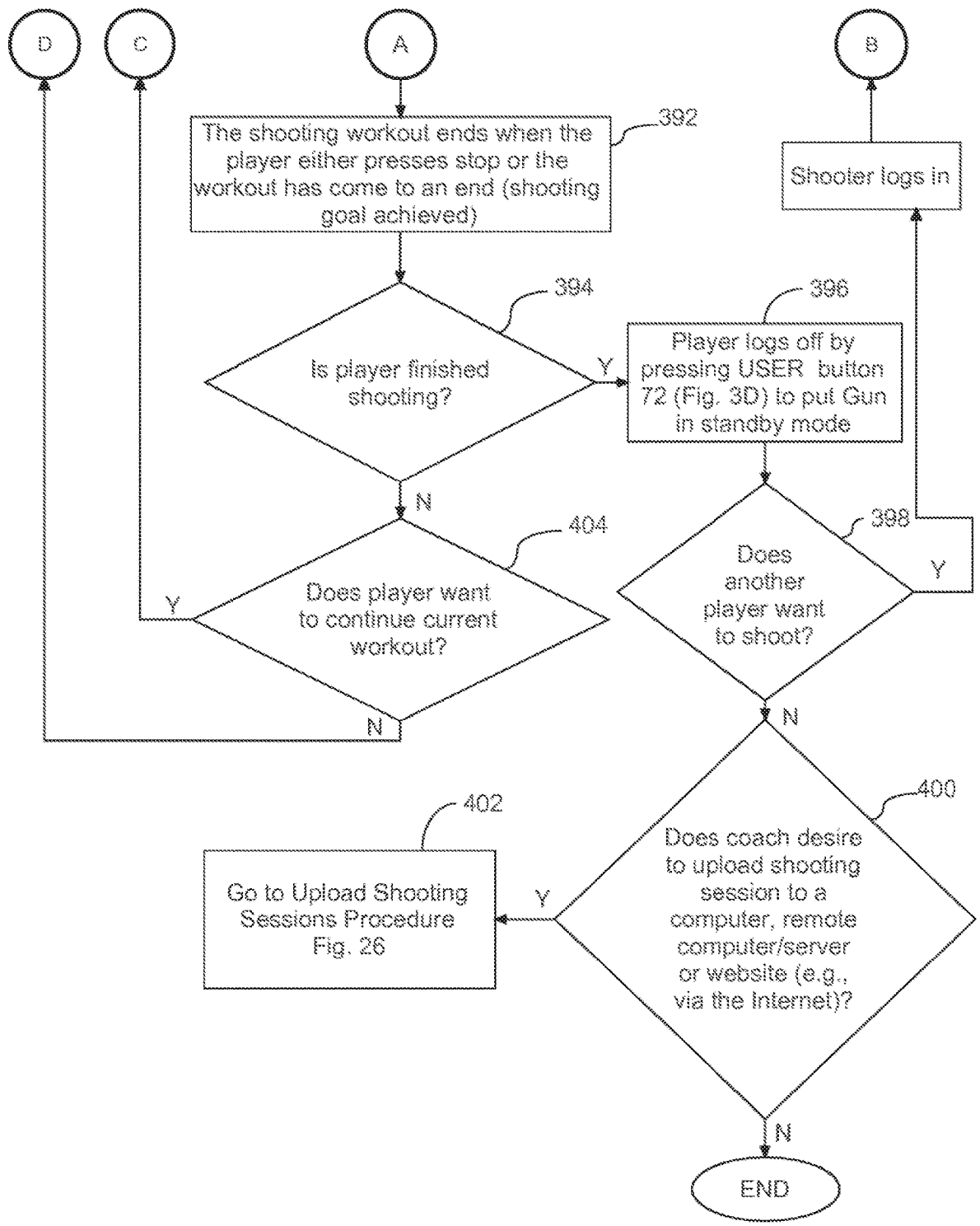

Referring now to FIGS. 23A and 23B, a process is shown for the user to select a shooting workout for the gun or ejector 20' to collect and save statistics and data relative to the workout, such as the number of shots made, number of total shots taken and the like at each of the predetermined or preselected shooting locations (e.g., the locations associated with the buttons 0-16 and labeled 41 in FIGS. 3 and 3A-3D and the associated positions or locations 22' (FIG. 10). The routine starts at block 380 (FIG. 23A) wherein the shooter chooses his shooting locations 0-16 on the interface 40 (FIGS. 3 and 3A-3D) by actuating one or more of the plurality of buttons 41. Alternatively, the user may select the pre-programmed drills button 278 (FIG. 3B) to cause the gun or ejector 20' to run through one or more pre-programmed drills that are stored on the gun or ejector 20'. If no locations are selected by the user, the gun or ejector 20' will treat the shooting session as an "open" session during which the gun 20' will fire balls in the direction it is pointing set physically by the user pointing the gun to the left corner or top of the key. There is no random shooting to different spots.

The routine proceeds to block 382 (FIG. 23A) wherein the shooter chooses the time delay between the pass by using the area of the interface 40 (FIG. 3A) labeled step two with the plurality of buttons 43. Time between passes can be from approx 1.5 seconds to 99 seconds. The shooter then chooses the number of balls 12' to be passed to each location before the gun or ejector 20' moves to the next shooting location (block 384). The shooter actuates the up and down arrow button 77 (FIG. 3D) to enter the total number of shots to be passed to each of the shooting locations before the gun or ejector 20' moves to the next shooting location. In one illustrative embodiment, the shooter or user may choose (block 386) if he or she wants to require shots to make or made in a row before the gun or ejector 20' moves to the next shooting location by actuating the button 74 (FIG. 3C). Once the gun or ejector 20' is programmed, the user may press the start button 70 (FIG. 3D), as indicated at block 388 in FIG. 23A.

At block 390 in FIG. 23A, the shooter begins shooting at a first one of the selected shooting locations and the gun or ejector 20' saves or records each made shot at each shooting location on the storage device 44' (FIG. 10). The gun or ejector 20' will also save a total number of shots at each shooting location. If no spots or shooting locations were initially selected by the user at block 380 (FIG. 23A), the gun or ejector 20' will throw passes in the direction it is pointing and save the makes and misses in the "open" shooting location in the memory or storage device 44'.

The routine proceeds to block 392 (FIG. 23B) where the shooting session or workout ends when the player either presses button 72 (FIG. 3D) or the workout has come to an end. For example, a workout or shooting session may come to an end after the gun or ejector 20' has ejected or launched the total number of shots to each of the locations selected, the pre-determined drill selected has been performed, or a shooting goal or one of the shooting challenges described earlier herein has been achieved. The routine proceeds to decision block 394 (FIG. 23B) where it is determined if the player has finished shooting. If the player has, then the player or user powers off the gun or ejector 20' or logs off by pressing (block 396) the user button 116 (FIG. 3C). Thereafter, it is determined whether another player is desirous of shooting at decision block 398 and if he is, then the routine proceeds back to block 380 (FIG. 23A) as shown. If the decision at decision block 398 is negative, then it is determined whether or not an interested user, such as a coach or other user, desires to upload the shooting session data or statistics to a remote computer or server or website (block 400 in FIG. 23B). If he does not, then the routine ends, but if he does, then the routine proceed to the upload shooting sessions data and statistics routine (block 402), described later herein relative to FIG. 26, which will be described later herein.

If the decision at decision block 394 is negative, then the routine proceeds to decision block 404 where it is determined whether or not the player wants to continue the current shooting session or workout. If he does, then the routine loops back to block 388 (FIG. 23A) as shown. If not, then the routine loops back to block 380 as shown.

Having described the general procedure for one embodiment that is not dependent on the Doppler System 800, now the procedure for selecting a shooting work out and for collecting data and statistics relative to the shooting session that utilizes the Doppler System 800 and its measurement or calculations will now be described relative to FIGS. 24A and 24B.

Figure 24A:
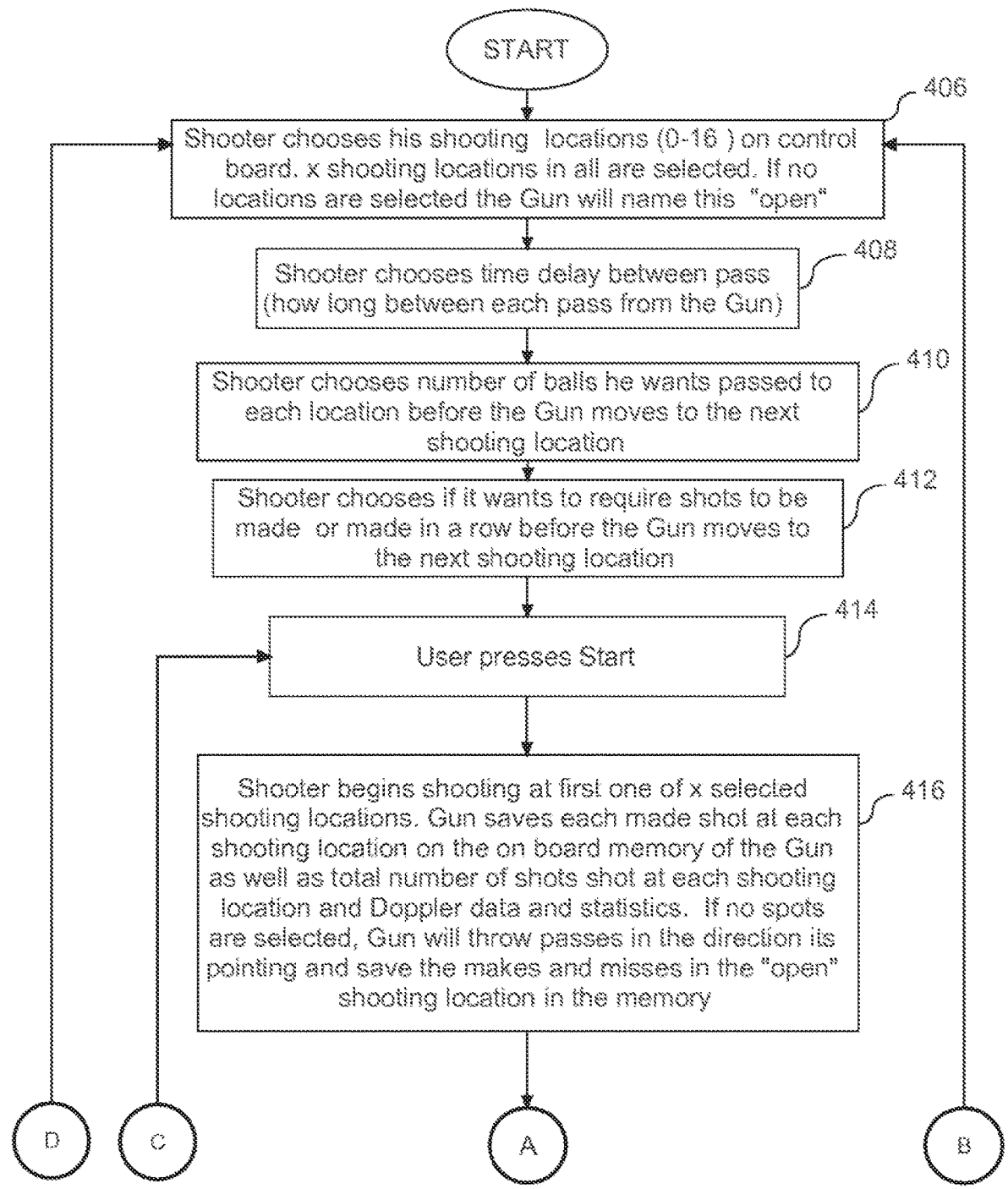
FIGS. 24A-24B is similar to the procedure shown in FIGS. 23A-23B, but includes Doppler measurements and statistics.

In FIG. 24A the routine begins at block 406 wherein the shooter chooses his shooting locations 0-16 on the interface 40 (FIG. 3 and FIGS. 3A-3D) by actuating one or more of the plurality of buttons 41 as described earlier. Alternatively, the user may select the pre-programmed drills button 278 (FIG. 3B) to cause the gun or ejector 20' to run through one or more pre-programmed drills that are stored on the gun or ejector 20'. If no locations are selected by the user the gun or ejector 20' will treat the shooting session as an "open" session during which the gun or ejector 20' will fire balls in the direction it is pointing set physically by the user pointing the gun say to the left corner or top of the key.

The routine proceeds to block 408 (FIG. 24A) wherein the shooter chooses the time delay between the pass by using the area of the interface 40' (FIGS. 3 and 3A-3D) labeled step two with the plurality of buttons 43. In the illustration, the shooter can choose between 15 seconds up to 60 seconds between passes from the gun or ejector 20'. The shooter then chooses the number of balls to be passed to each location before the gun or ejector 20' moves to the next shooting location (block 410). The shooter actuates the up and down arrow button 77 to enter the total number of shots to be passed to each of the shooting locations before the gun or ejector 20' moves to the next shooting location. In one illustrative embodiment, the shooter or user may choose (block 412) if he or she wants to require shots to made or made in a row before the gun or ejector 20' moves to the next shooting location by actuating the button 74 (FIG. 3C). Once the gun or ejector 20' is programmed, the user may press the start button 70 (FIG. 3D) as indicated at block 414 in FIG. 24A.

At block 416 in FIG. 24A, the shooter begins shooting at a first one of the selected shooting locations and the gun or ejector 20' saves or records each made shot at each shooting location on the storage device 44'. The gun or ejector 20' will also save a total number of shots at each shooting location. If no spots or shooting locations were initially selected by the user at block 406 (FIG. 24A), the gun or ejector 20' will throw passes in the direction it is pointing and save the makes and misses in the "open" shooting location in the memory or storage device 44'. The routine proceeds to block 418 (FIG. 24B) where the shooting session or workout ends when the player either presses button 72 (FIG. 3D) or the workout has come to an end. For example, a workout or shooting session may come to an end after the gun or ejector 20' has ejected or launched the total number of shots to each of the locations selected, the pre-determined drill selected has been performed or a shooting goal or one of the shooting challenges described earlier herein has been achieved. The routine proceeds to decision block 420 (FIG. 24B) where it is determined if the player has finished shooting. If the player has, then the player or user powers off the gun or ejector 20' or logs off by pressing (block 422) the user button 116 (FIG. 3C). Thereafter, it is determined whether another player is desirous of shooting at decision block 424 and if he is, then the routine proceeds back to block 406 (FIG. 24A) as shown. If the decision at decision block 424 is negative, then it is determined whether or not an interested user, such as a coach or other user, desires to upload the shooting session data or statistics to a remote computer or server or website (block 428 in FIG. 24B). If he does not, then the routine ends, but if he does, then the routine proceed to the upload shooting sessions data and statistics routine, described later herein relative to FIG. 26, which will be described later herein.

After the decision block 420, it is determined whether or not the player wants to continue to work the current shooting session or workout (block 420). If the decision at decision block 420 is negative, then the routine proceeds to decision block 432 where it is determined whether or not the player wants to continue the current shooting session or workout. If he does, then the routing loops back to block 414 (FIG. 24A) as shown. If not, then the routine loops back to block 406 as shown.

Figure 24B:
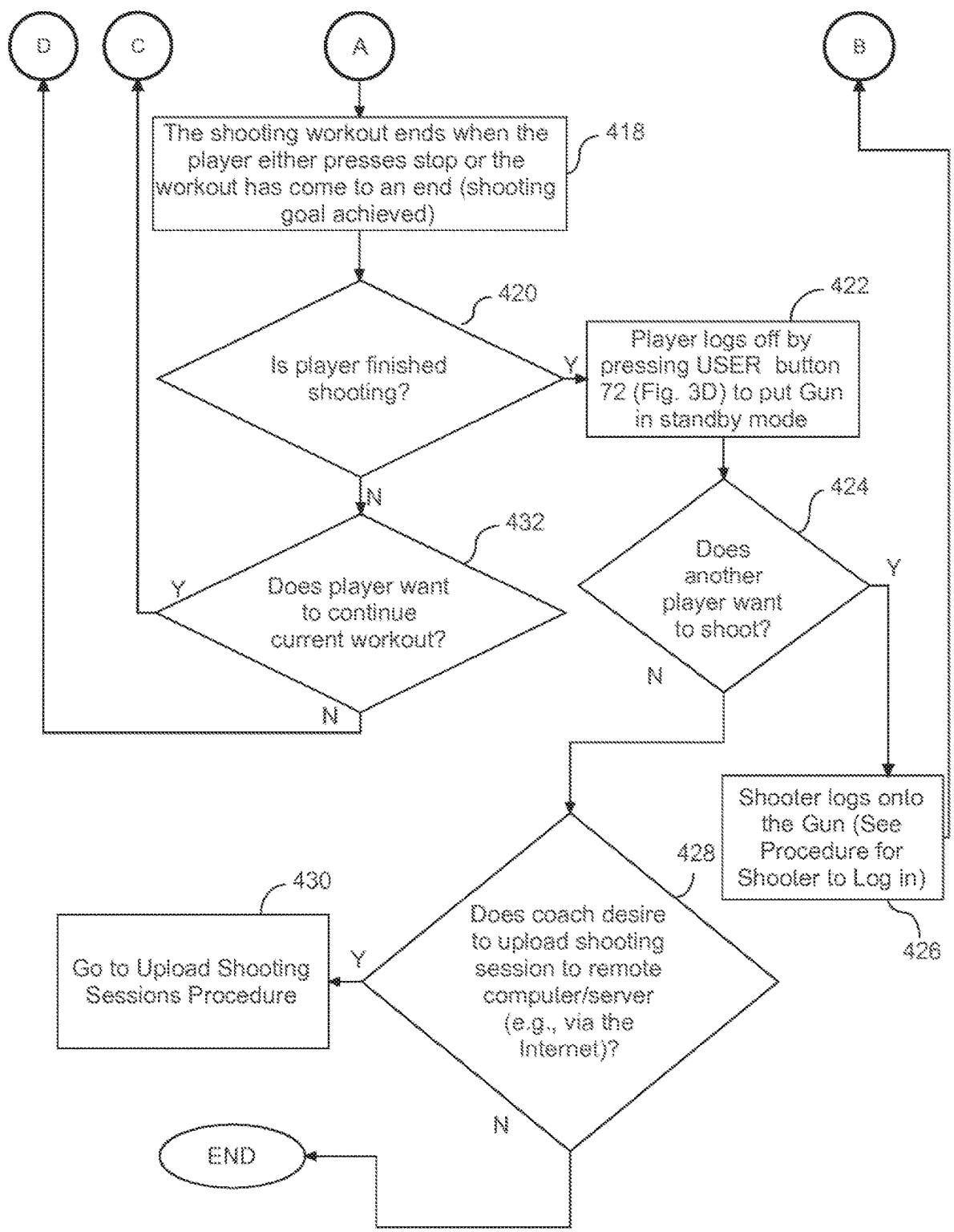

It is extremely important to note a difference between the procedure described and shown in FIGS. 24A and 24B relative to the procedure in FIGS. 23A and 23B. The procedure in FIGS. 24A and 24B, the system 200 and Doppler system 800 includes Doppler data and statistics. As mentioned earlier herein, these Doppler data, statistics, measurements or calculations include measurements and calculations of distance between the player and the gun or ejector 20', the shooter's release time (i.e., the time it takes from when the shooter receives the ball and then shoots the ball towards the hoop 14'), the arc or angle of the shooter's release, and the arc or entry angle of the shot as the shot enters the hoop 14'. In the manner described later herein, this Doppler data and statistics may also be used for comparisons, creating reports and the like as described later in. The user holds spot 0 button 41 (FIG. 3A) for 4 seconds to disable or to turn on the Shot Tracker feature. In the illustration being described, the gun or ejector 20' is always in an "on" state (unless the user has turned off the Shot Tracker feature) so that gun or ejector 20' is always collecting Doppler data and statistics, but collecting and using this data is not mandatory.

Referring back to FIG. 24B, if the decision at decision block 424 is affirmative, then the new shooter logs onto the gun or ejector 20' using the log in procedure described earlier herein relative to FIG. 22, as shown at block 426 in FIG. 24B. Thereafter, the routine loops back to decision block 406 as shown. If the decision at decision block 424 is negative, then the routine proceeds to decision block 428.

If the decision at decision block 424 (FIG. 24B) is negative, then it is determined whether or not an interested user, such as a coach, desires to upload the shooting session data or statistics to a remote computer or server or website (block 428). If he does not, then the routine ends, but if he does, then the routine proceed to the upload shooting sessions data and statistics routine (block 430) described later herein relative to FIG. 26.

After the decision block 420 (FIG. 24B), it is determined whether or not the player wants to continue to work the current shooting session or workout. If the decision at decision block 420 is negative, then the routine proceeds to decision block 432 where it is determined whether or not the player wants to continue the current shooting session or workout. If he does, then the routine loops back to block 414 (FIG. 23A) as shown. If not, then the routine loops back to block 406 as shown.

The user may power off the Gun by pressing the POWER SWITCH button in FIG. 3C (bottom left corner of interface 40) the machine is powered down and the procedures in FIGS. 23B and 24B will automatically go to END and the shooting data is stored.

Figure 25:
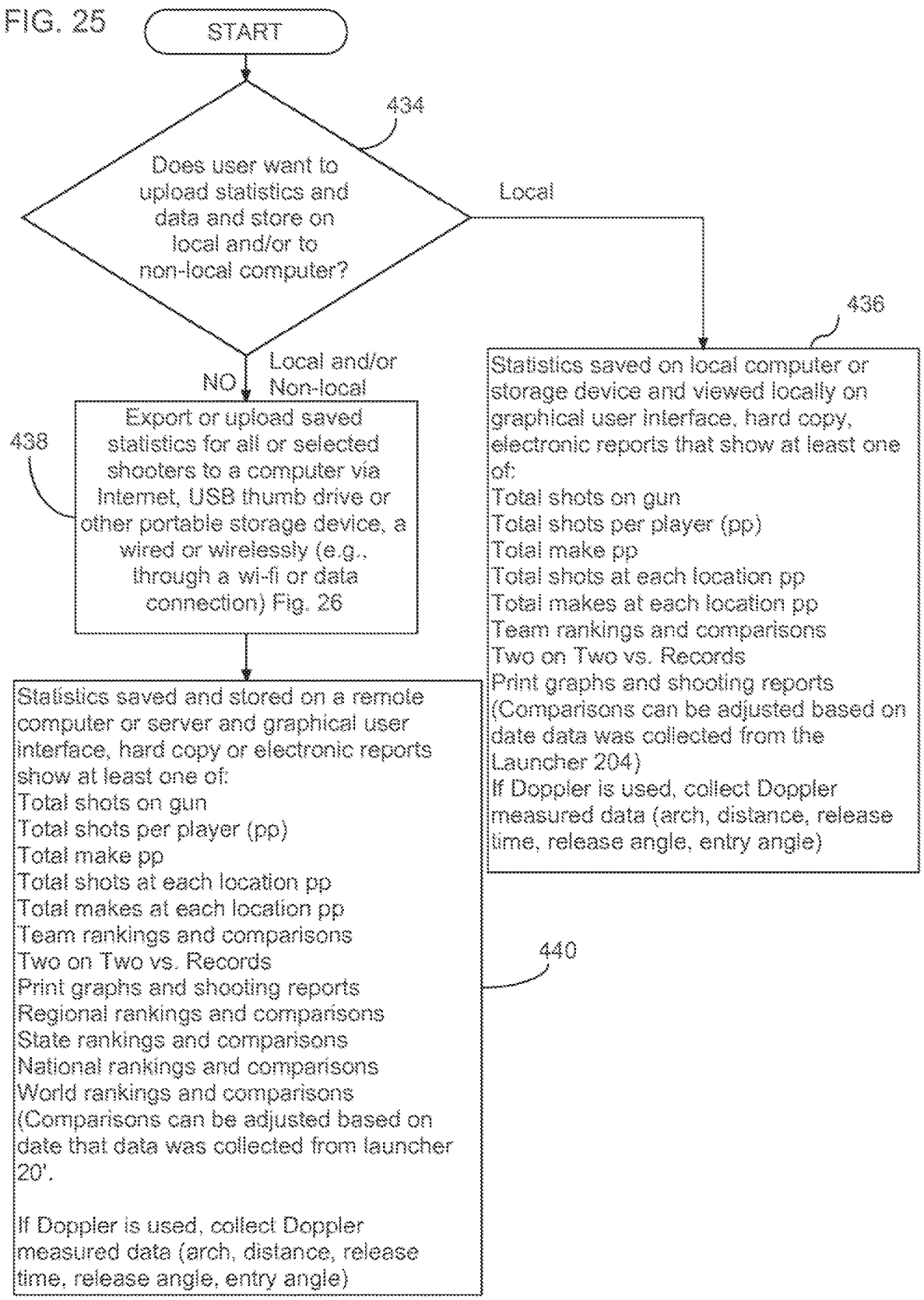
FIG. 25 is a general procedure for uploading statistics and measurements to a local or non-local computer or website.

After shooting is complete and the normal data and statistics and Doppler data and statistics are gathered, calculated and stored, for example, by controller 32' (FIG. 10) on the storage device 44', the statistics may be uploaded and stored to a local or remote computer, such as computer 202 or 204, or on a remote server or computer, such as the server 206 associated with the website WS. FIG. 25 addresses this feature of one embodiment.

In FIG. 25, it is determined at decision block 434 whether the user wants to upload data and statistics and store them on the local computer associated with the user, such as a computer 202 or remote server or computer 204, in the example. If he does, then the routine proceeds to block 436 whereupon the statistics are saved on the local computer 202, 204 or other storage device so that they may be viewed locally using a conventional program such as Windows Internet Explorer or Windows Explorer both of which are available from Microsoft Corporation of Redmond, Wash., Safari available from Apple Computers of Cupertino, Calif. or other program capable of viewing html files. Note that the data and statistics may be exported from the gun or ejector 20' using the export button 120 (FIG. 3D) mentioned and described earlier herein. As mentioned earlier herein, the data and statistics may be exported using the portable storage device 210 (FIG. 10), such as the thumb drive or flash drive mentioned earlier herein, may be downloaded to the computer using a wired (e.g., RS232 cable) or wirelessly transmitted (e.g., through a Wi-Fi connection) from the gun or ejector 20' as mentioned earlier using conventional wireless technology.

As illustrated in FIG. 25, block 436, one or more of the following data or statistics may be saved, used, displayed on, printed into report and the like using the local computer 202, 204:

Total shots on gun
Total shots per player
Total make per player
Total shots at each location per player
Total makes at each location per player
Team rankings and comparisons
Two on two vs. Records
Print graphs and shooting reports
(Comparisons can be adjusted based on date data was collected from gun or ejector 20')

If Doppler System 800 is used, collect Doppler measured data (arch, distance, release time, release angle, entry angle).

A user may also wish to not only store, use and print data on the local computer, such as computers 202 or 204, but may also wish to upload the data and statistics to, for example, a remote site or server, such as server 206 in FIG. 10, or remote website WS. The user would then proceed to block 438 in FIG. 25 to export and upload the saved statistics and data that are saved on the gun or ejector 20' for all or only selected ones of the shooters who were shooting during a shooting session to a computer, such as computers 202 and 204 or to the remote website WS and the server 206 associated therewith. Again, the data could be uploaded using the internet, or wirelessly, such as through a Wi-Fi connection or other data connection. As mentioned earlier herein, the portable storage device 210 (FIG. 10) may also be used to store the data and statistics so that they can be accessed using a computer which can be used to upload the statistics to the website WS, for example.

In one illustrative embodiment, it is important to note that if the statistics and data are uploaded to the website WS, the system 200 comprises a tracking system that is adapted to enable and permit a collection of measured and comparison statistics and data to be generated, stored, saved, viewed, published and used. For example, regional rankings and comparisons may be performed to rank and compare players who perform during the shooting session to other players in the region. Similar rankings and comparisons could be made on a state-wide basis (e.g., all players within the state of Ohio), a nationwide, basis, or international rankings and comparison comparing all players throughout the United States of America, Italy, China, Japan and the like. The system 200 and method described herein provide means and device for generating and using comparisons that can be adjusted based upon numerous various parameters described later herein, such as a shooting date or date range when a shooting session occurred, age of players, gender of players and the like. As illustrated in block 440 (FIG. 25), the statistics and data that may be gathered, calculated, saved and stored:

Total shots on gun
Total shots per player (pp)
Total make pp
Total shots at each location pp Total makes at each location pp
Team rankings and comparisons
Two on Two vs. Records
Print graphs and shooting reports
Regional rankings and comparisons
State rankings and comparisons
National rankings and comparisons
World rankings and comparisons (Again, comparisons can be adjusted based on the date the data was collected from gun or ejector 20') It should be understand that the graphs and shooting reports could be printed by using, for example, a ticket printer 46' or any other printer, such as a local or remote printer associated with computer or server 202, 204, server 208 or website WS.

If Doppler System 800 is used, Doppler measured data (arc, distance, release time, release angle $\theta_r$, entry angle $\theta_e$ is also collected) in the manner described earlier relative to FIGS. 13A-13B, 14 and 15A-15D.

The procedure for uploading the shooting sessions to the website WS will now be described relative to FIG. 26. The procedure for uploading shooting sessions data and statistics begins in FIG. 26 at block 442 wherein the user powers up the gun or ejector 20' into standby mode which may be manually selected by actuating the stop or standby button 72 (FIG. 3). If the data and statistics are to be uploaded non-wirelessly or without a hardwire connection to, for example, a computer 202, 204 or to the website WS, then in one illustration this may be done using the portable storage device 210 (FIG. 10 as mentioned earlier). In this event, the user inserts the portable storage device 210 (FIG. 10) which in the illustration being described could be a USB thumb drive into the USB port (not shown) of the gun or ejector 20'. Once the portable storage device 210 is inserted into the port (not shown) of the gun or ejector 20' control board or controller 32', the user may actuate the export data button 120 (FIG. 3D) to save the sessions file (block 442 in FIG. 26).

It is important to understand that in one illustrative embodiment, the sessions data and statistics file includes all shooters' dates and statistics and data associated with all shooting sessions they completed since the last export of data, their nametag to the three digit player code described earlier herein, number of makes and total shots in each session they shot each time from each shooting location. If the user wants to export the data without the use of the portable storage device 210, then the user may do so, for example, wirelessly. For example, the user would power up the computer 202 and use a wireless communication device 145' (FIG. 10), which in the illustration being described is coupled to the controller 32' and mounted on the gun or ejector 20'. In the illustration being described, the wireless communication device 145' may comprise conventional Bluetooth technology or other dedicated wireless or wired internet connection. If Gun is equipped with wireless communication device 145' that includes a wireless receiver and transmitter (FIG. 10), which is optional, the user would press the import or export buttons 118, 120 to effect the import or export of data (FIG. 3D). Alternatively, a hard wire connection between an RS232 port on the gun or ejector 20' may be used.

Figure 26:
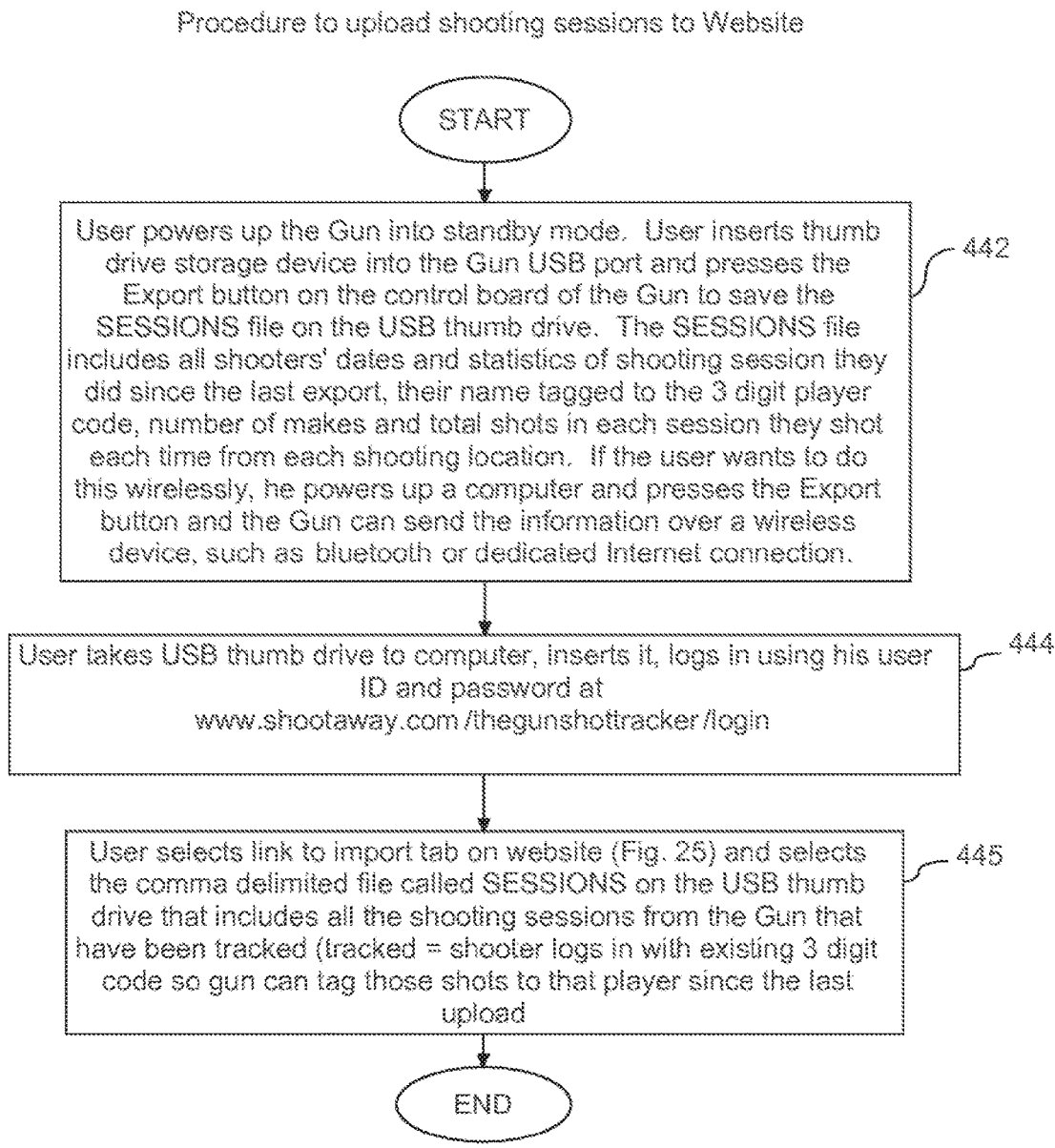
FIG. 26 is a general procedure for uploading shooting session data and statistics to a website in accordance with one embodiment.
Figure 41:
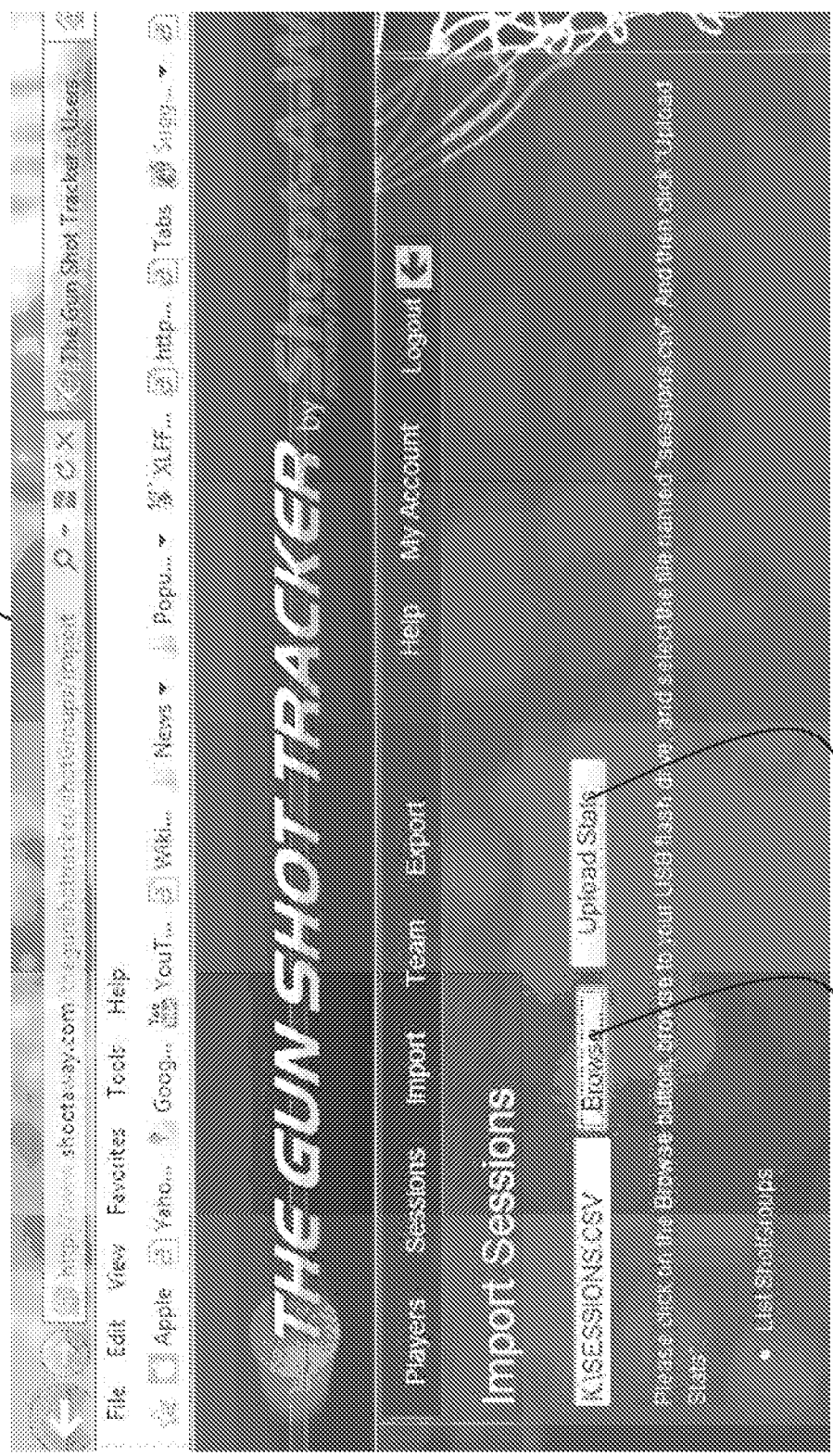

In the illustration shown in FIG. 26, it is contemplated that the portable storage device 210 is used and the user takes the portable storage device 210 to the computer 202 (block 444 in FIG. 26), inserts it, logs into the website WS using the graphical user interface 284 described earlier herein relative to FIG. 34. The user then selects the link to import button 280 (block 445 in FIG. 26). In response to the user actuating the import button 280 (FIG. 35), the user is prompted with another graphical user interface 446 (FIG. 41) and with a browse button 448 which, when actuated, presents the user with view(s) of their computer so they can import the file. The screen shot of the graphical user interface 451 (FIG. 40) is illustrative. The illustrative file is shown as "SESSIONS" and labeled as 453 in FIG. 40. After it is selected, the user may actuate the button 455 in FIG. 40 whereupon the file is imported from the portable storage device 210 or computer 202 and linked to the import sessions user interface 446 as illustrated in FIG. 41. The user may then actuate the upload stats button 457 (FIG. 41) whereupon the system 10 causes the file to be uploaded to the website WS and the server 206 associated therewith.

As mentioned, the data is stored in a database 206a (FIG. 10) associated with the server 206. It is important to note that the database 206a is updated and retains cumulative shooting statistics for each shooter on a team or roster. Thus, for example, if only two of ten shooters on a team shot during a shooting session, their data could be uploaded as described, but the database 206a maintains cumulative data for all members of the team regardless of when shooting occurred. This is useful for generating the comparison reports described later herein, some of which utilize lifetime shooting statistics.

Advantageously and as described, graphical user interface 451 (FIG. 40) shows the sessions file as stored on the portable storage device 210, which is shown in the illustration as "removable disk (K)". The user selects the "SESSIONS" file shown on the portable storage device 210 and actuates the open button 455 in FIG. 40 whereupon the sessions file data and statistics are uploaded to the website WS and in the illustration being described, stored on the server 206 associated with the website WS. In the illustration being described, the "SESSIONS" file includes all the information and data captured and referenced relative to the data mentioned earlier herein relative to FIG. 25. The website WS receives the information and data and updates the database 206a (FIG. 10) that maintains a continuous cumulative database for each player and all the statistics and data associated with the player for all the shooting statistics that were captured. In the illustration being described, the database 206a is set up that each session is tagged to a unique number which happens the date and time to the minute that it was started. Thus, the files can continuously be updated and added to.

Returning to FIG. 26, it is important to note that if the Doppler statistics and measurements that were gathered and/or calculated during an embodiment that used the Doppler System 800, then at the block 442, the sessions file referenced therein would also include the Doppler measurements and statistics which include distance of the shot, the release time for the shot, the release arc of the shot and entry angle or arc of the shot. The Doppler measurement and statistics are embodied and included in the sessions file and uploaded in the manner described herein. As mentioned earlier herein relative to FIG. 16, once the data and statistics are captured and uploaded to the server 206 (FIG. 10) associated therewith, the users may create, view, save, use and/or print customized reports and use the customized reports. The creation of the reports, use of the reports and the reports themselves will now be described.

As mentioned earlier herein relative to block 234 in FIG. 16, after the data and statistics are captured, measured and/or calculated, they can be viewed, stored, saved and used. In the embodiment being described, customized reports can be created and used. For example, the customized reports can be viewed by a user, such as a coach, trainer or player, to improve the player's basketball playing skills. For example, if a player learns and understands that his shooting efficiency at one location or area on the basketball floor is below a predetermined desired shooting efficiency, then the player can program the gun or ejector 20' to increase the frequency of practice shots at that position in order to improve the player's efficiency. The procedure for creating the customized reports will now be described relative to FIG. 27.

Figure 37:
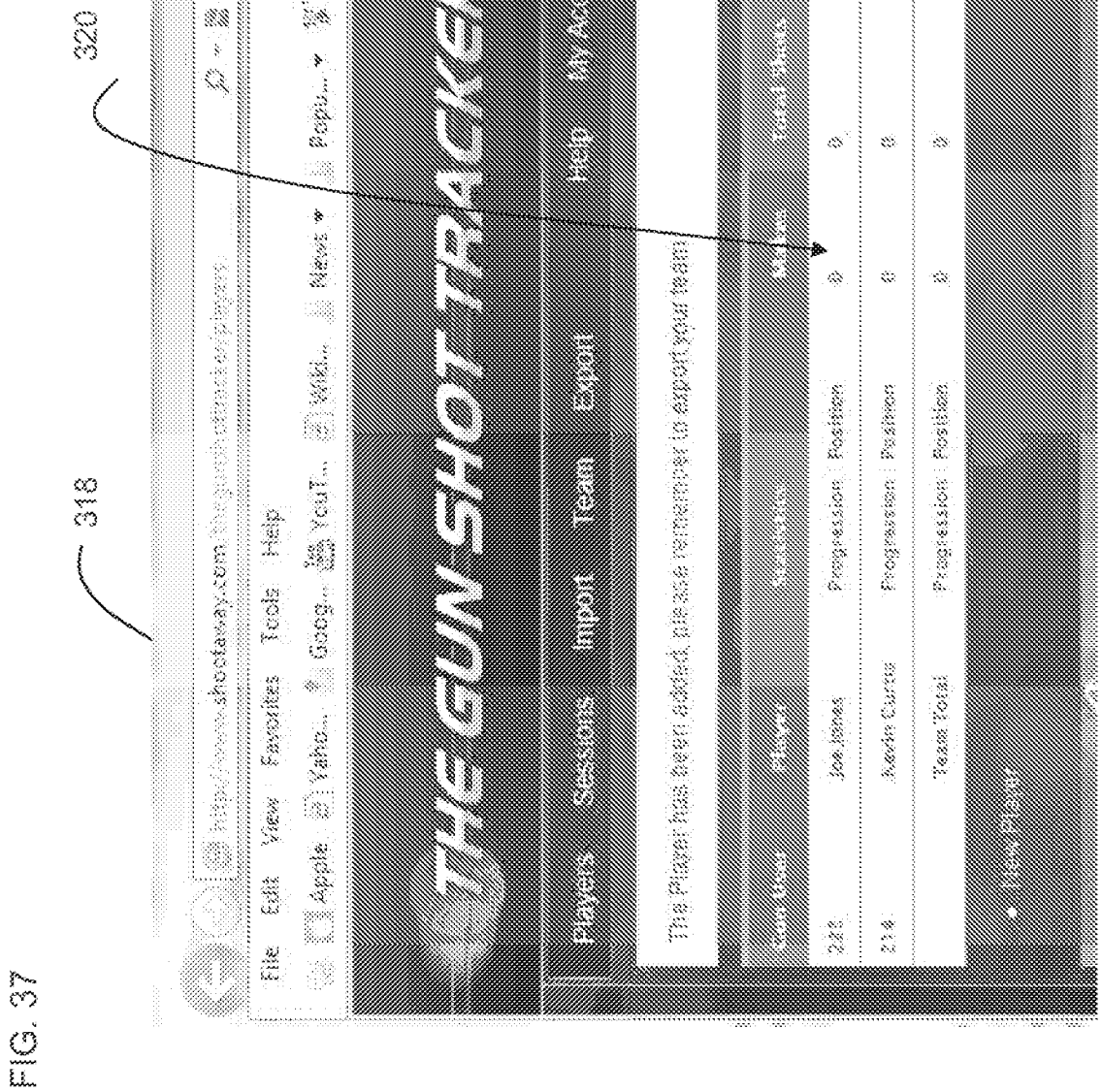
Figure 38:
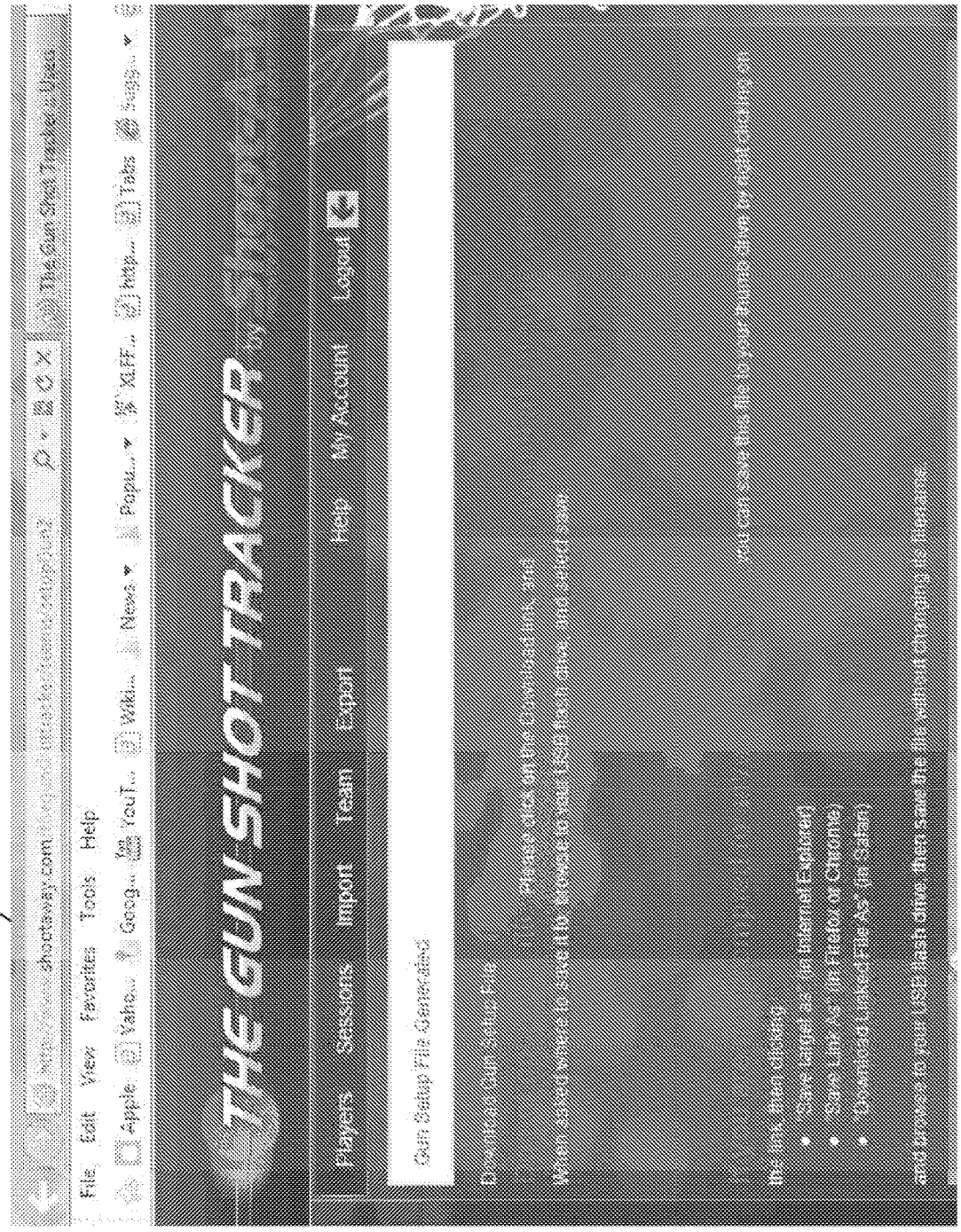
Figure 39:
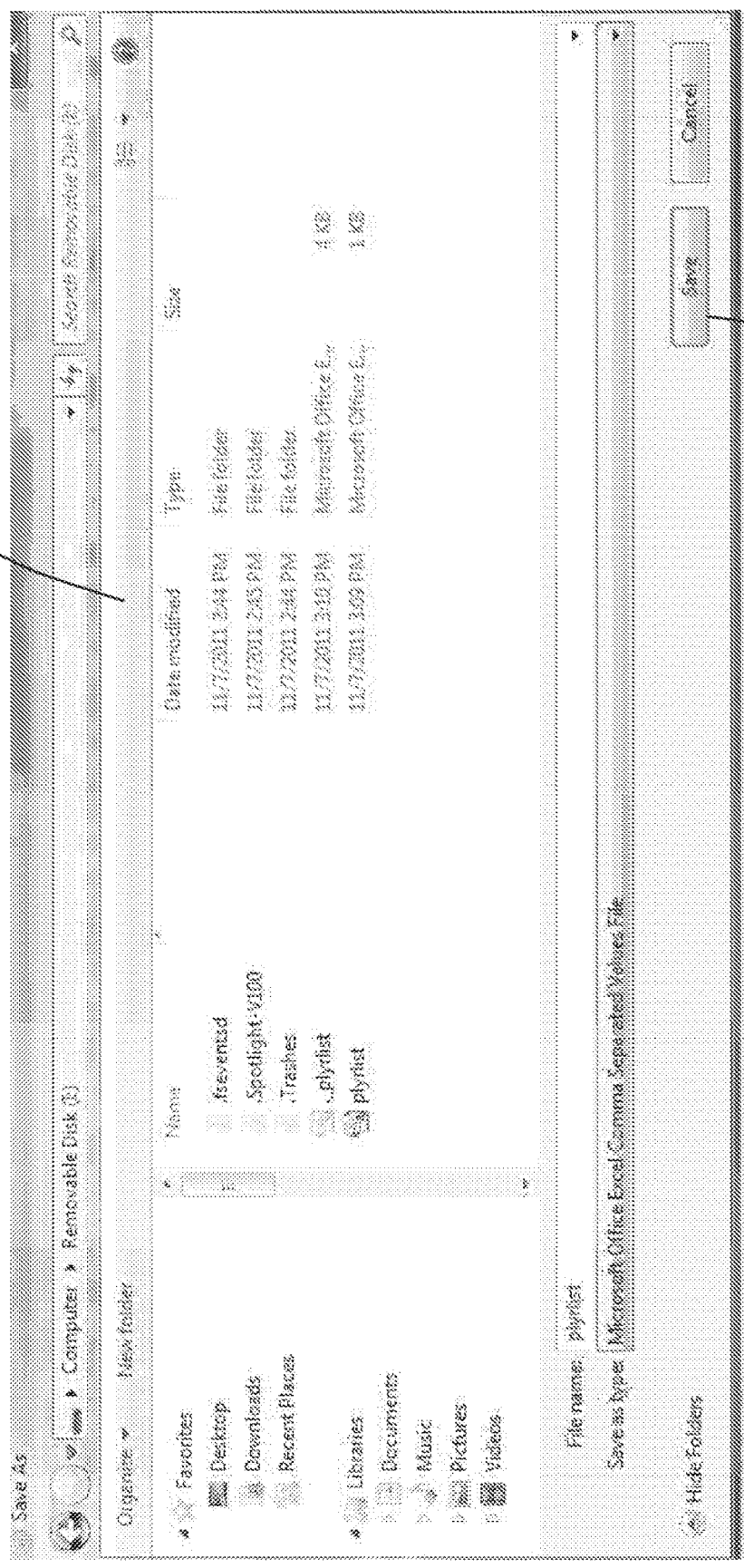
Figure 40:
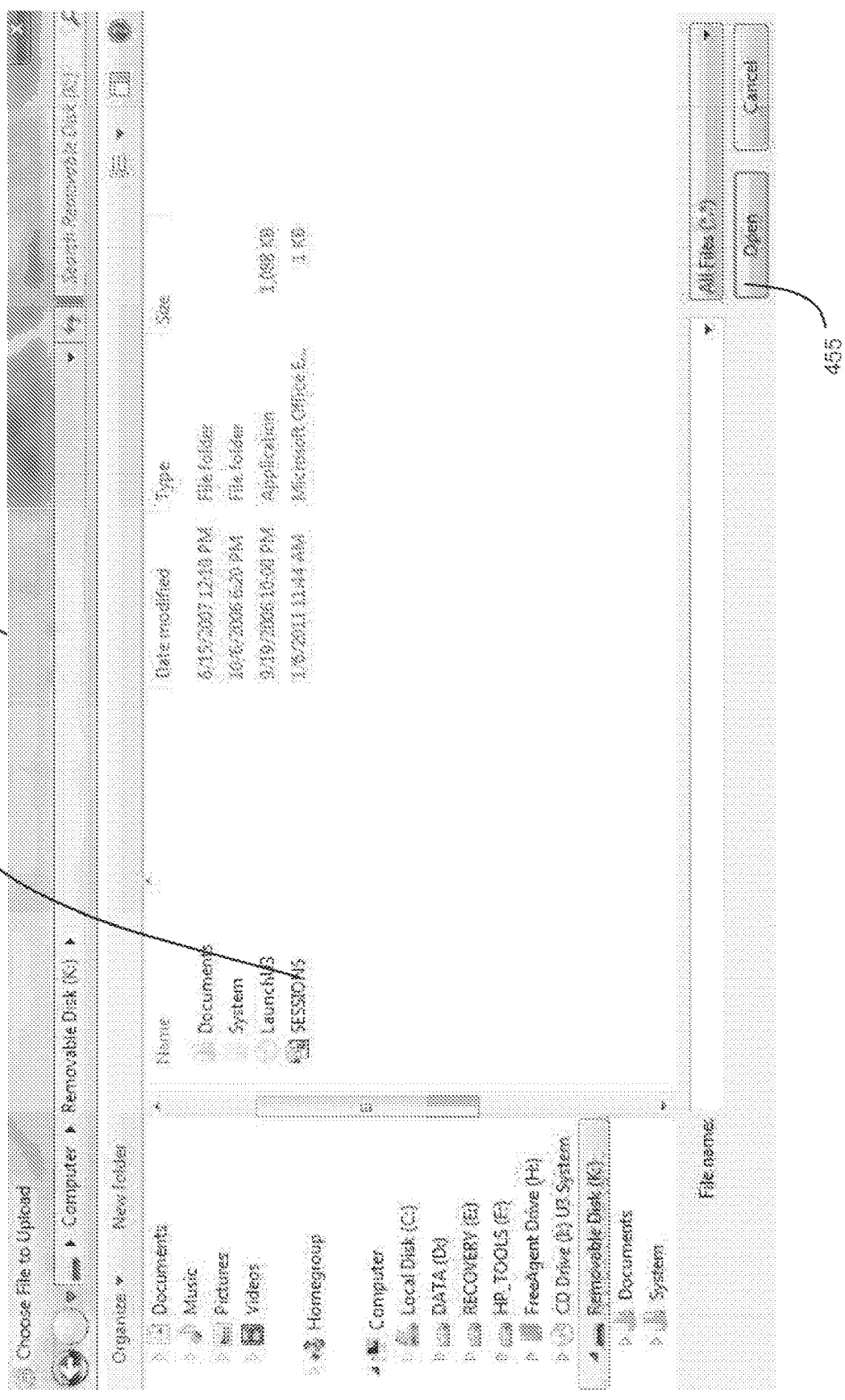

After the player has tracked their shooting data and statistics and the user uploads the "SESSIONS" file containing the data and statistics to the website WS, the user goes to the website WS login graphical user interface 284 (FIG. 34) and logs into the website WS using his or her username and password (block 450 in FIG. 27). The user may then actuate the player's button 304 in the graphical user interface 306 (FIG. 36) and is then presented with the listing of the players in area 320, as illustrated in FIG. 37 described earlier herein. At block 452 in FIG. 27, the user selects a particular shooter or shooters or even a team for which they would like an in-depth report.

The routine continues to decision block 454 wherein the user determines whether or not it wants to do a chart type comparing to other shooters. If not, the routine continues to decision block 456 where it is determined whether the chart type for an individual shooter is a progression chart. If it is not, the routine proceeds to block 458 and the user selects chart type; Made/total Shots, Shots, Percentage, Percentile at each Shooting Location and/or Doppler data of statistics.

If the decision at decision block 456 is yes, then the routine proceeds to block 460 whereupon the user selects the date range they would like the chart to include. For example, a beginning date, an ending date or total shots in a career which covers all dates is selected (block 460). After the procedures in block 458 and 460, the routine proceeds to allowing the user to select the rankings/chart at block 468 described later herein.

If the decision at decision block 454 is affirmative, then the user wishes to do comparisons to other shooters and the routine proceeds to block 462 where the user selects the location they would like to include which could be shooters from the local team only, the local county only, the state (e.g., all shooters in the state of Ohio), the country (e.g., all shooters in the U.S.A., France, Italy or China), or shooters from around the world. At block 464, the user selects the minimum and maximum age so that the report includes other shooters in the age range. Alternatively, the user may select all ages so that the report will compare the player, such as player A, to one or more other players of all ages. The routine continues where the user then selects (block 466) the shooting locations they wish to include in the chart or report. In the illustration being described, the shooting locations correspond to the buttons labeled 0-16 in FIG. 3 and the shooting locations 0-16 in FIG. 10. It should be understood that the selections mentioned in blocks 462-466 do not necessarily have to occur in any particular sequence.

The routine proceeds to block 468 where the user selects the rankings or chart type so that the chart or report is displayed on a screen, terminal or display, such as a monitor (not shown) coupled to the computer 202 or 204 or other display that the user is using to access the website WS. As mentioned earlier herein, the display may be associated with a computer, such as computers 202, 204, or other smart device, such as an iPad, iPhone, Android, Blackberry or other device that has the capability of allowing a user to access, view and use the website WS. Note that when the user selects which shooting locations they wish to include, they proceed to block 460 where the user selects the date range they would like the chart to include, including the beginning date, ending date or the total shots in a career which covers all dates as explained earlier herein relative to block 460. After block 460, the routine proceeds to block 468 where the user selects "show rankings" chart or report. As mentioned earlier herein relative to blocks 458 and 460, which concerns creating a chart or report when a comparison is not desired, after the user makes the selections referred to in block 458 and 460, the user selects the show rankings/ chart at block 468 as shown. It should be understood that the order of selection in blocks 462-466 is not strict, and a user can select criteria in any order as described herein.

After block 468, the routine continues to block 470 where the user views the rankings chart or report and then proceeds to decision block 472 where it is determined whether or not the user wishes to print the chart or report created. If he does, then the chart or report is printed (block 474), and thereafter or if the decision at decision block 472 is negative, then the user determines (block 476) whether or not he desires to email or publish the newly-created chart or ranking. If he does, then the routine proceeds to block 478 or the user is provided with a graphical user interface in which the user can elect to email the chart or report or ranking or otherwise publish it. In this regard, the website WS provides process and means for conventionally publishing the chart or report on website WS or using conventional social media, such as Twitter®, Facebook®, YouTube® or the like.

If the decision at decision block 476 is negative or after the publication referred to in block 478, the user determines at decision block 479 (FIG. 27) whether or not he wishes to create another chart or report. If he does not, then the procedure ends, but if he does, then the procedure proceeds to block 452 where the user may again select the shooter, shooters or team they would like an in-depth report on. It is important to note that the general procedure and steps referred to in FIG. 27 are shown in the order mentioned, but they do not have to occur in this exact order and the user may create reports for an individual player, group of players or team and also create comparison reports using the graphical user interface and the criteria described herein which may be selected in any order. In one form of the invention, the sorting variables may be presented on website WS as shown in FIGS. 46 and 51 with selection buttons or boxes (not shown) next to the variables for selection.

It should also be noted that the procedure for creating the customized reports on the website WS relative to FIG. 27 is useful for creating reports that have data and statistics that are not dependent on or that do not utilize or list Doppler measurements of the type mentioned earlier. Alternatively and in another embodiment of the invention, the charts and reports may also comprise Doppler data and statistics that include the Doppler measurements and calculations provided by the Doppler System 800 described earlier herein. If this is the case, then at blocks 458 and 460, the user can also select the specific Doppler data measurements or calculations, such as the distance from the basket from each shot, the player's release time, the release angle and the entry angle or arc at which the ball is being received in the hoop 14', that will be included in the chart or report.

After the user selects the chart or report criteria referred to in block 458 and 460 and/or the Doppler data or statistics, then the routine proceeds to block 468 as described earlier herein. Thus, it should be appreciated that reports or charts including the Doppler data and statistics are optional and may be selected by the user when creating the charts or reports for comparison or for an individual player or team of players. As mentioned earlier herein relative to FIG. 25 and blocks 436 and 440 in that figure, note that all of the variables mentioned earlier therein may be picked in any combination or permutation and the system 200 provides means for doing so. As mentioned earlier, in one form of the invention, the sorting variables may be presented on website WS as shown in FIGS. 46 and 51 with selection buttons or boxes (not shown) next to the variables for selection.

Advantageously, the system 200 and method described herein provides means, apparatus and methods adapted to enable shooting games and challenges, including the challenges mentioned and described earlier herein, as well as real-time or non real-time challenges between or among players of the same team or players of different teams and regardless of where those players are located or the time when they are shooting or the like. The system 200 and procedures and methods described herein also permit real-time competition and non real-time competitions between players of the same or different teams and regardless of where those players are located. By calibrating the gun or ejector 20' in the manner described earlier herein and providing the means and apparatus for saving, viewing and printing reports, including comparison reports, the user can compare himself or herself to others.

Figure 28A:
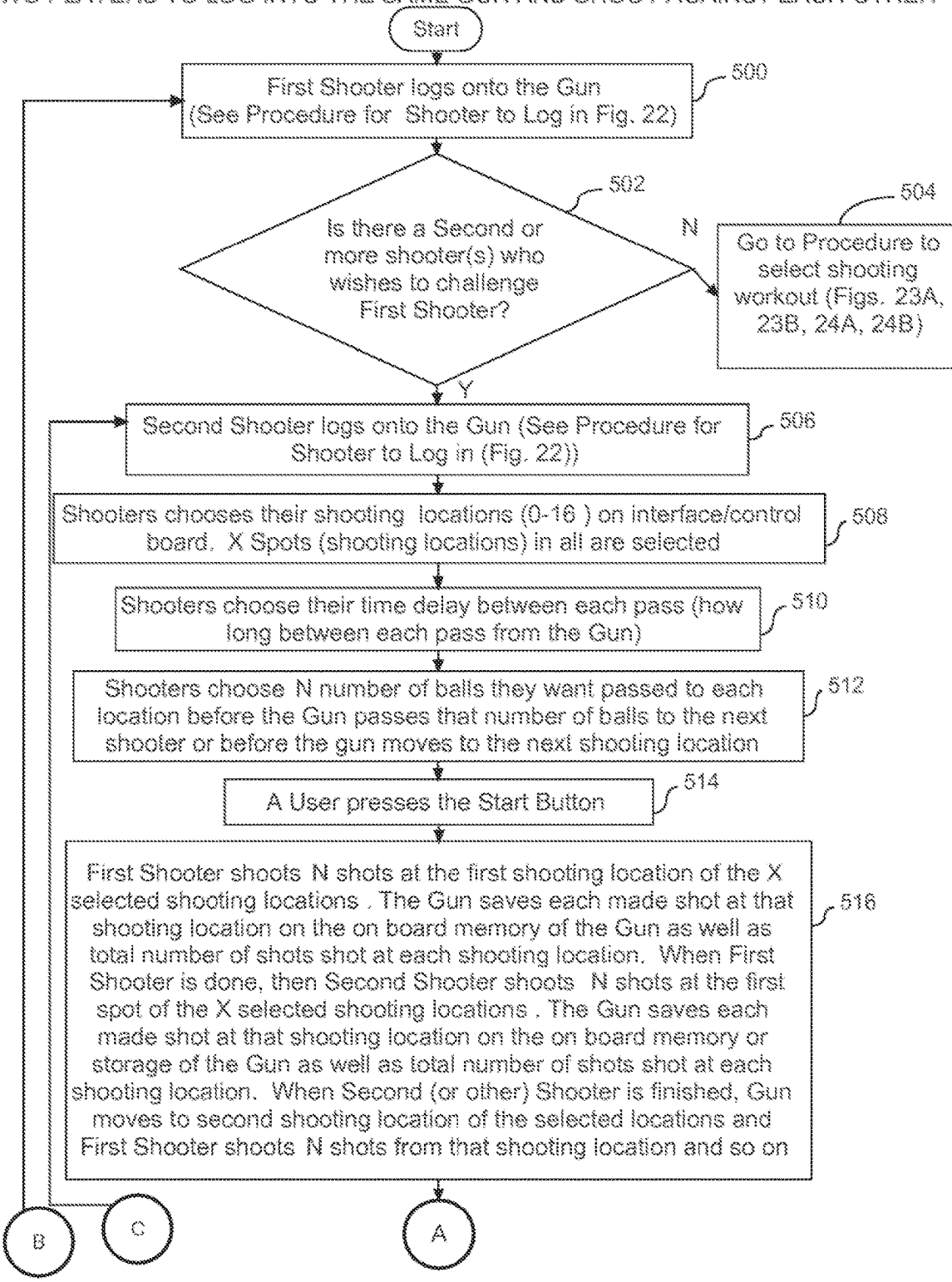
FIGS. 28A-28B is another illustrative challenge mode, which is a real-time challenge in the illustration.
Figure 28B:
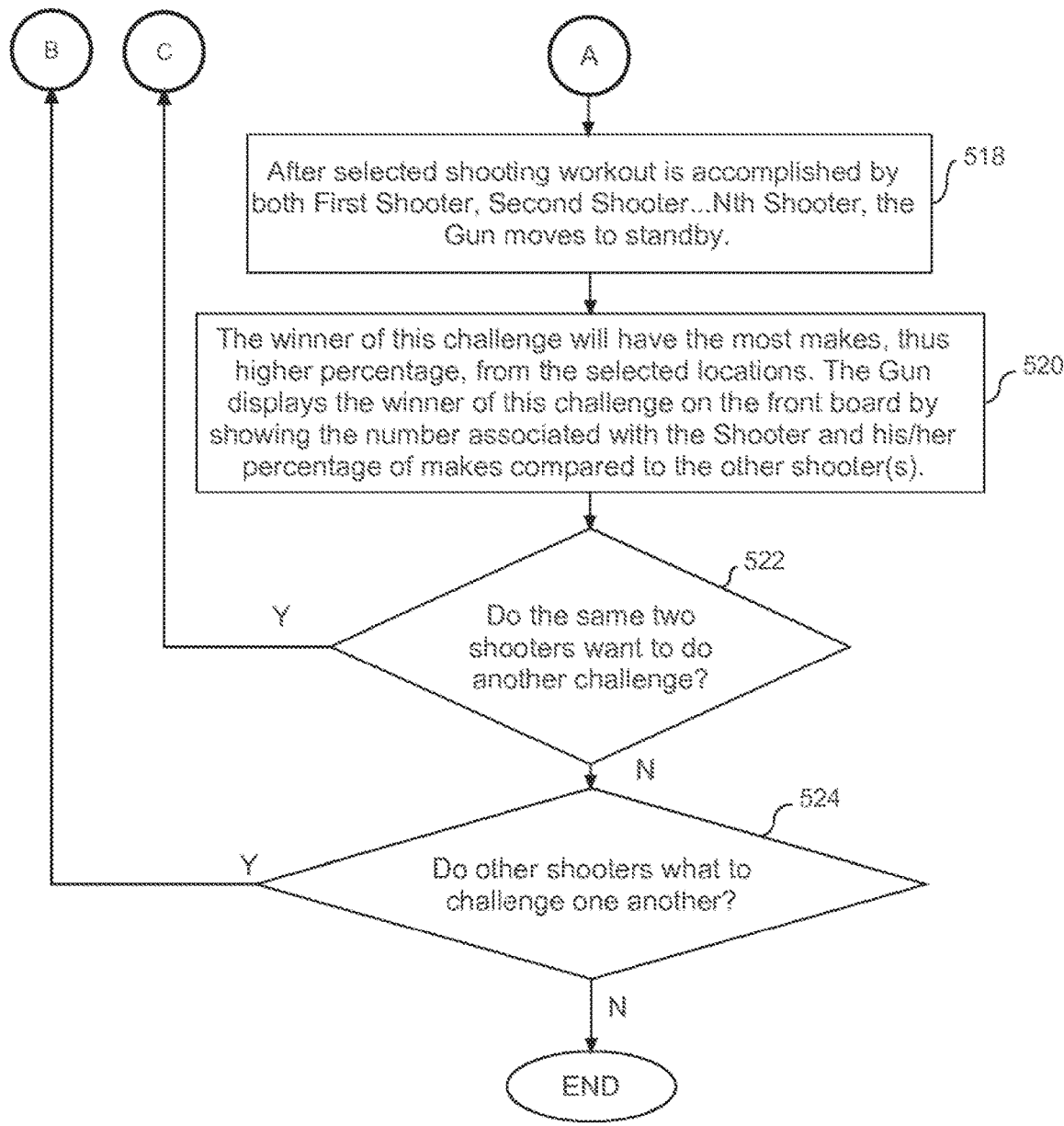

FIGS. 28A, 28B and 29 provide two illustrative shooting challenges or routines. It should be understood, however, that other shooting challenges are contemplated and the system 200 and methods described herein enable users to develop customized shooting challenges for use by players on the same team or players on different teams, regardless of the geographic location of the players or the time which the players shoot. In an alternative embodiment, the system 200 and method provide a procedure for real-time challenge for two players who may use the same gun or ejector 20' at the same location. This procedure will now be described relative to FIGS. 28A-28B.

This procedure starts at block 500 wherein the first player or shooter, such as Player A, logs onto the gun or ejector 20' using the shooting logon procedure described earlier herein relative to FIG. 22. It is then determined whether one or more other players or shooters, such as Player B, wishes to challenge the first player and if not, then the routine proceeds to block 502. Then, the routine proceeds to block 504 where the user proceeds to login and use the gun or ejector 20'. If the decision at decision block 502 is affirmative, then there is at least one or more other players or shooters who wish to challenge the first shooter, and so, the routine proceeds to block 506 where the second shooter also logs into the gun or ejector 20' using the procedure described earlier herein relative to FIG. 22, as shown at block 506 in FIG. 28A. The shooters choose their shooting locations (block 508), the time delay using the buttons 43 (FIG. 3B) on the interface 40 as described earlier herein (block 510 in FIG. 28A) and the shooter(s) choose the number of balls (block 512) that they want passed to each selected location or pre-programmed location (if a pre-programmed drill was selected). The Players A and B alternate shooting in the illustration. Player A first shoots at a location, then Player B and so on. After shooting is complete at a location, the gun or ejector 20' passes the number of balls to the next shooting location where Player A shoots, then Player B and so on. After Players A and B have shot at the second location, the gun or ejector 20' launches balls to the next selected location. Thus, the system 200 has the players alternate after shooting the number of shots at each location. It should be understood however, that the system 200 could have player A go through the entire program and then have player B shoot or it could have them alternate every shot.

As mentioned earlier herein, one feature of the embodiment being described is that the shooters can select any arrangement or order of the positions by actuating one or more of the plurality of buttons 41 (FIG. 3A). The controller 32' stores the selected locations and in the order in which the buttons 41 (FIG. 3A) were actuated, thereby giving the users the ability to customize the shooting locations and the order in which the gun or ejector 20' will eject or launch balls to the shooting locations. This has been found to be very advantageous when simulating a game condition. For example, a shooter may shoot the ball from the top of the key at position 8 (illustrated in FIG. 10) and then immediately move to another position, such as a position along a vector along the "0". This simulates a game condition when the basketball 12' hits a side of the rim 14' when a shot is missed and is deflected after a shot from the top of the key, straight toward a sideline. It may be important for the player to practice shooting at both positions in that order and the system 200 and method described herein enable the players or shooters to select positions along imaginary vectors, lines or direction extending from the gun or ejector 20' in the directions identified by the numbers or locations 0-16 in FIG. 10 in the illustration. For example, actuating the button 41 labeled "8" in FIG. 3A and then actuate the button 41 labeled "0" on the interface 40, the gun or ejector 20' launches basketballs along the vectors toward the position 8 (FIG. 10) and then toward the position 0. As mentioned earlier, in one embodiment, the gun or ejector 20' launches the number of balls programmed to each position in the order that the positions were selected using the interface 40.

At block 514 in FIG. 28A, the user presses the start button 70' (FIG. 3D) to begin the routine. At block 516 (FIG. 28A), the gun or ejector 20' begins launching basketballs 12' to the first shooter who shoots the preselected "n" number of shots programmed at block 512 at the first of the shooting locations selected at block 508. The gun or ejector 20' saves each shot that it senses being made using the sensor 33' at each shooting location on the controller or board 32', which stores the information in the storage device 44'. Note that the gun or ejector 20' also saves and stores the total number of shots taken on the storage device 44'.

When the first shooter is done shooting at each of the locations selected at block 508, then the second shooter begins shooting "n" number of balls selected at block 512 at the various shooting locations programmed at block 508. The gun or ejector 20' again saves this data along with the shots made as sensed by the sensor 33' and the total number of shots taken at each of the shooting locations programmed at block 508. When the next or other shooters is/are finished, the gun or ejector 20' begins ejecting balls to the first shooter at the next location that was programmed at block 508. Again, Player A shoots shots at a spot 1, then Player B shoots shots at spot 1, then Player A shoots shots at the next spot, then Player B shoots shots at the next spot and so on.

Note that the gun or ejector 20' delays the time between each pass at a shooting location in accordance with that which the user programmed at block 510. An additional delay time may also be used as in the first embodiment described earlier herein to delay the time between which the shooter begins shooting basketballs when changing from one location to the next location. For example, an additional delay time of five seconds may be required for a player or the first shooter to move to the next shooting location and the delay time that the user selected at block 510 may not be sufficient to enable the player to get to the next position.

Accordingly, the gun or ejector 20' controller 32' may comprise an additional pre-programmed delay time for ejecting basketballs 12' when the location of shooting changes.

The routine continues to block 518 (FIG. 28B) where after the selected shooting workout is accomplished by the first shooter, second shooter . . . to the nth shooter, the gun or ejector 20' enters a standby mode. The winner of the challenge may be displayed on the display 45' (FIG. 10) by the user code or number assigned to the player. At block 520 (FIG. 28B), the gun or ejector 20' displays the winner of the challenge as being the player with the most makes, thus the highest percentage of makes from the selected or programmed locations. Again, the controller 32' of the gun or ejector 20' causes the number associated with the shooter/player to be displayed along with his or her percentage of makes compared to the other shooter's percentages.

The routine proceeds to decision block 522 (FIG. 28B) wherein it is determined whether the same shooters want to do another shooting challenge, and if they do, then the routine returns to block 506 as shown. If they do not, then it is determined (decision block 524) whether other shooters want to challenge one another to a shooting challenge. If they do, then the routine proceeds to block 500 wherein other shooters can perform the shooting challenge. If they do not, then the procedure ends.

It should be understood that the procedure is not dependent on Doppler statistics or measurements or data provided by the Doppler System 800, but such Doppler data or statistics may also be incorporated into the shooting challenge. The system 200 can detect where ball is being shot from within a certain accuracy and require the second player or shooter, to retake said shot until he takes the shot from "about" (e.g., within a foot in the illustration) of the first shooter's general shot distance. The system 200 notifies shooter of this by flashing timing lights or other notice on Display 45' (FIG. 10) to make shooter aware that last shot did not count.

It should be understood that the procedure described in FIGS. 28A-28B is a real-time challenge mode during which two or more players are competing against each other using the same gun or ejector 20'. In another illustrative embodiment shown in FIG. 29, a shooting challenge is provided for players from different teams at different locations. For ease of description, it will be assumed that at least one gun or ejector 20' is located at two or more geographically distinct locations and they have been calibrated (as described relative to FIG. 21) for a first team, such as team A in the illustration, and a second team, such as team B, that is using a different or second gun or ejector 20' at a different geographic location. One or more players on team A shoot until the routine ends (block 528). The data associated with one or more players from team A shooting at the various positions are uploaded and stored on the website WS server 206 (block 530) in the manner described earlier herein.

The second system 208 having a gun or ejector 20' launches balls to the same or different positions that were pre-programmed or user-programmed positions for the players on team B (block 532 in FIG. 29). One or more players shoot until the routine ends (block 534) and then data and statistics for the one or more players from the second team B shooting at the various positions are uploaded and stored on the website WS server 206 as shown in block 536. It should be understood that the players from each of the teams A and B may shoot at the same time or at different times. It should also be understood that in one embodiment, the players at the second location of team B may program the gun or ejector 20' with the exact same pattern of programmed locations that were programmed by team A. Alternatively, the teams may program their gun or ejector 20' so that they shoot at totally different locations or where only a few locations overlap, the statistics and data for each of the locations is gathered and stored cumulatively for each location by the system 208 so that shooting data for various distance and locations are stored cumulatively and comparisons may be made over a period of time using data captured over a period of time.

Figure 42:
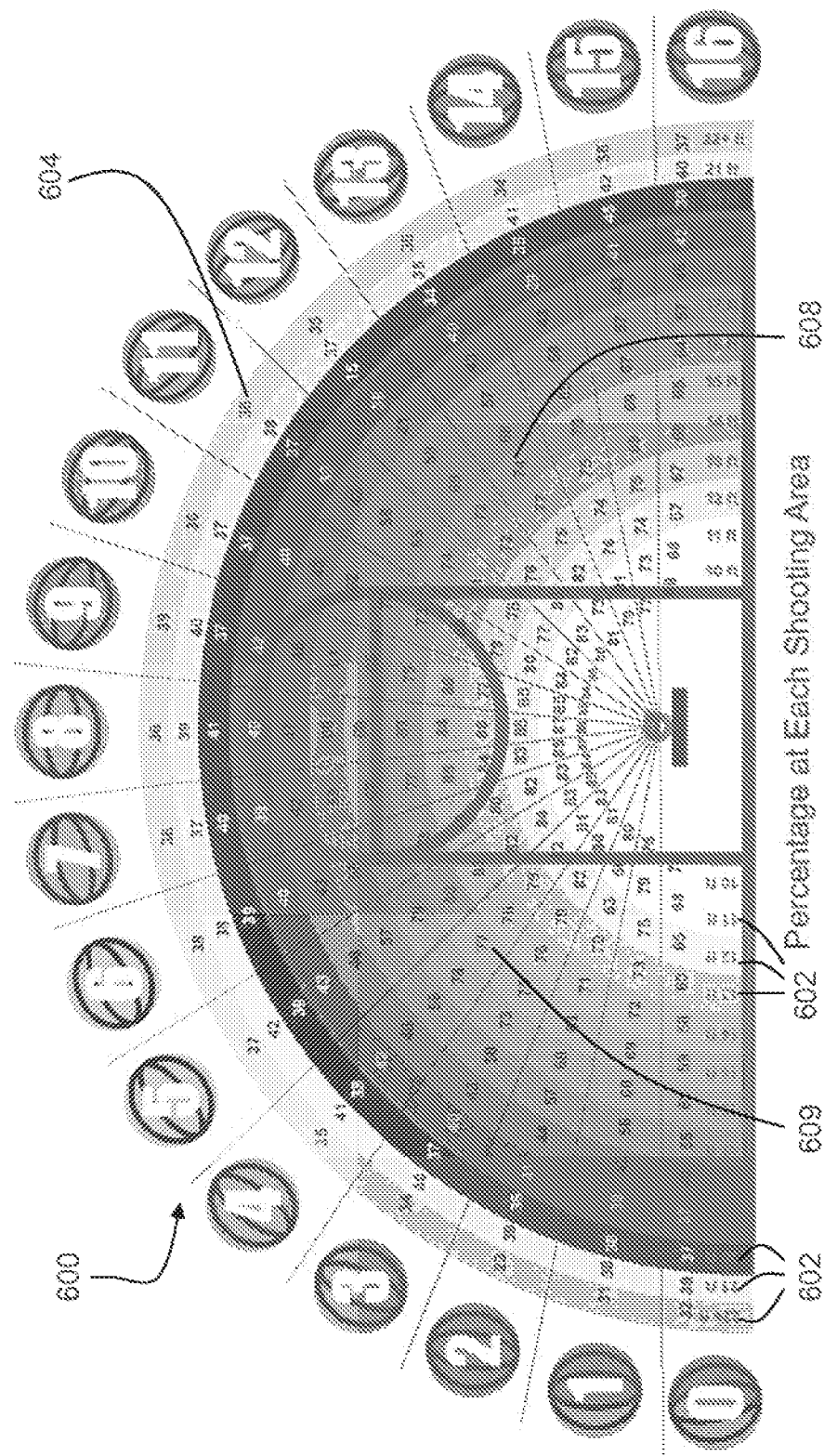
FIG. 42 is a scatter diagram or matrix illustrating various Doppler statistics and shooting percentages for various distances along various vectors corresponding to the shooting locations selected by a user.
Figure 43:
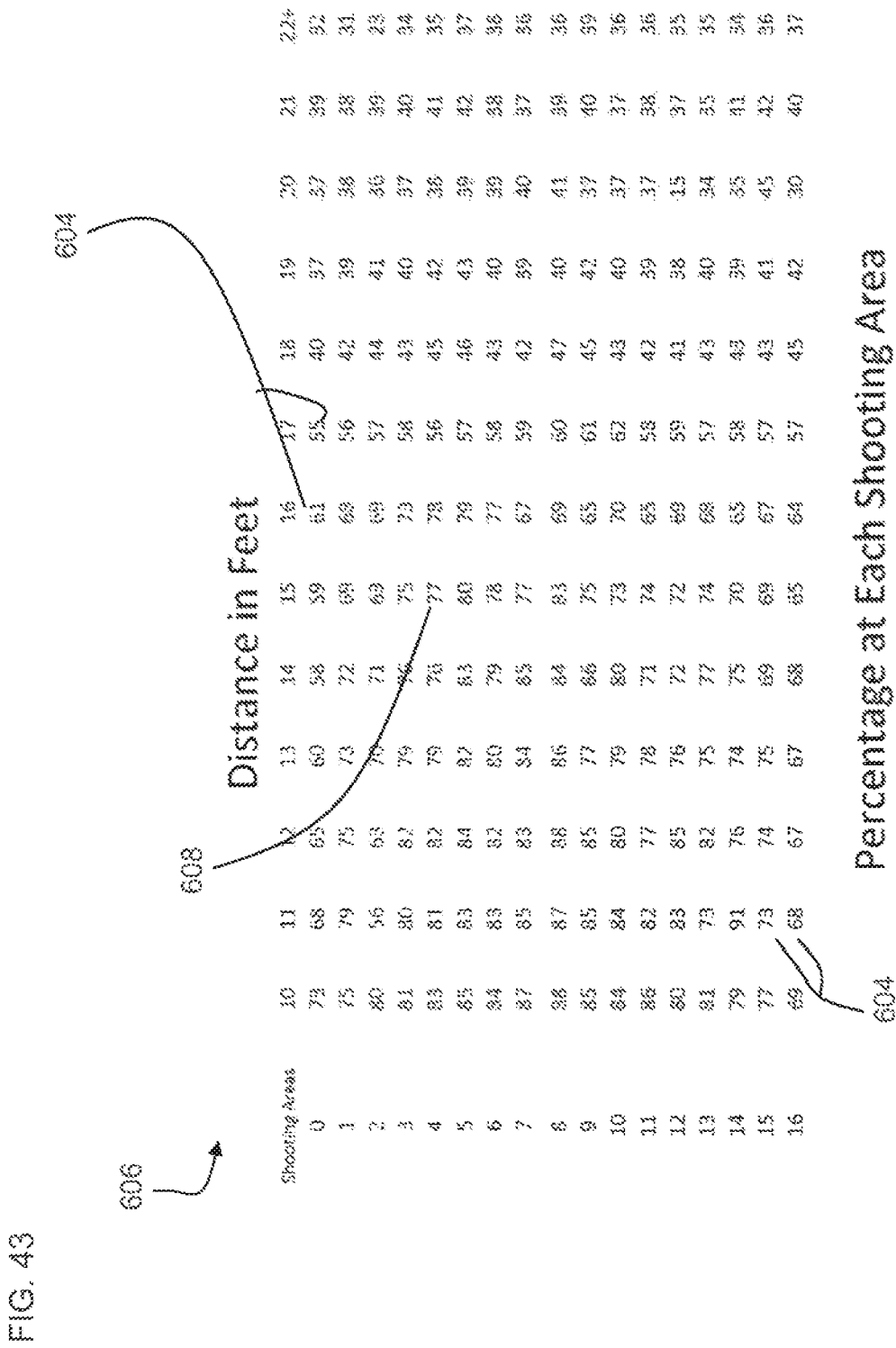
FIG. 43 is a table illustrating the data visually shown in the scatter diagram in FIG. 42.

Thus, the system 200 enables the users to compete in real-time or in non real-time because it is capable of collecting and storing data and statistics, including Doppler data, associated with one or more shooting sessions and then accumulating and storing the data over time and storing it on the website WS system and/or server 206. This is particularly useful when using the Doppler data and statistical measurements provided by the Doppler System 800 described earlier herein. In this regard, the Doppler measurements are captured, measured and/or calculated by the microprocessor 910 (FIGS. 14 and 15A) and schematically shown as 32' in FIG. 10 and may be stored on the website WS. Thereafter, a player's percentage of makes at numerous distances and positions, may be stored, viewed, published, printed and the like. For example, FIG. 42 illustrates a scatter or mapping diagram and FIG. 43 shows a report 600, both of which may be stored on the server 206 and used for competitions and comparisons as described herein.

Returning to the illustration in FIG. 29, recall that it is presumed that the players of team A are using a first gun or ejector 20' at a first geographic location and the players from team B are using the second system 208 (FIG. 10) having second gun or ejector 20' at a second geographic location. At decision block 538 (FIG. 29), it is determined whether more players from team A and/or team B are shooting in addition to the first players that have shot from those teams. If they are, then the routine loops back to block 526 where the second and subsequent players may shoot from the pre-programmed positions. If not, then the shooting challenge is complete for the teams A and B and the routine proceeds to block 540 where it is determined whether other players from other teams (i.e., teams other than A and B) are shooting. If they are, then a gun or ejector 20' which may be the first gun or ejector 20', second gun or ejector 20' or a third gun or ejector 20' located at a third geographic location launches balls to the pre-programmed or user programmed position for the next team (block 542 in FIG. 29). The players shoot until the routine ends (block 544).

Thereafter, data and statistics from the one or more players from the subsequent team(s) at the various positions are uploaded and stored on the website WS server 206 (block 546). If the decision at decision block 540 is negative or after the data and statistics are uploaded and stored as described relative to block 546, the system 200 enables users, such as teams, players, coaches and other interested parties, to view and compare player and team statistics of one team, such as team A, against the player and team statistics for another team, such as team B or other teams, as shown at block 548. The shooting challenge is then complete. Reports may be created and printed and the like as described herein.

As mentioned earlier herein relative to FIG. 20, FIG. 27, FIG. 29 and the like, the system 200 provides means for saving, viewing, printing, publishing the reports comprising data and statistics, comparisons, competitions and the like. The user may access the website WS with a conventional internet connection using a computer (e.g., computers 202, 204), smart phone or other smart device, such as an iPad, iPhone, Blackberry or the like. The user logs onto their account to access, publish, view and print out multiple detailed reports comparing local shooters' statistics and data, including but not limited to the number of made shots, number of shots taken, percentage of made shots relative to number of shots taken and comparisons of such statistics to a local, regional, national or international bank or data base of other shooters across the region, state, country or the world. The comparison reports and charts may be created on a cumulative basis, average basis and/or percentile basis and can be sorted in any particular arrangement using a plurality of criteria, such as age, date, time, gender, distance or other criteria as mentioned earlier herein.

The system 200 also enables the players' statistics and data to be stored in the storage device 44' (FIG. 10) coupled to the controller 32' and located on the gun or ejector 20' so that when a user uses the gun or ejector 20', the controller 32' can cause the shooting statistics and data for the positions being selected to be displayed on display 45' during a shooting session. For example, if a first player in Ohio has programmed the gun or ejector 20' to shoot one or more balls to the location 8 before beginning the shooting session, the controller 32' will cause the gun or ejector 20' to eject or launch balls to the position 8. The gun or ejector 20' may cause the display 45' to display the position number (i.e., "8"), the historical percentage of made shots at the position 8 by the local player, the shooting percentage for that position based on either average, median totals or total shots for a work out depending on what the user prefers. Alternatively, the controller 32' may cause a percentage of made shots at a position or location on a team-wide, regional, state-wide, national and international basis.

With the Doppler measurement capability provided by the Doppler System 800, it should be understood that each of the positions 0-16 (FIG. 10) in the example may be viewed as imaginary vectors having an originating point associated with the gun or ejector 20' and which extend outwardly away from hoop 14' in the direction of the locations or spots 0-16. One vector is illustrated in FIG. 10 and labeled $V_{13}$ for position 13. The Doppler measurement system 800 enables Doppler measurements and data to be captured at any position along the vector. For example, the Doppler System 800 enables the Doppler data and measurements to be captured along the base line vector position 0 at any distance from the gun or ejector 20', such as three feet, three-and-a-half feet, four feet, . . . twenty feet, etc. Typically, the Doppler will cease providing precise measurement data at about 35 feet. It should also be understood that the Doppler measurement system 800 rounds the measurements to the nearest foot so that, for example, if the Doppler System measures a shot taken at ten feet, seven inches, it rounds the measurement to eleven feet for ease of simplicity in comparisons.

As mentioned earlier herein, the server 206 (FIG. 10) comprises the database 206a on which the data and statistics have been uploaded to the website WS are saved. The user may access the website WS in the manner described earlier herein and then may generate the various reports, charts, comparisons and the like as described herein relative to FIG. 27. Some of these reports and charts will now be illustrated.

One illustrative report is shown in FIG. 42 wherein the individual shooting statistics report, scatter or mapping diagram for a particular shooter, Kevin Curtis in the illustration, is shown. Note the shooting positions 0-16 in the report and the Doppler data or statistics associated with the player's shooting. Thus, notice in the illustrative report shown in FIG. 42 that distance data measurements or calculations for a plurality of locations have been rounded off to the nearest foot, which are shown and labeled 602 in the illustration. The system 200 and the controller 32' and shooting efficiency calculator 32b' (FIG. 10) uses the Doppler measurement system 800 which measures, senses and/or calculates the measurements of the various distances and the sensor 33' is used to capture the number of made shots at each distance. The controller 32' and shooting efficiency calculator 32b' can then calculate a makes percentage which is associated with each distance along the vectors as shown. Again, one should understand that the various positions or shooting locations 0-16 may be considered as vectors along which the ball is ejected or launches by the gun or ejector 20' and the Doppler System 800 captures the measurement from where the player caught the ball and shot the ball from. As mentioned earlier herein, the Doppler System 800 also enables the calculation of the player's release time, which is the time between the point in time when the player captures the basketball and then shoots it toward the rim 14'. Other Doppler statistics, such as an arc of the shot as released by the player and the entry arc of the ball 12' as it approaches the hoop or rim 14' are calculated by the Doppler System 800 as described herein.

The report 600 (FIG. 42) may be visually displayed on a display associated with the computer 202 or 204 or other device in the form shown. Of course, the unique layout of the scatter diagram 600 provides the user with the means and ability to quickly view a player's performance at the various distances and positions on the basketball playing area. Note that the report 600 has the percentages 604 listed for each of the distance positions measured by the Doppler System 800. The report 600 may also be provided in a table format, such as a table 606 in FIG. 43. Note that the percentages are shown in the table along with the shooting area and the distance in feet as measured by the Doppler System 800 herein. For example, as illustrated in FIGS. 42 and 43, the shooter's percentage when shooting from fifteen feet along an imaginary vector $V_{13}$ (FIG. 10) is 74%, as illustrated by the data labeled 608 in FIGS. 42 and 43. In contrast, the percentage from fifteen feet along vector or location 4 is 77% as shown by the data labeled 609.

Advantageously, the system 200 provides a convenient and easy means and process for gathering, calculating, displaying, printing or publishing shooting data and statistics regarding a player's shooting ability at one or more of the shooting locations. The Doppler measurements provide accurate shooting measurements and comparisons because the player shooting, for example, along the vector $V_{13}$ (FIG. 10) associated with different shooting positions 13. This is valuable and important because players may shoot along a common vector, but not at the same distance along that vector. For example, one player may be shooting from sixteen feet, while an opposing player or subsequent player or even the same player may be shooting along the same vector $V_{16}$, but at a shorter or longer distance. Thus, unless the player was shooting from the exact same distance along a vector $V_{0-16}$ from the gun or ejector 20', the comparisons could be inaccurate.

Advantageously, the Doppler System 800 provides accurate measurements of the distances where the player(s) shoot the basketball from, and the system 200 collects statistics associated with each of those positions and the controller 32'/microprocessor 910 (FIGS. 10, 14 and 15C) measures, calculates and stores the data and statistics associated with each shot and its associated distance for use in creating the reports, comparisons and the like described herein. This feature of the embodiment provides for accurate analysis and comparisons of a player's efficiency in shooting and also accurate comparisons of a player's shooting efficiency and statistics when compared to one or more other players from the same or different teams.

The report 600 in FIG. 42 and table 606 in FIG. 43 may be displayed and viewed by the user using conventional means such as the user's computer 202, 204 or other device that the user uses to access the website WS. The report 600 and table 606 may be printed out and/or published in the manner described herein for use by the user.

It should also be understood that the reports for a team may also be generated in the same format or in a different desired format. Also, shooting percentage comparisons may be made, for example, for a region, state, nation or the world and may be created by the user using the website WS. The system, means and process for accomplishing this will now be described.

If the user desires to upload sessions data, it will follow the upload routine described earlier herein relative to FIG. 25. A representation or example of the "SESSIONS" file that is uploaded is shown in a format that is illustrated in FIG. 44. Note that the file format comprises the player's identification number in the column 700, the player's name 702, the date the session occurred in column 703 and then the shooting results from any of the shooting locations selected by the player or user. Note that the table is broken out by showing each location (0-16 in the illustration) being described and the total number of shots taken and made at each shooting of the shooting locations 0-16 in the illustration being described. For example, the report shows that the player Kevin Curtis (identified as "P214" in column 700) had a shooting session on May 20, 2010, that lasted for 58.04 seconds. At position or shooting location 7, the player took seven shots, as indicated by the data 706 in FIG. 44 and made five of those shots as indicated by data 708 in FIG. 44. Note that the player took a total number of nineteen shots and made twelve of those shots, as indicated by the data 710 and 712, respectively. The last column in the sessions data file identified by the part number 714 refers to the specific player number that differentiates each player in the data base no matter the team. In other words, 700 is the player number on that team and every team (Gun user) could have a 223 as a log in number for their Gun; but when it is uploaded to the internet, it is the number in column 714 that relates to this player and in the case of Joe Jones P223, his specific number tagged in the database is 19 in the illustration. In the illustration being described, the "SESSIONS" data file is a comma separated value file and will not have the actual first six rows illustrated in FIG. 44.

If the "SESSIONS" data includes Doppler measurements or calculations generated by the Doppler System 800, then the "SESSIONS" data file will include additional data as illustrated as shown in the FIG. 45. Note that in this "SESSIONS" data file the gun or ejector 20' collects or calculates six data points or facts including: 1) the shooting location, 2) the distance of the shot taken, 3) whether the shot was a make or miss, 4) the player's release time, 5) the player's release angle and 6) the entry angle into the hoop 14'. In the illustration being described, note that the player P223, Joe Jones, had a shooting session on May 20, 2010, and that his first shot, indicated by the column 720 in FIG. 45, shows that the shooting location was 0, corresponding to a base line shot identified by the location number 0 in FIG. 10. The column of data 720 also shows that the distance of his shot in feet was fifteen feet and that he made the shot, identified by the number 1 which represents a made shot (the number 0 represents a miss). The report shows the player's release time for the shot was 0.301 seconds, his release angle was 55° and the entry angle of the ball to hoop 14' was 45°.

Advantageously, a user, such as a coach, may note that the release angle, which represents the angle at which the player released the ball 12' toward the hoop 14', was 55°, but the entry angle was much shallower in that it was 45°. It may be a coach's desire to improve the player's entry angle to increase the probability that the basketball will approach the hoop 14' at a desired angle and thereby improve the player's probability of making the shot.

Note that the "SESSIONS" data represented in FIG. 45 shows the data for each and every shot taken by the player with the last column identified by the arrow 722 representing the last position of the last shooting location. Note that during any shooting session, the player may shoot from different positions. In the illustration shown in FIG. 45, Joe Jones shot in a serial order from shooting location 0, 1, 2, 3, 4 to the last shot taken, whereas in comparison, the player, Kevin Curtis, who had a shooting session on the same day, but he took all shots from the shooting location 8 in the illustration being described. Note also that the Doppler System 800 enabled the measurement and calculation of distances, release time, release arc or angle and entry arc or angle as shown. For example, Joe Jones shot at shooting location 0 from fifteen feet whereas at the shooting location 2 he shot from sixteen feet, as shown in FIG. 45. His corresponding release time, release angle and entry angle are different as well. Obviously, the Doppler measurements provide a user, such as a coach or trainer, extremely useful data in training a player to play basketball and to score.

As described earlier, once the sessions data is uploaded from the gun or ejector 20' or a computer, such as computer 202, 204, to the website WS server 206, the information can be used, evaluated, saved, viewed, stored, printed, published and the like. The following are some representative charts or reports that are selectively generated by the system 200 for use by the user.

FIG. 46 is a listing of the sorting variables that are presented to the user using drop down menus (not shown) in a graphical user interface. For example, all could be drop down decision boxes so if they were sorting on age, and did not want any above 10 years old, they would enter 10 in the box instead of "Any" and so on for the others. In the embodiment in FIG. 46, the sorting variables include:

| | Headings | Quantifiers | Explanation of Quantifiers |
|---|---|---|---|
| 1 | Choose Player | Roster List | Chose any player on your roster or entire team |
| 2 | Minimum Age | Any | range from 1-150 <= Maximum Age |
| 3 | Maximum Age | Any | range from 1-150 >= Minimum Age |
| 4 | Beginning Date | All | Beginning date <= Ending date |
| 5 | Ending Date | All | Ending date >= Beginning date |
| 6 | Gender | Both, M, F | Male, Female or include all shooters |
| 7 | Enter Shooting Locations | All | 0 through 17 |
| 8 | Chart Type | Makes/Total Shots/% | Sort based on makes, total shots or shooting % |
| 9 | City | All | Choose City |
| 10 | County | All | Choose County |
| 11 | State | All | Choose State |
| 12 | Country | All | Choose Country |

Once the user accesses the website and selects one or more of the sorting variables to be used in the report, the report accesses the website and is created in the manner described earlier relative to FIG. 27.

FIG. 47 illustrates an example where a user has selected various criteria for John Drew the website WS created the report 730 shown in FIG. 48. Thus, in the illustration, the user selected the player John Drew, the minimum age and the maximum age, 14 years and 25 years, respectively. The beginning and ending dates indicated in the example in FIG. 47 and the rest of the variables or criteria as illustrated in FIG. 47. In response, either the computer 202, 204 or and the website WS generated and displayed the chart or report 730 (FIG. 48). As mentioned earlier herein, the user may elect to publish this report or chart or may save it or print it out for use by him or others.

In the illustration in FIG. 48, the total shots for the criteria entered show the player John Drew to be ranked thirteenth when compared to other shooters around the world. In the illustration being described, the total shots shown in this report represent the total number of shots taken by a player at all shooting locations, which are the shooting locations 0-16 in the illustration being described. In this regard and as mentioned earlier, while the description herein has identified 0-16 locations, it should be understood that more or fewer locations may be provided on the interface 40 (FIG. 3) and programmed into the system 200 so that there are more or fewer identified shooting locations, respectively.

FIGS. 49 and 50 illustrate another example where a user has selected criteria including the entire team "Sangre" and identified all ages and a beginning date and an ending date. The user selected the shooting location 8 and identified the chart type as total makes, and the state and geographic territory as being All Cities and Counties within the State of Colorado. Note the resultant report 740 (FIG. 50) ranks the Sangre team second in total number of made shots at location 8 for the Colorado male teams. In this regard, note that the input information also includes gender, as illustrated in FIGS. 47 and 49 so that the data can be further sorted and organized based upon gender, as well as player, team and the other variables shown in the illustrations.

The examples illustrated in FIGS. 47, 48, 49 and 50 were not dependent upon or include Doppler measurements. In another embodiment of the invention, Doppler dependent measurements are provided and some illustrative examples of the input variables and reports generated will now be described.

It should be appreciated, again, that any number of reports and combinations of reports using one or more of the variables or criteria shown in the preceding and subsequent illustrations can be used. In other words, reports and charts may be created using any number of combinations or permutations of the input criteria or variables described in FIGS. 46 and 51. FIG. 51 illustrates the plurality of variables or criteria 742, which include Doppler measurements that may be presented to the user from the website WS and made available for selection. Note that the criteria or variables include:

| Headings | Quantifiers | Explanation of Quantifiers |
|---|---|---|
| 1 Choose Player | Roster List | Chose any player on your roster |
| 2 Minimum Age | Any | range from 1-150 <= Maximum Age |
| 3 Maximum Age | Any | range from 1-150 >= Minimum Age |
| 4 Beginning Date | All | Beginning date <= Ending date |
| 5 Ending Date | All | Ending date >= Beginning date |
| 6 Gender | Both, M, F | Male, Female or include all shooters |
| 7 Enter Shooting Locations | All | 0 through 16 |
| 8 Shooting Distance | All | 13, 14, 15, 16, 17, 18, 19, 20, 21+, all |

-continued

| Headings | Quantifiers | Explanation of Quantifiers |
|---|---|---|
| 9 Chart Type | Makes/Total Shots/% | Sort based on makes, total shots or shooting % |
| 10 City | All | Choose City |
| 11 County | All | Choose County |
| 12 State | All | Choose State |
| 13 Country | All | Choose Country |

Thus, the criteria or variable entries are provided to the user and the user can select the variables to create any type of chart desired based upon the variables selected. For example, FIG. 52 shows and illustrative selection of variables. In this example, John Drew was selected with the minimum/maximum ages indicated in the FIG. 52, and the other variables or criteria shown and described were selected. In response, the computer, such as computer 202, 204 or website WS created and generated the chart or report 743 which system 200 (FIG. 10) generated in response to the variables or criteria selected. Note in the illustration being described, the user-selected input criteria, shown in FIG. 52, that a shooting distance of twenty feet away from the hoop 14' was selected and a total shots taken at all locations (one or more of the locations identified 0-16 in FIG. 10 and on the interface 40 in FIG. 3). Note that the player chosen in the example was John Drew and in the report, it shows that John Drew of the Sangre school or team was thirteenth in total shots taken from all shooting locations of a distance of 20 feet between the dates Jun. 1, 2009 to Dec. 15, 2010 for males ages 14-25 in the illustration being described.

Another example is shown in FIGS. 54 and 55. Notice the input information shown in this example of FIG. 54 identifies a team, "Sangre", the position 8 and the distance of fifteen feet. The chart type was identified as "Total Makes" in the drop-down menu screen. The resulting chart or report 744 created by a computer, such as computer 202, 204 or website WS in response to this input information of FIG. 54 is illustrated in FIG. 55. Again, it shows the Sangre team's total makes for all dates for the shooting location or position 8 at a distance of fifteen feet along the vector defined by a line between the gun or ejector 20' and the position 8 shown in FIG. 10. In the illustration being described, the position 8 is at the center of the top of the key or an imaginary line bisecting and radially extending from a center axis of the basketball hoop 14' perpendicular to the backboard 16'.

Thus, it should be understood that the user can identify and select any combination or permutation of criteria or variables and the computer, such as computer 202, 204 or website WS will generate the corresponding report or chart for display, viewing, saving, printing, exporting, publishing and the like.

FIG. 56 illustrates a comparison chart or report showing a list of the top twenty rankings for shooters using a gun or ejector 20' on a given day. In the illustration being described, the day was Dec. 15, 2011, and the chart shows the top twenty national rankings. In the illustration being described, the team Upper Sandusky, Ohio generated this chart using the system 200. Note that its player identified at row 2 of the ranking was identified as T. Tedford of Upper Sandusky, Ohio who had a total number of shots taken of 7,644 as illustrated in the chart 750 in FIG. 56.

FIG. 57A illustrates a chart or report based on total shots made by the player and also illustrates player T. Tedford being ranked second among all shooters in the nation as illustrated in the report 752 shown in FIG. 57A. Note in the examples being described in FIGS. 56 and 57A-57B, the user of the system 200 identified or selected to show the national rankings for the team Upper Sandusky, Ohio. The top twenty players are indicated in the reports 750 (FIG. 56) and 752 (FIG. 57A), while the rest of the Upper Sandusky, Ohio team players and their associated ranking are identified as 750*a* (FIG. 56) and 752*a* (FIG. 57A) of the reports.

FIGS. 57B and 58 illustrate additional exemplary reports. FIG. 57B illustrates the ranking based upon percentage of shots made, indicating that M. Watson, for example, of the team Upper Sandusky, Ohio shot 99.85% and was second in the national ranking as illustrated in the chart or report 754 in FIG. 57B. Another exemplary report 756 is shown in FIG. 58 wherein a top twenty national rankings for the team Upper Sandusky, Ohio is shown. This illustration in FIG. 58 shows the list of rankings using the gun or ejector 20' for a given age range, minimum age sixteen and maximum age eighteen in the illustrative chart shown in FIG. 58. Note that the player T. Tedford of the Upper Sandusky, Ohio team ranked second with total shots taken of 993,343.

In still another example shown in FIG. 59, another report 758 is shown as being generated based upon the top twenty rankings for shooter's using the gun or ejector 20' during a particular date range. In the illustration being described, the date range selected by user was Dec. 23, 2011-Dec. 22, 2012. Note that for that year and date range, T. Tedford of the Upper Sandusky, Ohio team was also ranked second with the identified number of shots, total shots taken being the same as in the illustration shown in FIG. 58.

Advantageously, the system and method, again, permits sorting and comparisons based upon using Doppler measurements and without Doppler measurements and using any number of combinations or permutations of selected criteria or variables. In the illustration being described, several pre-programmed standard reports or chart formats are provided or generated by the website WS. In this regard, the following charts or reports are provided for use by the user:

| Type of Chart | Description |
| --- | --- |
| Total Makes | provides a chart based on total number of shots made at a location or distance (with or without Doppler measurements) |
| Total Shots Taken | provides a chart based on total number of shots taken at a location or distance (with or without Doppler measurements) |
| Percentage of Shots Made | provides a ranking and comparison based upon the shooting accuracy of the player, namely, the total shots made over the number of shots taken (with or with Doppler measurements) |

Again, as mentioned earlier herein, the comparisons can be made on a player basis, on a team basis and such comparisons can be made versus other players on the same or different teams, other geographic regions, such as city, county, state, national, international, age range, date range, gender and the other variables mentioned earlier herein relative to FIGS. 46 and 51.

The system 200 may provide other formats of charts as well. FIGS. 60-63 illustrate various examples of such charts. In FIG. 60, a chart showing the rankings for a particular shooting area was generated by the user. In the illustration shown, the chart was generated for a player, namely Kevin Curtis of the team Upper Sandusky, Ohio, and it shows his ranking compared to various geographic areas such as on his local team in the area 760*a*, regional compared to his ranking regionally (e.g., in the county in which his team is located) at area 760*b* in the chart or report 760. His statewide rankings, national shooting rankings and international shooting rankings are also shown in the areas 760*c*, 760*d* and 760*e*, respectively. Note that the charts in each area 760*a*-760*e* show the total shots made and the shooting percentage and his relative ranking based upon those criteria for the day (Dec. 15, 2011 in the illustration), week, month, year and even lifetime as shown in the columns indicated in report 760 in FIG. 60.

FIG. 61 illustrates still another exemplary report or chart 770. In this report, the player or team shooting percentages are presented for comparison to the local teams, regional teams, statewide teams, national teams and international teams as illustrated. Similar to the chart 760 in FIG. 60, the chart 770 shows the rankings for total shots, total shots made, shooting percentages for the day, week, month, year and lifetime for the player when compared to a local shooting team (area 770*a* in FIG. 61), a regional team (such as all teams in a particular geographic county in area 770*b* in FIG. 61), statewide (area 770*c*), nationwide within a nation, such as the United States of America (area 770*d*) and internationally in area 770*e* of chart 770 in FIG. 61.

FIGS. 62 and 63 illustrate yet another exemplary embodiment of charts that may be generated using the system 200. In this embodiment, a chart 772 is shown. In the embodiment shown in FIGS. 62 and 63 one of the variables used for comparison is one or more Doppler measurements. In the illustrative chart 772, which was created by the user using statistics website WS, the chart 772 shows the player or team versus the national shooting report. Note in top area of the chart 772*a*, the chart identifies a particular distance which could also be any distance measured by the Doppler System 800. Thus, at the distance of fifteen feet, the chart or report 772 was created for the player Kevin Curtis. Note that at a distance of fifteen feet, his statistics or rankings are shown in areas 772*b* of the chart 772. Likewise, in the area 772*c* his regional rankings or statistics are shown, and his statewide statistics are shown in the area 772*d*. The national rankings or statistics for the player are shown in the area 772*e* and the international data or statistics are shown in the area 772*f* as shown.

Thus, in this illustrative chart 772 in FIG. 62, the player Kevin Curtis' ranking was first on his team for total shots made from a distance of fifteen feet for the date Dec. 15, 2011, the week, the month of December, but he was ranked second for both the year 2011 and over his lifetime in comparison to other players on the team. Similar rankings and statistics are shown in the other areas 772*c*-772*f*.

Still another exemplary chart or report 774 is shown in FIG. 63. In this illustrative embodiment, the shooter selected a single shooting location, shooting location 8 in the illustration being described, and the Doppler measured distances of fifteen to nineteen feet. Again, the user selected a player, Kevin Curtis in the illustration, and his rankings are listed in the chart or reports 774. In this regard, note that his local shooting statistics compared to other shooters on his team is shown in the area 774*a*, regional shooting rankings or statistics in the area 774*b*, statewide shooting rankings or statistics in the area 774*c*, nationwide shooting rankings or statistics in the area 774*d* and international shooting rankings or statistics in the area 774*e* of the chart 774. Again, the preceding charts and reports are illustrative, and it should be understood that other shooting locations (0-16 in the illustration being described), distances or other criteria could be selected to generate other reports or charts.

Advantageously, the system and method described herein enable the user to gather, collect and analyze shooting data and use that shooting data to compare a player or a team's shooting efficiency and ranking versus other players or teams on a local, regional, statewide, national or even international basis. Using the information, a coach can focus the player on practicing shooting on different areas and with different techniques to improve the player's efficiency. The generation of these reports will greatly improve a shooter's efficiency based on two primary, but different reasons. First, the actual data can be studied and a user (both coach and shooter) can find areas that need improvement, whether it be more or less shots at that giving location or if the user is struggling on a certain side of the court, a coach may devise a game plan that would keep the user from shooting from those locations. Secondly, a player or coach will be able to see what others are doing and compare his body of work to theirs. This becomes a competition between users and thus more and more shots are taken and tracked since typically users of this machine are competitive. This collection of data can then be reviewed at a later time by users, including the player P, the coaches who advise the player P or other third parties in order to assess and improve the performance of the player P. In this regard, the collection of data can be made available to select other interested parties, such as players and coaches on other teams of a basketball league with which the player is affiliated, for example. Each individual player or a collection of players on a team or at a given school or club can maintain the website WS on which the statistics and data described above are posted. This posting allows a world-wide comparison of the performances of the players among themselves, their coaches, associates, and rivals. The system 200 also permits competitions among players, teams and the like.

Advantageously, the system and method permit gathering and configuring shooting statistics of the shooter and team across any territory, such as the United States, via the website WS and various graphical user interface showing graphical tables, charts and illustrations (not shown), on the website WS, with the data and statistics being downloadable, printable and/or visible for comparison. For example, the computer 202 (FIG. 10) may communicate with the remote computer or server 206 or a computer associated with a remote launcher 204 to cause players at remote locations to shoot the same shots. The data and statistics from those shots are collected and stored on, for example, computers 202 and server 206 and may be uploaded and stored on the server 206 associated with the website WS. Players, coaches and other interested parties may then view the data and statistics for comparison by visiting the website WS. For example, Player A from University X may compare his statistics to Player B from University Y. This enables virtual play, practice and comparison among at least one or a plurality of players on the same team or different teams and thereby enables a team to compare their data and statistics to one or more other teams.

Comparisons can be done in real-time, thereby allowing a plurality of players at remote locations, for example, to directly compete against each other in real-time if desired. For example, a given pass (in terms of speed, direction, and inclination angle) in FIG. 10 is made to Player A, who catches it and shoots. His performance data is recorded on the gun or ejector 20' or by computer 202 associated with that gun or ejector 20' on storage device 44'. The computer 202 or controller 32' controlling the gun or ejector 20' which launched the pass to Player A informs (e.g., wirelessly, directly or via website WS) the remote launcher 20' in a remote system, such as system 200 in FIG. 10, of the characteristics of that pass. The remote computer 204 then makes an identical pass to Player B using the remote gun or ejector 20', and the two computers 202, 204 and website WS allow an immediate comparison of the performances of the two players on those computers or on the remote website WS. For example, guns at different locations could be online and a prompt (not shown) on each machine allowing a shooter to challenge a remote shooter on another machine. When the challenge is accepted, the challenger programs his Gun and that program automatically programs (via the Internet) the remote Gun. The challenger then starts his gun and the real time challenge begins. The results may be displayed on display 45' (FIG. 10).

ADDITIONAL ADVANTAGES OR CONSIDERATIONS

1. It is contemplated that the data can be made available on other networks as well. For example, an intra-net can, in effect, be established, either by direct communication lines, or by using the Internet for communication, but by restricting access, as by using passwords. In this case, the data is not made available publicly, but to a limited audience. As a specific example, the data can be held in a remote or local server and made available through a dial-up line or other conventional communication link, such as a wireless link, to specific parties, such as members of a player's P league, members of other teams in any league, across the United State or anywhere around the world. In effect, the server 206 or website WS may deliver a display via a graphical user interface (not shown), an electronic or hard copy reprint of the data, although extensive, on demand to a limited audience.

2. In one embodiment, the data and statistics can be presented visually, such as by the scatter diagram 600 (FIG. 42) superimposed over a bird's eye view of a basketball court. The scatter diagram 600 indicates the area at each point where a shot 604 was taken, and indicates the distance, number of shots taken, the percentage of shots which scored and the like percentage which scored as swishers.

The statistics, data, reports and charts, or a selected subset of them, can be stored and printed for the player P when he finishes a practice session.

3. It was stated above that, after a launch of the basketball 12' by gun or ejector 20', the speed of the basketball 12' is computed and when the speed drops to zero, it is concluded that the player P has caught the basketball 12' at that time. However, if the player P is moving when the basketball 12' is caught, the speed may not drop to zero. Therefore, in one embodiment of the invention, the basketball 12' catch is concluded when the speed of the basketball 12' drops below a threshold. That threshold can be based on an average running speed of a player P, under the reasoning that a basketball in flight has a significantly higher speed than that running speed. Then, when a player P catches such a basketball 12', the speed of the basketball 12' will abruptly be constrained to conform to the player's P running speed. Thus, when the flight speed of the basketball 12' changes to the running speed of a player P, a catch may be concluded.

4. The speed of the basketball 12' along its flight path running from the gun or ejector 20' to the player P need not be constant. Thus, a more accurate computation of distance will (1) break the flight path into segments, (2) compute a speed S for each segment, (3) assign a time T to each segment, (4) compute a distance for each segment as S×T, and (5) compute a total distance as the sum of the distances for all segments.

5. In one embodiment of the invention, the actual, precise distance occurring between a player P and the gun or ejector 20' is not necessarily always the most important variable.

Rather, the response of the player P at a given location to a given pass is considered a paramount consideration. The player's P location is deduced from measured data. In a precise technical sense, the basketball 12' in FIG. 10 which is launched by the gun or ejector 20' will not maintain a constant speed. Further, the flight path followed by the basketball 12' will usually, but not always, resemble a parabola, but will not be a precise parabola because of the changing speed. Therefore, multiplying the measured speed of the basketball 12' by the time of flight will only give an approximation of the length of the flight path. This length is not the same as the distance from the gun or ejector 20' to the player P, although a good approximation of distance can probably be derived from the measured speed and time. The algorithms presented and described relative to FIGS. 13A-13I enable calculations of such distances.

Nevertheless, one embodiment of the invention is not necessarily concerned with precise measurement of these parameters. Rather, one embodiment of the invention is concerned with repeatability of the challenge presented to the player P by each pass. That is, the invention knows the release angle, $\theta_r$, at which the basketball 12' is launched, together with the compass direction of the launch. In addition, the invention knows the initial speed of the basketball 12'. These three parameters (ball speed, inclination angle, and compass direction) allow a given launch, or pass, to be repeated accurately. Thus, the same pass can be presented to the same player at different times and to different players at the same or different times and/or at the same or different places. The players' responses to the challenges can be measured, in terms of hold times and accuracy of their shots, recorded and then compared as mentioned earlier.

In regard to comparisons, because the players' responses are determined as provided herein, the player(s) responses can be compared in a meaningful way. This is despite the fact that the actual distance from the player P to the gun or ejector 20' may not be known with high precision.

From another perspective, the flight distance of the pass made by the gun or ejector 20' can be considered secondary data. The flight distance is computed, based on measured data, but the more relevant information lies in the detailed characteristics of the pass made by the gun or ejector 20'.

One goal or use of another embodiment may be to reproduce a given type of pass, for a given player or for comparison between multiple players. This reproduction can be made by repeating the gun's or ejector's 20' performance, in terms of (1) ball speed, (2) entry angle, (3) release direction, and so on. It is not necessary to work backward from the computed travel distance of a given pass in order to reproduce that pass.

Thus, from this other perspective, the measured information, such as distance of a pass delivered by the gun or ejector 20', is a useful approximation to the player P from the gun or ejector 20'.

6. Another consideration is that there are significant differences between the system 200 and prior art ball throwers, such as a baseball or tennis ball throwers. These differences include:

a) A typical women's basketball weighs about 20 ounces and a men's 22 ounces. Tennis balls weigh about 2 and $2\frac{1}{16}$ ounces and a baseball weighs about 5.13 ounces. One form of the invention launches a basketball with a velocity of about 30 feet per second at maximum spring setting. A baseball pitch traveling 100 miles per hour travels roughly 150 feet per second, as does a similar tennis ball. Because the basketball 12' travels at a significantly lower speed, compared to a baseball or tennis ball thrower, for example, from a baseball or tennis ball thrower machine (not shown), the basketball player can make reliable and repeatable catches of a launched basketball 12' in a bare-handed manner. As one specific example, the player can reliably and repeatably catch, bare-handed, the basketball 12' pass every ten seconds for ten minutes. That is not possible with a high speed baseball pitch, for example.

b) The basketball player catches and holds, at least momentarily, the launched basketball 12', and then makes a shot. That is not intended with baseball pitches and tennis ball guns.

c) The basketball launcher has associated equipment which calculates the distance of the player from the launcher 20, 20'. That is not done with the other prior art launchers that throw other balls, nor is there a reason to do so.

d) The basketball player does not use a bat, racket, or other instrument to strike the ball.

e) The basketball gun or ejector 20, 20' can require the player to move to different pre-programmed locations, to catch the ball. An automated tennis ball gun may require the player to move, but that is not done in baseball pitching, and, again, the player is not catching the ball, shooting and the ball launcher is not monitoring and measuring the distance from where the ball is shot to a hoop 14, 14'.

f) The basketball gun or ejector 20, 20' does not impose side spin on the ball, in order to cause deviations in the ball's path, as is done in tennis or in a baseball "curve ball."

7. Under one embodiment of the invention, a detection of (1) the speed of the launched basketball, (2) the entry angle, and (3) the release angle of the launched pass are all done without human intervention. This is different from having a database of basketball statistics that is kept and used. For example, the database may indicate that, in a given game, player X caught a pass from player Z who was positioned at a certain location, and then player X scored a three-point shot. Again, system 200 stores this information and allows one to re-construct the pass using the gun or ejector 20' in FIG. 10 and without human intervention.

A similar comment applies to the detection of whether a shot scores a goal.

8. In Table V a listing of each component in the circuits shown in the FIGS. 15A-15D is provided. It should be understood that these are merely representative and other values and arrangement of components could be used and the invention is not limited precisely thereto:

TABLE V

| Component | Type | Value | Available From |
| --- | --- | --- | --- |
| C1, C2, C200, C201, C205, C207, C217 | ceramic | .001 | Digi-Key Corporation of Thief River Falls, MN |
| C3, C4, C202, C203, C204, C206 | ceramic | .1 | Digi-Key Corporation of Thief River Falls, MN |

TABLE V-continued

| Component | Type | Value | Available From |
|---|---|---|---|
| C5, C8, C212, C213, C214, C215, C216 | tantalum | 1.0u | Digi-Key Corporation of Thief River Falls, MN |
| C6, C7 | ceramic | .047 | Digi-Key Corporation of Thief River Falls, MN |
| C9, C16, C17, C218, C219, C308, C303 | tantalum | 4.7u | Digi-Key Corporation of Thief River Falls, MN |
| C301 | COG | 2.0u | Digi-Key Corporation of Thief River Falls, MN |
| C302 | COG | 1.0u | Digi-Key Corporation of Thief River Falls, MN |
| C304 | aluminum | 20u | Digi-Key Corporation of Thief River Falls, MN |
| C305 | aluminum | 47u | Digi-Key Corporation of Thief River Falls, MN |
| C306 | 200 uF | Cap | Digi-Key Corporation of Thief River Falls, MN |
| C307, C311 | tantalum | 10u | Digi-Key Corporation of Thief River Falls, MN |
| C309 | ceramic | 330 pf | Digi-Key Corporation of Thief River Falls, MN |
| C310 | ceramic | .22u | Digi-Key Corporation of Thief River Falls, MN |
| C312 | ceramic | .01u | Digi-Key Corporation of Thief River Falls, MN |
| D1 | 160-1087 | LED-RED | Digi-Key Corporation of Thief River Falls, MN |
| D4, D2 | diode | 1N4148 | Digi-Key Corporation of Thief River Falls, MN |
| D3 | 160-1089 | GRN LED | Digi-Key Corporation of Thief River Falls, MN |
| D5 | 160-1088 | YEL LED | Digi-Key Corporation of Thief River Falls, MN |
| D205, D206, D207, D208, D209, D210, D211, D212, D300 | Schottky | 1N5711 | Digi-Key Corporation of Thief River Falls, MN |
| L300, L301 | 308-1486 | 47 uH | Digi-Key Corporation of Thief River Falls, MN |
| Q1 | PNP | 2N3906 | Digi-Key Corporation of Thief River Falls, MN |

TABLE V-continued

| Component | Type | Value | Available From |
|---|---|---|---|
| Q2, Q3, Q4, Q5, Q301 | NPN | 2N3904 | Digi-Key Corporation of Thief River Falls, MN |
| Q300 | Pchan | IRFR5305 | Digi-Key Corporation of Thief River Falls, MN |
| R1 | 1% metal film | 39.2k | Digi-Key Corporation of Thief River Falls, MN |
| R2 | 1% metal film | 43.2k | Digi-Key Corporation of Thief River Falls, MN |
| R3 | 1% metal film | 1.0k | Digi-Key Corporation of Thief River Falls, MN |
| R4, R13, R16, R17, R25, R209, R214 | 1% metal film | 100k | Digi-Key Corporation of Thief River Falls, MN |
| R5 | 1% metal film | 750 | Digi-Key Corporation of Thief River Falls, MN |
| R6 | 1% metal film | 2.49k | Digi-Key Corporation of Thief River Falls, MN |
| R7, R302 | 1% metal film | 2k | Digi-Key Corporation of Thief River Falls, MN |
| R8, R9, R10, R20, R22, R26, R204, R205, R207, R212, R303, | 1% metal film | 10K | Digi-Key Corporation of Thief River Falls, MN |
| R11 | 1% metal film | 33k | Digi-Key Corporation of Thief River Falls, MN |
| R12, R14 | 1% metal film | 8.45k | Digi-Key Corporation of Thief River Falls, MN |
| R15 | 1% metal film | 1 meg | Digi-Key Corporation of Thief River Falls, MN |
| R18, R19 | 1% metal film | 249 | Digi-Key Corporation of Thief River Falls, MN |
| R21 | 1% metal film | 3.01k | Digi-Key Corporation of Thief River Falls, MN |
| R23, R28, R31, R317 | 1% metal film | 4.99k | Digi-Key Corporation of Thief River Falls, MN |
| R27, R203, R208, R213, R301, R305 | 1% metal film | 1k | Digi-Key Corporation of Thief River Falls, MN |
| R29, R32 | 1% metal film | 15k | Digi-Key Corporation of Thief River Falls, MN |
| R202 | 1% metal film | 6.65k | Digi-Key Corporation of Thief River Falls, MN |

TABLE V-continued

| Component | Type | Value | Available From |
|---|---|---|---|
| R206 | 1% metal film | 4.9k | Digi-Key Corporation of Thief River Falls, MN |
| R210, R211 | 1% metal film | 374k | Digi-Key Corporation of Thief River Falls, MN |
| R216, R215 | 1% metal film | 1.82k | Digi-Key Corporation of Thief River Falls, MN |
| R304 | 1% metal film | 9.09k | Digi-Key Corporation of Thief River Falls, MN |
| R310 | 1% metal film | 30.1k | Digi-Key Corporation of Thief River Falls, MN |
| OSC1 | CTX306CT | 20 MHz | Digi-Key Corporation of Thief River Falls, MN |
| U1 | microprocessor | 18F2520 | Digi-Key Corporation of Thief River Falls, MN |
| U4, U201 | opamp | TL074 | Digi-Key Corporation of Thief River Falls, MN |
| U5 | digital pot | MCP4013 | Digi-Key Corporation of Thief River Falls, MN |
| U6 | Gunn | MAC7801 | MAcom available from Richardson RFPD, Inc. of LaFox, IL |
| U8 | regulator | MC7805D2 | Digi-Key Corporation of Thief River Falls, MN |
| U200 | reference | LTC1634smt | Digi-Key Corporation of Thief River Falls, MN |
| U204 | serial driver | MAX232A | Digi-Key Corporation of Thief River Falls, MN |
| U300 | neg voltage | LT1931AES5 | Digi-Key Corporation of Thief River Falls, MN |

While the system, procedure and methods constitute preferred or illustrative embodiments, it is to be understood that the invention is not limited to these precise methods, and that changes may be made in either without departing from the scope of the invention, which is defined in the appended claims.

What is claimed is:

1. An apparatus for assisting a user during basketball practice on a basketball playing surface having a basketball goal, the apparatus comprising:
a frame;
an ejector mounted to said frame and configured to launch at least one basketball toward each of a plurality of predetermined locations on said basketball playing surface;
a user interface connected to said frame, wherein said user interface comprises a rendering of the basketball playing surface, including a three-point line, and a plurality of selectable locations at spaced angular positions on the interface, adjacent to the rendering of the three-point line, wherein each one of said selectable locations mark a distinct location on said rendering corresponding to said predetermined locations on said basketball playing surface, and wherein each of said selectable locations are configured to be individually, directly, and sequentially actuated by physical touch from the user to create a first custom basketball practice arrangement;
a programmable control system in electronic communication with the ejector and the user interface, wherein said control system is configured to receive data representing the first custom basketball practice arrangement created by the user at the interface and command said ejector to launch at least one basketball in the direction(s) of each of said predetermined locations corresponding with selectable locations of the first custom basketball practice arrangement;

a detector associated with the basketball goal and in electronic communication with the control system, said detector configured to detect basketballs passing through the goal; and a report generator in electronic communication with the control system and the detector, wherein said report generator is configured to generate and transmit a report comprising shooting data for each of said predetermined locations of said first custom basketball practice arrangement;

wherein said control system is adapted to end said first custom basketball practice arrangement and to monitor for subsequent actuation of said selectable locations at the user interface by the user to create a second custom basketball practice arrangement different from said first custom basketball practice arrangement;

wherein the shooting data comprises a shooting efficiency score for each of the predetermined locations of said first custom basketball practice arrangement.

2. The apparatus of claim 1 wherein:
the control system is configured to determine and record the distance the at least one basketball was ejected; and
the shooting data further comprises the distance the at least one basketball was ejected.

3. The apparatus of claim 1 wherein:
the control system is configured to determine and record information regarding the travel path of the at least one basketball; and
the shooting data further comprises the information regarding the travel path of the at least one basketball.

4. The apparatus of claim 1 wherein:
the report generator is configured to make the shooting data available on a website.

5. The apparatus of claim 1 wherein:
the report generator is configured to make the shooting data available on an application.

6. The apparatus of claim 1 further comprising:
a remote control device in wireless communication with the control system configured to permit programming of the ejector from a remote location.

7. A system for assisting a user during basketball practice comprising:
a launcher configured to eject a series of basketballs to predetermined locations;
a housing for said launcher;
a user interface located on said housing and comprising a rendering of a basketball playing area, including a rendering of a three-point arc, and a plurality of selectable locations configured to be actuated individually and directly by physical touch of the user to create custom basketball shooting routines, wherein said selectable locations are located at spaced angular positions on or along said three-point arc;
a control device in electronic communication with said user interface, wherein said control device is configured to receive data representing a user created custom basketball shooting routine and command the launcher to eject the series of basketballs to each of the predetermined locations corresponding with the selectable locations actuated by the user in the user created custom basketball shooting routine;

a sensor associated with a basketball goal, wherein said sensor is configured to detect basketballs passing through the basketball goal; and a calculation device in electronic communication with the tracking device and the sensor, wherein said calculation device is configured to receive data from said control device indicating the number of passes in the user created custom basketball shooting routine and data from the sensor indicting the number of made basketball shots during the time the launcher was commanded to launch basketballs as part of the user created custom basketball shooting routine and generate a report comprising shooting data.

8. The system of claim 7 wherein:
the shooting data comprises the predetermined locations of the user created custom basketball practice routine corresponding with the selectable locations touched at the user interface, the number of times a basketball was ejected as part of the user created custom basketball practice routine as commanded by the control device, and the number of successful basketball goals detected by the sensor Lduring the user created basketball practice routine.

9. The system of claim 8 further comprising:
a network connection device in communication with the calculation device and a network, the network connection device configured to receive and transmit the shooting data.

10. The system of claim 9 wherein:
the calculation device is configured format the shooting data for display on a website.

11. The system of claim 9 wherein:
the calculation device is configured to format the shooting data for display on an application installed on a connected device.

12. A basketball launching apparatus for assisting a user performing a basketball practice routine comprising:
a frame;
a rotatable ejector connected to said frame and capable of launching a plurality of basketballs in a user programmed sequence to a number of predetermined spaced angular locations along a basketball playing area;
an interface connected to said frame and comprising:
a panel comprising a rendering of a basketball playing surface comprising a rendering of a baseline, a key, and a three-point line;
a plurality of selectable locations at said panel, wherein each of said selectable locations are configured to be selected by a user through physical touch in a direct, individual, and sequential fashion;
at least one input receiver for receiving the user selection of the plurality of selectable locations which define a user created custom basketball practice routine;
a time delay selection area configured to permit the user to select a time delay between said passes of said user created custom basketball practice routine; and
a shots per location selection area configured to permit the user to select the number of basketballs to be passed to each of said predetermined locations in said user created custom basketball practice routine;
wherein said plurality of selectable locations are arranged in spaced angular positions at said interface along the rendering of the three-point line;
a controller in electronic communication with the interface and the ejector, wherein controller is configured to receive said user created custom basketball practice routine from the interface, determine which of the predetermined locations said basketball passes will be launched to by said ejector to perform the user created custom basketball practice routine, and command said ejector to launch the number of basketballs selected by the user at the shots per location selection area to each of said predetermined locations forming the user created custom basketball practice routine at intervals corresponding with the user selection made at the time delay selection area; and a counter configured to determine the number shots which pass through the basketball hoop during the user created custom basketball practice routine; and a calculation device in electronic communication with the interface and the counter, wherein said calculation device is configured to receive data from the counter regarding the number of basketballs passing through the basketball hoop during the user created custom basketball practice routine and data from the controller regarding the number of passes made during the user created custom basketball practice routine and calculate a user efficiency score for each of the predetermined locations forming the user created custom basketball practice routine.

13. The system of claim 7 wherein:

the tracking device is configured to determine and record the distance each of the basketballs were ejected; and the shooting data further comprises the distance each of the basketballs where ejected.

14. The apparatus of claim 2 wherein:

said report comprises a second rendering of the basketball playing surface, including a second rendering of the three-point line; and the shooting efficiency score for each of the predetermined locations is displayed on the second rendering of the basketball playing surface to correspond with the distance the at least one basketball was ejected such that the report is capable of displaying the shooting efficiency scores in front of or behind the rendering of the three-point line.

* * * * *

UNITED STATES PATENT AND TRADEMARK OFFICE
CERTIFICATE OF CORRECTION

PATENT NO. : 10,518,153 B2
APPLICATION NO. : 14/984051
DATED : December 31, 2019
INVENTOR(S) : Joseph et al.

Page 1 of 1

It is certified that error appears in the above-identified patent and that said Letters Patent is hereby corrected as shown below:

In the Claims

In Claim 8, Line 22:
Please delete "Lduring" and insert --during--.

In Claim 10, Line 30:
Please insert --to-- after "configured".

Signed and Sealed this
Twenty-fifth Day of February, 2020

Andrei Iancu
*Director of the United States Patent and Trademark Office*